US008304431B2

(12) United States Patent
Buntinx

(10) Patent No.: US 8,304,431 B2
(45) Date of Patent: *Nov. 6, 2012

(54) USE OF D4 AND 5-HT2A ANTAGONISTS, INVERSE AGONISTS OR PARTIAL AGONISTS

(75) Inventor: Erik Buntinx, Alken (BE)

(73) Assignee: PharmaNeuroBoost N.V., Alken (BE)

( * ) Notice: Subject to any disclaimer, the term of this patent is extended or adjusted under 35 U.S.C. 154(b) by 1007 days.

This patent is subject to a terminal disclaimer.

(21) Appl. No.: 10/580,962

(22) PCT Filed: Dec. 2, 2004

(86) PCT No.: PCT/BE2004/000172
§ 371 (c)(1),
(2), (4) Date: May 31, 2006

(87) PCT Pub. No.: WO2005/053796
PCT Pub. Date: Jun. 16, 2005

(65) Prior Publication Data
US 2007/0078162 A1  Apr. 5, 2007

(30) Foreign Application Priority Data

| Dec. 2, 2003 | (CA) | 2451798 |
|---|---|---|
| Dec. 2, 2003 | (EP) | 03447279 |
| Jan. 5, 2004 | (EP) | 04447001 |
| Mar. 18, 2004 | (CA) | 2461248 |
| Mar. 18, 2004 | (EP) | 04447066 |
| Oct. 21, 2004 | (EP) | 04025035 |
| Nov. 4, 2004 | (JP) | 2004-349085 |
| Nov. 15, 2004 | (CA) | 2487529 |

(51) Int. Cl.
*A01N 43/40* (2006.01)
*A01N 43/08* (2006.01)
*A61K 31/445* (2006.01)
*A61K 31/34* (2006.01)
*C07D 211/00* (2006.01)
*C07D 307/00* (2006.01)

(52) U.S. Cl. ......... 514/316; 514/469; 546/186; 549/469
(58) Field of Classification Search .................. 514/316, 514/469; 546/186; 549/469
See application file for complete search history.

(56) References Cited

U.S. PATENT DOCUMENTS

| 4,797,419 A | 1/1989 | Moos et al. |
|---|---|---|
| 5,364,857 A | 11/1994 | Bode Greuel |
| 5,446,070 A | 8/1995 | Mantelle |
| 5,554,383 A | 9/1996 | Dodman |
| 5,635,213 A | 6/1997 | Nystrom et al. |
| 5,723,467 A | 3/1998 | Mesens et al. |
| 5,759,837 A | 6/1998 | Kuhajda et al. |
| 5,762,960 A | 6/1998 | Dodman |
| 5,780,474 A | 7/1998 | Peglion et al. |
| 5,955,459 A | 9/1999 | Bradley et al. |
| 6,150,353 A | 11/2000 | Broekkamp et al. |
| 6,191,133 B1 | 2/2001 | Coppen |
| 6,300,354 B1 | 10/2001 | Steiner et al. |
| 6,358,698 B1 | 3/2002 | Weiner et al. |
| 6,486,153 B1 | 11/2002 | Pineiro et al. |
| 2002/0086899 A1* | 7/2002 | Sanchez et al. ............... 514/469 |
| 2003/0032636 A1 | 2/2003 | Cremers et al. |
| 2004/0002482 A1 | 1/2004 | Dudley et al. |
| 2004/0213816 A1 | 10/2004 | Weiner et al. |
| 2004/0266790 A1 | 12/2004 | Bartl et al. |
| 2005/0119248 A1 | 6/2005 | Buntinx |
| 2005/0119249 A1 | 6/2005 | Buntinx |
| 2005/0119253 A1 | 6/2005 | Buntinx |
| 2005/0148018 A1 | 7/2005 | Weiner et al. |
| 2005/0203130 A1 | 9/2005 | Buntinx |
| 2005/0261278 A1 | 11/2005 | Weiner et al. |
| 2005/0261340 A1 | 11/2005 | Weiner et al. |
| 2005/0288328 A1 | 12/2005 | Weiner et al. |
| 2006/0199842 A1 | 9/2006 | Weiner et al. |
| 2006/0264465 A1 | 11/2006 | Weiner et al. |
| 2006/0264466 A1 | 11/2006 | Weiner et al. |
| 2011/0136865 A1 | 6/2011 | Buntinx |

(Continued)

FOREIGN PATENT DOCUMENTS

CA  2461248  9/2009

(Continued)

OTHER PUBLICATIONS

Van Oekelen et. al., Eur. J. Pharm., 2001, Elsevier Science, vol. 425, pp. 21-32.*
Meyer, U. A., J. Pharmacokinetics & Biopharmaceutics,1996, Plenum Publishing Corp., vol. 24, pp. 449-459.*
Müller T, entitled "Drug treatment of non-motor symptoms in Parkinson's disease," Expert Opinion on Pharmacotherapy, 2002, vol. 3, No. 4, pp. 381-388.
PERMAX prescription information, Eli Lilly Company, (http://www.fda.gov/medwatch/safety/2003/permax_Pl.pdf), revised Oct. 2, 2003, pp. 1-2.

(Continued)

*Primary Examiner* — Shengjun Wang
*Assistant Examiner* — Sarah Pihonak
(74) *Attorney, Agent, or Firm* — Amster, Rothstein & Ebenstein LLP

(57) ABSTRACT

The present invention relates to the use of compounds and compositions of compounds having D4 and 5-HT2A antagonistic, partial agonistic or inverse agonistic activity for the treatment of the underlying dysregulation of the emotional functionality of mental disorders (i.e. affect instability-hypersensitivity-hyperaesthesia-dissociative phenomena-etc). The invention also relates to methods comprising administering to a patient diagnosed as having a neuropsychiatric disorder a pharmaceutical composition containing (i) compounds having D4 antagonistic, partial agonistic or inverse agonistic activity and (ii) compounds having 5-HT2A antagonistic, partial agonistic or inverse agonistic, and (iii) any known medicinal compound and compositions of said compounds. The combined D4 and 5-HT2A antagonistic, partial agonistic or inverse agonistic effects may reside within the same chemical or biological compound or in two different chemical and/or biological compounds.

33 Claims, 15 Drawing Sheets

U.S. PATENT DOCUMENTS

Figure 1:
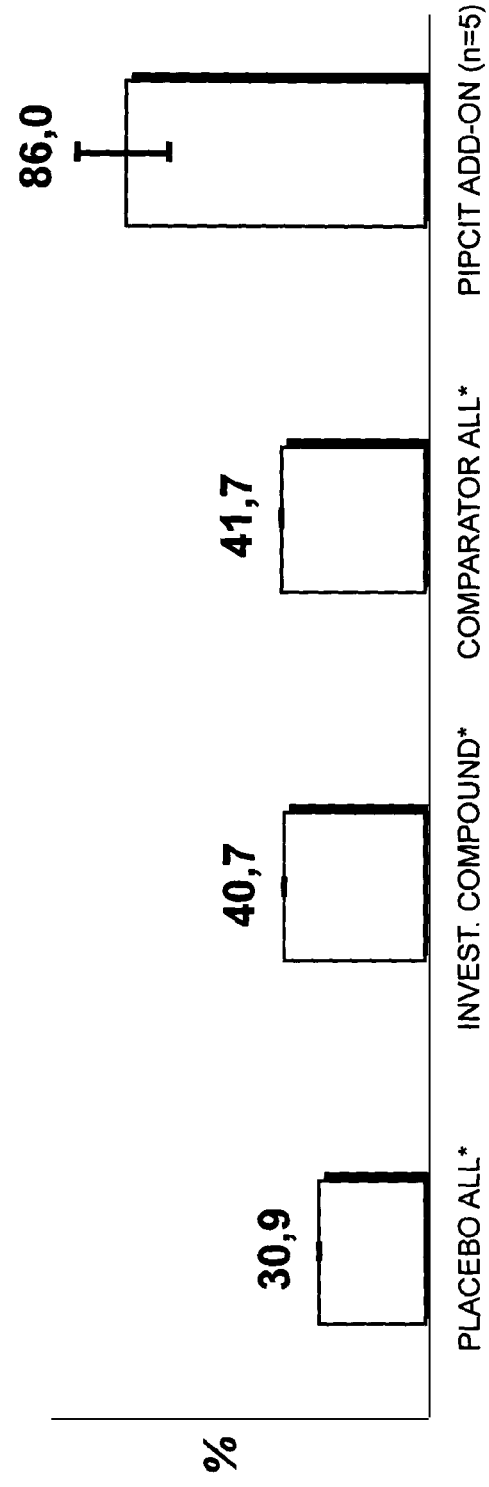

| | | | |
|---|---|---|---|
| 2011/0172251 A1 | 7/2011 | Buntinx | |
| 2011/0207776 A1 | 8/2011 | Buntinx | |
| 2012/0010242 A1 | 1/2012 | Buntinx | |

FOREIGN PATENT DOCUMENTS

| | | | |
|---|---|---|---|
| DE | 4039631 A1 | 6/1992 | |
| WO | WO 98/11897 A | 3/1998 | |
| WO | WO 98/43646 A | 10/1998 | |
| WO | WO 00/64441 A | 11/2000 | |
| WO | WO0103694 A1 * | 1/2001 | |
| WO | WO 01/41701 A2 * | 6/2001 | |
| WO | WO 01/98298 A | 12/2001 | |
| WO | WO 02/051833 A | 7/2002 | |

OTHER PUBLICATIONS

USPTO Office Action dated May 3, 2007 in connection with related U.S. Appl. No. 10/803,793, filed Mar. 18, 2004.
USPTO Office Action dated Aug. 10, 2007 in connection with related U.S. Appl. No. 10/984,683, filed Nov. 9, 2004.
USPTO Office Action dated Oct. 2, 2007 in connection with related U.S. Appl. No. 10/752,423, filed Jan. 6, 2004.
USPTO Office Action dated Oct. 19, 2007 in connection with related U.S. Appl. No. 10/803,793, filed Mar. 18, 2004.
USPTO Office Action dated Feb. 22, 2008 in connection with related U.S. Appl. No. 10/984,683, filed Nov. 9, 2004.
USPTO Office Action dated Jan. 23, 2008 in connection with related U.S. Appl. No. 10/725,965, filed Dec. 2, 2003.
USPTO Office Action dated Mar. 13, 2007 in connection with U.S. Appl. No. 10,725,965, filed Dec. 2, 2003.
USPTO Office Action dated Sep. 15, 2008 in connection with U.S. Appl. No. 10,725,965, filed Dec. 2, 2003.
USPTO Office Action dated Mar. 6, 2009 in connection with U.S. Appl. No. 10/580,962, filed May 31, 2006.
USPTO Office Action dated Oct. 21, 2008 in connection with U.S. Appl. No. 10/984,683, filed Nov. 9, 2004.
USPTO Office Action dated Feb. 20, 2009 in connection with U.S. Appl. No. 10/803,793, filed Mar. 18, 2004.
USPTO Office Action dated Sep. 2, 2008 in connection with U.S. Appl. No. 10/803,793, filed Mar. 18, 2004.
USPTO Office Action dated Feb. 19, 2009 in connection with U.S. Appl. No. 10/752,423 filed Jan. 6, 2004.
USPTO Office Action dated May 13, 2008 in connection with U.S. Appl. No. 10/752,423, filed Jan. 6, 2004.
USPTO Office Action dated Jun. 20, 2007 in connection with U.S. Appl. No. 10/752,423, filed Jan. 6, 2004.
USPTO Office Action dated Feb. 16, 2007 in connection with U.S. Appl. No. 10/803,793, filed Mar. 18, 2004.
USPTO Office Action dated May 14, 2007 in connection with U.S. Appl. No. 10/984,683, filed Nov. 9, 2004.
Janssen-Cilab B.V instructions for Dipiperon tablets 40 mg. and Dipiperon drops 40 mg/ml.
Wirz-Justice A et al., "Haloperidol Disrupts, Clozapine Reinstates the Circadian Rest-Activity Cycle in a Patient With Early-Onset Alzheimer Disease," Alzheimer Disease and Associated Disorders, vol. 14, No. 4, pp. 212-215, 2000.
Decision to Grant a European Patent Pursuant to Article 97(1) EPC, dated Feb. 19, 2009 in connection with EP Patent Application No. 04025035.9, 2 pages.
Communication Under Rule 71(3) EPC, dated Oct. 13, 2008, in connection with EP Patent Application No. 04025035.9, 95 pages.
Marek G J et al., "Synergistic Action of 5-HT2A Antagonists and Selective Serotonin Reuptake Inhibitors in Neuropsychiatric Disorders," Online publication: Sep. 13, 2002 at http://www.acnp.org/citations/Npp091302378,Neuropsychopharmacology 28: 402-12, 2003.
"Atypical Antipsychotic Agents: Medicaid Drug Use Review Criteria for Outpatient Use," Sep. 15, 2008 Office Action in U.S. Appl. No. 10/725,965, pp. 1-14.
Heiser P et al., entitled "The selective serotonin reuptake inhibitors and the newer antidepressants in child and adolescent psychiatry," Zeitschrift fur Kinder—und Jugendpsychiatrie und Psychotherpie Switzerland 30: 2002, 173-183.

Carlier PR et al., Synthesis of a Potent Wide-Spectrum Serotonin-, Norepinephrine-, Dopamine- reuptake inhibitor (SNDRI) and a species-selective dopamine reuptake inhibitor based on the gamma-amino alcohol functional group, Bioorgan. Medicin. Chem. Let. 8, 1998, 487-492.
Fitzgerald K D et al., entitled "Risperidone Augmentation of Serotonin Reuptake Inhibitor Treatment of Pediatric Obsessive Compulsive Disorder," Journal of Child and Adolescent Psychopharmacology, vol. 9, No. 2, 1999, 115-123.
McDougle C J et al., entitled "A Double-blind. Placebo-Dontrolled Study of Risperidone Addition in Serotonin Reuptake Inhibitor-Refractory Obsessive-complusive Disorder," Arch Gen Psychiatry, vol. 57, Aug. 2000, 794-801.
Maina G et al., entitled "antipsychotic agumentation for treatment resistant obsessive-compulsive disorder: what if antipsychotic is discontinued," Int. Clin. Psychopharm, 18, 2003, 23-28.
Hirose S et al., entitled "An Open Pilot Study Combining Risperidone and a Selective Serotonin Reuptake Inhibitor as Initial Antidepresant Therapy," J. Clin. Psych. 63, 2002, 733-736.
Truffinet P et al., Placebo-controlled study of the D4/5-HT2A antagonist fananserin in the treatment of schizophrenia. Am J. Psychiatry 156: 419-425, 1999.
Squelart P, et al., "Pipamperone (Dipiperon), a useful sedative neuroleptic drug in troublesome chronic pyschotic patients." Acta Psychiatrica Belgica, vol. 77, No. 2, Mar. 1977, pp. 284-293.
Koch HJ, et al., "Successful therapy of tardive dyskinesia in a 71-year-old woman with a combination of tetrabenazine, olanzapinr and tiapride." International Journal of Clinical Practice, vol. 57, No. 2, Mar. 2003, pp. 147-149.
Diebold K, et al., "Are psychoactive-drug-induced changes in plasma lipid and lipoprotein levels of significance for clinical remission in psychiatric disorders?" Pharmacopsychiatry, 1998, vol. 31, pp. 60-67.
Grozinger M, et al., "Melperone is an inhibitor of the CYP2D6 catalyzed O-demethylation of venlafaxine." Pharmacopsychiatry, vol. 36, No. 1, Jan. 2003, pp. 3-6.
Perugi G, et al., "Effectiveness of adjunctive gabapentin in resistant bipolar disorder: Is it due to anxious-alcohol abuse comorbidity?" Journal of Clinical Psychopharmacology, vol. 22, No. 6, 2002, pp. 584-591.
Wieling, W et al., "Initial orthostatic hypotension as a cause of recurrent syncope: A case report." Clinical Autonomic Research, vol. 11 (4), 2001, pp. 269-270.
Database Pharmaprojects Online! PJB Publications Ltd., Dec. 1999. Caesar Accession No. 1498 (2 pages).
Adler L, et al., "Praxis Der Stationaeren Akutbenhandlung Von Manien Restrospektive Vergleichsuntersuchung An Je 100 Patienten Zweier Psychiatrischer Zentren. Practice of In-Patient Acute Treatment of Manias." Fortschritte Der Neurologie Psychiatrie, Stuttgart, vol. 62, No. 12, 1994, pp. 479-488.
Ansoms C, et al., "Sleep disorders in patents with severe mental depression: double-blind placebo-controlled evaluation of the value of pipamerone (Dipiperone)." Acta Psychiatrica Scandinavica, vol. 55, No. 2, Feb. 1977, pp. 116-122.
Leysen JE, et al., "Receptor interactions of new antipsychotics: relation to pharmacodynamic and clinical effects." International Journal of Psychiatry in Clinical Practice, vol. 2, No. 1, 1998, pp. S3-S17.
Vanhoenacker P, et al., "Efficient expression of the human dopamine D4.2 receptor: Pinitive influence of pipamperone on expression levels." Abstracts of the Society for Neuroscience, vol. 26 No. 1/2, 2000.
Schotte A, et al., "Risperidone compared with new and reference antipsychotic drugs: in vitro and in vivo receptor binding." Psychopharmacology, vol. 124, No. 1-2, 1996, pp. 57-73.
Van De Vijver Damc, et al., "Antipsychotic and Parkinson's disease: Association with disease and drug choice during the first 5 years of antiparkinsonian drug treatment." Eur. J. Clin. Pharmacology, vol. 58, 2002, pp. 157-161.
Jovic NI, et al., "Phenomenology and treatment of delirium in Alzheimer's disease" Revue Medicate De La Suisse Romande, vol. 117, No. 9, Sep. 1997, pp. 655-658.
Engelborghs S, et al., "Amino acids of biogenic amines in cerbrospinal fluid of patients with Parkinson's disease." Neurochemical Research, vol. 28 No. 8, Aug. 2003, pp. 1145-1150.

Newman-Tancredi A, et al., "[35S]-guansosine-5'-O-(3-thio) triphosphate binding as a measure of efficacy at human recombinant dopamine D4.4 receptors: Actions of antiparkinsonian and antipsychotic agents." Journal of Pharmacology and Experimental Therapeutics, vol. 282 (1), 1997, pp. 181-191.

Tarzi FI, et al., "Role of dopamine D4 receptors in neuropsychiatric disorders." Journal of Neurochemistry, vol. 81, supp. 1, Jun. 2002, p. 33, Abstract.

Tarzi FI, et al., "Dopamine D4 receptors: Significance for molecular psychiatry at the millennium." Molecular Psychiatry, vol. 4, No. 6, Nov. 1999, pp. 529-538.

Leopold NA, "Risperidone treatment of drug-related psychosis in patients with parkinsonism." Movement Disorders, vol. 15, No. 2, Mar. 2000, pp. 301-304.

Tahar AH, et al., "Antidyskinetic effect of JL-18, a clozapine analog, in parkinsonian monkeys." European Journal of Pharmacology, vol. 399, No. 2-3, Jul. 7, 2000, pp. 183-186.

Zesiewicz TA, et al., "Clozapine withdrawal symptoms in a Parkinson's disease patient." Movement Disorders, vol. 17, No. 6, Nov. 2002, pp. 1365-1367.

Faltraco F, et al., "Akuelle therapeimoglichkeiten der alzheimer demenz (current therapeutical strategies in dementia)." Neurol. Rehabil. 2003, 9(1), pp. 15-22.

Etchepareborda MC, "Neurocognitive and pharmacological approach to specific learning disorders." Database Medline Online, US National Library of Medicine, Feb. 1999, and Revista De Neurologia, vol. 28, suppl. 2, Feb. 1999, pp. S81-S93, Abstract.

Stahl SM, et al., "Examination of nightime sleep-related problems during double-blind, placebo-controlled trials of galantamine in patients with Alzheimer's disease." Current Medical Research and Opinion 2004, vol. 20, No. 4, pp. 517-524.

Meneses, A, "Are 5-HT 1B/1D and 5-HT 2A/2B/2C receptors involved in learning and memory processes?" Drugs 1999, vol. 2 (8), 1999, pp. 796-801.

Wirz-Justice A, et al., "Haloperidol disrupts, clozapine reinstates the circadian rest-activity cycle in a patient with early-onset Alzheimer disease." Alzheimer Disease and Associated Disorders, vol. 14, No. 4, 2000, pp. 212-215.

Fahs H, et al., "Thymoregulateurs Dans L'Agitation et les Troubles Du Comportement Chez le Sujet Dement a Propos de Huit Cas, Anticonvulsivants and Aggresive Behaviors in Alzheimer's Disease. Eight Cases Reports." L'Encephale, vol. 25, No. 2, 1999, pp. 169-174.

Werth E, et al., "Decline in long-term circadian rest-activity cycle organization in a patient with dementia." Journal of Geriatric Psychiatry and Neurology, vol. 15, No. 1, Apr. 2002, pp. 55-59.

Meltzer HY, et al., "Plasma clozapine levels and the treatment of L-Dopa-induced psychosis in Parkinson's disease. A high potency effect of clozapine." Neuropsychopharmacology, vol. 12, No. 1, 1995, pp. 39-45.

Munchau A, et al., "Pharmacological treatment of Parkinson's disease." Postgraduate Medical Journal, vol. 76, Oct. 2000, pp. 602-610.

Hubble J P et al., entitled "Pre-clinical studies of pramipexole: clinical relevance," European Journal of Neurology Supplement, 2000, vol. 7 (Suppl. 1), pp. 15-20.

Silver D E et al., entitled "Initiating therapy for Parkinson's disease," Neurology, 1998, vol. 50 (Suppl. 6), pp. S18-S22.

Stein D J et al, entitled "Risperidone augmentation of serotonin reuptake inhibitors in obsessive-compulsive and related disorders," J Clin Psychiatry, 1997, 58(3):119-122.

Albert U et al., entitled "Management of treatment resistant obsessive-compulsive disorder. Algorithms for Pharmacotherapy," Panminerva Med, 2002, 44(2):83-91.

Mohr N et al., entitled "Quetiapine augmentation of serotonin reuptake inhibitors in obsessive-compulsive disorders," Int J Psychopharmacol, 2002, 17(1):37-40.

Silver H, entitled "Selective serotonin reuptake inhibitor augmentation in the treatment of negative symptoms of schizophrenia," 2003, Int Clin Psychopharmacol, 18(6):305-313.

USPTO Office Action dated Jun. 10, 2009 in connection with related U.S. Appl. No. 10/725,965, filed Dec. 2, 2003.

USPTO Office Action dated Aug. 5, 2009 in connection with related U.S. Appl. No. 10/752,423, filed Jan. 6, 2004.

USPTO Office Action dated Nov. 10, 2009 in connection with related U.S. Appl. No. 10/803,793, filed Mar. 18, 2004.

USPTO Office Action dated Jul. 21, 2009 in connection with related U.S. Appl. No. 10/984,683, filed Nov. 9, 2004.

Interview Summary dated Oct. 22, 2009 in connection with related U.S. Appl. No. 10/725,965.

Khan, Arif, MD et al., "Symptom Reduction and Suicide Risk in Patients Treated With Placebo in Antidepressant Clinical Trials—An Analysis of the Food and Drug Administration Database." Arch Gen Psychiatry, vol. 57, Apr. 2000, pp. 311-317.

Montgomery, Stuart A. et al., "Escitaloprarn versus venlafaxine XR in the treatment of depression." International Clinical Psychopharmacol, 21:297-309, 2006.

Moore, Nicholas et al., "Prospective, multicentre, randomized double-blind study of the efficacy of escitalopram versus citalopram in outpatient treatment of major depressive disorder." International Clinical Psychopharmacol, 20:131-137, 2005.

Nelson, Craig J., et al., "Atypical Antipsychotic Augmentation in Major Depressive Disorder: A Meta-Analysis of Placebo-Controlled Randomized Trials." Am J Psychiatry, Sep. 2009, 166:980-991.

Peremans, Kathelijne et al., "Evaluation of serotonin-2A receptor occupancy with 123 I-5-I-R91150 and single-photon emission tomography before and after low-dose pipamperone administration in the canine brain." Nuclear Medicine Communications, 29:724-729, 2008. Published and Page Proofs.

Prinssen, Eric P.M. et al., "The effects of antipsychotics with 5-HT2C receptor affinity in behavioral assays selective for 5-HT2C receptor antagonist properties of compounds." European Journal of Pharmacology, 2000, 388:57-67.

Download from www.whocc.no/atcddd/welcome.html dated Aug. 20, 2009, 2 pages.

Buntinx, E. et al., Preclinical and clinical evidence for the efficacy of pipamperone in augmenting the antidepressant effects of the SSRI citalopram. International Journal of Neuropsychopharmaccology, vol. 1, supplement 1, p. 190, Jul. 2008.

Buntinx E et al., Preclinical and Clinical Evidence for the Efficacy of Pipamperone in Augmenting the Antidepressant Effects of the SSRI Citalopram. Poster presented at the XXVI Collegium Internationale Neuro-Psychopharmacologicum (CINP) Congress Jul. 13-17, 2008, Munich, Germany and Summary Expected Receptor Occupancy (RO) of Pipamperone in vivo.

USPTO Office Action dated Jun. 8, 2010 in connection with U.S. Appl. No. 10/725,965, filed Dec. 2, 2003.

USPTO Office Action dated Mar. 18, 2010 in connection with U.S. Appl. No. 10/752,423, filed Jan. 6, 2004.

USPTO Office Action dated Apr. 28, 2010 in connection with U.S. Appl. No. 10/752,423, filed Jan. 6, 2004.

USPTO Office Action dated Jun. 9, 2010 in connection with U.S. Appl. No. 10/752,423, filed Jan. 6, 2004.

USPTO Office Action dated Jun. 8, 2010 in connection with U.S. Appl. No. 10/803,793, filed Mar. 18, 2004.

USPTO Office Action dated Jun. 23, 2010 in connection with U.S. Appl. No. 10/984,683, filed Nov. 9, 2004.

USPTO Notice of Allowance and Fee(s) Due dated Jun. 23, 2010 in connection with U.S. Appl. No. 10/752,423, filed Jan. 6, 2004.

Dierick M et al., entitled "A Double-Blind Comparison of Venlafaxine and Fluoxetine for Treatment of Major Depression in Outpatients," Prog. Neuro-Psychopharmacol & Biol. Psychiat., 1996, vol. 20, pp. 57-71.

Remington's Pharmaceutical Sciences, 1980, 420-425.

Stella V J et al., entitled "Prodrug strategies to overcome poor water solubility," Advanced Drug Delivery Reviews 59 (2007) 677-694.

Hegerl U et al., entitled "The serotonin syndrome scale: first results on validity," Eur Arch Psychiatry Clin Neurosci (1998) 248: 96-103.

USPTO Notice of Allowance and Fee(s) Due dated Aug. 10, 2010 in connection with U.S. Appl. No. 10/725,965, filed Dec. 2, 2003.

Brown E S, entitled "Extrapyramidal Side Effects with Low-Dose Risperidone," Can J Psychiatry (1997), vol. 42(3). pp. 325-326.

Caley C F, entitled "Extrapyramidal Reactions from Concurrent SSRI and Atypical Antipsychotic Use," Can J Psychiatry (1998), vol. 43(3), pp. 307-308.

CITALOPRAM 10mg, 20mg and 40mg Tablets, 2 pages Actavis Date of last revisions Mar. 2007.

Buntinx E et al., Low dose pipamperone, enhancing antidepressant effect of citalopram, occupies 5HT2A 50-60% leaving D2 nearly drug free, European Neuropsychopharmacology, vol. 20, Supp. 3, Aug. 2010, S396-5397, along with poster.

Bonaccorso S et al., entitled "SR46349-B, a 5-HT 2A/SC Receptor Antagonist, Potentiates Haloperidol-induced Dopamine Release in Rat Medial Prefrontal Cortex and Nucleus Accumbens," Neuropsychopharmacology 2002—vol. 27, No. 3, 430-441.

Gelders Y G et al., entitled Thymosthenic Agents, A Novel Approach in the Treatment of Schizophrenia, British Journal of Psychiatry (1989), 155 (suppl. 5), 33-36.

Nasrallah H A, et al., entitled "Combination therapy is here to stay," Current Psychiatry, vol. 9, No. 5, (May 11-12, 2010).

USPTO Office Action dated Jun. 23, 2011 in connection with U.S. Appl. No. 12/931,313, filed Jan. 26, 2011.

USPTO Office Action dated Jan. 31, 2012 in connection with U.S. Appl. No. 12/931,313, filed Jan. 26, 2011.

USPTO Office Action dated Feb. 28, 2012 in connection with U.S. Appl. No. 13/065,638, filed Mar. 25, 2011.

Marsh L M, entitled "Neuropsychiatric Aspects of Parkinson's Disease," Psychosomatics 41:1, Jan.-Feb. 2000, 15-23.

Haan H, entitled "So viel wie notig, so wenig wie moglich," TW Neurologie Psychiatre 8, Heft 7/8, Jul./Aug. 1994, 396-397.

Verdeau-Pailles J entitled "Traitement du syndrome neuroleptique par le chlorhydrate de biperidene sous sa forme retard Etude sur 9 mois de 55 malades hospitalises," Encephale, 1976, 2(4):341-347.

Thase M E et al., , entitled "Remission rates during treatment with venlafaxine or selective serotonin reuptake inhibitors," British Journal of Psychiatry, 2001, 178:234-241.

Stahl S M et al., entitled A Critical Review of Atypical Antipsychotic Utilization:Comparing Monotherapy with Polypharmacy and Augmentation, Current Medicinal Chemistry, 2004, 11, 313-327.

Chalamet M-J, entitled Les troubles caracteriels du vieillard, Psychologie Medicale, 1981, 13, 2, 365-369.

Fahs I et al., entitled "Thymoregulateurs dans l'agitation et les troubles du comportement chez le sujet dement a propos de huit cas," Encephale, 1999, 25, (2):169-174.

Introduction—Common Medications for Anxiety Disorders, http://www.anxieties.com/med-intro-.php, 4 pages.

"Diagnostic and Statistical Manual of Mental Disorders, Fourth Edition, Text Revision," http://www.behavenet.com/diagnostic-and-statistical-manual-mental-disorders-fourth-edition-text-revision#301, 1 page, (May 10, 2012).

* cited by examiner

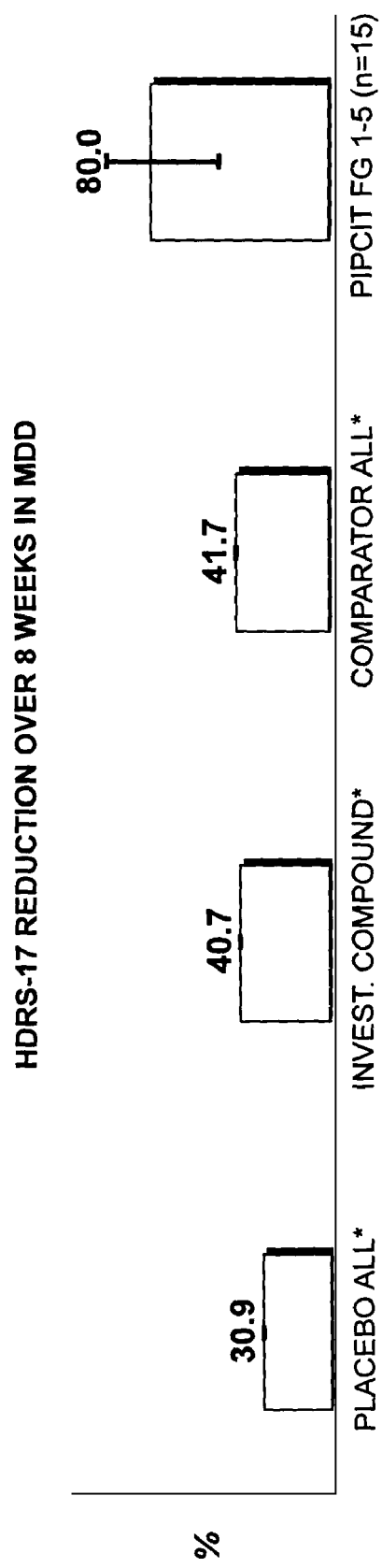

Figure 4

Foregoing Treatment During 1-5 (mean 4) days with Pipamperon 8-12 (mean 10) mg/day (bid) Followed With the Combination Treatment of Pipamperon and Citalopram 20-50 (mean 26) mg/day (bid) (PIPCIT FG 1-5) in MDD (HDRS-17 at BL = 23) in Comparison with the Standard Efficacy of Antidepressants in Clinical Trials*

* A. KHAN et al, Symptom Reduction and Suicide Risk in Patients Treated With Placebo in Antidepressant Clinical Trials, ARCH. OF GENERAL PSYCHIATRY / VOL 57, APR 2000)

Figure 6:
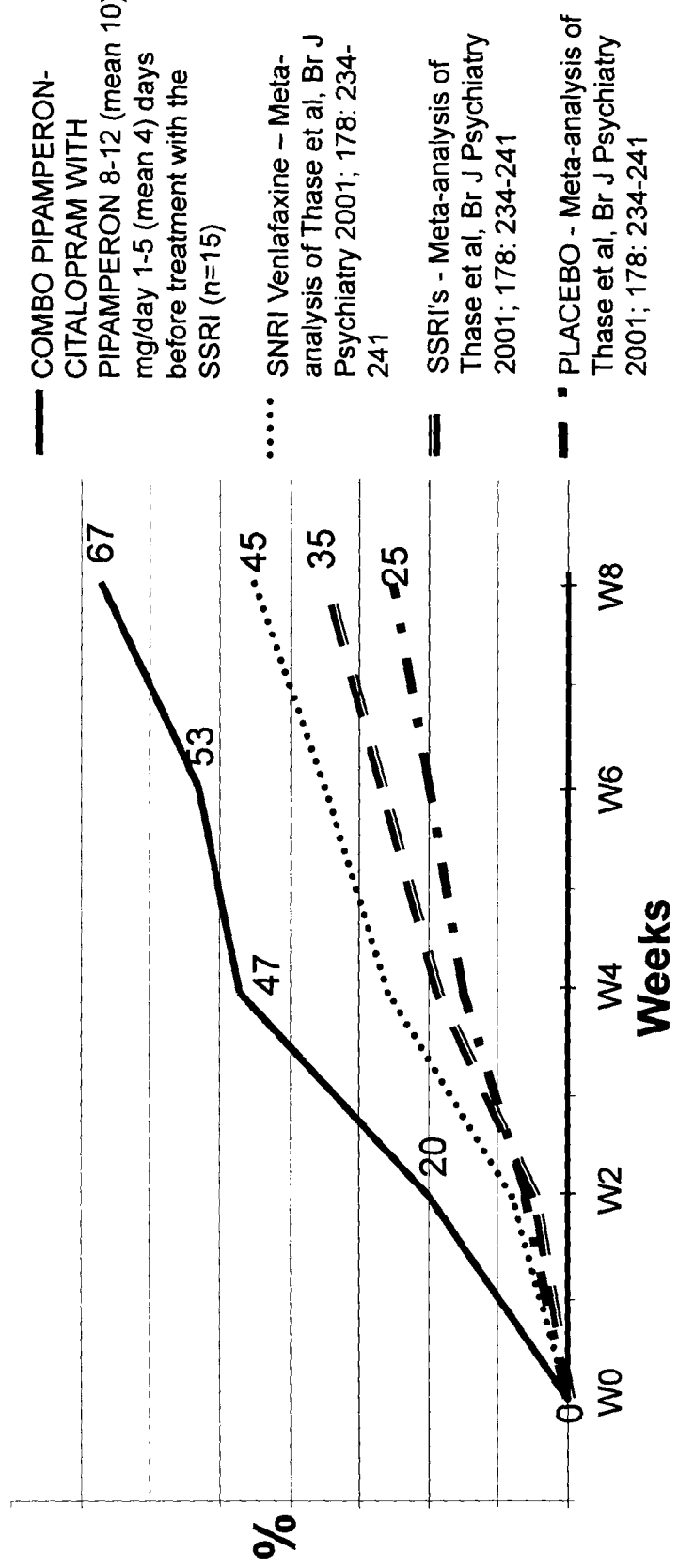

Figure 6 REMISSION RATES (HDRS-17 <=7): COMBO PIPAMPERON-CITALOPRAM WITH A FORE-GOING TREATMENT OF 4 DAYS WITH PIPAMPERON 10mg/day vs SNRI (venlafaxine) in MAJOR DEPRESSION Foregoing & Add-On Treatment with Pipamperon 8-12 mg/day (bid) and Citalopram 20-40 mg/day (bid) in MDD in Comparison with the Standard Efficacy of Antidepressants in Clinical Trials*

* A. KHAN et al, Symptom Reduction and Suicide Risk in Patients Treated With Placebo in Antidepressant Clinical Trials, ARCH. OF GENERAL PSYCHIATRY / VOL 57, APR 2000)

Figure 12:
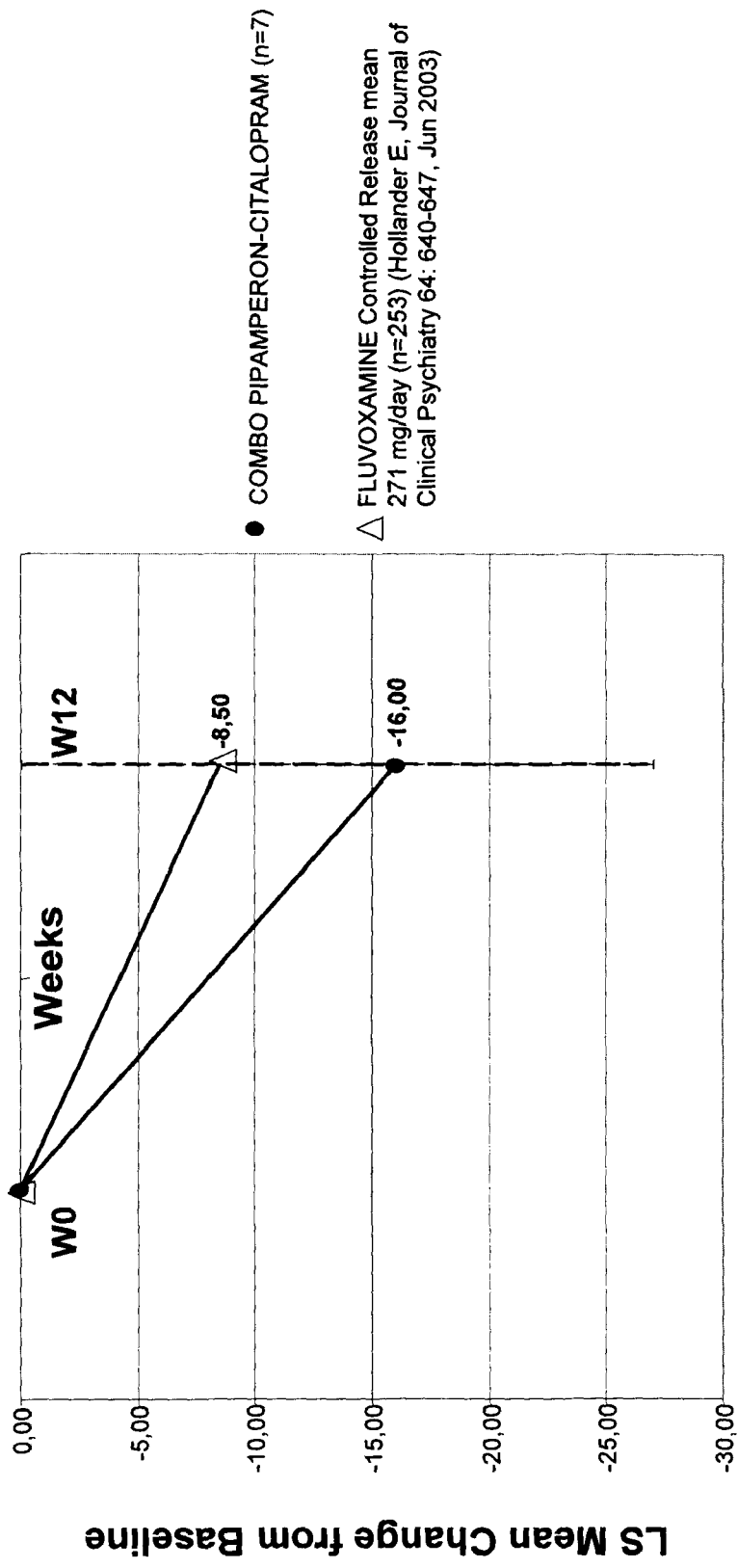

Figure 12  Y-BOCS TOTALSCORE: Foregoing & Add-On Treatment with Pipamperon 8-15 mg/day (bid) and Citalopram 30-80 mg/day (bid) in comparison with the SSRI fluvoxamine in OCD

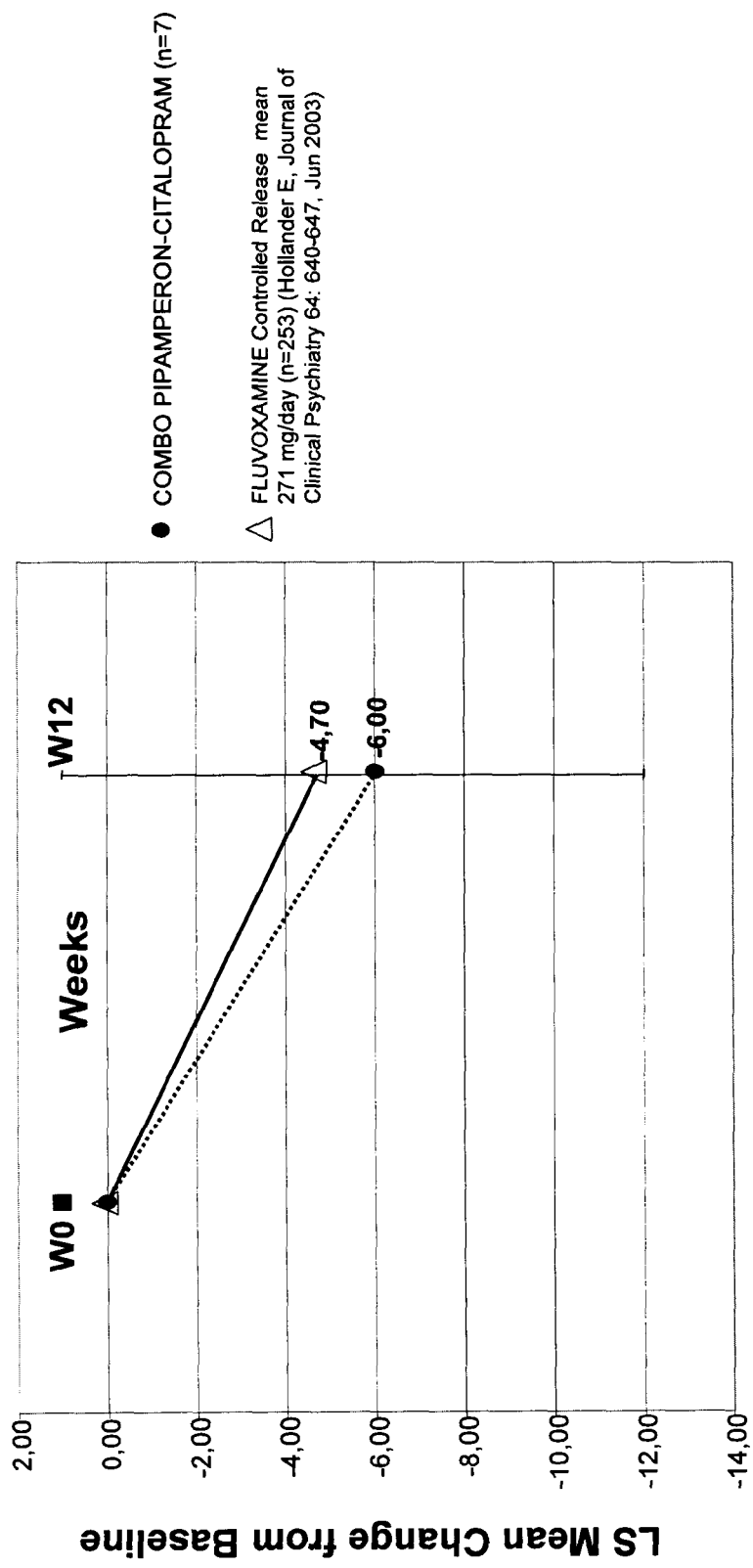
Figure 14    Y-BOCS COMPULSION SCORE: Foregoing & Add-On Treatment with Pipamperon 8-15 mg/day (bid) and Citalopram 30-80 mg/day (bid) in comparison with the SSRI fluvoxamine in OCD

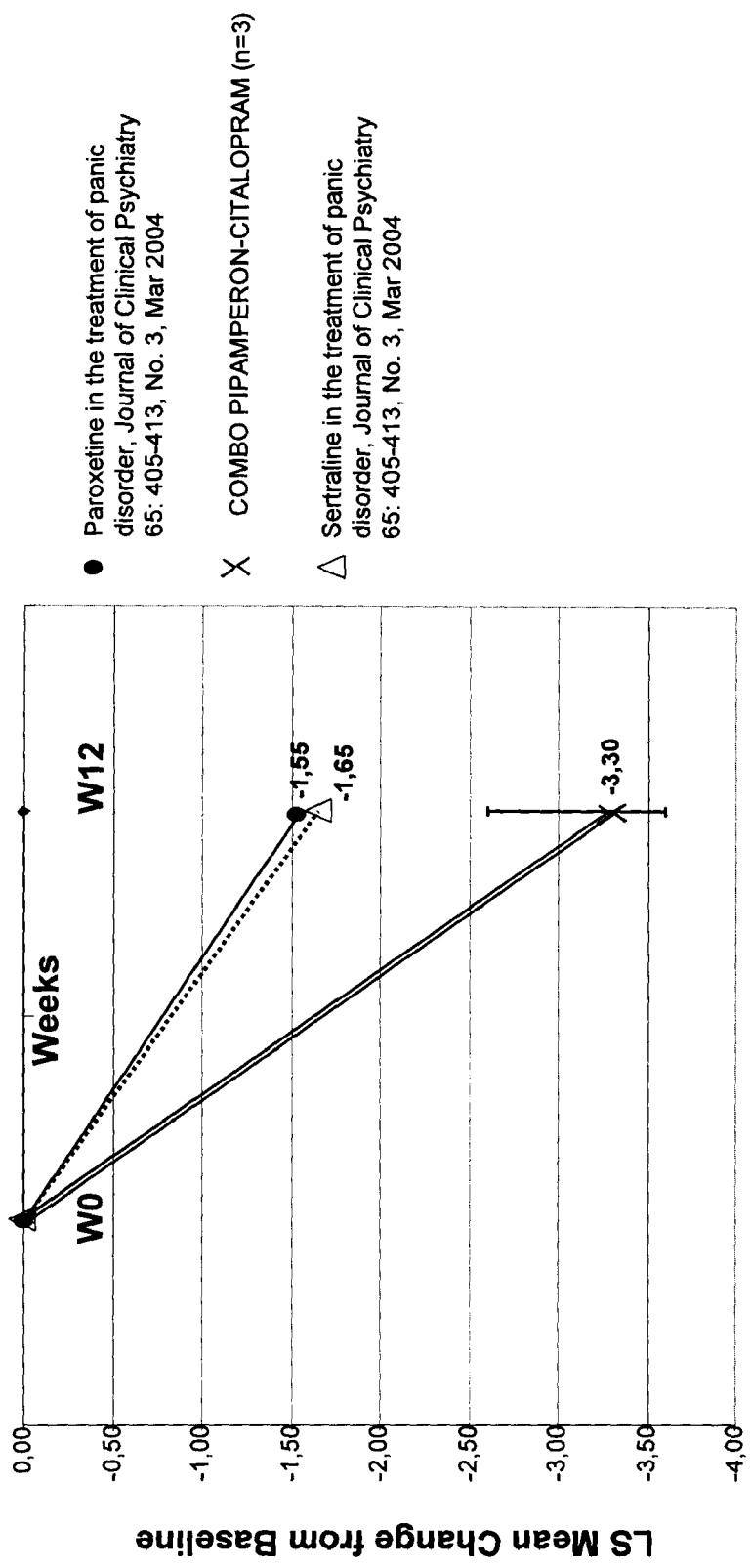
Figure 15 CGI-SEVERITY SCORE: Foregoing & Add-On Treatment with Pipamperon 8 mg/day (bid) and Citalopram 20-40 mg/day (bid) in comparison with the SSRI in Panic Disorder

USE OF D4 AND 5-HT2A ANTAGONISTS, INVERSE AGONISTS OR PARTIAL AGONISTS

CROSS REFERENCE TO RELATED APPLICATIONS

This application is a national stage entry under 35 U.S.C. §371 of PCT International Application No. PCT/BE2004/000172, filed Dec. 2, 2004, which claims priority of U.S. patent application Ser. No. 10/725,965, filed Dec. 2, 2003, now U.S. Pat. No. 7,884,096, Canadian Patent Application No. 2,451,798, filed Dec. 2, 2003, European Patent Application No. 03447279.5, filed Dec. 2, 2003, European Patent Application No. 04447001.1, filed Jan. 5, 2004, U.S. patent application Ser. No. 10/752,423, filed Jan. 6, 2004, now U.S. Pat. No. 7,855,195, European Patent Application No. 04447066.4, filed Mar. 18, 2004, U.S. patent application Ser. No. 10/803,793, filed Mar. 18, 2004, Canadian Patent Application No. 2,461,248, filed Mar. 18, 2004, European Patent Application No. 04025035.9, filed Oct. 21, 2004, Japanese Patent Application No. 2004-349085, filed Nov. 4, 2004, U.S. patent application Ser. No. 10/984,683, filed Nov. 9, 2004, and Canadian Patent Application No. 2,487,529, filed Nov. 15, 2004.

FIELD OF THE INVENTION

The invention relates to the field of neuropsychiatry. More specifically, the invention relates to the use of compounds, which have D4 and 5-HT2A antagonist, inverse agonist or partial agonist activity, for the preparation of medicaments.

BACKGROUND OF THE INVENTION

Conventionally, mental disorders are divided into types based on criteria sets with defining features. DSM-IV (*American Psychiatric Association*, (1993-ISBN 0-89042-061-0)) is the in the art well-known golden standard of such a categorical classification. In DSM-IV, there is no assumption that each category of mental disorder is a completely discrete entity with absolute boundaries dividing it from other mental disorders or from no mental disorder. There is also no assumption that all individuals described as having the same mental disorder are alike in all important ways. Individuals sharing a diagnosis are likely to be heterogeneous even in regard to the defining features of the diagnosis. Thus, the categorical defined mental disorders as mood and anxiety disorders are having an external and even internal variable co-incidence of symptoms concerning e.g. mood, anxiety, perception, feeding, somatic sensations, sexual functions, sleep, cognitive functioning, impulse control, attention, substance use, personality, bereavement, identity, phase of life, abuse or neglect and other aspects of behavior.

In a dimensional system, clinical presentations are classified based on quantification of attributes i.e. dysfunctions rather than the assignment to categories and works best in describing phenomena that are distributed continuously and that do not have clear boundaries.

Emotion dysregulation is known as such an attribution or dysfunction that plays an important role in the development and course of mental disorders (Gross, J. J. & Munoz. R. F., 1995, *Emotion regulation and mental health, Clinical Psychology: Science and Practice*, 2, 151-164; Mennin, D. S., Heimberg, R. G., Turk, C. L. & Fresco, D. M., 2002, *Applying an emotion regulation framework to integrative approaches to generalized anxiety disorder, Clinical Psychology: Science and Practice*, 9, 85-90; Linehan, M. M., 1993, *Cognitive-behavioral treatment of borderline personality disorder*, New York, The Guilford Press; Gratz, K. L., Roemer, L., 2001 & 2004, *Multidimensional assessment of emotion regulation and dysregulation: development, factor structure, and initial validation of the Difficulties in Emotion Regulation Scale*, Annual meeting of the Association for Advancement of Behavior Therapy, November 2001 & *Journal of Psychopathology and Behavioral Assessment*, Vol. 26, No. 1, March 2004) besides behavioural and cognitive dysfunctions. D4 dopamine receptors (D4DR), almost exclusively present in the mesocortical and mesolimbic systems (O'Malley, K. L., Harmon, S., Tang, L., Todd, R. D., *The rat dopamine D4 receptor; sequence, gene structure, and demonstration of expression in the cardiovascular system, New Biol.*, 4, 137-46, 1992), are in the art known as modulators of emotion and cognition. D4DR agonistic activity gives a behavioural sensitisation; D4DR antagonistic activity leads to an emotion modulation (Svensson, T. H., Mathé, A. A., *Monoaminergic Transmitter Systems, Biological Psychiatry* (eds. D'Haenen, H., et al.), 45-66, 2002, John Wiley & Sons, Ltd). Data demonstrate that agonism of the dopamine D4 receptors play an important role in the induction of behavioral sensitization to amphetamine and accompanying adaptations in pre- and postsynaptic neural systems associated with the mesolimbocortical dopamine projections (D. L. Feldpausch et al.; *The Journal of Pharmacology and Experimental Therapeutics* Vol. 286, Issue 1, 497-508, July 1998).

Results suggest that the antagonisms of cortical D2 dopamine receptors are a common target of traditional and atypical antipsychotics for therapeutic action. Higher in vivo binding to the D2 receptors in the cortex than in the basal ganglia is suggested as an indicator of favorable profile for a putative antipsychotic compound (X. Xiberas and J. L. Martinot; *The British Journal of Psychiatry* (2001) 179: 503-508). Results show that dopamine D4 receptor antagonism in the brain does not result in the same neurochemical consequences (increased dopamine metabolism or hyperprolactinemia) observed with typical neuroleptics (Smite Patel at al., *The Journal of Pharmacology and Experimental Therapeutics* Vol. 283, Issue 2, 636-647, 1997). The selective D4 dopamine receptor antagonist L-745,870 was ineffective as an antipsychotic for the treatment of neuroleptic responsive patients with acute schizophrenia (Kramer, M. S. et al., *Arch. Gen. Psychiatry* 1997 December; 54(12):1080).

Finally, in the biological system, mental disorders are defined on other levels of abstraction than in the categorical and dimensional system. Structural pathology (e.g. amyloid plaques in Alzheimer Disease), etiology (e.g. HIV Dementia) and deviance from a physiological norm (e.g. reduced cerebral blood flow) are often used as indicative biological markers for a mental disorder. The underlying dysregulation of various neurotransmittor systems (glutaminergic, GABAergic, cholinergic, monoaminergic (nor-adrenergic, dopaminergic, serotonergic), etc.) is the in the art used model for the explanation of the biological determinants of the clinical presentation of mental disturbances. It is known that the Serotonin 2A Receptor (5-HT2A receptor)—which is widespread in the Central Nervous System (CNS)—has a regulating role on the dysregulation of various neuro-transmitter systems. 5-HT2A agonism gives several behavioural disturbances; 5-HT2A antagonism leads to a governance of mood, social behaviour, anxiety, cognitive function, stress, sleep functions, nociception, sexual functions, feeding and other aspects of behaviour (J. E. Leysen (2004) 5-HT2 *Receptors; Current Drug Targets—CNS & Neurological Disorders*, 2004, 3, 11-26).

Dysregulation of the HPA axis (hypothalamic-pituitary-adrenal axis) has frequently been reported in patients with psychiatric disorders, and is among the most robustly demonstrated neurobiological changes among psychiatric patients (D. A. Gutman and C. B. Nemeroff, *Neuroendocrinology, Biological Psychiatry* (eds. D'Haenen, H., et al), 99, 2002, John Wiley & Sons, Ltd). The resulting elevated plasma cortisol concentrations leads to an enhanced binding of serotonin for the 5-HT2A receptor (E. A. Young, *Mineralocorticoid Receptor Function in Major Depression, Arch. Gen. Psychiatry*, January 2003; 60: 24-28) and thus agonism.

Additionally 5-HT2A antagonism gives a des-inhibiting of the inhibitory effect of the 5-HT2A receptor on (i) the 5-HT1A receptor stimulation by serotonin (S. M. Stahl, *Newer Antidepressants and Mood Stabilizers, Essential Psychopharmacology*, 265, University Press; 2 edition (Jun. 15, 2000); ISBN: 0521646154) and on (ii) the dopamine release in the mesocortical systems (S. M. Stahl, *Classical Antidepressants, Serotonin Selective and Noradrenargic Reuptake Inhibitors, Essential Psychopharmacology*, 233, University Press; 2 edition (Jun. 15, 2000); ISBN: 0521646154).

Clinical or real effectiveness of psychopharma is very rare via common pooping-out; many treatment-refractory patients and up to half of patients fail to attain remission (S. M. Stahl, *Essential Psychopharmacology, Depression and Bipolar Disorders*, 151, University Press; 2 edition (Jun. 15, 2000); ISBN: 0521646154). Implications of not attaining remission for Mental Disorders are increased relapse rates, continuing functional impairment and increased suicide rate (S. M. Stahl, *Essential Psychopharmacology, Depression and Bipolar Disorders*, 152, University Press; 2 edition (Jun. 15, 2000); ISBN: 0521646154). Clinical causes of not attaining remission by the Current Psychopharmacological Compounds are inadequate early treatment, underlying emotion dysregulation (affecting instability-hypersensitivity-hyperaesthesia-dissociative phenomena, etc.) and competitive antagonism. There is thus a growing need for a more efficient therapy and more efficient, selective and efficacious medicaments for treating mental disorders.

SUMMARY OF THE INVENTION

The present invention relates to the use of compounds and pharmaceutical compositions having D4 and 5-HT2A antagonistic, partial agonistic or inverse agonistic activity for the treatment of the underlying emotion dysregulation of mental disorders (e.g. affecting instability-hypersensitivity-hyperaesthesia-dissociative phenomena-etc.) and to methods entailing administering to a patient diagnosed as having a mental disorder a pharmaceutical composition containing (i) compounds having specific high selective D4 and 5-HT2A antagonistic, partial agonistic or inverse agonistic activity and (ii) a known medicinal compound and/or compositions of compounds. The combined D4 and 5-HT2A antagonistic, partial agonistic or inverse agonistic effects may reside within the same chemical or biological compound.

Taken into account the above mentioned (i) rare clinical or real effectiveness of psycho tropics, (ii) the governance of the features and dysfunctions responsible—in a variable co-incidentally—for the clinical state of the mental disorders by D4 dopamine receptor (D4DR) and 2A serotonin receptor (5-HT2A) antagonism and (iii) the fact that 5-HT2A antagonism gives a des-inhibiting of the inhibitory effect of the 5-HT2A receptor on (a) the 5-HT1A receptor stimulation by serotonin and on (b) the dopamine release in the mesocortical systems, the present invention relates to the use of a compound for the preparation of a medicament for treating a disease or disorder with an underlying emotion dysregulation, characterised in that said compound has (i) a selective affinity for the Dopamine-4 (D4) receptor with a pKi value equal to or higher than 8 towards the D4 receptor and less than 8 towards other Dopamine receptors, and (ii) a selective affinity for the 5-HT2A receptor with a pKi value equal to or higher than 8 towards the 5-HT2A receptor and less than 8 towards other 5-HT receptors and wherein said compound is administered to a patient in a dose ranging between 5 and 15 mg of the active ingredient. Preferably, said compound is pipamperon.

In a preferred embodiment, in a mono therapeutic context, the invention relates to the use of a compound as defined above, preferably pipamperon, for preparing a medicament for treating a disease or disorder selected from the group comprising anxiety disorders, eating disorders, premenstrual syndrome, somatoform disorders, factitious disorders, dissociative disorders, sexual and gender identity disorders, sleep disorders, adjustment disorders, cognitive disorders, impulse control disorders, pervasive development, attention-deficit and disruptive behaviour disorders, substance-related disorders, personality disorders, psychological factors affecting medical conditions, malingering, antisocial behaviour, bereavement, occupational, identity, phase of life, academic problem, problems related to abuse or neglect.

According to a further embodiment the invention relates to the use of a first compound as defined above for the preparation of a medicament for treating a mental disease or disorder with an underlying emotion dysregulation whereby a second compound is administered simultaneously with, separate from or sequential to said first compound to augment the therapeutic effect of said second compound on said disease, or to provide a faster onset of the therapeutic effect of said second compound on said disease.

The mental diseases or disorders characterized by an underlying emotion dysregulation can be grouped into subclasses as follows: (i) non-cognitive mental disorders comprising mood disorders, anxiety disorders, psychotic disorders, eating disorders, premenstrual syndrome, somatoform disorders (excluding pain disorders), factitious disorders, dissociative disorders, sexual and gender identity disorders, sleep disorders, adjustment disorders, impulse control disorders, pervasive development disorders, attention-deficit disorders, disruptive behaviour disorders, substance-related disorders, personality disorders, psychological factors affecting medical conditions, malingering, antisocial behaviour, bereavement, occupational problems, identity problem, phase of life problem, academic problem and problems related to abuse or neglect; (ii) cognitive diseases comprising delirium, Alzheimer Disease, substance-related persisting dementia, vascular dementia, dementia due to HIV disease, dementia due to head trauma, dementia due to Parkinson Disease, dementia due to Huntington Disease, dementia due to Pick Disease, dementia due to Creutzfeldt-Jacob Disease, amnestic disorders due to a general medical condition, substance-induced persisting amnestic disorder, mild cognitive impairment disorder, other cognitive disorders; (iii) pain disorders; and (iv) Parkinson Disease.

In a preferred embodiment, the first compound is administered daily at least one day before administering said second compound.

Preferably, said second compound is characterized by the physiological property of influencing positively the activity of the Central Nervous System.

The invention also relates to a method for preparing a compound having a selective D4 and 5-HT2A antagonist, reverse agonist or partial agonist activity comprising the following steps: (a) measuring the selective affinity of a test compound to the D4 receptor and selecting a compound that has a pKi value equal to or greater than 8 towards the D4 receptor in respect to all the other D receptors, and measuring the selective efficacy of the selected compound to the D4 receptor and selecting a compound which is a selective antagonist, inverse agonist or partial agonist of the D4 receptor; (b) measuring the selective affinity of a test compound to the 5-HT2A receptor and selecting a compound that has a pKi value equal to or greater than 8 towards the 5-HT2A receptor in respect to all the other 5HT receptors, and measuring the selective efficacy of the selected compound to the 5-HT2A receptor and selecting a compound which is a selective antagonist, inverse agonist or partial agonist of the 5-HT2A receptor; (c) identifying a compound which is selected in (a) and (b), (d) preparing the compound identified in (c).

The invention further also relates to a compound prepared by the described method.

DETAILED DESCRIPTION OF THE INVENTION

The present inventors surprisingly found that compounds which have a high selective affinity towards the 5-HT2A receptor and which, at the same time have a high selective affinity towards the dopamine-4 (D4) receptor show an improved effect in treating underlying emotion dysregulation of mental disorders.

The compounds according to the invention may be chemical or biological in nature, or may be chemically synthesised. Preferably, the compounds of the invention are provided as a pharmaceutically acceptable salt.

One example of such a compound which has both a selective affinity for the 5-HT2A receptor with a pKi value equal to or higher than 8 towards the 5-HT2A receptor and less than 8 towards other 5HT receptors, and a selective affinity for the D4 receptor with a pKi value equal to or higher than 8 towards the D4 receptor and less than 8 towards other dopamine receptors is pipamperon. Pipamperon is the conventional name given for the compound of the formula 1'-[3-(p-Fluorobenzoyl)propyl]-[1,4'-bipiperidine]-4'-carboxamide. Pipamperon is also the active ingredient of for instance the commercially available Dipiperon (Janssen, Cilag B.V).

Further, the present inventors surprisingly found that the dosage of active ingredient for pipamperon in treatment (in monotherapy as well as in combination therapy as described in more detail further) could be very low compared to conventionally used dosages. Preferred dosages which, according to the invention, have been shown to be effective for treating these mental disorders, range between 5 and 15 mg per day or between 5 and 10 mg per day. More preferably, dosages of 5, 6, 7, 8, 9, 10, 11, 12, 13, 14 or 15 mg per day are used in treatment of the diseases of the invention. In conventional pipamperon treatment, the active ingredient is available in tablets of 40 mg per tablet or in solutions of 2 mg per drop. Conventional usage of high doses ranging from 40 to 360 mg is prescribed. For instance, for children up to the age of 14, doses corresponding with 2 to 6 mg per kg body weight are conventionally prescribed. The high selective affinity of pipamperon towards the 5-HT2A receptor and the D4 receptor is reflected in the low dosage which is needed for the treatment of the mental diseases listed below and also contributes to the efficacy of the treatment.

The mental disorders which can be treated using pipamperon in a mono therapy at such low doses are for instance anxiety disorders, eating disorders, premenstrual syndrome, somatoform disorders, factitious disorders, dissociative disorders, sexual and gender identity disorders, sleep disorders, adjustment disorders, cognitive disorders, impulse control disorders, pervasive development, attention-deficit and disruptive behaviour disorders, substance-related disorders, personality disorders, psychological factors affecting medical conditions, malingering, antisocial behaviour, bereavement, occupational, identity, phase of life, academic problem, problems related to abuse or neglect.

Mental disorders such as depression are commonly treated with serotonin re-uptake inhibitors. Unfortunately, however, these compounds can give rise to side effects in use. Moreover, a substantial problem in most treatment of mental disorders is the non-response to selective serotonin re-uptake inhibitors (SSRIs). Also the onset of the therapeutic effect can be delayed undesirable.

A problem to be solved by the present invention is thus the provision of a more efficient therapy and efficient, highly selective and efficacious medicaments for treating mental disorders.

The inventors found that, for instance, the non-response to selective serotonin re-uptake inhibitors (SSRIs) in depression may be declared by (partial) inhibition of the 5-HT1A stimulation via 5-HT2A stimulation. Des-inhibition thereof via 5-HT2A antagonism seems to be an answer to this problem.

The present inventors found that a simultaneous or foregoing treatment with a compound having a high selective 5-HT2A antagonist, inverse agonist or partial agonist activity, could lead to a greater response towards, for instance, SSRIs. However, not all compounds exhibiting 5-HT2A antagonism are useful: competition between 5-HT2A stimulation via serotonin and 5-HT2A antagonism via the compound could be responsible for the lack of more efficacy of compounds which have both a selective serotonin re-uptake inhibitory and 5-HT2A antagonist profile, such as trazodone and nefazodone.

The present inventors further surprisingly found that a simultaneous or foregoing treatment with a compound having a high selective D4 antagonist, inverse agonist or partial agonist activity in combination with a compound having a high selective 5-HT2A antagonist, inverse agonist or partial agonist activity could lead to a greater response towards, for instance, SSRIs, or any of the compounds listed in Table 6 or below. In addition, the inventors found that a combination treatment provides less residual symptoms and more remission relative to a mono therapy with these compounds.

As such, in a combination treatment, the doses of the compounds listed in Table 6 for treating patients with mental disorders may be decreased to about 10-90% of the conventional dose, preferably to about 20-80%, or 30-70%, or 40-60% or to about 50% of the conventional dose. Even if the administered dose of the compound is decreased in the combination therapy, the therapeutical effect may be sustained or ameliorated relative to the conventional dose. The danger of side effects of a treatment with such compounds can be decreased or minimized in the combination therapy of the invention. In this regard, the term conventional dose refers to the dose used heretofor for a particular compound in treating patients with a mental disorder, for instance, according to the supplier's or physician's description or as listed in Table 6.

In this invention, the term "antagonist" refers to an interaction between chemicals in which one partially or completely inhibits the effect of the other, in particular agents having high affinity for a given receptor, but which do not activate this receptor.

In this invention, the term "inverse agonist" refers to a ligand which produces an effect opposite to that of the agonist by occupying the same receptor.

In this invention, the term "agonist" relates to an agent which both binds to a receptor and has an intrinsic effect.

In this invention, the term "partial agonist" relates to an agent with lower intrinsic activity than a full agonist, and which produces a lower maximum effect.

The present inventors found that a compound which binds to the 5-HT2A receptor with a pKi of at least 8 but for which the binding affinity, i.e. pKi, towards other 5HT receptors is less than 8 in combination with a high selective affinity for the D4 receptor, i.e. which bind to the D4 receptor with a pKi of at least 8 but for which the binding affinity, i.e. pKi, towards other dopamine receptors is less than 8 also show such an improved effect in treatment. These effects, i.e. D4 antagonism, inverse agonism or partial agonism and 5-HT2A antagonism, inverse agonism or partial agonism, may reside in the same compound.

The term "other 5HT receptors" as used herein relate to for instance 5-HT1 receptors (e.g. 5-HT1A, 5-HT1B, 5-HT1D, 5-HT1E, 5-HT1F), 5-HT2B, 5-HT2C, 5-HT6 (rat) and 5-HT7 (rat).

By the expression "selective affinity for the 5-HT2A receptor" is meant that the receptor has a higher affinity for the 5-HT2A receptor than for other 5-HT receptors.

The expression "selective affinity for the D4 receptor" means that the receptor has a higher affinity for the dopamine D4 receptor than for other dopamine receptors.

The term "other dopamine receptors" are, for instance, D1, D2 and D3 dopamine receptors.

pKi values of test compounds for dopamine receptors as well as 5-HT2A receptors can be measured using commonly known assays.

Compounds which have a selective affinity for the D4 receptor preferably have a pKi value equal to or higher than 8 towards the D4 receptor and less than 8 towards other dopamine receptors.

Preferably, the compounds of the invention which have a selective affinity for the 5-HT2A receptor (or the D4 receptor), are compounds which have a pKi value equal to or higher than 8 towards the 5-HT2A receptor and the D4 receptor, and less than 8 towards other 5-HT receptors or dopamine receptors, respectively, as can be measured, for instance by methods known in the art. For instance, the "NIMH Psychoactive Drug Screening Program (PDSP)" K, database (http://kidb.cwru.edu/nimh/5htp.php), is a unique resource in the public domain which provides information on the abilities of drugs to interact with an expanding number of molecular targets. The PDSP K database serves as a data warehouse for published and internally-derived pKi, or affinity, values for a large number of drugs and drug candidates at an expanding number of G-protein coupled receptors, ion channels, transporters and enzymes. The PDSP internet site also provides for commonly used protocols and assays for measuring pKi values of 5-HT and dopamine receptors.

A preferred example of a compound which has both a selective affinity for the 5-HT2A receptor with a pKi value equal to or higher than 8 towards the 5-HT2A receptor and less than 8 towards other 5-HT receptors, and a selective affinity for the D4 receptor with a pKi value equal to or higher than 8 towards the D4 receptor and less than 8 towards other Dopamine receptors and which is therefore useful in a combination therapy is pipamperon.

Table 1 illustrates the selective affinity of for instance pipamperon for the 5-HT2A and for the D4 receptor. In addition, Table 1 also illustrates the low or absence of affinity of pipamperon for other receptors such as the adrenergic receptors Alpha 1A, Alpha 2A, Alpha 2B, Alpha 2C, Beta 1, Beta 2, and the histamine receptor H1. As such, treating patients with pipamperon will provide for less side effects which otherwise result from simultaneous stimulation of other receptors. Therefore, and according to preferred embodiments, useful compounds according to the invention not only have a selective 5-HT2A and/or D4 affinity but also a low affinity for other receptors such as the adrenergic and histamine receptors.

The low dosage which can be used in pipamperon treatment, as already described earlier, contributes to the high selective affinity of the compound towards the 5-HT2A receptor and the D4 receptor and therefore also to the efficacy of the treatment.

The mental diseases or disorders characterized by an underlying emotion dysregulation can be grouped into subclasses as follows: (i) the non-cognitive mental disorders comprising mood disorders, anxiety disorders, psychotic disorders, eating disorders, premenstrual syndrome, somatoform disorders (excluding pain disorders), factitious disorders, dissociative disorders, sexual and gender identity disorders, sleep disorders, adjustment disorders, impulse control disorders, pervasive development disorders, attention-deficit disorders, disruptive behaviour disorders, substance-related disorders, personality disorders, psychological factors affecting medical conditions, malingering, antisocial behaviour, bereavement, occupational problems, identity problem, phase of life problem, academic problem and problems related to abuse or neglect; (ii) cognitive diseases comprising delirium, Alzheimer Disease, substance-related persisting dementia, vascular dementia, dementia due to HIV disease, dementia due to head trauma, dementia due to Parkinson Disease, dementia due to Huntington Disease, dementia due to Pick Disease, dementia due to Creutzfedt-Jacob Disease, amnestic disorders due to a general medical condition, substance-induced persisting amnestic disorder, mild cognitive impairment disorder, other cognitive disorders; (iii) the pain disorders; and (iv) Parkinson Disease. In Table 5, this classification has been used for summarizing the diseases and disorders relative to known psychotropics. In Table 6, an overview of pharmacological grouping is provided, indicating the pharmalogical profile numbering, the pharmalogical profile, the main disease or disorder indication(s), the name of the compound, the dose range, and the company producing or selling said compound.

These diseases and their diagnosis are very clearly defined in the "Diagnostic and Statistical Manual of Mental Disorders (DSM-IV)" published by the American Psychiatric Association. This manual sets forth diagnostic criteria, descriptions and other information to guide the classification and diagnosis of mental disorders and is commonly used in the field of neuropsychiatry. It is for instance available on the internet under:

http://www.behavenet.com/capsules/disorders/dsm4tr.htm.

The expression "non-cognitive diseases or disorders" used in some of the embodiments of the invention comprises the following group of diseases or disorders: mood disorders, anxiety disorders, psychotic disorders, eating disorders, premenstrual syndrome, somatoform disorders (excluding pain disorders), factitious disorders, dissociative disorders, sexual and gender identity disorders, sleep disorders, adjustment disorders, impulse control disorders, pervasive development disorders, attention-deficit disorders, disruptive behaviour disorders, substance-related disorders, personality disorders, psychological factors affecting medical conditions, malingering, antisocial behaviour, bereavement, occupational problems, identity problem, phase of life problem, academic problem and problems related to abuse or neglect.

In other embodiments of the invention, the mental diseases or disorders that are characterized by an underlying emotion dysregulation belong to the group of pain disorders. For instance, the combination therapy with pipamperon is especially advantageous for management of acute pain in diseases such as, but not limited to, musculoskeletal diseases, rheumatoid arthritis, osteoarthritis and ankylosing spondylitis. For the classification of pain disorders, reference is also made to the DSM-IV where these disorders are clearly described in the section of somatoform disorders by way of internationally accepted diagnostic criteria.

In other embodiments of the invention, the 5-HT2A receptor and/or Dopamine-4 receptor antagonist, inverse agonist or partial agonist (e.g. pipamperon) is used in treatment of patients having neuro-degenerative diseases or disorders, or related cognitive diseases or disorders. The diseases or disorders of the present invention are characterized by an underlying degeneration of the Central Nervous System (CNS), preferably selected from the group consisting of, but not limited to, neurodegenerative diseases such as Parkinson Disease, and in other embodiments of the invention, selected from the group of (related) cognitive diseases or disorders such as Alzheimer Disease.

For instance, Parkinson Disease, which is a chronic progressive nervous disease chiefly of later life, is linked to decreased dopamine production in the substantia nigra and is marked by tremor and weakness of resting muscles and by a shuffling gait. Dopamine agonists and even levodopa, widely used in Parkinson Disease, gives via a dopamine D4 receptor stimulation psychiatric manifestations. The induced release of serotonin acts via 5-HT2A stimulation as a "brake" on dopamine release (Young B. K., Camicioli R., Ganzini L., *Neuropsychiatric adverse effects of antiparkinsonian drugs. Characteristics, evaluation and treatment. Drugs Aging.* 1997 May; 10(5): 367-83). Because of the need of specific D4 and 5-HT2A antagonism in the treatment of Parkinson Disease with dopamine agonists and even levodopa, it seems reasonable to combine with a compound with a high selective D4 and 5-HT2A antagonism i.e. having merely no activity towards the other receptors especially the D2 receptor because of the primary need of the relieve of the excessive burden of remaining dopaminergic neurons. Therefore, the use of the so-called atypical anti-psychotics or serotonin-dopamine antagonists (SDAs) is absolutely contra-indicated since their high affinity for the D2 receptor. Even the use of serotonin releasing compounds such as SSRIs in the absence of an effective 5-HT2A antagonism are contra-productive towards the Parkinson Disease symptoms although many Parkinson patients are in need for an antidepressant since major depression is a very common and disabling condition in this kind of patients.

The expression "(related) cognitive diseases or disorders" according to the invention comprises, the following group of diseases or disorders: delirium (F05), dementia (such as Alzheimer Disease (F00), vascular dementia (F01), dementia due to other general medical conditions (HIV disease (F02.4), head trauma (F06.8), Parkinson Disease (F02.3), Huntington Disease (F02.2), Pick Disease (F02.0), Creutzfeldt-Jacob Disease (F02.1) and other (F02.8)), substance-induced persisting dementia (F1x.6)), amnestic disorders due to a general medical condition (F06.8) or a substance-induced persisting amnestic disorder (F1x.6), mild cognitive impairment disorder (F06.7) and other cognitive disorders (F04). The above list of diseases is provided by way of example and is not intended to limit the invention.

For instance, Alzheimer Disease is a degenerative brain disease of unknown cause that is the most common form of dementia. Alzheimer Disease usually starts in late middle age or in old age as a memory loss for recent events spreading to memories for more distant events and progresses over the course of five to ten years to a profound intellectual decline characterized by dementia and personal helplessness. The disease is marked histologically by the degeneration of brain neurons especially in the cerebral cortex and by the presence of neurofibrillary tangles and plaques containing beta-amyloid. Because dopamine receptor D4 (DRD4) antagonism can inhibit the behavioral disturbances—merely aggression and confusion—caused by the degeneration of dopamine D2 receptors (Esiri, M. M., *The basis for behavioural disturbances in dementia, J. Neurol. Neurosurg. Psychiatry,* 1996; 61(2):127-130.2) accompanied with Alzheimer disease and 5-HT2A antagonism has an important boosting effect towards the effect of cholinesterase inhibitors such as used in the treatment by facilitating the affected dopamine release in the mesocortical dopamine pathways, a high selective D4/5-HT2A-antagonist would be a more preferable compound to combine with a cholinesterase inhibitor since this avoids the counteracting effect of the in the art used SDAs on the cognitive functioning by its dopamine receptor D2-antagonism.

These diseases and their diagnoses are very clearly defined in the "*International Statistical Classification of Diseases and Related Health Problems,* 1989 Revision, Geneva, World Health Organization, 1992 (ICD-10). This manual sets forth diagnostic criteria, descriptions and other information to guide the classification and diagnosis of neurodegenerative disorders and is commonly used in the field of neurology. According to the ICD-10 classification, the cognitive disorders are classified under several classes of disorders, i.e. dispersed under categories F00 to F19 (see above: respective classification between parentheses). Following the DSM classification, however, they are grouped in one class of diseases or disorders.

The terms "treatment", "treating", and the like, as used herein include amelioration or elimination of a developed mental disease or condition once it has been established or alleviation of the characteristic symptoms of such disease or condition. As used herein these terms a so encompass, depending on the condition of the patient, preventing the onset of a disease or condition or of symptoms associated with a disease or condition, including reducing the severity of a disease or condition or symptoms associated therewith prior to affliction with said disease or condition. Such prevention or reduction prior to affliction refers to administration of the compound or composition of the invention to a patient that is not at the time of administration afflicted with the disease or condition. "Preventing" also encompasses preventing the recurrence or relapse-prevention of a disease or condition or of symptoms associated therewith, for instance after a period of improvement. It should be clear that mental conditions may be responsible for physical complaints. In this respect, the term "treating" also includes prevention of a physical disease or condition or amelioration or elimination of the developed physical disease or condition once it has been established or alleviation of the characteristic symptoms of such conditions.

As used herein, the term "medicament" also encompasses the terms "drug", "therapeutic", "potion" or other terms which are used in the field of medicine to indicate a preparation with therapeutic or prophylactic effect.

The present inventors not only found that the selective 5-HT2A and D4 antagonists, inverse agonists or partial agonists have an effect in augmenting the therapeutic effect or in providing a faster onset of the therapeutic effect of a diversity of other pharmaceutical compounds, i.e. also named "second compounds" in the present invention, in the treatment of specific diseases or disorders. A few examples of other pharmaceutical compounds whose effects are augmented or where the onset of the effect is fastened upon simultaneous or fore-going treatment with a selective 5-HT2A and D4 antagonist, preferably pipamperon in a low dose, are nor-epinephrine re-uptake inhibitors, neuroleptic agents, dopamine antagonists, or compounds used for treating or alleviating musculoskeletal diseases or disorders. A further list of other pharmaceutical compounds or second compounds useful according to the invention is provided in Table 5. It should be clear, given the general applicable character of the invention, that this list of other pharmaceutical compounds is very brief and that the invention should not be restricted to the ones exemplified herein. It should be clear that in the present invention, pipamperon is never to be seen as a "second compound".

According to the invention, it thus has been found that the compounds having a selective 5-HT2A and D4 antagonist, inverse agonist or partia agonist activity as described above are useful for augmenting the therapeutic effect of a second compound on a disease.

According to another embodiment of the invention, it has also been found that the compounds having a selective 5-HT2A and D4 antagonist, inverse agonist or partial agonist activity as described above are useful for providing a faster onset of the therapeutic effect of a second compound on a disease.

From the above it should be clear that the selective 5-HT2A and D4 antagonist, inverse agonist or partial agonist is also named 'the first compound' in the embodiments of the invention.

According to the invention, when the 5-HT2A and D4 antagonist, inverse agonist or partial agonist activity reside in separate compounds, the term "composition" may be used. Compositions of the invention comprise a first element having (i) a selective affinity for the D4 receptor with a pKi value equal to or higher than 8 towards the D4 receptor and less than 8 towards other dopamine receptors, and a second element having (ii) a selective affinity for the 5-HT2A receptor with a pKi value equal to or higher than 8 towards the 5-HT2A receptor and less than 8 towards other 5-HT receptors.

The expression "the 5-HT2A and D4 antagonist, inverse agonist or partial agonist" is used herein to indicate a single compound having both activities or to indicate the composition comprising the activities in separate elements.

It should be clear that when, in the present invention, a composition of separate elements is used instead of a single compound, this composition of separate elements may be used in combination with another, i.e. a second, compound to augment the therapeutic effect of the other, i.e. the second, compound on the same or another disease.

When the 5-HT2A and D4 antagonist, inverse agonist or partial agonist or the composition comprising both elements and the second compound are administered simultaneously, the compounds or active ingredients may be present in a single pharmaceutical composition or formulation. Alternatively the compounds or active ingredients are administered in separate pharmaceutical compositions or formulations for simultaneous or separate use. The invention thus also relates to pharmaceutical compositions comprising pipamperon and a second compound of the invention and to the uses of these pharmaceutical compositions.

When the 5-HT2A and D4 antagonist, inverse agonist or partial agonist or the composition comprising both elements of the invention are administered prior to the second compound as defined, the 5-HT2A and D4 antagonist, inverse agonist or partial agonist or the composition comprising both elements is administered at least during 1 day prior to said second compound. Preferably, the 5-HT2A and D4 antagonist, inverse agonist or partial agonist (e.g. pipamperon) or the composition compressing both elements is administered for at least 1, 2, 3, 4, 5, 6, 7, 8, 9 or 10 days prior to the administration of the second compound. Preferably, the 5-HT2A and D4 antagonist, inverse agonist or partial agonist (e.g. pipamperon) or the composition comprising both elements is administered for at least 2, 3, 4 or 5 weeks prior to the administration of the second compound, or even for at least 1, 2, 3, 4, 5, 6, 7, 8, 9, 10, 11 or 12 months prior to the administration of the second compound.

According to a preferred embodiment of the invention, the above described compounds or the composition comprising both elements having a 5-HT2A and D4 antagonist, inverse agonist or partial agonist activity are useful for augmenting the therapeutic effect of citalopram or for providing a faster onset of the therapeutic effect of citalopram.

Citalopram or citalopram hydrobromide is a selective serotonin (5-hydroxytryptamine/5-HT) re-uptake inhibitor (SSRI) and is the conventional name given for the compound of the formula (RS)-1-[3-(dimethylamino)propyl]-1-(p-fluorophenyl)-5-phthalancarbonitrile hydro-bromide.

According to an embodiment, a daily dose of active ingredient of SSRI, preferably citalopram, ranges between 10 and 40 mg per day. Preferably, daily doses of active ingredient ranging between 20 and 30 mg per day are administered. More preferably, a daily dose of 10, 15, 20, 25, 30, 35 or 40 mg per day is administered.

According to another preferred embodiment of the invention, the above described compounds or the composition comprising both elements having a 5-HT2A and D4 antagonist, inverse agonist or partial agonist activity are useful for augmenting the therapeutic effect of fluvoxamine or for providing a faster onset of the therapeutic effect of fluvoxamine.

Fluvoxamine or fluvoxamine maleate (luvox, fevarin) is a selective serotonin (5-HT) reuptake inhibitor (SSRI) belonging to a new chemical series, the 2-aminoethyl oxime ethers of aralkylketones. It is chemically unrelated to other SSRIs and clomipramine. It is chemically designated as 5-methoxy-4'-(trifluoromethyl)valerophenone (E)-O-(2-aminoethyl) oxime maleate (1:1).

According to an embodiment, a daily dose of active ingredient of fluvoxamine maleate ranges between 100 and 300 mg per day. Preferably, daily doses of active ingredient ranging between 150 and 200 mg per day are administered. More preferably, a daily dose of 100, 150, 200, 250 or 300 mg per day is administered.

According to a preferred embodiment of the invention, the above described compounds or the composition comprising both elements having a 5-HT2A and D4 antagonist, inverse agonist or partial agonist activity are useful for augmenting the therapeutic effect of seiegiline or for providing a faster onset of the therapeutic effect of selegiline.

Selegiline or L-deprenyl or phenylisopropyl methyl propynyl amine is a monoamine oxidase B inhibitor (MAO-B inhibitor) and is the conventional name given for the compound of the formula (R)-(−)-N, α-dimethyl-N-(2-propynyl) phenethylamine-HCl.

According to an embodiment, a daily dose of active ingredient of MAO-B inhibitor, preferably selegiline, ranges between 5 and 60 mg per day. Preferably, daily doses of active ingredient ranging between 20 and 40 mg per day are administered. More preferably, a daily dose of 10, 15, 20, 25, 30, 35 or 40 mg per day is administered.

Most of the second compounds herein described are known in the art and may be used in doses according to the supplier's or physician's prescription, or may be used according to specific embodiments described herein.

Also encompassed by the invention are pro-drugs to these second compounds or active metabolites of these compounds. For instance, for risperidone it is known that, among other products, bio transformation in the liver produces 9-hydroxyrisperidone, which is of the same pharmacological activity and intensity as parent risperidone. Therefore, also 9-hydroxyrisperidone, naturally produced or chemically synthesized may be used in the methods and uses according to the invention.

The term "active metabolite" as used herein relates to a therapeutically active compound produced by the metabolism of a parent drug. Drugs administered to treat diseases are usually transformed (metabolized) within the body into a variety of related chemical forms (metabolites), some of which may have therapeutic activity (an active metabolite).

The present invention also encompasses the use of these second compounds, administered in the form of a pharmaceutically acceptable salt in admixture with a suitable pharmaceutically acceptable excipient.

To prepare the pharmaceutical compositions, comprising the compounds or the combination of the first and second compound described herein, an effective amount of the active ingredients, in acid or base addition salt form or base form, is combined in admixture with a pharmaceutically acceptable carrier, which can take a wide variety of forms depending on the form of preparation desired for administration. These pharmaceutical compositions are desirably in unitary dosage form suitable, for administration orally, nasal, rectally, percutaneously, transdermally, by parenteral, intramuscular, intravascular injection or intrathecal administration. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included.

The pharmaceutical compounds for treatment are intended for parenteral, topical, oral or local administration and generally comprise a pharmaceutically acceptable carrier and an amount of the active ingredient sufficient to reverse or prevent the bad effects of mental disorders. The carrier may be any of those conventionally used and is limited only by chemico-physical considerations, such as solubility and lack of reactivity with the compound, and by the route of administration.

Examples of pharmaceutically acceptable acid addition salts for use in the present inventive pharmaceutical composition include those derived from mineral acids, such as hydrochloric, hydrobromic, phosphoric, metaphosphoric, nitric and sulfuric acids, and organic acids, such as tartaric, acetic, citric, malic, lactic, fumaric, benzoic, glycolic, gluconic, succinic, p-toluenesulphonic acids, and arylsulphonic, for example.

The pharmaceutically acceptable excipients described herein, for example, vehicles, adjuvants, carriers or diluents, are well-known to those who are skilled in the art and are readily available to the public. It is preferred that the pharmaceutically acceptable carrier be one that is chemically inert to the active compounds and one that has no detrimental side effects or toxicity under the conditions of use.

The following formulations for oral, aerosol, parenteral, subcutaneous, intravenous, intramuscular, interperitoneal, rectal, and vaginal administration are merely exemplary and are in no way limiting. Overall, the requirements for effective pharmaceutical carriers for parenteral compositions are well known to those of ordinary skill in the art. See Pharmaceutics and Pharmacy Practice, J.B. Lippincott Company, Philadelphia, Pa., Banker and Chalmers, eds., pages 238-250, (1982), and ASHP Handbook on Injectable Drugs, Toissel, 4th ed., pages 622-630 (1986). Topical formulations, including those that are useful for transdermal drug release, are well-known to those of skill in the art and are suitable in the context of the present invention for application to skin.

Formulations suitable for oral administration require extra considerations considering the nature of the compounds and the possible breakdown thereof if such compounds are administered orally without protecting them from the digestive secretions of the gastrointestinal tract. Such a formulation can consist of (a) liquid solutions, such as an effective amount of the compound dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible excipients. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such excipients as are known in the art.

The compounds of the present invention, alone or in combination with other suitable components, can be made into aerosol formulations to be administered via inhalation. For aerosol administration, the compounds are preferably supplied in finely divided form along with a surfactant and propellant. Typical percentages of compounds are 0.01%-20% by weight, preferably 1%-10%. The surfactant must, of course, be nontoxic, and preferably soluble in the propellant. Representative of such agents are the esters or partial esters of fatty acids containing from 6 to 22 carbon atoms, such as caproic, octanoic, lauric, palmitic, stearic; linoleic, linolenic, olesteric and oleic acids with an aliphatic polyhydric alcohol or its cyclic anhydride. Mixed esters, such as mixed or natural glycerides may be employed. The surfactant may constitute 0.1%-20% by weight of the compounds, preferably 0.25-5%. The balance of the compounds is ordinarily propellant. A carrier can also be included as desired, e.g., lecithin for intranasal delivery. These aerosol formulations can be placed into acceptable pressurized propellants, such as dichlorodifluoromethane, propane, nitrogen, and the like. They also may be formulated as pharmaceuticals for non-pressured preparations, such as in a nebulizer or an atomizer. Such spray formulations may be used to spray mucosa.

It will be understood that, apart from daily doses, the compounds can be administered by other schedules. For instance, the present invention also contemplates depot injection, in which a long acting form of the active compound is injected into the body, such as the muscles. From there the active compound slowly enters the rest of the body, so one injection can last from 1 to 4 weeks or even multiple months. Other form of dosage administrations relate to "once-a-week" pills, in which the ingredient is slowly released over a period of a week, and slow-release patches, e.g. a CDS (Continuous Delivery System), or Once-a-Day Transdermal Patches.

According to a further embodiment, the invention also relates to a method for preparing a compound or composition having a selective D4 and 5-HT2A antagonist, reverse agonist or partial agonist. The invention also relates to the compounds prepared by the claimed method, with the proviso that said compound is not an already known compound, such as pipamperon.

It should be clear that the compounds and compositions described herein are useful for treating any patient in need thereof. As used herein the term "patient" is not restricted to humans but also to other mammals, for instance, domestic animals which may also suffer from any form of a mental disease or disorder described herein.

The second compounds of the invention can be further grouped according to their pharmacological profile, which is summarized in Table 6.

The present invention is now described in more detail by the following embodiments. The compounds belonging to different pharmacological profiles can be further grouped according to their action on the same pathway or system as follows.

1: Combination Therapy with a 5-HT (Serotonin) Reuptake Enhancer

The mental disorders which can be treated using compounds having a high selective affinity for the 5-HT2A and D4 receptor, for instance pipamperon, in a combination therapy with a 5-HT (serotonin) reuptake enhancer, are chosen from the group of diseases or disorders consisting of mood disorders, anxiety disorders, eating disorders, premenstrual syndrome, somatoform disorders (excluding pain disorders), factitious disorders, dissociative disorders, sexual and gender identity disorders, sleep disorders, adjustment disorders, impulse control disorders, substance related disorder, personality disorders, antisocial behaviour, bereavement, occupational problem, problems related to abuse or neglect and pain disorders.

The present invention thus relates to the use of pipamperon or a pharmaceutically acceptable salt thereof for the preparation of a medicament for treating the underlying emotion dysregulation of a non-cognitive mental disease or disorder selected from the group of diseases or disorders consisting of mood disorders, anxiety disorders, eating disorders, premenstrual syndrome, somatoform disorders (excluding pain disorders), factitious disorders, dissociative disorders, sexual and gender identity disorders, sleep disorders, adjustment disorders, impulse control disorders, substance related disorder, personality disorders, antisocial behaviour, bereavement, occupational problem and problems related to abuse or neglect, characterized in that pipamperon or said pharmaceutically acceptable salt thereof is administered simultaneously with, separate from or prior to the administration of a 5-HT (serotonin) reuptake enhancer compound to augment the therapeutic effect or to provide a faster onset of the therapeutic effect of said 5-HT (serotonin) reuptake enhancer compound, further characterized in that pipamperon is to be administered to a patient in a daily dose ranging between 5 and 15 mg of the active ingredient.

The present invention thus relates to the use of pipamperon or a pharmaceutically acceptable salt thereof for the preparation of a medicament for treating the underlying emotion dysregulation of pain disorders, characterized in that pipamperon or said pharmaceutically acceptable salt thereof is administered simultaneously with, separate from or prior to the administration of a 5-HT (serotonin) reuptake enhancer compound to augment the therapeutic effect or to provide a faster onset of the therapeutic effect of said 5-HT (serotonin) reuptake enhancer compound, further characterized in that pipamperon is to be administered to a patient in a daily dose ranging between 5 and 15 mg of the active ingredient.

According to a preferred embodiment, the invention relates to the uses as described above, wherein said 5-HT (serotonin) reuptake enhancer compound is tianeptine or a pro-drug or an active metabolite thereof, or a pharmaceutically acceptable salt thereof. Preferably, tianeptine is to be administered in a daily dose ranging between 25 and 50 mg of the active ingredient.

The invention a' so relates to a pharmaceutical composition comprising (a) pipamperon, and (b) a 5-HT (serotonin) reuptake enhancer, preferably tianeptine or a pro-drug or an active metabolite thereof, or a pharmaceutically acceptable salt thereof, as a combined preparation for simultaneous, separate or sequential use for treating the underlying emotion dysregulation of a mental disease or disorder which is chosen from the group of diseases or disorders consisting of mood disorders, anxiety disorders, eating disorders, premenstrual syndrome, somatoform disorders (excluding pain disorders), factitious disorders, dissociative disorders, sexual and gender identity disorders, sleep disorders, adjustment disorders, impulse control disorders, substance related disorder, personality disorder, antisocial behaviour, bereavement, occupational problem, problems related to abuse or neglect and pain disorders.

A pharmaceutical composition as described above wherein pipamperon is provided in a unitary dose of between 5 and 15 mg of the active ingredient and wherein said 5-HT (serotonin) reuptake enhancer is tianeptine, preferably provided in a unitary dose of between 25 and 50 mg of the active ingredient.

2: Combination Therapy with a 5-HT1 Autoreceptor Agonist

The mental disorders which can be treated using compounds having a high selective affinity for the 5-HT2A and D4 receptor, for instance pipamperon, in a combination therapy with a 5-HT1 autoreceptor agonist, are chosen from the group of diseases or disorders consisting of mood disorders, anxiety disorders, eating disorders, premenstrual syndrome, somatoform disorders (excluding pain disorders), factitious disorders, dissociative disorders, sexual and gender identity disorders, sleep disorders, adjustment disorders, impulse control disorders, substance related disorder, personality disorders, antisocial behaviour, bereavement, occupational problem, problems related to abuse or neglect and pain disorders.

The present invention thus relates to the use of pipamperon or a pharmaceutically acceptable salt thereof for the preparation of a medicament for treating the underlying emotion dysregulation of a non-cognitive mental disease or disorder selected from the group of diseases or disorders consisting of mood disorders, anxiety disorders, eating disorders, premenstrual syndrome, somatoform disorders (excluding pain disorders), factitious disorders, dissociative disorders, sexual and gender identity disorders, sleep disorders, adjustment disorders, impulse control disorders, substance related disorder, personality disorders, antisocial behaviour, bereavement, occupational problem and problems related to abuse or neglect, characterized in that pipamperon or said pharmaceutically acceptable salt thereof is administered simultaneously with, separate from or prior to the administration of a 5-HT1 autoreceptor agonist compound to augment the therapeutic effect or to provide a faster onset of the therapeutic effect of said 5-HT1 autoreceptor agonist compound, further characterized in that pipamperon is to be administered to a patient in a daily dose ranging between 5 and 15 mg of the active ingredient.

The present invention thus relates to the use of pipamperon or a pharmaceutically acceptable salt thereof for the preparation of a medicament for treating the underlying emotion dysregulation of pain disorders, characterized in that pipamperon or said pharmaceutically acceptable salt thereof is administered simultaneously with, separate from or prior to the administration of a 5-HT1 autoreceptor agonist compound to augment the therapeutic effect or to provide a faster onset of the therapeutic effect of said 5-HT1 autoreceptor agonist compound, further characterized in that pipamperon is to be administered to a patient in a daily dose ranging between 5 and 15 mg of the active ingredient.

According to a preferred embodiment, the invention relates to the uses as described above, wherein said 5-HT1 autoreceptor agonist compound is sunepitron or a pro-drug or an active metabolite thereof, or a pharmaceutically acceptable salt thereof.

The invention also relates to a pharmaceutical composition comprising (a) pipamperon, and (b) a 5-HT1 autoreceptor agonist, preferably sunepitron or a pro-drug or an active metabolite thereof, or a pharmaceutically acceptable salt thereof, as a combined preparation for simultaneous, separate or sequential use for treating the underlying emotion dysregulation of a mental disease or disorder which is chosen from the group of diseases or disorders consisting of mood disorders, anxiety disorders, eating disorders, premenstrual syndrome, somatoform disorders (excluding pain disorders), factitious disorders, dissociative disorders, sexual and gender identity disorders, sleep disorders, adjustment disorders, impulse control disorders, substance related disorder, personality disorder, antisocial behaviour, bereavement, occupational problem, problems related to abuse or neglect and pain disorders.

3: Combination Therapy with a 5-HT1A (Serotonin 1A Receptor) Agonist Compound

The mental disorders which can be treated using compounds having a high selective affinity for the 5-HT2A and D4 receptor, for instance pipamperon, in a combination therapy with a 5-HT1A (serotonin 1A receptor) agonist compound, are chosen from the group of diseases or disorders consisting of mood disorders, anxiety disorders, eating disorders, premenstrual syndrome, somatoform disorders (excluding pain disorders), factitious disorders, dissociative disorders, sexual and gender disorders, sleep disorders, adjustment disorders, impulse control disorders, attention-deficit disorders, substance-related disorder, personality disorders, antisocial behaviour, bereavement, occupational problem, problems related to abuse or neglect and pain disorders.

The present invention thus relates to the use of pipamperon or a pharmaceutically acceptable salt thereof for the preparation of a medicament for treating the underlying emotion dysregulation of a non-cognitive mental disease or disorder selected from the group of diseases and disorders consisting of mood disorders, anxiety disorders, eating disorders, premenstrual syndrome, somatoform disorders (excluding pain disorders), factitious disorders, dissociative disorders, sexual and gender disorders, sleep disorders, adjustment disorders, impulse control disorders, attention-deficit disorders, substance-related disorder, personality disorders, antisocial behaviour, bereavement, occupational problem and problems related to abuse or neglect, characterized in that pipamperon or said pharmaceutically acceptable salt thereof is administered simultaneously with, separate from or prior to the administration of a 5-HT1A (serotonin 1A receptor) agonist compound to augment the therapeutic effect or to provide a faster onset of the therapeutic effect of said 5-HT1A (serotonin 1A receptor) agonist compound, further characterized in that pipamperon is to be administered to a patient in a daily dose ranging between 5 and 15 mg of the active ingredient.

The present invention further also relates to the use of pipamperon or a pharmaceutically acceptable salt thereof for the preparation of a medicament for treating the underlying emotion dysregulation of pain disorders, characterized in that pipamperon or said pharmaceutically acceptable salt thereof is administered simultaneously with, separate from or prior to the administration of a 5-HT1A (serotonin 1A receptor) agonist compound to augment the therapeutic effect or to provide a faster onset of the therapeutic effect of said 5-HT1A (serotonin 1A receptor) agonist compound, further characterized in that pipamperon is to be administered to a patient in a daily dose ranging between 5 and 15 mg of the active ingredient.

According to a preferred embodiment, the invention relates to the uses as described above, wherein said 5-HT1A (serotonin 1A receptor) agonist compound is chosen from the group consisting of MN-305, zalospirone, xaliproden, VPI-013 (also known as OPC-14523), tandosprione, sarizotan, PRX-00023, metanospirone, lesopitron, gepirone, flesinoxan, EMD 68843, buspirone, bupropion (preferably controlled release formulation) and alnespirone, preferably xaliproden, sarizotan, gepirone, flesinoxan and bupropion (preferably controlled release formulation) or a pro-drug or an active metabolite thereof, or a pharmaceutically acceptable salt thereof. More preferably, said 5-HT1A (serotonin 1A receptor) agonist is xaliproden and is to be administered in a daily dose ranging between 1 and 2 mg of the active ingredient. Even more preferably, said 5-HT1A (serotonin 1A receptor) agonist is buproprion (controlled release formulation) and is to be administered in a daily dose ranging between 150 and 450 mg of the active ingredient. Even more preferably, said 5-HT1A (serotonin 1A receptor) agonist is gepirone and is to be administered in a daily dose, ranging between 20 and 80 mg of the active ingredient per day.

The invention also relates to a pharmaceutical composition comprising (a) pipamperon, and (b) a 5-HT1A (serotonin 1A receptor) agonist, preferably chosen from the group consisting of MN-305, zalospirone, xaliproden, VPI-013 (also known as OPC-14523), tandosprione, sarizotan, PRX-00023, metanospirone, lesopitron, gepirone, fiesinoxan, EMD 68843, buspirone, bupropion (preferably controlled release formulation) and alnespirone, more preferably xaliproden, sarizotan, gepirone, flesinoxan and bupropion (preferably controlled release formulation), or a pro-drug or an active metabolite thereof, or a pharmaceutically acceptable salt thereof, as a combined preparation for simultaneous, separate or sequential use for treating the underlying emotion dysregulation of a mental disease or disorder which is chosen from the group of diseases or disorders consisting of mood disorders, anxiety disorders, eating disorders, premenstrual syndrome, somatoform disorders (excluding pain disorders), factitious disorders, dissociative disorders, sexual and gender disorders, sleep disorders, adjustment disorders, impulse control disorders, attention-deficit disorders, substance-related disorder, personality disorders, antisocial behaviour, bereavement, occupational problem, problems related to abuse or neglect and pain disorders.

The present invention also relates to a pharmaceutical composition as described above wherein pipamperon is provided in a unitary dose of between 5 and 15 mg of the active ingredient and wherein said 5-HT1A (serotonin 1A receptor) agonist is xaliproden, preferably provided in a unitary dose of between 1 and 2 mg of the active ingredient.

The present invention also relates to a pharmaceutical composition as described above wherein pipamperon is provided in a unitary dose of between 5 and 15 mg of the active ingredient and wherein said 5-HT1A (serotonin 1A receptor) agonist is buproprion (controlled release formulation), preferably provided in a unitary dose of between 150 and 450 mg of the active ingredient.

The present invention also relates to a pharmaceutical composition as described above wherein pipamperon is provided in a unitary dose of between 5 and 15 mg of the active ingredient and wherein said 5-HT1A (serotonin 1A receptor) agonist is gepirone, preferably provided in a unitary dose of between 20 and 80 mg of the active ingredient.

4: Combination Therapy with a 5-HT1A (Serotonin 1A Receptor) Antagonist Compound The mental disorders which can be treated using compounds having a high selective affinity for the 5-HT2A and D4 receptor, for instance pipamperon, in a combination therapy with a 5-HT1A (serotonin 1A receptor) antagonist compound, are chosen from the group of diseases or disorders consisting of mood disorders, anxiety disorders, eating disorders, premenstrual syndrome, somatoform disorders (excluding pain disorders), factitious disorders, dissociative disorders, sexual and gender disorders, adjustment disorders, impulse control disorders, substance-related disorder, personality disorders, antisocial behaviour, bereavement, occupational problem and problems related to abuse or neglect.

The present invention thus relates to the use of pipamperon or a pharmaceutically acceptable salt thereof for the preparation of a medicament for treating the underlying emotion dysregulation of a non-cognitive mental disease or disorder selected from the group of diseases and disorders consisting of mood disorders, anxiety disorders, eating disorders, premenstrual syndrome, somatoform disorders (excluding pain disorders), factitious disorders, dissociative disorders, sexual and gender disorders, adjustment disorders, impulse control disorders, substance-related disorder, personality disorders, antisocial behaviour, bereavement, occupational problem and problems related to abuse or neglect, characterized in that pipamperon or said pharmaceutically acceptable salt thereof is administered simultaneously with, separate from or prior to the administration of a 5-HT1A antagonist compound to augment the therapeutic effect or to provide a faster onset of the therapeutic effect of said 5-HT1A antagonist compound, further characterized in that pipamperon is to be administered to a patient in a daily dose ranging between 5 and 15 mg of the active ingredient.

According to a preferred embodiment, the invention relates to the uses as described above, wherein said 5-HT1A antagonist compound is chosen from the group consisting of robalzotan tartrate hydrate and NAD299 or a pro-drug or an active metabolite thereof, or a pharmaceutically acceptable salt thereof.

The invention also relates to a pharmaceutical composition comprising (a) pipamperon, and (b) a 5-HT1A antagonist, preferably chosen from the group consisting of robalzotan tartrate hydrate and NAD299, or a pro-drug or an active metabolite thereof, or a pharmaceutically acceptable salt thereof, as a combined preparation for simultaneous, separate or sequential use for treating the underlying emotion dysregulation of a non-cognitive mental disease or disorder which is chosen from the group of diseases or disorders consisting of mood disorders, anxiety disorders, eating disorders, premenstrual syndrome, somatoform disorders (excluding pain disorders), factitious disorders, dissociative disorders, sexual and gender disorders, adjustment disorders, impulse control disorders, substance-related disorder, personality disorders, antisocial behaviour, bereavement, occupational problem and problems related to abuse or neglect.

5: Combination Therapy with a 5-HT1B (Serotonin 1B Receptor) Antagonist Compound The mental disorders which can be treated using compounds having a high selective affinity for the 5-HT2A and D4 receptor, for instance pipamperon, in a combination therapy with a 5-HT1B (serotonin 13 receptor) antagonist compound, are chosen from the group of diseases or disorders consisting of mood disorders, anxiety disorders, eating disorders, premenstrual syndrome, somatoform disorders (excluding pain disorders), factitious disorders, dissociative disorders, sexual and gender disorders, sleep disorders, adjustment disorders, impulse control disorders, substance-related disorder, personality disorders, antisocial behaviour, bereavement, occupational problem and problems related to abuse or neglect.

The present invention thus relates to the use of pipamperon or a pharmaceutically acceptable salt thereof for the preparation of a medicament for treating the underlying emotion dysregulation of a non-cognitive mental disease or disorder selected from the group of diseases and disorders consisting of mood disorders, anxiety disorders, eating disorders, premenstrual syndrome, somatoform disorders (excluding pain disorders), factitious disorders, dissociative disorders, sexual and gender disorders, sleep disorders, adjustment disorders, impulse control disorders, substance-related disorder, personality disorders, antisocial behaviour, bereavement, occupational problem and problems related to abuse or neglect, characterized in that pipamperon or said pharmaceutically acceptable salt thereof is administered simultaneously with, separate from or prior to the administration of a 5-HT1B antagonist compound to augment the therapeutic effect or to provide a faster onset of the therapeutic effect of said 5-HT1B antagonist compound, further characterized in that pipamperon is to be administered to a patient in a daily dose ranging between 5 and 15 mg of the active ingredient.

According to a preferred embodiment, the invention relates to the use as described above, wherein said 5-HT1B antagonist compound is chosen from the group consisting of elzasonan, AZD1134 and AR-A2, preferably elzasonan, or a pro-drug or an active metabolite thereof, or a pharmaceutically acceptable salt thereof.

The invention also relates to a pharmaceutical composition comprising (a) pipamperon, and (b) a 5-HT1B antagonist, preferably chosen from the group consisting of elzasonan, AZD1134 and AR-A2, preferably elzasonan, or a pro-drug or an active metabolite thereof, or a pharmaceutically acceptable salt thereof, as a combined preparation for simultaneous, separate or sequential use for treating the underlying emotion dysregulation of a non-cognitive mental disease or disorder which is chosen from the group of diseases or disorders consisting of mood disorders, anxiety disorders, eating disorders, premenstrual syndrome, somatoform disorders (excluding pain disorders), factitious disorders, dissociative disorders, sexual and gender disorders, sleep disorders, adjustment disorders, impulse control disorders, substance-related disorder, personality disorders, antisocial behaviour, bereavement, occupational problem and problems related to abuse or neglect.

6: Combination Therapy with a 5-HT2B (Serotonin 2B Receptor) Antagonist Compound The mental disorders which can be treated using compounds having a high selective affinity for the 5-HT2A and D4 receptor, for instance pipamperon, in a combination therapy with a 5-HT2B (serotonin 2B receptor) antagonist compound, are chosen from the group of diseases or disorders consisting of mood disorders, anxiety disorders, eating disorders, premenstrual syndrome, somatoform disorders (excluding pain disorders), factitious disorders, dissociative disorders, sexual and gender disorders, sleep disorders, adjustment disorders, impulse control disorders, substance-related disorder, personality disorders, antisocial behaviour, bereavement, occupational problem, problems related to abuse or neglect and pain disorders.

The present invention thus relates to the use of pipamperon or a pharmaceutically acceptable salt thereof for the preparation of a medicament for treating the underlying emotion dysregulation of a non-cognitive mental disease or disorder selected from the group of diseases and disorders consisting of mood disorders, anxiety disorders, eating disorders, premenstrual syndrome, somatoform disorders (excluding pain disorders), factitious disorders, dissociative disorders, sexual and gender disorders, sleep disorders, adjustment disorders, impulse control disorders, substance-related disorder, personality disorders, antisocial behaviour, bereavement, occupational problem, problems related to abuse or neglect, characterized in that pipamperon or said pharmaceutically acceptable salt thereof is administered simultaneously with, separate from or prior to the administration of a 5-HT2B antagonist compound to augment the therapeutic effect or to provide a faster onset of the therapeutic effect of said 5-HT2B antagonist compound, further characterized in that pipamperon is to be administered to a patient in a daily dose ranging between 5 and 15 mg of the active ingredient.

The present invention thus relates to the use of pipamperon or a pharmaceutically acceptable salt thereof for the preparation of a medicament for treating the underlying emotion dysregulation of pain disorders, characterized in that pipamperon or said pharmaceutically acceptable salt thereof is administered simultaneously with, separate from or prior to the administration of a 5-HT2B antagonist compound to augment the therapeutic effect or to provide a faster onset of the therapeutic effect of said 5-HT2B antagonist compound, further characterized in that pipamperon is to be administered to a patient in a daily dose ranging between 5 and 15 mg of the active ingredient.

According to a preferred embodiment, the invention relates to the uses as described above, wherein said 5-HT2B antagonist compound is agomelatine or a pro-drug or an active metabolite thereof, or a pharmaceutically acceptable salt thereof. Preferably, agomelatine is to be administered in a daily dose ranging between 25 and 50 mg of the active ingredient.

The invention also relates to a pharmaceutical composition comprising (a) pipamperon, and (b) a 5-HT2B antagonist, preferably agomelatine or a pro-drug or an active metabolite thereof, or a pharmaceutically acceptable salt thereof, as a combined preparation for simultaneous, separate or sequential use for treating the underlying emotion dysregulation of a mental disease or disorder which is chosen from the group of diseases or disorders consisting of mood disorders, anxiety disorders, eating disorders, premenstrual syndrome, somatoform disorders (excluding pain disorders), factitious disorders, dissociative disorders, sexual and gender disorders, sleep disorders, adjustment disorders, impulse control disorders, substance-related disorder, personality disorders, antisocial behaviour, bereavement, occupational problem, problems related to abuse or neglect and pain disorders.

A pharmaceutical composition as described above wherein pipamperon is provided in a unitary dose of between 5 and 15 mg of the active ingredient and wherein said 5-HT2B antagonist is agomelatine, preferably provided in a unitary dose of between 25 and 50 mg of the active ingredient.

7: Combination Therapy with a 5-HT2C (Serotonin 2C Receptor) Antagonist Compound The mental disorders which can be treated using compounds having a high selective affinity for the 5-HT2A and D4 receptor, for instance pipamperon, in a combination therapy with a 5-HT2C (serotonin 2C receptor) antagonist compound, are chosen from the group of diseases or disorders consisting of mood disorders, anxiety disorders, eating disorders, premenstrual syndrome, somatoform disorders (excluding pain disorders), factitious disorders, dissociative disorders, sexual and gender disorders, sleep disorders, adjustment disorders, impulse control disorders, substance-related disorder, personality disorders, antisocial behaviour, bereavement, occupational problem, problems related to abuse or neglect and pain disorders.

The present invention thus relates to the use of pipamperon or a pharmaceutically acceptable salt thereof for the preparation of a medicament for treating the underlying emotion dysregulation of a non-cognitive mental disease or disorder selected from the group of diseases and disorders consisting of mood disorders, anxiety disorders, eating disorders, premenstrual syndrome, somatoform disorders (excluding pain disorders), factitious disorders, dissociative disorders, sexual and gender disorders, sleep disorders, adjustment disorders, impulse control disorders, substance-related disorder, personality disorders, antisocial behaviour, bereavement, occupational problem, problems related to abuse or neglect, characterized in that pipamperon or said pharmaceutically acceptable salt thereof is administered simultaneously with, separate from or prior to the administration of a 5-HT2C antagonist compound to augment the therapeutic effect or to provide a faster onset of the therapeutic effect of said 5-HT2C antagonist compound, further characterized in that pipamperon is to be administered to a patient in a daily dose ranging between 5 and 15 mg of the active ingredient.

The present invention thus relates to the use of pipamperon or a pharmaceutically acceptable salt thereof for the preparation of a medicament for treating the underlying emotion dysregulation of pain disorders, characterized in that pipamperon or said pharmaceutically acceptable salt thereof is administered simultaneously with, separate from or prior to the administration of a 5-HT2C antagonist compound to augment the therapeutic effect or to provide a faster onset of the therapeutic effect of said 5-HT2C antagonist compound, further characterized in that pipamperon is to be administered to a patient in a daily dose ranging between 5 and 15 mg of the active ingredient.

According to a preferred embodiment, the invention relates to the uses as described above, wherein said 5-HT2C antagonist compound is chosen from the group consisting of SB 243213 and agomelatine or a pro-drug or an active metabolite thereof, or a pharmaceutically acceptable salt thereof. Preferably, agomelatine is to be administered in a daily dose ranging between 25 and 50 mg of the active ingredient.

The invention also relates to a pharmaceutical composition comprising (a) pipamperon, and (b) a 5-HT2C antagonist, preferably chosen from the group consisting of SB 243213 and agomelatine or a pro-drug or an active metabolite thereof, or a pharmaceutically acceptable salt thereof, as a combined preparation for simultaneous, separate or sequential use for treating the underlying emotion dysregulation of a mental disease or disorder which is chosen from the group of diseases or disorders consisting of mood disorders, anxiety disorders, eating disorders, premenstrual syndrome, somatoform disorders (excluding pain disorders), factitious disorders, dissociative disorders, sexual and gender disorders, sleep disorders, adjustment disorders, impulse control disorders, substance-related disorder, personality disorders, antisocial behaviour, bereavement, occupational problem, problems related to abuse or neglect and pain disorders.

The present invention also relates to a pharmaceutical composition as described above wherein pipamperon is provided in a unitary dose of between 5 and 15 mg of the active ingredient and wherein said 5-HT2C antagonist is agomelatine, preferably provided in a unitary dose of between 25 and 50 mg of the active ingredient.

8: Combination Therapy with a 5-HT3 (Serotonin 3 Receptor) Antagonist Compound

The mental disorders which can be treated using compounds having a high selective affinity for the 5-HT2A and D4 receptor, for instance pipamperon, in a combination therapy with a 5-HT3 (serotonin 3 receptor) antagonist compound, are substance-related disorders.

The present invention thus relates to the use of pipamperon or a pharmaceutically acceptable salt thereof for the preparation of a medicament for treating the underlying emotion dysregulation of substance-related disorders, characterized in that pipamperon or said pharmaceutically acceptable salt thereof is administered simultaneously with, separate from or prior to the administration of a 5-HT3 antagonist compound to augment the therapeutic effect or to provide a faster onset of the therapeutic effect of said 5-HT3 antagonist compound, further characterized in that pipamperon is to be administered to a patient in a daily dose ranging between 5 and 15 mg of the active ingredient.

According to a preferred embodiment, the invention relates to the use as described above, wherein said 5-HT3 antagonist compound is ondansetron or a pro-drug or an active metabolite thereof, or a pharmaceutically acceptable salt thereof. Preferably, ondansetron is to be administered in a daily dose ranging between 8 and 32 mg of the active ingredient.

The invention also relates to a pharmaceutical composition comprising (a) pipamperon, and (b) a 5-HT3 antagonist, preferably ondansetron or a pro-drug or an active metabolite thereof, or a pharmaceutically acceptable salt thereof, as a combined preparation for simultaneous, separate or sequential use for treating the underlying emotion dysregulation of substance-related disorders.

The invention also relates to a pharmaceutical composition as described above wherein pipamperon is provided in a unitary dose of between 5 and 15 mg of the active ingredient and wherein said 5-HT3 antagonist is ondansetron, preferably provided in a unitary dose of between 8 and 32 mg of the active ingredient.

9: Combination Therapy with a 5-HT6 (Serotonin 6 Receptor) Antagonist Compound

The mental disorders which can be treated using compounds having a high selective affinity for the 5-HT2A and D4 receptor, for instance pipamperon, in a combination therapy with a 5-HT6 (serotonin 6 receptor) antagonist compound, are chosen from the group of diseases or disorders consisting of Alzheimer Disease, substance-induced persisting dementia, vascular dementia, dementia due to HIV disease, dementia due to head trauma, dementia due to Parkinson Disease, dementia due to Huntington Disease, dementia due to Pick Disease, dementia due to Creutzfeldt-Jacob Disease, amnestic disorders due to a general medical condition, substance-induced persisting amnestic disorder, mild cognitive impairment disorder and other cognitive disorders.

The present invention thus relates to the use of pipamperon or a pharmaceutically acceptable salt thereof for the preparation of a medicament for treating the underlying emotion dysregulation of a cognitive disorder selected from the group of diseases and disorders consisting of Alzheimer Disease, substance-induced persisting dementia, vascular dementia, dementia due to HIV disease, dementia due to head trauma, dementia due to Parkinson Disease, dementia due to Huntington Disease, dementia due to Pick Disease, dementia due to Creutzfeldt-Jacob Disease, amnestic disorders due to a general medical condition, substance-induced persisting amnestic disorder, mild cognitive impairment disorder and other cognitive disorders, characterized in that pipamperon or said pharmaceutically acceptable salt thereof is administered simultaneously with, separate from or prior to the administration of a 5-HT6 antagonist compound to augment the therapeutic effect or to provide a faster onset of the therapeutic effect of said 5-HT6 antagonist compound, further characterized in that pipamperon is to be administered to a patient in a daily dose ranging between 5 and 15 mg of the active ingredient.

According to a preferred embodiment, the invention relates to the use as described above, wherein said 5-HT6 antagonist compound is chosen from the group consisting of SB-271046, 742457 and 271046 or a pro-drug or an active metabolite thereof, or a pharmaceutically acceptable salt thereof.

The invention also relates to a pharmaceutical composition comprising (a) pipamperon, and (b) a 5-HT6 antagonist, preferably chosen from the group consisting of SB-271046, 742457 and 271046 or a pro-drug or an active metabolite thereof, or a pharmaceutically acceptable salt thereof, as a combined preparation for simultaneous, separate or sequential use for treating the underlying emotion dysregulation of a mental disease or disorder which is chosen from the group of diseases or disorders consisting of Alzheimer Disease, substance-induced persisting dementia, vascular dementia, dementia due to HIV disease, dementia due to head trauma, dementia due to Parkinson Disease, dementia due to Huntington Disease, dementia due to Pick Disease, dementia due to Creutzfeldt-Jacob Disease, amnestic disorders due to a general medical condition, substance-induced persisting amnestic disorder, mild cognitive impairment disorder and other cognitive disorders.

10: Combination Therapy with an Acetylcholinesterase Inhibitor Compound

The mental disorders which can be treated using compounds having a high selective affinity for the 5-HT2A and D4 receptor, for instance pipamperon, in a combination therapy with an acetylcholinesterase inhibitor compound, are chosen from the group of diseases or disorders consisting of Alzheimer Disease, substance-induced persisting dementia, vascular dementia, dementia due to HIV disease, dementia due to head trauma, dementia due to Parkinson Disease, dementia due to Huntington Disease, dementia due to Pick Disease, dementia due to Creutzfeldt-Jacob Disease, amnestic disorders due to a general medical condition, substance-induced persisting amnestic disorder, mild cognitive impairment disorder and other cognitive disorders.

The present invention thus relates to the use of pipamperon or a pharmaceutically acceptable salt thereof for the preparation of a medicament for treating the underlying emotion dysregulation of a cognitive disorder selected from the group of diseases and disorders consisting of Alzheimer Disease, substance-induced persisting dementia, vascular dementia, dementia due to HIV disease, dementia due to head trauma, dementia due to Parkinson Disease, dementia due to Huntington Disease, dementia due to Pick Disease, dementia due to Creutzfeldt-Jacob Disease, amnestic disorders due to a general medical condition, substance-induced persisting amnestic disorder, mild cognitive impairment disorder, other cognitive disorders, characterized in that pipamperon or said pharmaceutically acceptable salt thereof is administered simultaneously with, separate from or prior to the administration of an acetylcholinesterase inhibitor compound to augment the therapeutic effect or to provide a faster onset of the therapeutic effect of said acetylcholinesterase inhibitor compound, further characterized in that pipamperon is to be administered to a patient in a daily dose ranging between 5 and 15 mg of the active ingredient.

According to a preferred embodiment, the invention relates to the use as described above, wherein said acetylcholinesterase inhibitor compound is chosen from the group consisting of tacrine, rivastigmine tartrate, rivastigmine, physostigmine, phenserine tartrate, metrifonate, huperzine A, galantamine (preferably extended release formulation), donezepil, dichlorvos and anseculin hydrochloride, preferably tartrate, or a pro-drug or an active metabolite thereof, or a pharmaceutically acceptable sat thereof. Preferably, rivastigmine tartrate is to be administered in a daily dose ranging between 3 and 12 mg of the active ingredient. Preferably, phenserine tartrate is to be administered in a daily dose ranging between 20 and 30 mg of the active ingredient. Preferably, galantamine (extended release formulation) is to be administered in a daily dose ranging between 8 and 24 mg of the active ingredient.

The invention also relates to a pharmaceutical composition comprising (a) pipamperon, and (b) an acetylcholinesterase inhibitor, preferably chosen from the group consisting of tacrine, rivastigmine tartrate, rivastigmine, physostigmine, phenserine tartrate, metrifonate, huperzine A, galantamine (preferably extended release formulation), donezepil, dichlorvos and anseculin hydrochloride, preferably tartrate, or a pro-drug or an active metabolite thereof, or a pharmaceutically acceptable salt thereof, as a combined preparation for simultaneous, separate or sequential use for treating the underlying emotion dysregulation of a mental disease or disorder which is chosen from the group of diseases or disorders consisting of Alzheimer Disease, substance-related persisting dementia, vascular dementia, dementia due to HIV disease, dementia due to head trauma, dementia due to Parkinson Disease, dementia due to Huntington Disease, dementia due to Pick Disease, dementia due to Creutzfeldt-Jacob Disease, amnestic disorders due to a general medical condition, substance-induced persisting amnestic disorder, mild cognitive impairment disorder and other cognitive disorders.

The invention also relates to a pharmaceutical composition as described above wherein pipamperon is provided in a unitary dose of between 5 and 15 mg of the active ingredient and wherein said acetylcholinesterase inhibitor is rivastigmine tartrate, preferably provided in a unitary dose of between 3 and 12 mg of the active ingredient.

The invention further relates to a pharmaceutical composition as described above wherein pipamperon is provided in a unitary dose of between 5 and 15 mg of the active ingredient and wherein said acetylcholinesterase inhibitor is phenserine tartrate, preferably provided in a unitary dose of between 20 and 30 mg of the active ingredient.

In addition, the invention relates to a pharmaceutical composition as described above wherein pipamperon is provided in a unitary dose of between 5 and 15 mg of the active ingredient and wherein said acetylcholinesterase inhibitor is galantamine (preferably extended release formulation), preferably provided in a unitary dose of between 8 and 24 mg of the active ingredient.

11: Combination Therapy with an Adenosine A2a Receptor Antagonist Compound

The mental disorder which can be treated using compounds having a high selective affinity for the 5-HT2A and D4 receptor, for instance pipamperon, in a combination therapy with an adenosine A2a receptor antagonist compound, is Parkinson disease.

The present invention thus relates to the use of pipamperon or a pharmaceutically acceptable salt thereof for the preparation of a medicament for treating the underlying emotion dysregulation of Parkinson disease, characterized in that pipamperon or said pharmaceutically acceptable salt thereof is administered simultaneously with, separate from or prior to the administration of an adenosine A2a receptor antagonist compound to augment the therapeutic effect or to provide a faster onset of the therapeutic effect of said adenosine A2a receptor antagonist compound, further characterized in that pipamperon is to be administered to a patient in a daily dose ranging between 5 and 15 mg of the active ingredient.

According to a preferred embodiment, the invention relates to the use as described above, wherein said adenosine A2a receptor antagonist compound is KW-6002 or a pro-drug or an active metabolite thereof, or a pharmaceutically acceptable salt thereof. Preferably, KW-6002 is to be administered in a daily dose ranging between 40 and 80 mg of the active ingredient.

The invention also relates to a pharmaceutical composition comprising (a) pipamperon, and (b) an adenosine A2a receptor antagonist, preferably KW-6002 or a pro-drug or an active metabolite thereof, or a pharmaceutically acceptable salt thereof, as a combined preparation for simultaneous, separate or sequential use for treating the underlying emotion dysregulation of Parkinson disease.

The invention also relates to a pharmaceutical composition as described above wherein pipamperon is provided in a unitary dose of between 5 and 15 mg of the active ingredient and wherein said acetylcholinesterase inhibitor is KW-6002, preferably provided in a unitary dose of between 40 and 80 mg of the active ingredient.

12: Combination Therapy with an Adrenergic Transmitter Releaser

The mental disorders which can be treated using compounds having a high selective affinity for the 5-HT2A and D4 receptor, for instance pipamperon, in a combination therapy with an adrenergic transmitter releaser, are chosen from the group of diseases or disorders consisting of mood disorders, anxiety disorders, eating disorders, premenstrual syndrome, somatoform disorders (excluding pain disorders), factitious disorders, dissociative disorders, sexual and gender identity disorders, adjustment disorders, impulse control disorders, personality disorders, bereavement, occupational problem, problems related to abuse or neglect and pain disorders.

The present invention thus relates to the use of pipamperon or a pharmaceutically acceptable salt thereof for the preparation of a medicament for treating the underlying emotion dysregulation of a non-cognitive mental disease or disorder selected from the group of diseases and disorders consisting of mood disorders, anxiety disorders, eating disorders, premenstrual syndrome, somatoform disorders (excluding pain disorders), factitious disorders, dissociative disorders, sexual and gender identity disorders, adjustment disorders, impulse control disorders, personality disorders, bereavement, occupational problem and problems related to abuse or neglect, characterized in that pipamperon or said pharmaceutically acceptable salt thereof is administered simultaneously with, separate from or prior to the administration of an adrenergic transmitter releaser compound to augment the therapeutic effect or to provide a faster onset of the therapeutic effect of said adrenergic transmitter releaser compound, further characterized in that pipamperon is to be administered to a patient in a daily dose ranging between 5 and 15 mg of the active ingredient.

The present invention thus relates to the use of pipamperon or a pharmaceutically acceptable salt thereof for the preparation of a medicament for treating the underlying emotion dysregulation of pain disorders, characterized in that pipamperon or said pharmaceutically acceptable salt thereof is administered simultaneously with, separate from or prior to the administration of an adrenergic transmitter releaser compound to augment the therapeutic effect or to provide a faster onset of the therapeutic effect of said adrenergic transmitter releaser compound, further characterized in that pipamperon is to be administered to a patient in a daily dose ranging between 5 and 15 mg of the active ingredient.

According to a preferred embodiment, the invention relates to the uses as described above, wherein said adrenergic transmitter releaser compound is pipoxazole or a pro-drug or an active metabolite thereof, or a pharmaceutically acceptable salt thereof. Preferably, pipoxazole is to be administered in a daily dose ranging between 30 and 60 mg of the active ingredient.

The invention also relates to a pharmaceutical composition comprising (a) pipamperon, and (b) an adrenergic transmitter releaser, preferably pipoxazole, or a pro-drug or an active metabolite thereof, or a pharmaceutically acceptable salt thereof, as a combined preparation for simultaneous, separate or sequential use for treating the underlying emotion dysregulation of a mental disease or disorder which is chosen from the group of diseases or disorders consisting of mood disorders, anxiety disorders, eating disorders, premenstrual syndrome, somatoform disorders (excluding pain disorders), factitious disorders, dissociative disorders, sexual and gender identity disorders, adjustment disorders, impulse control disorders, personality disorders, bereavement, occupational problem, problems related to abuse or neglect and pain disorders.

The invention also relates to a pharmaceutical composition as described above wherein pipamperon is provided in a unitary dose of between 5 and 15 mg of the active ingredient and wherein said adrenergic transmitter releaser is pipoxazole, preferably provided in a unitary dose of between 30 and 60 mg of the active ingredient.

13: Combination Therapy with an Alpha 1 Adrenoreceptor Antagonist

The mental disorders which can be treated using compounds having a high selective affinity for the 5-HT2A and D4 receptor, for instance pipamperon, in a combination therapy with an alpha 1 adrenoreceptor antagonist, are chosen from the group of diseases or disorders consisting of mood disorders, anxiety disorders, eating disorders, premenstrual syndrome, somatoform disorders (excluding pain disorders), factitious disorders, dissociative disorders, sexual and gender identity disorders, sleep disorders, adjustment disorders, impulse control disorders, personality disorders, bereavement, occupational problem, problems related to abuse or neglect, pain disorders and Parkinson disease.

The present invention thus relates to the use of pipamperon or a pharmaceutically acceptable salt thereof for the preparation of a medicament for treating the underlying emotion dysregulation of a non-cognitive mental disease or disorder selected from the group of diseases and disorders consisting of mood disorders, anxiety disorders, eating disorders, premenstrual syndrome, somatoform disorders (excluding pain disorders), factitious disorders, dissociative disorders, sexual and gender identity disorders, sleep disorders, adjustment disorders, impuse control disorders, personality disorders, bereavement, occupational problem and problems related to abuse or neglect, characterized in that pipamperon or said pharmaceutically acceptable salt thereof is administered simultaneously with, separate from or prior to the administration of a alpha 1 adrenoreceptor antagonist compound to augment the therapeutic effect or to provide a faster onset of the therapeutic effect of said alpha 1 adrenoreceptor antagonist compound, further characterized in that pipamperon is to be administered to a patient in a daily dose ranging between 5 and 15 mg of the active ingredient.

The present invention thus relates to the use of pipamperon or a pharmaceutically acceptable salt thereof for the preparation of a medicament for treating the underlying emotion dysregulation of pain disorders, characterized in that pipamperon or said pharmaceutically acceptable salt thereof is administered simultaneously with, separate from or prior to the administration of an alpha 1 adrenoreceptor antagonist compound to augment the therapeutic effect or to provide a faster onset of the therapeutic effect of said alpha 1 adrenoreceptor antagonist compound, further characterized in that pipamperon is to be administered to a patient in a daily dose ranging between 5 and 15 mg of the active ingredient.

The present invention thus relates to the use of pipamperon or a pharmaceutically acceptable salt thereof for the preparation of a medicament for treating the underlying emotion dysregulation of Parkinson disease, characterized in that pipamperon or said pharmaceutically acceptable salt thereof is administered simultaneously with, separate from or prior to the administration of an alpha 1 adrenoreceptor antagonist compound to augment the therapeutic effect or to provide a faster onset of the therapeutic effect of said alpha 1 adrenoreceptor antagonist compound, further characterized in that pipamperon is to be administered to a patient in a daily dose ranging between 5 and 15 mg of the active ingredient.

According to a preferred embodiment, the invention relates to the uses as described above, wherein said alpha 1 adrenoreceptor antagonist compound is chosen from the group consisting of SDZ NVI 085 and flesinoxan or a pro-drug or an active metabolite thereof, or a pharmaceutically acceptable salt thereof.

The invention also relates to a pharmaceutical composition comprising (a) pipamperon, and (b) an alpha 1 adrenoreceptor antagonist, preferably chosen from the group consisting of SDZ NVI 085 and flesinoxan or a pro-drug or an active metabolite thereof, or a pharmaceutically acceptable salt thereof, as a combined preparation for simultaneous, separate or sequential use for treating the underlying emotion dysregulation of a mental disease or disorder which is chosen from the group of diseases or disorders consisting of mood disorders, anxiety disorders, eating disorders, premenstrual syndrome, somatoform disorders (excluding pain disorders), factitious disorders, dissociative disorders, sexual and gender identity disorders, sleep disorders, adjustment disorders, impulse control disorders, personality disorders, bereavement, occupational problem, problems related to abuse or neglect, pain disorders and Parkinson disease.

14: Combination Therapy with an Alpha 2 Adrenoreceptor Antagonist

The mental disorders which can be treated using compounds having a high selective affinity for the 5-HT2A and D4 receptor, for instance pipamperon, in a combination therapy with an alpha 2 adrenoreceptor antagonist, are chosen from the group of diseases or disorders consisting of mood disorders, anxiety disorders, psychotic disorders, eating disorders, premenstrual syndrome, somatoform disorders (excluding pain disorders), factitious disorders, dissociative disorders, sexual and gender identity disorders, sleep disorders, adjustment disorders, impulse control disorders, substance related disorders, personality disorders, bereavement, occupational problem, problems related to abuse or neglect and pain disorders.

The present invention thus relates to the use of pipamperon or a pharmaceutically acceptable salt thereof for the preparation of a medicament for treating the underlying emotion dysregulation of a non-cognitive mental disease or disorder selected from the group of diseases and disorders consisting of mood disorders, anxiety disorders, psychotic disorders, eating disorders, premenstrual syndrome, somatoform disorders (excluding pain disorders), factitious disorders, dissociative disorders, sexual and gender identity disorders, sleep disorders, adjustment disorders, impulse control disorders, substance related disorders, personality disorders, bereavement, occupational problem and problems related to abuse or neglect, characterized in that pipamperon or said pharmaceutically acceptable salt thereof is administered simultaneously with, separate from or prior to the administration of a alpha 2 adrenoreceptor antagonist compound to augment the therapeutic effect or to provide a faster onset of the therapeutic effect of said alpha 2 adrenoreceptor antagonist compound, further characterized in that pipamperon is to be administered to a patient in a daily dose ranging between 5 and 15 mg of the active ingredient.

The present invention thus relates to the use of pipamperon or a pharmaceutically acceptable salt thereof for the preparation of a medicament for treating the underlying emotion dysregulation of pain disorders, characterized in that pipamperon or said pharmaceutically acceptable salt thereof is administered simultaneously with, separate from or prior to the administration of an alpha 2 adrenoreceptor antagonist compound to augment the therapeutic effect or to provide a faster onset of the therapeutic effect of said alpha 2 adrenoreceptor antagonist compound, further characterized in that pipamperon is to be administered to a patient in a daily dose ranging between 5 and 15 mg of the active ingredient.

According to a preferred embodiment, the invention relates to the uses as described above, wherein said alpha 2 adrenoreceptor antagonist compound is chosen from the group consisting of UK-14304, sunepitron, mirtazepine, idazoxan, fluparoxan, A75200 and (R)-A 75200, preferably sunepitron or idazoxan, or a pro-drug or an active metabolite thereof, or a pharmaceutically acceptable salt thereof. Preferably, idazoxan is to be administered in a daily dose ranging between 5 and 40 mg of the active ingredient.

The invention also relates to a pharmaceutical composition comprising (a) pipamperon, and (b) an alpha 2 adrenoreceptor antagonist, preferably chosen from the group consisting of UK-14304, sunepitron, mirtazepine, idazoxan, fluparoxan, A75200 and (R)-A 75200, preferably sunepitron or idazoxan, or a pro-drug or an active metabolite thereof, or a pharmaceutically acceptable salt thereof, as a combined preparation for simultaneous, separate or sequential use for treating the underlying emotion dysregulation of a mental disease or disorder which is chosen from the group of diseases or disorders consisting of mood disorders, anxiety disorders, psychotic disorders, eating disorders, premenstrual syndrome, somatoform disorders (excluding pain disorders), factitious disorders, dissociative disorders, sexual and gender identity disorders, sleep disorders, adjustment disorders, impulse control disorders, substance related disorders, personality disorders, bereavement, occupational problem, problems related to abuse or neglect and pain disorders.

The invention also relates to a pharmaceutical composition as described above wherein pipamperon is provided in a unitary dose of between 5 and 15 mg of the active ingredient and wherein said alpha 2 adrenoreceptor antagonist is Idazoxan, preferably provided in a unitary dose of between 5 and 40 mg of the active ingredient.

15: Combination Therapy with an AMPA Receptor Mediator Compound

The mental disorders which can be treated using compounds having a high selective affinity for the 5-HT2A and D4 receptor, for instance pipamperon, in a combination therapy with an AMPA (alpha-amino-3-hydroxy-5-methyl-4-isoxazole propionate) receptor mediator compound, are chosen from the group of diseases or disorders consisting of mood disorders, anxiety disorders, psychotic disorders, eating disorders, premenstrual syndrome, somatoform disorders (excluding pain disorders), factitious disorders, dissociative disorders, sleep disorders, adjustment disorders, impulse control disorders, pervasive development disorders, disruptive behaviour disorders, substance-induced disorders, personality disorders, psychological factors affecting medical conditions, malingering, antisocial behaviour, bereavement, occupational problem, identity problem, problems related to abuse or neglect, pain disorders, delirium, Alzheimer Disease, substance-related persisting dementia, vascular dementia, dementia due to HIV disease, dementia due to head trauma, dementia due to Parkinson Disease, dementia due to Huntington Disease, dementia due to Pick Disease, dementia due to Creutzfeldt-Jacob Disease, amnestic disorders due to a general medical condition, substance-induced persisting amnestic disorder, mild cognitive impairment disorder and other cognitive disorders.

The present invention thus relates to the use of pipamperon or a pharmaceutically acceptable salt thereof for the preparation of a medicament for treating the underlying emotion dysregulation of a non-cognitive mental disease or disorder selected from the group of diseases and disorders consisting of mood disorders, anxiety disorders, psychotic disorders, eating disorders, premenstrual syndrome, somatoform disorders (excluding pain disorders), factitious disorders, dissociative disorders, sleep disorders, adjustment disorders, impulse control disorders, pervasive development disorders, disruptive behaviour disorders, substance-related disorders, personality disorders, psychological factors affecting medical conditions, malingering, antisocial behaviour, bereavement, occupational problem, identity problem and problems related to abuse or neglect, characterized in that pipamperon or said pharmaceutically acceptable salt thereof is administered simultaneously with, separate from or prior to the administration of an AMPA receptor mediator compound to augment the therapeutic effect or to provide a faster onset of the therapeutic effect of said AMPA receptor mediator compound, further characterized in that pipamperon is to be administered to a patient in a daily dose ranging between 5 and 15 mg of the active ingredient.

The present invention thus relates to the use of pipamperon or a pharmaceutically acceptable salt thereof for the preparation of a medicament for treating the underlying emotion dysregulation of pain disorders, characterized in that pipamperon or said pharmaceutically acceptable salt thereof is administered simultaneously with, separate from or prior to the administration of an AMPA receptor mediator compound to augment the therapeutic effect or to provide a faster onset of the therapeutic effect of said AMPA receptor mediator compound, further characterized in that pipamperon is to be administered to a patient in a daily dose ranging between 5 and 15 mg of the active ingredient.

The present invention thus relates to the use of pipamperon or a pharmaceutically acceptable salt thereof for the preparation of a medicament for treating the underlying emotion dysregulation of a cognitive mental disease or disorder selected from the group of diseases and disorders consisting of delirium, Alzheimer Disease, substance-induced persisting dementia, vascular dementia, dementia due to HIV disease, dementia due to head trauma, dementia due to Parkinson Disease, dementia due to Huntington Disease, dementia due to Pick Disease, dementia due to Creutzfeldt-Jacob Disease, amnestic disorders due to a general medical condition, substance-induced persisting amnestic disorder, mild cognitive impairment disorder and other cognitive disorders, characterized in that pipamperon or said pharmaceutically acceptable salt thereof is administered simultaneously with, separate from or prior to the administration of an AMPA receptor mediator compound to augment the therapeutic effect or to provide a faster onset of the therapeutic effect of said AMPA receptor mediator compound, further characterized in that pipamperon is to be administered to a patient in a daily dose ranging between 5 and 15 mg of the active ingredient.

According to a preferred embodiment, the invention relates to the uses as described above, wherein said AMPA receptor mediator compound is chosen from the group consisting of ampakine ORG 24448/CX-619, ampakine CX-717, ampakine CX-691 and ampakine CX-516, preferably ampakine ORG 24448/CX-619, ampakine CX-717 or ampakine CX-691, or a pro-drug or an active metabolite thereof, or a pharmaceutically acceptable salt thereof.

The invention also relates to a pharmaceutical composition comprising (a) pipamperon, and (b) an AMPA receptor mediator, preferably chosen from the group consisting of ampakine ORG 24448/CX-619, ampakine CX-717, ampakine CX-691 and ampakine. CX-516, preferably ampakine ORG 24448/CX-619, ampakine CX-717 or ampakine CX-691, or a pro-drug or an active metabolite thereof, or a pharmaceutically acceptable salt thereof, as a combined preparation for simultaneous, separate or sequential use for treating the underlying emotion dysregulation of a mental disease or disorder which is chosen from the group of diseases or disorders consisting of mood disorders, anxiety disorders, psychotic disorders, eating disorders, premenstrual syndrome, somatoform disorders (excluding pain disorders), factitious disorders, dissociative disorders, sleep disorders, adjustment disorders, impulse control disorders, pervasive development disorders, disruptive behaviour disorders, substance-related disorders, personality disorders, psychological factors affecting medical conditions, malingering, antisocial behaviour, bereavement, occupational problem, identity problem, problems related to abuse or neglect, pain disorders, delirium, Alzheimer Disease, substance-induced persisting dementia, vascular dementia, dementia due to HIV disease, dementia due to head trauma, dementia due to Parkinson Disease, dementia due to Huntington Disease, dementia due to Pick Disease, dementia due to Creutzfeldt-Jacob Disease, amnestic disorders due to a general medical condition, substance-induced persisting amnestic disorder, mild cognitive impairment disorder and other cognitive disorders.

16: Combination Therapy with an Amphetamine Compound

The mental disorders which can be treated using compounds having a high selective affinity for the 5-HT2A and D4 receptor, for instance pipamperon, in a combination therapy with an amphetamine compound, are attention-deficit disorders.

The present invention thus relates to the use of pipamperon or a pharmaceutically acceptable salt thereof for the preparation of a medicament for treating the underlying emotion dysregulation of attention deficit disorders, characterized in that pipamperon or said pharmaceutically acceptable salt thereof is administered simultaneously with, separate from or prior to the administration of an amphetamine compound to augment the therapeutic effect or to provide a faster onset of the therapeutic effect of said amphetamine compound, further characterized in that pipamperon is to be administered to a patient in a daily dose ranging between 5 and 15 mg of the active ingredient.

According to a preferred embodiment, the invention relates to the use as described above, wherein said amphetamine compound is methylphenidate (preferably administered by a transdermal system) or a pro-drug or an active metabolite thereof, or a pharmaceutically acceptable salt thereof.

The invention also relates to a pharmaceutical composition comprising (a) pipamperon, and (b) an amphetamine, preferably methylphenidate (preferably administered by a transdermal system) or a pro-drug or an active metabolite thereof, or a pharmaceutically acceptable salt thereof, as a combined preparation for simultaneous, separate or sequential use for treating the underlying emotion dysregulation of attention deficit disorders.

17: Combination Therapy with an Amyloid Aggregation-Inhibitor Compound

The mental disorders which can be treated using compounds having a high selective affinity for the 5-HT2A and D4 receptor, for instance pipamperon, in a combination therapy with an amyloid aggregation-inhibitor compound, are chosen from the group of diseases or disorders consisting of Alzheimer Disease, substance-related persisting dementia, vascular dementia, dementia due to HIV disease, dementia due to head trauma, dementia due to Parkinson Disease, dementia due to Huntington Disease, dementia due to Pick Disease, dementia due to Creutzfeldt-Jacob Disease, amnestic disorders due to a general medical condition, substance-induced persisting amnestic disorder, mild cognitive impairment disorder and other cognitive disorders.

The present invention thus relates to the use of pipamperon or a pharmaceutically acceptable salt thereof for the preparation of a medicament for treating the underlying emotion dysregulation of a cognitive mental disease or disorder selected from the group of diseases and disorders consisting of Alzheimer Disease, substance-related persisting dementia, vascular dementia, dementia due to HIV disease, dementia due to head trauma, dementia due to Parkinson Disease, dementia due to Huntington Disease, dementia due to Pick Disease, dementia due to Creutzfeldt-Jacob Disease, amnestic disorders due to a general medical condition, substance-induced persisting amnestic disorder, mild cognitive impairment disorder and other cognitive disorders, characterized in that pipamperon or said pharmaceutically acceptable salt thereof is administered simultaneously with, separate from or prior to the administration of an amyloid aggregation-inhibitor compound to augment the therapeutic effect or to provide a faster onset of the therapeutic effect of said amyloid aggregation-inhibitor compound, further characterized in that pipamperon is to be administered to a patient in a daily dose ranging between 5 and 15 mg of the active ingredient.

According to a preferred embodiment, the invention relates to the use as described above, wherein said amyloid aggregation-inhibitor compound is chosen from the group consisting of APAN and Alzhemed, or a pro-drug or an active metabolite thereof, or a pharmaceutically acceptable salt thereof. Preferably, Alzhemed is to be administered in a daily dose of between 200 and 300 mg of the active ingredient.

The invention also relates to a pharmaceutical composition comprising (a) pipamperon, and (b) an amyloid aggregation-inhibitor, preferably chosen from the group consisting of APAN and Alzhemed, or a pro-drug or an active metabolite thereof, or a pharmaceutically acceptable salt thereof, as a combined preparation for simultaneous, separate or sequential use for treating the underlying emotion dysregulation of a mental disease or disorder which is chosen from the group of diseases or disorders consisting of Alzheimer Disease, substance-related persisting dementia, vascular dementia, dementia due to HIV disease, dementia due to head trauma, dementia due to Parkinson Disease, dementia due to Huntington Disease, dementia due to Pick Disease, dementia due to Creutzfeldt-Jacob Disease, amnestic disorders due to a general medical condition, substance-induced persisting amnestic disorder, mild cognitive impairment disorder and other cognitive disorders.

The invention also relates to a pharmaceutical composition as described above wherein pipamperon is provided in a unitary dose of between 5 and 15 mg of the active ingredient and wherein said amyloid aggregation-inhibitor is Alzhemed, preferably provided in a unitary dose of between 200 and 300 mg of the active ingredient.

18: Combination Therapy with an Androgen Receptor Modulator Compound

The mental disorders which can be treated using compounds having a high selective affinity for the 5-HT2A and D4 receptor, for instance pipamperon, in a combination therapy with an androgen receptor modulator compound, are sexual and gender identity disorders.

The present invention thus relates to the use of pipamperon or a pharmaceutically acceptable salt thereof for the preparation of a medicament for treating the underlying emotion dysregulation of sexual and gender identity disorders, characterized in that pipamperon or said pharmaceutically acceptable salt thereof is administered simultaneously with, separate from or prior to the administration of an androgen receptor modulator compound to augment the therapeutic effect or to provide a faster onset of the therapeutic effect of said androgen receptor modulator compound, further characterized in that pipamperon is to be administered to a patient in a daily dose ranging between 5 and 15 mg of the active ingredient.

According to a preferred embodiment, the invention relates to the use as described above, wherein said androgen receptor modulator compound is LGD2226 or a pro-drug or an active metabolite thereof, or a pharmaceutically acceptable salt thereof.

The invention also relates to a pharmaceutical composition comprising (a) pipamperon, and (b) an androgen receptor modulator, preferably LGD2226 or a pro-drug or an active metabolite thereof, or a pharmaceutically acceptable salt thereof, as a combined preparation for simultaneous, separate or sequential use for treating the underlying emotion dysregulation of sexual and gender identity disorders.

19: Combination Therapy with an Beta 3 Adrenoreceptor Agonist

The mental disorders which can be treated using compounds having a high selective affinity for the 5-HT2A and D4 receptor, for instance pipamperon, in a combination therapy with an beta 3 adrenoreceptor agonist, are chosen from the group of diseases or disorders consisting of mood disorders, anxiety disorders, eating disorders, premenstrual syndrome, somatoform disorders (excluding pain disorders), factitious disorders, dissociative disorders, sexual and gender identity disorders, sleep disorders, adjustment disorders, impulse control disorders, substance related disorders, personality disorders, bereavement, occupational problem, problems related to abuse or neglect and pain disorders.

The present invention thus relates to the use of pipamperon or a pharmaceutically acceptable salt thereof for the preparation of a medicament for treating the underlying emotion dysregulation of a non-cognitive mental disease or disorder selected from the group of diseases and disorders consisting of mood disorders, anxiety disorders, eating disorders, premenstrual syndrome, somatoform disorders (excluding pain disorders), factitious disorders, dissociative disorders, sexual and gender identity disorders, sleep disorders, adjustment disorders, impulse control disorders, substance related disorders, personality disorders, bereavement, occupational problem and problems related to abuse or neglect, characterized in that pipamperon or said pharmaceutically acceptable salt thereof is administered simultaneously with, separate from or prior to the administration of a beta 3 adrenoreceptor agonist compound to augment the therapeutic effect or to provide a faster onset of the therapeutic effect of said beta 3 adrenoreceptor agonist compound, further characterized in that pipamperon is to be administered to a patient in a daily dose ranging between 5 and 15 mg of the active ingredient.

The present invention thus relates to the use of pipamperon or a pharmaceutically acceptable salt thereof for the preparation of a medicament for treating the underlying emotion dysregulation of pain disorders, characterized in that pipamperon or said pharmaceutically acceptable salt thereof is administered simultaneously with, separate from or prior to the administration of an beta 3 adrenoreceptor agonist compound to augment the therapeutic effect or to provide a faster onset of the therapeutic effect of said beta 3 adrenoreceptor agonist compound, further characterized in that pipamperon is to be administered to a patient in a daily dose ranging between 5 and 15 mg of the active ingredient.

According to a preferred embodiment, the invention relates to the uses as described above, wherein said beta 3 adrenoreceptor agonist compound is SR 586'1 or a pro-drug or an active metabolite thereof, or a pharmaceutically acceptable salt thereof.

The invention also relates to a pharmaceutical composition comprising (a) pipamperon, and (b) a beta 3 adrenoreceptor agonist, preferably SR 58611 or a pro-drug or an active metabolite thereof, or a pharmaceutically acceptable salt thereof, as a combined preparation for simultaneous, separate or sequential use for treating the underlying emotion dysregulation of a mental disease or disorder which is chosen from the group of diseases or disorders consisting of mood disorders, anxiety disorders, eating disorders, premenstrual syndrome, somatoform disorders (excluding pain disorders), factitious disorders, dissociative disorders, sexual and gender identity disorders, sleep disorders, adjustment disorders, impulse control disorders, substance related disorders, personality disorders, bereavement, occupational problem, problems related to abuse or neglect and pain disorders.

20: Combination Therapy with a Calcium Channel Modulator Compound

The mental disorders which can be treated using compounds having a high selective affinity for the 5-HT2A and D4 receptor, for instance pipamperon, a combination therapy with a calcium channel modulator compound, are chosen from the group of diseases or disorders consisting of Alzheimer Disease, substance-related persisting dementia, vascular dementia, dementia due to HIV disease, dementia due to head trauma, dementia due to Parkinson Disease, dementia due to Huntington Disease, dementia due to Pick Disease, dementia due to Creutzfeldt-Jacob Disease, amnestic disorders due to a general medical condition, substance-induced persisting amnestic disorder, mild cognitive impairment disorder, other cognitive disorders and Parkinson disease.

The present invention thus relates to the use of pipamperon or a pharmaceutically acceptable salt thereof for the preparation of a medicament for treating the underlying emotion dysregulation of a cognitive mental disease or disorder selected from the group of diseases and disorders consisting of Alzheimer Disease, substance-related persisting dementia, vascular dementia, dementia due to HIV disease, dementia due to head trauma, dementia due to Parkinson Disease, dementia due to Huntington Disease, dementia due to Pick Disease, dementia due to Creutzfeldt-Jacob Disease, amnestic disorders due to a general medical condition, substance-induced persisting amnestic disorder, mild cognitive impairment disorder and other cognitive disorders, characterized in that pipamperon or said pharmaceutically acceptable salt thereof is administered simultaneously with, separate from or prior to the administration of a calcium channel modulator compound to augment the therapeutic effect or to provide a faster onset of the therapeutic effect of said calcium channel modulator compound, further characterized in that pipamperon is to be administered to a patient in a daily dose ranging between 5 and 15 mg of the active ingredient.

The present invention thus relates to the use of pipamperon or a pharmaceutically acceptable salt thereof for the preparation of a medicament for treating the underlying emotion dysregulation of Parkinson disease, characterized in that pipamperon or said pharmaceutically acceptable salt thereof is administered simultaneously with, separate from or prior to the administration of a calcium channel modulator compound to augment the therapeutic effect or to provide a faster onset of the therapeutic effect of said calcium channel modulator compound, further characterized in that pipamperon is to be administered to a patient in a daily dose ranging between 5 and 15 mg of the active ingredient.

According to a preferred embodiment, the invention relates to the uses as described above, wherein said calcium channel modulator compound is chosen from the group consisting of safinamide and MEM 1003, or a pro-drug or an active metabolite thereof, or a pharmaceutically acceptable salt thereof.

The invention also relates to a pharmaceutical composition comprising (a) pipamperon, and (b) a calcium channel modulator, preferably chosen from the group consisting of safinamide and MEM 1003, or a pro-drug or an active metabolite thereof, or a pharmaceutically acceptable salt thereof, as a combined preparation for simultaneous, separate or sequential use for treating the underlying emotion dysregulation of a mental disease or disorder which is chosen from the group of diseases or disorders consisting of Alzheimer Disease, substance-related persisting dementia, vascular dementia, dementia due to HIV disease, dementia due to head trauma, dementia due to Parkinson Disease, dementia due to Huntington Disease, dementia due to Pick Disease, dementia due to Creutzfeldt-Jacob Disease, amnestic disorders due to a general medical condition, substance-induced persisting amnestic disorder, mild cognitive impairment disorder, other cognitive disorders and Parkinson disease.

21: Combination Therapy with a Cannabioid Receptor 1 (CB1) Antagonist

The mental disorders which can be treated using compounds having a high selective affinity for the 5-HT2A and D4 receptor, for instance pipamperon, in a combination therapy with a cannabioid receptor 1 (CB1) antagonist, are chosen from the group of diseases or disorders consisting of mood disorders, anxiety disorders, psychotic disorders, somatoform disorders (excluding pain disorders), factitious disorders, dissociative disorders, sleep disorders, adjustment disorders, impulse control disorders, pervasive development disorders, disruptive behaviour disorders, substance-related disorders, personality disorders, psychological factors affecting medical conditions, malingering, antisocial behaviour, bereavement, occupational problem, identity problem, problems related to abuse or neglect, pain disorders and delirium.

The present invention thus relates to the use of pipamperon or a pharmaceutically acceptable salt thereof for the preparation of a medicament for treating the underlying emotion dysregulation of a non-cognitive mental disease or disorder selected from the group of diseases and disorders consisting mood disorders, anxiety disorders, psychotic disorders, somatoform disorders (excluding pain disorders), factitious disorders, dissociative disorders, sleep disorders, adjustment disorders, impulse control disorders, pervasive development disorders, disruptive behaviour disorders, substance-related disorders, personality disorders, psychological factors affecting medical conditions, malingering, antisocial behaviour, bereavement, occupational problem, identity problem and problems related to abuse or neglect, characterized in that pipamperon or said pharmaceutically acceptable salt thereof is administered simultaneously with, separate from or prior to the administration of a cannabioid receptor 1 antagonist compound to augment the therapeutic effect or to provide a faster onset of the therapeutic effect of said cannabioid receptor antagonist compound, further characterized in that pipamperon is to be administered to a patient in a daily dose ranging between 5 and 15 mg of the active ingredient.

The present invention thus relates to the use of pipamperon or a pharmaceutically acceptable salt thereof for the preparation of a medicament for treating the underlying emotion dysregulation of pain disorders, characterized in that pipamperon or said pharmaceutically acceptable salt thereof is administered simultaneously with, separate from or prior to the administration of a cannabioid receptor 1 antagonist compound to augment the therapeutic effect or to provide a faster onset of the therapeutic effect of said cannabioid receptor 1 antagonist compound, further characterized in that pipamperon is to be administered to a patient in a daily dose ranging between 5 and 15 mg of the active ingredient.

The present invention thus relates to the use of pipamperon or a pharmaceutically acceptable salt thereof for the preparation of a medicament for treating the underlying emotion dysregulation of delirium, characterized in that pipamperon or said pharmaceutically acceptable salt thereof is administered simultaneously with, separate from or prior to the administration of a cannabioid receptor 1 antagonist compound to augment the therapeutic effect or to provide a faster onset of the therapeutic effect of said cannabioid receptor 1 antagonist compound, further characterized in that pipamperon is to be administered to a patient in a daily dose ranging between 5 and 15 mg of the active ingredient.

According to a preferred embodiment, the invention relates to the uses as described above, wherein said cannabioid receptor antagonist compound is SR 141716 or a pro-drug or an active metabolite thereof, or a pharmaceutically acceptable salt thereof.

The invention also relates to a pharmaceutical composition comprising (a) pipamperon, and (b) a cannabioid receptor antagonist, preferably SR 141716 or a pro-drug or an active metabolite thereof, or a pharmaceutically acceptable salt thereof, as a combined preparation for simultaneous, separate or sequential use for treating the underlying emotion dysregulation of a mental disease or disorder which is chosen from the group of diseases or disorders consisting of mood disorders, anxiety disorders, psychotic disorders, somatoform disorders (excluding pain disorders), factitious disorders, dissociative disorders, sleep disorders, adjustment disorders, impulse control disorders, pervasive development disorders, disruptive behaviour disorders, substance-related disorders, personality disorders, psychological factors affecting medical conditions, malingering, antisocial behaviour, bereavement, occupational problem, identity problem, problems related to abuse or neglect, pain disorders and delirium.

22: Combination Therapy with a Cathepsin K Inhibitor Compound

The mental disorders which can be treated using compounds having a high selective affinity for the 5-HT2A and D4 receptor, for instance pipamperon, in a combination therapy with a cathepsin K inhibitor compound, are pain disorders.

The present invention thus relates to the use of pipamperon or a pharmaceutically acceptable salt thereof for the preparation of a medicament for treating the underlying emotion dysregulation of pain disorders, characterized in that pipamperon or said pharmaceutically acceptable salt thereof is administered simultaneously with, separate from or prior to the administration of a cathepsin K inhibitor compound to augment the therapeutic effect or to provide a faster onset of the therapeutic effect of said cathepsin K inhibitor compound, further characterized in that pipamperon is to be administered to a patient in a daily dose ranging between 5 and 15 mg of the active ingredient.

According to a preferred embodiment, the invention relates to the use as described above, wherein said cathepsin K inhibitor compound is 462795 or a pro-drug or an active metabolite thereof, or a pharmaceutically acceptable salt thereof.

The invention also relates to a pharmaceutical composition comprising (a) pipamperon, and (b) a cathepsin K inhibitor, preferably 462795 or a pro-drug or an active metabolite thereof, or a pharmaceutically acceptable salt thereof, as a combined preparation for simultaneous, separate or sequential use for treating the underlying emotion dysregulation of pain disorders.

23: Combination Therapy with a Choline Uptake Enhancer Compound

The mental disorders which can be treated using compounds having a high selective affinity for the 5-HT2A and D4 receptor, for instance pipamperon, in a combination therapy with a choline uptake enhancer compound, are chosen from the group of diseases o' disorders consisting of Alzheimer Disease, substance-induced persisting dementia, vascular dementia, dementia due to HIV disease, dementia due to head trauma, dementia due to Parkinson Disease, dementia due to Huntington Disease, dementia due to Pick Disease, dementia due to Creutzfeldt-Jacob Disease, amnestic disorders due to a general medical condition, substance-induced persisting amnestic disorder, mild cognitive impairment disorder and other cognitive disorders.

The present invention thus relates to the use of pipamperon or a pharmaceutically acceptable salt thereof for the preparation of a medicament for treating the underlying emotion dysregulation of a cognitive mental disease or disorder selected from the group of diseases and disorders consisting of Alzheimer Disease, substance-induced persisting dementia, vascular dementia, dementia due to HIV disease, dementia due to head trauma, dementia due to Parkinson Disease, dementia due to Huntington Disease, dementia due to Pick Disease, dementia due to Creutzfeldt-Jacob Disease, amnestic disorders due to a general medical condition, substance-induced persisting amnestic disorder, mild cognitive impairment disorder and other cognitive disorders, characterized in that pipamperon or said pharmaceutically acceptable salt thereof is administered simultaneously with, separate from or prior to the administration of a choline uptake enhancer compound to augment the therapeutic effect or to provide a faster onset of the therapeutic effect of said choline uptake enhancer compound, further characterized in that pipamperon is to be administered to a patient in a daily dose ranging between 5 and 15 mg of the active ingredient.

According to a preferred embodiment, the invention relates to the use as described above, wherein said choline uptake enhancer compound is MKC-231 or a pro-drug or an active metabolite thereof, or a pharmaceutically acceptable salt thereof. Preferably, MKC-231 is to be administered in a daily dose of between 20 and 160 mg of the active ingredient.

The invention also relates to a pharmaceutical composition comprising (a) pipamperon, and (b) a choline uptake enhancer, preferably MKC-231 or a pro-drug or an active metabolite thereof, or a pharmaceutically acceptable salt thereof, as a combined preparation for simultaneous, separate or sequential use for treating the underlying emotion dysregulation of a mental disease or disorder which is chosen from the group of diseases or disorders consisting of Alzheimer Disease, substance-induced persisting dementia, vascular dementia, dementia due to HIV disease, dementia due to head trauma, dementia due to Parkinson Disease, dementia due to Huntington Disease, dementia due to Pick Disease, dementia due to Creutzfeldt-Jacob Disease, amnestic disorders due to a general medical condition, substance-induced persisting amnestic disorder, mild cognitive impairment disorder and other cognitive disorders.

The invention also relates to a pharmaceutical composition as described above wherein pipamperon is provided in a unitary dose of between 5 and 15 mg of the active ingredient and wherein said choline uptake enhancer is MKC-231, preferably provided in a unitary dose of between 20 and 160 mg of the active ingredient.

24: Combination Therapy with a COX-2 Inhibitor Compound

The mental disorders which can be treated using compounds having a high selective affinity for the 5-HT2A and D4 receptor, for instance pipamperon, in a combination therapy with a COX-2 inhibitor compound, are pain disorders.

The present invention thus relates to the use of pipamperon or a pharmaceutically acceptable salt thereof for the preparation of a medicament for treating the underlying emotion dysregulation of pain disorders, characterized in that pipamperon or said pharmaceutically acceptable salt thereof is administered simultaneously with, separate from or prior to the administration of a COX-2 inhibitor compound to augment the therapeutic effect or to provide a faster onset of the therapeutic effect of said COX-2 inhibitor compound, further characterized in that pipamperon is to be administered to a patient in a daily dose ranging between 5 and 15 mg of the active ingredient.

According to a preferred embodiment, the invention relates to the use as described above, wherein said COX-2 inhibitor compound is chosen from the group consisting of valdecoxib, rofecoxib, parecoxib, etoricoxib, COX 189, celecoxib and ABT-963, preferably parecoxib, etoricoxib or COX 189, or a pro-drug or an active metabolite thereof, or a pharmaceutically acceptable salt thereof. Preferably, parecoxib is to be administered in a daily dose of between 20 and 80 mg of the active ingredient. Preferably, etoricoxib is to be administered in a daily dose of between 20 and 120 mg of the active ingredient. Preferably, COX 189 is to be administered in a daily dose of between 100 and 800 mg of the active ingredient.

The invention also relates to a pharmaceutical composition comprising (a) pipamperon, and (b) a COX-2 inhibitor, preferably chosen from the group consisting of valdecoxib, rofecoxib, parecoxib, etoricoxib, COX 189, celecoxib and ABT-963, preferably parecoxib, etoricoxib or COX 189, or a pro-drug or an active metabolite thereof, or a pharmaceutically acceptable salt thereof, as a combined preparation for simultaneous, separate or sequential use for treating the underlying emotion dysregulation of pain disorders.

The invention also relates to a pharmaceutical composition as described above wherein pipamperon is provided in a unitary dose of between 5 and 15 mg of the active ingredient and wherein said COX-2 inhibitor is parecoxib, preferably provided in a unitary dose of between 20 and 80 mg of the active ingredient.

The invention also relates to a pharmaceutical composition as described above wherein pipamperon is provided in a unitary dose of between 5 and 15 mg of the active ingredient and wherein said COX-2 inhibitor is etoricoxib, preferably provided in a unitary dose of between 20 and 120 mg of the active ingredient.

The invention also relates to a pharmaceutical composition as described above wherein pipamperon is provided in a unitary dose of between 5 and 15 mg of the active ingredient and wherein said COX-2 inhibitors COX 189, preferably provided in a unitary dose of between 100 and 800 mg of the active ingredient.

25: Combination Therapy with a COX-Inhibiting Nitric Oxide Donator (CINOD) Compound The mental disorders which can be treated using compounds having a high selective affinity for the 5-HT2A and D4 receptor, for instance pipamperon, in a combination therapy with a COX-inhibiting nitric oxide donator (CINOD) compound, are pain disorders.

The present invention thus relates to the use of pipamperon or a pharmaceutically acceptable salt thereof for the preparation of a medicament for treating the underlying emotion dysregulation of pain disorders, characterized in that pipamperon or said pharmaceutically acceptable salt thereof is administered simultaneously with, separate from or prior to the administration of a COX-inhibiting nitric oxide donator (CINOD) compound to augment the therapeutic effect or to provide a faster onset of the therapeutic effect of said COX-inhibiting nitric oxide donator (CINOD) compound, further characterized in that pipamperon is to be administered to a patient in a daily dose ranging between 5 and 15 mg of the active ingredient.

According to a preferred embodiment, the invention relates to the use as described above, wherein said COX-inhibiting nitric oxide donator (CINOD) compound is chosen from the group consisting of AZD4717 and AZD3582 or a pro-drug or an active metabolite thereof, or a pharmaceutically acceptable salt thereof. Preferably, AZD3582 is to be administered in a daily dose ranging between 93.75 and 750 mg of the active ingredient.

The invention also relates to a pharmaceutical composition comprising (a) pipamperon, and (b) a COX-inhibiting nitric oxide donator (CINOD), preferably chosen from the group consisting of AZD4717 and AZD3582 or a pro-drug or an active metabolite thereof, or a pharmaceutically acceptable salt thereof, as a combined preparation for simultaneous, separate or sequential use for treating the underlying emotion dysregulation of pain disorders.

The invention also relates to a pharmaceutical composition as described above wherein pipamperon is provided in a unitary dose of between 5 and 15 mg of the active ingredient and wherein said COX-inhibiting nitric oxide donator (CINOD) is AZD3582, preferably provided in a unitary dose of between 93.75 and 750 mg of the active ingredient.

26: Combination Therapy with a CRF1 (Corticoid-Releasing Factor Receptor 1) Antagonist The mental disorders which can be treated using compounds having a high selective affinity for the 5-HT2A and D4 receptor, for instance pipamperon, in a combination therapy with a CRF1 (Corticotropin-Releasing Factor receptor 1) antagonist, are chosen from the group of diseases or disorders consisting of mood disorders, anxiety disorders, eating disorders, premenstrual syndrome, somatoform disorders (excluding pain disorders), factitious disorders, dissociative disorders, sexual and gender identity disorders, sleep disorders, adjustment disorders, impulse control disorders, substance related disorders, personality disorders, bereavement, occupational problem, problems related to abuse or neglect and pain disorders.

The present invention thus relates to the use of pipamperon or a pharmaceutically acceptable salt thereof for the preparation of a medicament for treating the underlying emotion dysregulation of a non-cognitive mental disease or disorder selected from the group of diseases and disorders consisting of mood disorders, anxiety disorders, eating disorders, premenstrual syndrome, somatoform disorders (excluding pain disorders), factitious disorders, dissociative disorders, sexual and gender identity disorders, sleep disorders, adjustment disorders, impulse control disorders, substance related disorders, personality disorders, bereavement, occupational problem and problems related to abuse or neglect, characterized in that pipamperon or said pharmaceutically acceptable salt thereof is administered simultaneously with, separate from or prior to the administration of a CRF1 antagonist compound to augment the therapeutic effect or to provide a faster onset of the therapeutic effect of said CRF1 antagonist compound, further characterized in that pipamperon is to be administered to a patient in a daily dose ranging between 5 and 15 mg of the active ingredient.

The present invention thus relates to the use of pipamperon or a pharmaceutically acceptable salt thereof for the preparation of a medicament for treating the underlying emotion dysregulation of pain disorders, characterized in that pipamperon or said pharmaceutically acceptable salt thereof is administered simultaneously with, separate from or prior to the administration of a CRF1 antagonist compound to augment the therapeutic effect or to provide a faster onset of the therapeutic effect of said CRF1 antagonist compound, further characterized in that pipamperon is to be administered to a patient in a daily dose ranging between 5 and 15 mg of the active ingredient.

According to a preferred embodiment, the invention relates to the uses as described above, wherein said CRF1 antagonist compound is chosen from the group consisting of R121919, NBI-34041, elzasonan, CP-448,187, CP-154-526, AAG 561 and 723620, preferably 8121919, elzasonan or AAG 561, or a pro-drug or an active metabolite thereof, or a pharmaceutically acceptable salt thereof. Preferably, R121919 is to be administered in a daily dose of between 5 and 80 mg of the active ingredient.

The invention also relates to a pharmaceutical composition comprising (a) pipamperon, and (b) a CRF1 antagonist, preferably chosen from the group consisting of R121919, NBI-34041, elzasonan, CP-448,187, CP-154-526, AAG 561 and 723620, preferably R121919, elzasonan or AAG 561, or a pro-drug or an active metabolite thereof, or a pharmaceutically acceptable salt thereof, as a combined preparation for simultaneous, separate or sequential use for treating the underlying emotion dysregulation of a mental disease or disorder which is chosen from the group of diseases or disorders consisting of mood disorders, anxiety disorders, eating disorders, premenstrual syndrome, somatoform disorders (excluding pain disorders), factitious disorders, dissociative disorders, sexual and gender identity disorders, sleep disorders, adjustment disorders, impulse control disorders, substance related disorders, personality disorders, bereavement, occupational problem, problems related to abuse or neglect and pain disorders.

The invention also relates to a pharmaceutical composition as described above wherein pipamperon is provided in a unitary dose of between 5 and 15 mg of the active ingredient and wherein said CRF1 antagonist is R121919, preferably provided in a unitary dose of between 5 and 80 mg of the active ingredient.

27: Combination Therapy with a D1 (Dopamine 1) Receptor Agonist

The mental disorders which can be treated using compounds having a high selective affinity for the 5-HT2A and D4 receptor, for instance pipamperon, in a combination therapy with a D1 (dopamine 1) receptor agonist, are chosen from the group of diseases or disorders consisting of substance related disorders and Parkinson disease.

The present invention thus relates to the use of pipamperon or a pharmaceutically acceptable salt thereof for the preparation of a medicament for treating the underlying emotion dysregulation of substance related disorders, characterized in that pipamperon or said pharmaceutically acceptable salt thereof is administered simultaneously with, separate from or prior to the administration of a D1 receptor agonist compound to augment the therapeutic effect or to provide a faster onset of the therapeutic effect of said D1 receptor agonist compound, further characterized in that pipamperon is to be administered to a patient in a daily dose ranging between 5 and 15 mg of the active ingredient.

The present invention thus relates to the use of pipamperon or a pharmaceutically acceptable salt thereof for the preparation of a medicament for treating the underlying emotion dysregulation of Parkinson disease, characterized in that pipamperon or said pharmaceutically acceptable salt thereof is administered simultaneously with, separate from or prior to the administration of a D1 receptor agonist compound to augment the therapeutic effect or to provide a faster onset of the therapeutic effect of said D1 receptor agonist compound, further characterized in that pipamperon is to be administered to a patient in a daily dose ranging between 5 and 15 mg of the active ingredient.

According to a preferred embodiment, the invention relates to the uses as described above, wherein said D1 receptor agonist compound is DAS-431 or a pro-drug or an active metabolite thereof, or a pharmaceutically acceptable salt thereof.

The invention also relates to a pharmaceutical composition comprising (a) pipamperon, and (b) a D1 receptor agonist, preferably DAS-431 or a pro-drug or an active metabolite thereof, or a pharmaceutically acceptable salt thereof, as a combined preparation for simultaneous, separate or sequential use for treating the underlying emotion dysregulation of a mental disease or disorder which is chosen from the group of diseases or disorders consisting of substance related disorders and Parkinson disease.

28: Combination Therapy with D2 (Dopamine 2) Receptor Antagonist

The mental disorders which can be treated using compounds having a high selective affinity for the 5-HT2A and D4 receptor, for instance pipamperon, in a combination therapy with D2 (dopamine 2) receptor antagonist, are chosen from the group of diseases or disorders consisting of mood disorders, psychotic disorders, somatoform disorders (excluding pain disorders), factitious disorders, dissociative disorders, sleep disorders, adjustment disorders, impulse control disorders, pervasive development disorders, disruptive behaviour disorders, substance-related disorders, personality disorders, psychological factors affecting medical conditions, malingering, antisocial behaviour, bereavement, occupational problem, identity problem, problems related to abuse or neglect, pain disorders and delirium.

The present invention thus relates to the use of pipamperon or a pharmaceutically acceptable salt thereof for the preparation of a medicament for treating the underlying emotion dysregulation of a non-cognitive mental disease or disorder selected from the group of diseases and disorders consisting mood disorders, psychotic disorders, somatoform disorders (excluding pain disorders), factitious disorders, dissociative disorders, sleep disorders, adjustment disorders, impulse control disorders, pervasive development disorders, disruptive behaviour disorders, substance-related disorders, personality disorders, psychological factors affecting medical conditions, malingering, antisocial behaviour, bereavement, occupational problem, identity problem and problems related to abuse or neglect, characterized in that pipamperon or said pharmaceutically acceptable salt thereof is administered simultaneously with, separate from or prior to the administration of a D2 receptor antagonist compound to augment the therapeutic effect or to provide a faster onset of the therapeutic effect of said D2 receptor antagonist compound, further characterized in that pipamperon is to be administered to a patient in a daily dose ranging between 5 and 15 mg of the active ingredient.

The present invention thus relates to the use of pipamperon or a pharmaceutically acceptable salt thereof for the preparation of a medicament for treating the underlying emotion dysregulation of pain disorders, characterized in that pipamperon or said pharmaceutically acceptable salt thereof is administered simultaneously with, separate from or prior to the administration of a D2 receptor antagonist compound to augment the therapeutic effect or to provide a faster onset of the therapeutic effect of said D2 receptor antagonist compound, further characterized in that pipamperon is to be administered to a patient in a daily dose ranging between 5 and 15 mg of the active ingredient.

The present invention thus relates to the use of pipamperon or a pharmaceutically acceptable salt thereof for the preparation of a medicament for treating the underlying emotion dysregulation of delirium, characterized in that pipamperon or said pharmaceutically acceptable salt thereof is administered simultaneously with, separate from or prior to the administration of a D2 receptor antagonist compound to augment the therapeutic effect or to provide a faster onset of the therapeutic effect of said D2 receptor antagonist compound, further characterized in that pipamperon is to be administered to a patient in a daily dose ranging between 5 and 15 mg of the active ingredient.

According to a preferred embodiment, the invention relates to the uses as described above, wherein said D2 receptor antagonist compound is chosen from the group consisting of bifeprunox and amisulpride, preferably bifeprunox, or a pro-drug or an active metabolite thereof, or a pharmaceutically acceptable salt thereof.

The invention also relates to a pharmaceutical composition comprising (a) pipamperon, and (b) a D2 receptor antagonist, preferably chosen from the group consisting of bifeprunox and amisulpride, preferably bifeprunox, or a pro-drug or an active metabolite thereof, or a pharmaceutically acceptable salt thereof, as a combined preparation for simultaneous, separate or sequential use for treating the underlying emotion dysregulation of a mental disease or disorder which is chosen from the group of diseases or disorders consisting of mood disorders, psychotic disorders, somatoform disorders (excluding pain disorders), factitious disorders, dissociative disorders, sleep disorders, adjustment disorders, impulse control disorders, pervasive development disorders, disruptive behaviour disorders, substance-related disorders, personality disorders, psychological factors affecting medical conditions, malingering, antisocial behaviour, bereavement, occupational problem, identity problem, problems related to abuse or neglect, pain disorders and delirium.

29: Combination Therapy with D3 (Dopamine 3) Receptor Antagonist

The mental disorders which can be treated using compounds having a high selective affinity for the 5-HT2A and D4 receptor, for instance pipamperon, in a combination therapy with D3 (dopamine 3) receptor antagonist, are chosen from the group of diseases or disorders consisting of psychotic disorders, somatoform disorders (excluding pain disorders), factitious disorders, dissociative disorders, sleep disorders, adjustment disorders, impulse control disorders, pervasive development disorders, disruptive behaviour disorders, substance-related disorders, personality disorders, psychological factors affecting medical conditions, malingering, antisocial behaviour, bereavement, occupational problem, identity problem, problems related to abuse or neglect, pain disorders, delirium and Parkinson disease.

The present invention thus relates to the use of pipamperon or a pharmaceutically acceptable salt thereof for the preparation of a medicament for treating the underlying emotion dysregulation of a non-cognitive mental disease or disorder selected from the group of diseases and disorders consisting of psychotic disorders, somatoform disorders (excluding pain disorders), factitious disorders, dissociative disorders, sleep disorders, adjustment disorders, impulse control disorders, pervasive development disorders, disruptive behaviour disorders, substance-related disorders, personality disorders, psychological factors affecting medical conditions, malingering, antisocial behaviour, bereavement, occupational problem, identity problem, problems related to abuse or neglect, characterized in that pipamperon or said pharmaceutically acceptable salt thereof is administered simultaneously with, separate from or prior to the administration of a D3 receptor antagonist compound to augment the therapeutic effect or to provide a faster onset of the therapeutic effect of said D3 receptor antagonist compound, further characterized in that pipamperon is to be administered to a patient in a daily dose ranging between 5 and 15 mg of the active ingredient.

The present invention thus relates to the use of pipamperon or a pharmaceutically acceptable salt thereof for the preparation of a medicament for treating the underlying emotion dysregulation of pain disorders, characterized in that pipamperon or said pharmaceutically acceptable salt thereof is administered simultaneously with, separate from or prior to the administration of a D3 receptor antagonist compound to augment the therapeutic effect or to provide a faster onset of the therapeutic effect of said D3 receptor antagonist compound, further characterized in that pipamperon is to be administered to a patient in a daily dose ranging between 5 and 15 mg of the active ingredient.

The present invention thus relates to the use of pipamperon or a pharmaceutically acceptable salt thereof for the preparation of a medicament for treating the underlying emotion dysregulation of delirium, characterized in that pipamperon or said pharmaceutically acceptable salt thereof is administered simultaneously with, separate from or prior to the administration of a D3 receptor antagonist compound to augment the therapeutic effect or to provide a faster onset of the therapeutic effect of said D3 receptor antagonist compound, further characterized in that pipamperon is to be administered to a patient in a daily dose ranging between 5 and 15 mg of the active ingredient.

The present invention thus relates to the use of pipamperon or a pharmaceutically acceptable salt thereof for the preparation of a medicament for treating the underlying emotion dysregulation of Parkinson disease, characterized in that pipamperon or said pharmaceutically acceptable salt thereof is administered simultaneously with, separate from or prior to the administration of a D3 receptor agonist compound to augment the therapeutic effect or to provide a faster onset of the therapeutic effect of said D3 receptor agonist compound, further characterized in that pipamperon is to be administered to a patient in a daily dose ranging between 5 and 15 mg of the active ingredient.

According to a preferred embodiment, the invention relates to the uses as described above, wherein said D3 receptor antagonist compound is chosen from the group consisting of BSF-201640 and PD 58491, or a pro-drug or an active metabolite thereof, or a pharmaceutically acceptable salt thereof.

The invention also relates to a pharmaceutical composition comprising (a) pipamperon, and (b) a D3 receptor antagonist, preferably chosen from the group consisting of BSF-201640 and PD 58491, or a pro-drug or an active metabolite thereof, or a pharmaceutically acceptable salt thereof, as a combined preparation for simultaneous, separate or sequential use for treating the underlying emotion dysregulation of a mental disease or disorder which is chosen from the group of diseases or disorders consisting of psychotic disorders, somatoform disorders (excluding pain disorders), factitious disorders, dissociative disorders, sleep disorders, adjustment disorders, impulse control disorders, pervasive development disorders, disruptive behaviour disorders, substance-related disorders, personality disorders, psychological factors affecting medical conditions, malingering, antisocial behaviour, bereavement, occupational problem, identity problem, problems related to abuse or neglect, pain disorders, delirium and Parkinson disease.

30: Combination Therapy with a DA (Dopamine) Uptake Inhibitor

The mental disorders which can be treated using compounds having a high selective affinity for the 5-HT2A and D4 receptor, for instance pipamperon, in a combination therapy with a DA (dopamine) uptake inhibitor, are chosen from the group of diseases or disorders consisting of substance related disorders and Parkinson disease.

The present invention thus relates to the use of pipamperon or a pharmaceutically acceptable salt thereof for the preparation of a medicament for treating the underlying emotion dysregulation of substance related disorders, characterized in that pipamperon or said pharmaceutically acceptable salt thereof is administered simultaneously with, separate from or prior to the administration of a DA uptake inhibitor compound to augment the therapeutic effect or to provide a faster onset of the therapeutic effect of said DA uptake inhibitor compound, further characterized in that pipamperon is to be administered to a patient in a daily dose ranging between 5 and 15 mg of the active ingredient.

The present invention thus relates to the use of pipamperon or a pharmaceutically acceptable salt thereof for the preparation of a medicament for treating the underlying emotion dysregulation of Parkinson disease, characterized in that pipamperon or said pharmaceutically acceptable salt thereof is administered simultaneously with, separate from or prior to the administration of a DA uptake inhibitor compound to augment the therapeutic effect or to provide a faster onset of the therapeutic effect of said DA uptake inhibitor compound, further characterized in that pipamperon is to be administered to a patient in a daily dose ranging between 5 and 15 mg of the active ingredient.

According to a preferred embodiment, the invention relates to the uses as described above, wherein said DA uptake inhibitor compound is chosen from the group consisting of safinamide and GBR 12909, or a pro-drug or an active metabolite thereof, or a pharmaceutically acceptable salt thereof.

The invention also relates to a pharmaceutical composition comprising (a) pipamperon, and (b) a D2 receptor antagonist, preferably chosen from the group consisting of safinamide and GBR 12909, or a pro-drug or an active metabolite thereof, or a pharmaceutically acceptable salt thereof, as a combined preparation for simultaneous, separate or sequential use for treating the underlying emotion dysregulation of a mental disease or disorder which is chosen from the group of diseases or disorders consisting of substance related disorders and Parkinson disease.

31: Combination Therapy with an Dopamine (Receptor) Agonist

The mental disorders which can be treated using compounds having a high selective affinity for the 5-HT2A and D4 receptor, for instance pipamperon, in a combination therapy with an dopamine (receptor) agonist, are chosen from the group of diseases or disorders consisting of mood disorders, anxiety disorders, eating disorders, premenstrual syndrome, somatoform disorders (excluding pain disorders), factitious disorders, dissociative disorders, adjustment disorders, impulse control disorders, attention-deficit disorders, substance-related disorders, personality disorders, problems related to abuse or neglect, pain disorders and Parkinson disease.

The present invention thus relates to the use of pipamperon or a pharmaceutically acceptable salt thereof for the preparation of a medicament for treating the underlying emotion dysregulation of a non-cognitive mental disease or disorder selected from the group of diseases and disorders consisting mood disorders, anxiety disorders, eating disorders, premenstrual syndrome, somatoform disorders (excluding pain disorders), factitious disorders, dissociative disorders, adjustment disorders, impulse control disorders, attention-deficit disorders, substance-related disorders, personality disorders and problems related to abuse or neglect, characterized in that pipamperon or said pharmaceutically acceptable salt thereof is administered simultaneously with, separate from or prior to the administration of a dopamine (receptor) agonist compound to augment the therapeutic effect or to provide a faster onset of the therapeutic effect of said dopamine (receptor) agonist compound, further characterized in that pipamperon is to be administered to a patient in a daily dose ranging between 5 and 15 mg of the active ingredient.

The present invention thus relates to the use of pipamperon or a pharmaceutically acceptable salt thereof for the preparation of a medicament for treating the underlying emotion dysregulation of pain disorders, characterized in that pipamperon or said pharmaceutically acceptable salt thereof is administered simultaneously with, separate from or prior to the administration of a dopamine (receptor) agonist compound to augment the therapeutic effect or to provide a faster onset of the therapeutic effect of said dopamine (receptor) agonist compound, further characterized in that pipamperon is to be administered to a patient in a daily dose ranging between 5 and 15 mg of the active ingredient.

The present invention thus relates to the use of pipamperon or a pharmaceutically acceptable salt thereof for the preparation of a medicament for treating the underlying emotion dysregulation of Parkinson disease, characterized in that pipamperon or said pharmaceutically acceptable salt thereof is administered simultaneously with, separate from or prior to the administration of a dopamine (receptor) agonist compound to augment the therapeutic effect or to provide a faster onset of the therapeutic effect of said dopamine (receptor) agonist compound, further characterized in that pipamperon is to be administered to a patient in a daily dose ranging between 5 and 15 mg of the active ingredient.

According to a preferred embodiment, the invention relates to the uses as described above, wherein said dopamine (receptor) agonist compound is chosen from the group consisting of sumanirole, SLV 308, sarizotan, S32504, rotigotine (preferably a Once-a-Day Transdermal Patch), ropinirole HCL (preferably controlled-release formulation), pramipexole, DAB452, cabergoline, bromocriptine, alaptide, cabergoline, lisuride, preferably sumanirole, rotigotine (preferably a Once-a-Day Transdermal Patch), pergolide or ropinirole HCL (preferably controlled-release formulation), or a pro-drug or an active metabolite thereof, or a pharmaceutically acceptable salt thereof. Preferably, sumanirole is to be administered in a daily dose of between 4 and 16 mg of the active ingredient. Preferably, rotigotine (Once-a-Day Transdermal Patch) is to be administered in a daily dose of between 4.5 and 13.5 mg of the active ingredient. Preferably, ropinirole HCL (controlled-release formulation) is to be administered in a daily dose of between 0.75 and 24 mg of the active ingredient. Preferably, pergolide is to be administered in a daily dose of between 0.5 and 10 mg of the active ingredient.

The invention also relates to a pharmaceutical composition comprising (a) pipamperon, and (b) a dopamine (receptor) agonist, preferably chosen from the group consisting of sumanirole, SLV 308, sarizotan, S32504, rotigotine (preferably a Once-a-Day Transdermal Patch), ropinirole HCL (preferably controlled-release formulation), pramipexole, DAB452, cabergoline, bromocriptine, alaptide, cabergoline, lisuride and pergolide, more preferably sumanirole, rotigotine (preferably a Once-a-Day Transdermal Patch), ropinirole HCL (preferably controlled-release formulation) or pergolide, or a pro-drug or an active metabolite thereof, or a pharmaceutically acceptable salt thereof, as a combined preparation for simultaneous, separate or sequential use for treating the underlying emotion dysregulation of a mental disease or disorder which is chosen from the group of diseases or disorders consisting of mood disorders, anxiety disorders, eating disorders, premenstrual syndrome, somatoform disorders (excluding pain disorders), factitious disorders, dissociative disorders, adjustment disorders, impulse control disorders, attention-deficit disorders, substance-related disorders, personality disorders, problems related to abuse or neglect, pain disorders and Parkinson disease.

The invention also relates to a pharmaceutical composition as described above wherein pipamperon is provided in a unitary dose of between 5 and 15 mg of the active ingredient and wherein said dopamine (receptor) agonist is sumanirole, preferably provided in a unitary dose of between 4 and 16 mg of the active ingredient.

The invention also relates to a pharmaceutical composition as described above wherein pipamperon is provided in a unitary dose of between 5 and 15 mg of the active ingredient and wherein said dopamine (receptor) agonist is rotigotine (Once-a-Day Transdermal Patch), preferably provided in a unitary dose of between 4.5 and 13.5 mg of the active ingredient.

The invention also relates to a pharmaceutical composition as described above wherein pipamperon is provided in a unitary dose of between 5 and 15 mg of the active ingredient and wherein said dopamine (receptor) agonist is ropinirole HCL (controlled-release formulation), preferably provided in a unitary dose of between 0.75 and 24 mg of the active ingredient.

The invention also relates to a pharmaceutical composition as described above wherein pipamperon is provided in a unitary dose of between 5 and 15 mg of the active ingredient and wherein said dopamine (receptor) agonist is pergolide, preferably provided in a unitary dose of between 0.5 and 10 mg of the active ingredient.

32: Combination Therapy with a Compound Activating ERK (Extracellular Signal-Related Kinase)

The mental disorders which can be treated using compounds having a high selective affinity for the 5-HT2A and D4 receptor, for instance pipamperon, in a combination therapy with a compound that activates ERK (extracellular signal-related kinase), are chosen from the group of diseases or disorders consisting of Alzheimer Disease, substance-induced persisting dementia, vascular dementia, dementia due to HIV disease, dementia due to head trauma, dementia due to Parkinson Disease, dementia due to Huntington Disease, dementia due to Pick Disease, dementia due to Creutzfeldt-Jacob Disease, amnestic disorders due to a general medical condition, substance-induced persisting amnestic disorder, mild cognitive impairment disorder and other cognitive disorders.

The present invention thus relates to the use of pipamperon or a pharmaceutically acceptable salt thereof for the preparation of a medicament for treating the underlying emotion dysregulation of a cognitive mental disease or disorder selected from the group of diseases and disorders consisting of Alzheimer Disease, substance-induced persisting dementia, vascular dementia, dementia due to HIV disease, dementia due to head trauma, dementia due to Parkinson Disease, dementia due to Huntington Disease, dementia due to Pick Disease, dementia due to Creutzfeldt-Jacob Disease, amnestic disorders due to a general medical condition, substance-induced persisting amnestic disorder, mild cognitive impairment disorder and other cognitive disorders, characterized in that pipamperon or said pharmaceutically acceptable salt thereof is administered simultaneously with, separate from or prior to the administration of a compound that activates ERK (extracellular signal-related kinase) to augment the therapeutic effect or to provide a faster onset of the therapeutic effect of said compound that activates ERK (extracellular signal-related kinase), further characterized in that pipamperon is to be administered to a patient in a daily dose ranging between 5 and 15 mg of the active ingredient.

According to a preferred embodiment, the invention relates to the use as described above, wherein said compound that activates ERK (extracellular signal-related kinase) is CPI-1189 or a pro-drug or an active metabolite thereof, or a pharmaceutically acceptable salt thereof. Preferably, CPI-1189 is to be administered in a daily dose of between 50 and 100 mg of the active ingredient.

The invention also relates to a pharmaceutical composition comprising (a) pipamperon, and (b) a compound that activates ERK (extracellular signal-related kinase), preferably CPI-1189 or a pro-drug or an active metabolite thereof, or a pharmaceutically acceptable salt thereof, as a combined preparation for simultaneous, separate or sequential use for treating the underlying emotion dysregulation of a mental disease or disorder which is chosen from the group of diseases or disorders consisting of Alzheimer Disease, substance-induced persisting dementia, vascular dementia, dementia due to HIV disease, dementia due to head trauma, dementia due to Parkinson Disease, dementia due to Huntington Disease, dementia due to Pick Disease, dementia due to Creutzfeldt-Jacob Disease, amnestic disorders due to a general medical condition, substance-induced persisting amnestic disorder, mild cognitive impairment disorder and other cognitive disorders.

The invention also relates to a pharmaceutical composition as described above wherein pipamperon is provided in a unitary dose of between 5 and 15 mg of the active ingredient and wherein said compound that activates ERK (extracellular signal-related kinase) is CPI-1189, preferably provided in a unitary dose of between 50 and 100 mg of the active ingredient.

33: Combination Therapy with a GABA (Gamma-Aminobutyric Acid) Agonist Compound

The mental disorders which can be treated using compounds having a high selective affinity for the 5-HT2A and D4 receptor, for instance pipamperon, in a combination therapy with a GABA (gamma-aminobutyric acid) agonist compound, are chosen from the group of diseases or disorders consisting of Alzheimer Disease, substance-induced persisting dementia, vascular dementia, dementia due to HIV disease, dementia due to head trauma, dementia due to Parkinson Disease, dementia due to Huntington Disease, dementia due to Pick Disease, dementia due to Creutzfeldt-Jacob Disease, amnestic disorders due to a general medical condition, substance-induced persisting amnestic disorder, mild cognitive impairment disorder and other cognitive disorders.

The present invention thus relates to the use of pipamperon or a pharmaceutically acceptable salt thereof for the preparation of a medicament for treating the underlying emotion dysregulation of a cognitive mental disease or disorder selected from the group of diseases and disorders consisting of Alzheimer Disease, substance-induced persisting dementia, vascular dementia, dementia due to HIV disease, dementia due to head trauma, dementia due to Parkinson Disease, dementia due to Huntington Disease, dementia due to Pick Disease, dementia due to Creutzfeldt-Jacob Disease, amnestic disorders due to a general medical condition, substance-induced persisting amnestic disorder, mild cognitive impairment disorder and other cognitive disorders, characterized in that pipamperon or said pharmaceutically acceptable salt thereof is administered simultaneously with, separate from or prior to the administration of a GABA agonist compound to augment the therapeutic effect or to provide a faster onset of the therapeutic effect of said GABA agonist compound, further characterized in that pipamperon is to be administered to a patient in a daily dose ranging between 5 and 15 mg of the active ingredient.

According to a preferred embodiment, the invention relates to the use as described above, wherein said GABA agonist compound is nefiracetam or a pro-drug or an active metabolite thereof, or a pharmaceutically acceptable salt thereof.

The invention also relates to a pharmaceutical composition comprising (a) pipamperon, and (b) a GABA agonist, preferably nefiracetam or a pro-drug or an active metabolite thereof, or a pharmaceutically acceptable salt thereof, as a combined preparation for simultaneous, separate or sequential use for treating the underlying emotion dysregulation of a mental disease or disorder which is chosen from the group of diseases or disorders consisting of Alzheimer Disease, substance-induced persisting dementia, vascular dementia, dementia due to HIV disease, dementia due to head trauma, dementia due to Parkinson Disease, dementia due to Huntington Disease, dementia due to Pick Disease, dementia due to Creutzfeldt-Jacob Disease, amnestic disorders due to a general medical condition, substance-induced persisting amnestic disorder, mild cognitive impairment disorder and other cognitive disorders.

34: Combination Therapy with a GABA-A Agonist Compound

The mental disorders which can be treated using compounds having a high selective affinity for the 5-HT2A and D4 receptor, for instance pipamperon, in a combination therapy with a GABA-A (gamma-aminobutyric acid receptor A) agonist compound, are sleep disorders.

The present invention thus relates to the use of pipamperon or a pharmaceutically acceptable salt thereof for the preparation of a medicament for treating the underlying emotion dysregulation of sleep disorders, characterized in that pipamperon or said pharmaceutically acceptable salt thereof is administered simultaneously with, separate from or prior to the administration of a GABA-A agonist compound to augment the therapeutic effect or to provide a faster onset of the therapeutic effect of said GABA-A agonist compound, further characterized in that pipamperon is to be administered to a patient in a daily dose ranging between 5 and 15 mg of the active ingredient.

According to a preferred embodiment, the invention relates to the use as described above, wherein said GABA-A agonist compound is gaboxadol or a pro-drug or an active metabolite thereof, or a pharmaceutically acceptable salt thereof. Preferably, gaboxadol is to be administered in a daily dose of between 5 and 20 mg of the active ingredient.

The invention also relates to a pharmaceutical composition comprising (a) pipamperon, and (b) an GABA-A agonist, preferably gaboxadol or a pro-drug or an active metabolite thereof, or a pharmaceutically acceptable salt thereof, as a combined preparation for simultaneous, separate or sequential use for treating the underlying emotion dysregulation of sleep disorders.

The invention also relates to a pharmaceutical composition as described above wherein pipamperon is provided in a unitary dose of between 5 and 15 mg of the active ingredient and wherein said GABA-A agonist is Gaboxadol, preferably provided in a unitary dose of between 5 and 20 mg of the active ingredient.

35: Combination Therapy with a GABA-A Modulator Compound

The mental disorders which can be treated using compounds having a high selective affinity for the 5-HT2A and D4 receptor, for instance pipamperon, in a combination therapy with a GABA-A (gamma-aminobutyric acid receptor A) modulator compound, are chosen from the group of diseases or disorders consisting of anxiety disorders, eating disorders, premenstrual syndrome, somatoform disorders (excluding pain disorders), factitious disorders, dissociative disorders, sexual and gender identity disorders, sleep disorders, adjustment disorders, impulse control disorders, personality disorders, bereavement, occupational problem and problems related to abuse or neglect.

The present invention thus relates to the use of pipamperon or a pharmaceutically acceptable salt thereof for the preparation of a medicament for treating the underlying emotion dysregulation of a non-cognitive mental disease or disorder selected from the group of diseases and disorders consisting of anxiety disorders, eating disorders, premenstrual syndrome, somatoform disorders (excluding pain disorders), factitious disorders, dissociative disorders, sexual and gender identity disorders, sleep disorders, adjustment disorders, impulse control disorders, personality disorders, bereavement, occupational problem and problems related to abuse or neglect, characterized in that pipamperon or said pharmaceutically acceptable salt thereof is administered simultaneously with, separate from or prior to the administration of a GABA-A modulator compound to augment the therapeutic effect or to provide a faster onset of the therapeutic effect of said GABA-A modulator compound, further characterized in that pipamperon is to be administered to a patient in a daily dose ranging between 5 and 15 mg of the active ingredient.

According to a preferred embodiment, the invention relates to the use as described above, wherein said GABA-A modulator compound is chosen from the group consisting of zolpidem (preferably MR sustained-release version), zaleplon (preferably extended-release formulation), SL 65.1498, SEP174559, pagoclone, NGD 96-3, indiplon, eszopiclone, CP-730,330 (NGD 96-3) and ocinaplon, preferably zolpidem (preferably MR sustained-release version), zaleplon (preferably extended-release formulation), pagoclone, indiplon or eszopiclone, or a pro-drug or an active metabolite thereof, or a pharmaceutically acceptable salt thereof. Preferably, zolpidem MR sustained-release version is to be administered in a daily dose of between 10 and 20 mg of the active ingredient. Preferably, zaleplon extended-release is to be administered in a daily dose ranging between 2.5 and 20 mg of the active ingredient. Preferably, pagoclone is to be administered in a daily dose ranging between 7.5 and 60 mg of the active ingredient. Preferably, indiplon is to be administered in a daily dose of between 10 and 20 mg of the active ingredient. Preferably, eszopiclone is to be administered in a daily dose of between 2 and 3 mg of the active ingredient. Preferably, ocinaplon is to be administered in a daily dose of between 10 and 60 mg of the active ingredient.

The invention also relates to a pharmaceutical composition comprising (a) pipamperon, and (b) a GABA-A modulator, preferably chosen from the group consisting of zolpidem (preferably MR sustained-release version), zaleplon (preferably extended-release formulation), SL 65.1498, SEP174559, pagoclone, indiplon, eszopiclone, CP-730,330 (NGD 96-3) and ocinaplon, preferably zolpidem (preferably MR sustained-release version), zaleplon (preferably extended-release formulation), pagoclone, NGD 96-3, indiplon or eszopiclone, or a pro-drug or an active metabolite thereof, or a pharmaceutically acceptable salt thereof, as a combined preparation for simultaneous, separate or sequential use for treating the underlying emotion dysregulation of a mental disease or disorder which is chosen from the group of diseases or disorders consisting of anxiety disorders, eating disorders, premenstrual syndrome, somatoform disorders (excluding pain disorders), factitious disorders, dissociative disorders, sexual and gender identity disorders, sleep disorders, adjustment disorders, impulse control disorders, personality disorders, bereavement, occupational problem and problems related to abuse or neglect.

The invention also relates to a pharmaceutical composition as described above wherein pipamperon is provided in a unitary dose of between 5 and 15 mg of the active ingredient and wherein said GABA-A modulator is zolpidem MR sustained-release version, preferably provided in a unitary dose of between 10 and 20 mg of the active ingredient.

The invention also relates to a pharmaceutical composition as described above wherein pipamperon is provided in a unitary dose of between 5 and 15 mg of the active ingredient and wherein said GABA-A modulator is zaleplon extended-release, preferably provided in a unitary dose of between 2.5 and 20 mg of the active ingredient.

The invention also relates to a pharmaceutical composition as described above wherein pipamperon is provided in a unitary dose of between 5 and 15 mg of the active ingredient and wherein said GABA-A modulator is Pagoclone, preferably provided in a unitary dose of between 7.5 and 60 mg of the active ingredient.

The invention also relates to a pharmaceutical composition as described above wherein pipamperon is provided in a unitary dose of between 5 and 15 mg of the active ingredient and wherein said GABA-A modulator is indiplon, preferably provided in a unitary dose of between 10 and 20 mg of the active ingredient.

The invention also relates to a pharmaceutical composition as described above wherein pipamperon is provided in a unitary dose of between 5 and 15 mg of the active ingredient and wherein said GABA-A modulator is eszopiclone, preferably provided in a unitary dose of between 2 and 3 mg of the active ingredient.

The invention also relates to a pharmaceutical composition as described above wherein pipamperon is provided in a unitary dose of between 5 and 15 mg of the active ingredient and wherein said GABA-A modulator is ocinaplon, preferably provided in a unitary dose of between 10 and 60 mg of the active ingredient.

36: Combination Therapy with a GABA-B Antagonist Compound

The mental disorders which can be treated using compounds having a high selective affinity for the 5-HT2A and D4 receptor, for instance pipamperon, in a combination therapy with a GABA-B (gamma-aminobutyric acid receptor B) antagonist compound, are chosen from the group of diseases or disorders consisting of anxiety disorders, eating disorders, premenstrual syndrome, somatoform disorders (excluding pain disorders), factitious disorders, dissociative disorders, sexual and gender identity disorders, sleep disorders, adjustment disorders, impulse control disorders, personality disorders, bereavement, occupational problem and problems related to abuse or neglect.

The present invention thus relates to the use of pipamperon or a pharmaceutically acceptable salt thereof for the preparation of a medicament for treating the underlying emotion dysregulation of a non-cognitive mental disease or disorder selected from the group of diseases and disorders consisting of anxiety disorders, eating disorders, premenstrual syndrome, somatoform disorders (excluding pain disorders), factitious disorders, dissociative disorders, sexual and gender identity disorders, sleep disorders, adjustment disorders, impulse control disorders, personality disorders, bereavement, occupational problem and problems related to abuse or neglect, characterized in that pipamperon or said pharmaceutically acceptable salt thereof is administered simultaneously with, separate from or prior to the administration of a GABA-B antagonist compound to augment the therapeutic effect or to provide a faster onset of the therapeutic effect of said GABA-B antagonist compound, further characterized in that pipamperon is to be administered to a patient in a daily dose ranging between 5 and 15 mg of the active ingredient.

According to a preferred embodiment, the invention relates to the use as described above, wherein said GABA-B antagonist compound is AVE 7398 or a pro-drug or an active metabolite thereof, or a pharmaceutically acceptable salt thereof.

The invention also relates to a pharmaceutical composition comprising (a) pipamperon, and (b) a GABA-B antagonist, preferably AVE 7398 or a pro-drug or an active metabolite thereof, or a pharmaceutically acceptable salt thereof, as a combined preparation for simultaneous, separate or sequential use for treating the underlying emotion dysregulation of a mental disease or disorder which is chosen from the group of diseases or disorders consisting of anxiety disorders, eating disorders, premenstrual syndrome, somatoform disorders (excluding pain disorders), factitious disorders, dissociative disorders, sexual and gender identity disorders, sleep disorders, adjustment disorders, impulse control disorders, personality disorders, bereavement, occupational problem and problems related to abuse or neglect.

37: Combination Therapy with a Glial-Cell Line Derived Neurotrophic Factor Compound The mental disorder which can be treated using compounds having a high selective affinity for the 5-HT2A and D4 receptor, for instance pipamperon, in a combination therapy with a Glial-cell Line Derived Neurotrophic Factor compound, is Parkinson disease.

The present invention thus relates to the use of pipamperon or a pharmaceutically acceptable salt thereof for the preparation of a medicament for treating the underlying emotion dysregulation of Parkinson disease, characterized in that pipamperon or said pharmaceutically acceptable salt thereof is administered simultaneously with, separate from or prior to the administration of a Glial-cell Line Derived Neurotrophic Factor compound to augment the therapeutic effect or to provide a faster onset of the therapeutic effect of said Glial-cell Line. Derived Neurotrophic Factor compound, further characterized in that pipamperon is to be administered to a patient in a daily dose ranging between 5 and 15 mg of the active ingredient.

According to a preferred embodiment, the invention relates to the use as described above, wherein said Glial-cell Line Derived Neurotrophic Factor compound is GDNF or a pro-drug or an active metabolite thereof, or a pharmaceutically acceptable salt thereof. Preferably, GDNF is to be administered in a daily dose ranging between 3.75 and 30 mg of the active ingredient.

The invention also relates to a pharmaceutical composition comprising (a) pipamperon, and (b) a Glial-cell Line Derived Neurotrophic Factor, preferably GDNF or a pro-drug or an active metabolite thereof, or a pharmaceutically acceptable salt thereof, as a combined preparation for simultaneous, separate or sequential use for treating the underlying emotion dysregulation of Parkinson disease.

The invention also relates to a pharmaceutical composition as described above wherein pipamperon is provided in a unitary dose of between 5 and 15 mg of the active ingredient and wherein said Glial-cell Line Derived Neurotrophic Factor is GDNF, preferably provided in a unitary dose of between 3.75 and 30 mg of the active ingredient.

38: Combination Therapy with a Glucocorticoid Synthesis Inhibitor Compound

The mental disorders which can be treated using compounds having a high selective affinity for the 5-HT2A and D4 receptor, for instance pipamperon, in a combination therapy with a glucocorticoid synthesis inhibitor compound, are chosen from the group of diseases or disorders consisting of substance related disorders and Parkinson disease.

The present invention thus relates to the use of pipamperon or a pharmaceutically acceptable salt thereof for the preparation of a medicament for treating the underlying emotion dysregulation of substance related disorders, characterized in that pipamperon or said pharmaceutically acceptable salt thereof is administered simultaneously with, separate from or prior to the administration of a glucocorticoid synthesis inhibitor compound to augment the therapeutic effect or to provide a faster onset of the therapeutic effect of said glucocorticoid synthesis inhibitor compound, further characterized in that pipamperon is to be administered to a patient in a daily dose ranging between 5 and 15 mg of the active ingredient.

The present invention thus relates to the use of pipamperon or a pharmaceutically acceptable salt thereof for the preparation of a medicament for treating the underlying emotion dysregulation of Parkinson disease, characterized in that pipamperon or said pharmaceutically acceptable salt thereof is administered simultaneously with, separate from or prior to the administration of a glucocorticoid synthesis inhibitor compound to augment the therapeutic effect or to provide a faster onset of the therapeutic effect of said glucocorticoid synthesis inhibitor compound, further characterized in that pipamperon is to be administered to a patient in a daily dose ranging between 5 and 15 mg of the active ingredient.

According to a preferred embodiment, the invention relates to the uses as described above, wherein said glucocorticoid synthesis inhibitor compound is metyrapone or a pro-drug or an active metabolite thereof, or a pharmaceutically acceptable salt thereof.

The invention also relates to a pharmaceutical composition comprising (a) pipamperon, and (b) a glucocorticoid synthesis inhibitor, preferably metyrapone or a pro-drug or an active metabolite thereof, or a pharmaceutically acceptable salt thereof, as a combined preparation for simultaneous, separate or sequential use for treating the underlying emotion dysregulation of a mental disease or disorder which is chosen from the group of diseases or disorders consisting of substance related disorders and Parkinson disease.

39: Combination Therapy with a Glutamate Receptor Antagonist Compound

The mental disorders which can be treated using compounds having a high selective affinity for the 5-HT2A and D4 receptor, for instance pipamperon, in a combination therapy with a glutamate receptor antagonist compound, are chosen from the group of diseases or disorders consisting of anxiety disorders, somatoform disorders (excluding pain disorders), factitious disorders, dissociative disorders, adjustment disorders, impulse control disorders, substance-related disorders, personality disorders, bereavement, occupational problem, problems related to abuse or neglect and pain disorders.

The present invention thus relates to the use of pipamperon or a pharmaceutically acceptable salt thereof for the preparation of a medicament for treating the underlying emotion dysregulation of a non-cognitive mental disease or disorder selected from the group of diseases and disorders consisting of anxiety disorders, somatoform disorders (excluding pain disorders), factitious disorders, dissociative disorders, adjustment disorders, impulse control disorders, substance-related disorders, personality disorders, bereavement, occupational problem, and problems related to abuse or neglect, characterized in that pipamperon or said pharmaceutically acceptable salt thereof is administered simultaneously with, separate from or prior to the administration of a glutamate receptor antagonist compound to augment the therapeutic effect or to provide a faster onset of the therapeutic effect of said glutamate receptor antagonist compound, further character-ized in that pipamperon is to be administered to a patient in a daily dose ranging between 5 and 15 mg of the active ingredient.

The present invention thus relates to the use of pipamperon or a pharmaceutically acceptable salt thereof for the preparation of a medicament for treating the underlying emotion dysregulation of pain disorders, characterized in that pipamperon or said pharmaceutically acceptable salt thereof is administered simultaneously with, separate from or prior to the administration of a glutamate receptor antagonist compound to augment the therapeutic effect or to provide a faster onset of therapeutic effect of said glutamate receptor antagonist compound, further characterized in that pipamperon is to be administered to a patient in a daily dose ranging between 5 and 15 mg of the active ingredient.

According to a preferred embodiment, the invention relates to the uses as described above, wherein said glutamate receptor antagonist compound is LY354740 or a pro-drug or an active metabolite thereof, or a pharmaceutically acceptable salt thereof.

The invention also relates to a pharmaceutical composition comprising (a) pipamperon, and (b) a glutamate receptor antagonist, preferably LY354740 or a pro-drug or an active metabolite thereof, or a pharmaceutically acceptable salt thereof, as a combined preparation for simultaneous, separate or sequential use for treating the underlying emotion dysregulation of a mental disease or disorder which is chosen from the group of diseases or disorders consisting of anxiety disorders, somatoform disorders (excluding pain disorders), factitious disorders, dissociative disorders, adjustment disorders, impulse control disorders, substance-related disorders, personality disorders, bereavement, occupational problem, problems related to abuse or neglect and pain disorders.

40: Combination Therapy with an GPCR (G-Protein-Coupled Receptor) Modulator

The mental disorders which can be treated using compounds having a high selective affinity for the 5-HT2A and D4 receptor, for instance pipamperon, in a combination therapy with an GPCR (G-protein-coupled receptor) modulator, are chosen from the group of diseases or disorders consisting of mood disorders, anxiety disorders, eating disorders, premenstrual syndrome, somatoform disorders (excluding pain disorders), factitious disorders, dissociative disorders, sexual and gender identity disorders, sleep disorders, adjustment disorders, impulse control disorders, substance-related disorders, personality disorders, bereavement, occupational problem, problems related to abuse or neglect and pain disorders.

The present invention thus relates to the use of pipamperon or a pharmaceutically acceptable salt thereof for the preparation of a medicament for treating the underlying emotion dysregulation of a non-cognitive mental disease or disorder selected from the group of diseases and disorders consisting of mood disorders, anxiety disorders, eating disorders, premenstrual syndrome, somatoform disorders (excluding pain disorders), factitious disorders, dissociative disorders, sexual and gender identity disorders, sleep disorders, adjustment disorders, impulse control disorders, substance-related disorders, personality disorders, bereavement, occupational problem and problems related to abuse or neglect, characterized in that pipamperon or said pharmaceutically acceptable salt thereof is administered simultaneously with, separate from or prior to the administration of a GPCR modulator compound to augment the therapeutic effect or to provide a faster onset of the therapeutic effect of said GPCR modulator compound, further characterized in that pipamperon is to be administered to a patient in a daily dose ranging between 5 and 15 mg of the active ingredient.

The present invention thus relates to the use of pipamperon or a pharmaceutically acceptable salt thereof for the preparation of a medicament for treating the underlying emotion dysregulation of pain disorders, characterized in that pipamperon or said pharmaceutically acceptable salt thereof is administered simultaneously with, separate from or prior to the administration of a GPCR modulator compound to augment the therapeutic effect or to provide a faster onset of the therapeutic effect of said GPCR modulator compound, further characterized in that pipamperon is to be administered to a patient in a daily dose ranging between 5 and 15 mg of the active ingredient.

According to a preferred embodiment, the invention relates to the uses as described above, wherein said GPCR modulator compound is R1204 or a pro-drug or an active metabolite thereof, or a pharmaceutically acceptable salt thereof.

The invention also relates to a pharmaceutical composition comprising (a) pipamperon, and (b) a GPCR modulator, preferably R1204 or a pro-drug or an active metabolite thereof, or a pharmaceutically acceptable salt thereof, as a combined preparation for simultaneous, separate or sequential use for treating the underlying emotion dysregulation of a mental disease or disorder which is chosen from the group of diseases or disorders consisting of mood disorders, anxiety disorders, eating disorders, premenstrual syndrome, somatoform disorders (excluding pain disorders), factitious disorders, dissociative disorders, sexual and gender identity disorders, sleep disorders, adjustment disorders, impulse control disorders, substance-related disorders, personality disorders, bereavement, occupational problem, problems related to abuse or neglect and pain disorders.

41: Combination Therapy with an GR (Glucocorticoid Receptor) Antagonist

The mental disorders which can be treated using compounds having a high selective affinity for the 5-HT2A and D4 receptor, for instance pipamperon, in a combination therapy with an GR (glucocorticoid receptor) antagonist, are chosen from the group of diseases or disorders consisting of mood disorders, anxiety disorders, eating disorders, premenstrual syndrome, somatoform disorders (excluding pain disorders), factitious disorders, dissociative disorders, sexual and gender identity disorders, sleep disorders, adjustment disorders, impulse control disorders, substance-related disorders, personality disorders, bereavement, occupational problem, problems related to abuse or neglect and pain disorders.

The present invention thus relates to the use of pipamperon or a pharmaceutically acceptable salt thereof for the preparation of a medicament for treating the underlying emotion dysregulation of a non-cognitive mental disease or disorder selected from the group of diseases and disorders consisting of mood disorders, anxiety disorders, eating disorders, premenstrual syndrome, somatoform disorders (excluding pain disorders), factitious disorders, dissociative disorders, sexual and gender identity disorders, sleep disorders, adjustment disorders, impulse control disorders, substance-related disorders, personality disorders, bereavement, occupational problem and problems related to abuse or neglect, characterized in that pipamperon or said pharmaceutically acceptable salt thereof is administered simultaneously with, separate from or prior to the administration of a GR antagonist compound to augment the therapeutic effect or to provide a faster onset of the therapeutic effect of said GR antagonist compound, further characterized in that pipamperon is to be administered to a patient in a daily dose ranging between 5 and 15 mg of the active ingredient.

The present invention thus relates to the use of pipamperon or a pharmaceutically acceptable salt thereof for the preparation of a medicament for treating the underlying emotion dysregulation of pain disorders, characterized in that pipamperon or said pharmaceutically acceptable salt thereof is administered simultaneously with, separate from or prior to the administration of a GR antagonist compound to augment the therapeutic effect or to provide a faster onset of the therapeutic effect of said GR antagonist compound, further characterized in that pipamperon is to be administered to a patient in a daily dose ranging between 5 and 15 mg of the active ingredient.

According to a preferred embodiment, the invention relates to the use as described above, wherein said GR antagonist compound is chosen from the group consisting of ORG 34517/34850 and mifepristone, preferably mifepristone, or a pro-drug or an active metabolite thereof, or a pharmaceutically acceptable salt thereof. Preferably, mifepristone is to be administered in a daily dose of between 600 and 1200 mg of the active ingredient.

The invention also relates to a pharmaceutical composition comprising (a) pipamperon, and (b) a GR antagonist, preferably chosen from the group consisting of ORG 34517/34850 and mifepristone, preferably mifepristone, or a pro-drug or an active metabolite thereof, or a pharmaceutically acceptable salt thereof, as a combined preparation for simultaneous, separate or sequential use for treating the underlying emotion dysregulation of a mental disease or disorder which is chosen from the group of diseases or disorders consisting of mood disorders, anxiety disorders, eating disorders, premenstrual syndrome, somatoform disorders (excluding pain disorders), factitious disorders, dissociative disorders, sexual and gender identity disorders, sleep disorders, adjustment disorders, impulse control disorders, substance-related disorders, personality disorders, bereavement, occupational problem, problems related to abuse or neglect and pain disorders.

The invention also relates to a pharmaceutical composition as described above wherein pipamperon is provided in a unitary dose of between 5 and 15 mg of the active ingredient and wherein said GR antagonist is Mifepristone, preferably provided in a unitary dose of between 600 and 1200 mg of the active ingredient.

42: Combination Therapy with a Histamine H3-Receptor Antagonist

The mental disorders which can be treated using compounds having a high selective affinity for the 5-HT2A and D4 receptor, for instance pipamperon, in a combination therapy with a histamine H3-receptor antagonist, are chosen from the group of diseases or disorders consisting of Alzheimer Disease, substance-induced persisting dementia, vascular dementia, dementia due to HIV disease, dementia due to head trauma, dementia due to Parkinson Disease, dementia due to Huntington Disease, dementia due to Pick Disease, dementia due to Creutzfeldt-Jacob Disease, amnestic disorders due to a general medical condition, substance-induced persisting amnestic disorder, mild cognitive impairment disorder and other cognitive disorders.

The present invention thus relates to the use of pipamperon or a pharmaceutically acceptable salt thereof for the preparation of a medicament for treating the underlying emotion dysregulation of a cognitive mental disease or disorder selected from the group of diseases and disorders consisting of Alzheimer Disease, substance-induced persisting dementia, vascular dementia, dementia due to HIV disease, dementia due to head trauma, dementia due to Parkinson Disease, dementia due to Huntington Disease, dementia due to Pick Disease, dementia due to Creutzfeldt-Jacob Disease, amnestic disorders due to a general medical condition, substance-induced persisting amnestic disorder, mild cognitive impairment disorder and other cognitive disorders, characterized in that pipamperon or said pharmaceutically acceptable salt thereof is administered simultaneously with, separate from or prior to the administration of a histamine H3-receptor antagonist compound to augment the therapeutic effect or to provide a faster onset of the therapeutic effect of said histamine H3-receptor antagonist compound, further characterized in that pipamperon is to be administered to a patient in a daily dose ranging between 5 and 15 mg of the active ingredient.

According to a preferred embodiment, the invention relates to the uses as described above, wherein said histamine H3-receptor antagonist compound is chosen from the group of compounds consisting of ABT-834 and ABT-239, or a pro-drug or an active metabolite thereof, or a pharmaceutically acceptable salt thereof.

The invention also relates to a pharmaceutical composition comprising (a) pipamperon, and (b) a histamine H3-receptor antagonist, preferably chosen from the group consisting of ABT-834 and ABT-239 or a pro-drug or an active metabolite thereof, or a pharmaceutically acceptable salt thereof, as a combined preparation for simultaneous, separate or sequential use for treating the underlying emotion dysregulation of a cognitive mental disease or disorder which is chosen from the group consisting of Alzheimer Disease, substance-related persisting dementia, vascular dementia, dementia due to HIV disease, dementia due to head trauma, dementia due to Parkinson Disease, dementia due to Huntington Disease, dementia due to Pick Disease, dementia due to Creutzfeldt-Jacob Disease, amnestic disorders due to a general medical condition, substance-induced persisting amnestic disorder, mild cognitive impairment disorder and other cognitive disorders.

43: Combination Therapy with a Hormonal Substance

The mental disorders which can be treated using compounds having a high selective affinity for the 5-HT2A and D4 receptor, for instance pipamperon, in a combination therapy with a hormonal substance, are chosen from the group of diseases or disorders consisting of premenstrual syndrome and sexual and gender identity disorders.

The present invention thus relates to the use of pipamperon or a pharmaceutically acceptable salt thereof for the preparation of a medicament for treating the underlying emotion dysregulation of a cognitive mental disease or disorder selected from the group of diseases and disorders consisting of premenstrual syndrome and sexual and gender identity disorders, characterized in that pipamperon or said pharmaceutically acceptable salt thereof is administered simultaneously with, separate from or prior to the administration of a hormonal substance to augment the therapeutic effect or to provide a faster onset of the therapeutic effect of said hormonal substance, further characterized in that pipamperon is to be administered to a patient in a daily dose ranging between 5 and 15 mg of the active ingredient.

According to a preferred embodiment, the invention relates to the uses as described above, wherein said hormonal substance is chosen from the group consisting of a testosterone transdermal spray, a testosterone gel, a female testosterone patch, synthetic conjugated estrogen A, methyltestosterone, a estrogens/methyltestosterone and a drosiperone/ethinyl estradiol composition, or a pro-drug or an active metabolite thereof, or a pharmaceutically acceptable salt thereof. More preferably, said hormonal substance is synthetic conjugated estrogen A and is to be administered in a daily dose ranging between 0.075 and 0.6 mg of the active ingredient. More preferably, said hormonal substance is a drosiperone/ethinyl estradiol composition and is to be administered as a daily dose in tablets, preferably comprising 3 mg drosiperone and 0.02 mg ethinyl estradiol of the active ingredients, respectively.

The invention also relates to a pharmaceutical composition comprising (a) pipamperon, and (b) a hormonal substance, preferably chosen from the group consisting of a testosterone transdermal spray, a testosterone gel, a female testosterone patch, synthetic conjugated estrogen A, methyltestosterone, a estrogens/methyltestosterone and a drosiperone/ethinyl estradiol composition, or a pro-drug or an active metabolite thereof, or a pharmaceutically acceptable salt thereof, as a combined preparation for simultaneous, separate or sequential use for treating the underlying emotion dysregulation of a cognitive mental disease or disorder which is chosen from the group consisting of premenstrual syndrome and sexual and gender identity disorders.

The invention also relates to a pharmaceutical composition as described above wherein pipamperon is provided in a unitary dose of between 5 and 15 mg of the active ingredient and wherein said hormonal substance is synthetic conjugated estrogen A, preferably provided in a unitary dose of between 0.075 and 0.6 mg of the active ingredient.

The invention also relates to a pharmaceutical composition as described above wherein pipamperon is provided in a unitary dose of between 5 and 15 mg of the active ingredient and wherein said hormonal substance is a drosiperone/ethinyl estradiol composition, preferably provided in tablets comprising a unitary dose of 3 mg drosiperone and 0.02 mg ethinyl estradiol of the active ingredients, respectively.

44: Combination Therapy with a Compound which Increases Brain Concentrations of 5-HT The mental disorders which can be treated using compounds having a high selective affinity for the 5-HT2A and D4 receptor, for instance pipamperon, in a combination therapy with a compound which increases brain concentrations of 5-HT (serotonin), are chosen from the group of diseases or disorders consisting of mood disorders, anxiety disorders, eating disorders, premenstrual syndrome, somatoform disorders (excluding pain disorders), factitious disorders, dissociative disorders, sexual and gender identity disorders, sleep disorders, adjustment disorders, impulse control disorders, substance-related disorders, personality disorders, bereavement, occupational problem, problems related to abuse or neglect and pain disorders.

The present invention thus relates to the use of pipamperon or a pharmaceutically acceptable salt thereof for the preparation of a medicament for treating the underlying emotion dysregulation of a non cognitive mental disease or disorder selected from the group of diseases and disorders consisting of mood disorders, anxiety disorders, eating disorders, premenstrual syndrome, somatoform disorders (excluding pain disorders), factitious disorders, dissociative disorders, sexual and gender identity disorders, sleep disorders, adjustment disorders, impulse control disorders, substance-related disorders, personality disorders, bereavement, occupational problem and problems related to abuse or neglect, characterized in that pipamperon or said pharmaceutically acceptable salt thereof is administered simultaneously with, separate from or prior to the administration of a compound which increases brain concentrations of 5-HT (serotonin) to augment the therapeutic effect or to provide a faster onset of the therapeutic effect of said compound which increases brain concentrations of 5-HT (serotonin), further characterized in that pipamperon is to be administered to a patient in a daily dose ranging between 5 and 15 mg of the active ingredient.

The present invention thus relates to the use of pipamperon or a pharmaceutically acceptable salt thereof for the preparation of a medicament for treating the underlying emotion dysregulation of pain, characterized in that pipamperon or said pharmaceutically acceptable salt thereof is administered simultaneously with, separate from or prior to the administration of a compound which increases brain concentrations of 5-HT (serotonin) to augment the therapeutic effect or to provide a faster onset of the therapeutic effect of said compound which increases brain concentrations of 5-HT (serotonin), further characterized in that pipamperon is to be administered to a patient in a daily dose ranging between 5 and 15 mg of the active ingredient.

According to a preferred embodiment, the invention relates to the uses as described above, wherein said compound which increases brain concentrations of 5-HT (serotonin) is chosen from the group consisting of triptosine, SP 186, PMD 145 and KW 6055, or a pro-drug or an active metabolite thereof, or a pharmaceutically acceptable salt thereof.

The invention also relates to a pharmaceutical composition comprising (a) pipamperon, and (b) a compound which increases brain concentrations of 5-HT (serotonin), preferably chosen from the group consisting of triptosine, SP 186, PMD 145 and KW 6055, or a pro-drug or an active metabolite thereof, or a pharmaceutically acceptable salt thereof, as a combined preparation for simultaneous, separate or sequential use for treating the underlying emotion dysregulation of a mental disease or disorder which is chosen from the group of diseases and disorders consisting of mood disorders, anxiety disorders, eating disorders, premenstrual syndrome, somatoform disorders (excluding pain disorders), factitious disorders, dissociative disorders, sexual and gender identity disorders, sleep disorders, adjustment disorders, impulse control disorders, substance-related disorders, personality disorders, bereavement, occupational problem, problems related to abuse or neglect and pain disorders.

45: Combination Therapy with a Compound which Increases Insulin Sensitivity

The mental disorders which can be treated using compounds having a high selective affinity for the 5-HT2A and D4 receptor, for instance pipamperon, in a combination therapy with a compound which increases insulin sensitivity, are chosen from the group of diseases or disorders consisting of Alzheimer Disease, substance-induced persisting dementia, vascular dementia, dementia due to HIV disease, dementia due to head trauma, dementia due to Parkinson Disease, dementia due to Huntington Disease, dementia due to Pick Disease, dementia due to Creutzfeldt-Jacob Disease, amnestic disorders due to a general medical condition, substance-induced persisting amnestic disorder, mild cognitive impairment disorder and other cognitive disorders.

The present invention thus relates to the use of pipamperon or a pharmaceutically acceptable salt thereof for the preparation of a medicament for treating the underlying emotion dysregulation of a cognitive mental disease or disorder selected from the group of diseases and disorders consisting of Alzheimer Disease, substance-induced persisting dementia, vascular dementia, dementia due to HIV disease, dementia due to head trauma, dementia due to Parkinson Disease, dementia due to Huntington Disease, dementia due to Pick Disease, dementia due to Creutzfeldt-Jacob Disease, amnestic disorders due to a general medical condition, substance-induced persisting amnestic disorder, mild cognitive impairment disorder and other cognitive disorders, characterized in that pipamperon or said pharmaceutically acceptable salt thereof is administered simultaneously with, separate from or prior to the administration of a compound which increases insulin sensitivity to augment the therapeutic effect or to provide a faster onset of the therapeutic effect of said compound which increases insulin sensitivity, further characterized in that pipamperon is to be administered to a patient in a daily dose ranging between 5 and 15 mg of the active ingredient.

According to a preferred embodiment, the invention relates to the use as described above, wherein said compound which increases insulin sensitivity is rosiglitazone maleate, or a pro-drug or an active metabolite thereof, or a pharmaceutically acceptable salt thereof.

The invention also relates to a pharmaceutical composition comprising (a) pipamperon, and (b) a compound which increases insulin sensitivity, preferably rosiglitazone maleate or a pro-drug or an active metabolite thereof, or a pharmaceutically acceptable salt thereof, as a combined preparation for simultaneous, separate or sequential use for treating the underlying emotion dysregulation of a cognitive mental disease or disorder which is chosen from the group consisting of Alzheimer Disease, substance-induced persisting dementia, vascular dementia, dementia due to HIV disease, dementia due to head trauma, dementia due to Parkinson Disease, dementia due to Huntington Disease, dementia due to Pick Disease, dementia due to Creutzfeldt-Jacob Disease, amnestic disorders due to a general medical condition, substance-induced persisting amnestic disorder, mild cognitive impairment disorder and other cognitive disorders.

46: Combination Therapy with a Compound Inhibiting the Mixed Lineage Kinase Family The mental disorder which can be treated using compounds having a high selective affinity for the 5-HT2A and D4 receptor, for instance pipamperon, in a combination therapy with a compound which is an inhibitor of the mixed lineage kinase family is Parkinson Disease.

The present invention thus relates to the use of pipamperon or a pharmaceutically acceptable salt thereof for the preparation of a medicament for treating the underlying emotion dysregulation of Parkinson Disease, characterized in that pipamperon or said pharmaceutically acceptable salt thereof is administered simultaneously with, separate from or prior to the administration of a compound which is an inhibitor of the mixed lineage kinase family to augment the therapeutic effect or to provide a faster onset of the therapeutic effect of said compound which is an inhibitor of the mixed lineage kinase family, further characterized in that pipamperon is to be administered to a patient in a daily dose ranging between 5 and 15 mg of the active ingredient.

According to a preferred embodiment, the invention relates to the use as described above, wherein said compound which is an inhibitor of the mixed lineage kinase family is CEP-1347 or a pro-drug or an active metabolite thereof, or a pharmaceutically acceptable salt thereof.

The invention also relates to a pharmaceutical composition comprising (a) pipamperon, and (b) a compound which is an inhibitor of the mixed lineage kinase family, preferably CEP-1347 or a pro-drug or an active metabolite thereof, or a pharmaceutically acceptable salt thereof, as a combined preparation for simultaneous, separate or sequential use for treating the underlying emotion dysregulation of Parkinson Disease.

47: Combination Therapy with an Interleukin-1 Beta Converting Enzyme Inhibitor Compound The mental disorder which can be treated using compounds having a high selective affinity for the 5-HT2A and D4 receptor, for instance pipamperon, in a combination therapy with an interleukin-1 beta converting enzyme inhibitor compound, is a pain disorder.

The present invention thus relates to the use of pipamperon or a pharmaceutically acceptable salt thereof for the preparation of a medicament for treating the underlying emotion dysregulation of a pain disorder, characterized in that pipamperon or said pharmaceutically acceptable salt thereof is administered simultaneously with, separate from or prior to the administration of an interleukin-1 beta converting enzyme inhibitor compound to augment the therapeutic effect or to provide a faster onset of the therapeutic effect of said interleukin-1 beta converting enzyme inhibitor compound, further characterized in that pipamperon is to be administered to a patient in a daily dose ranging between 5 and 15 mg of the active ingredient.

According to a preferred embodiment, the invention relates to the use as described above, wherein said interleukin-1 beta converting enzyme inhibitor is prainacasan or a pro-drug or an active metabolite thereof, or a pharmaceutically acceptable salt thereof.

The invention also relates to a pharmaceutical composition comprising (a) pipamperon, and (b) an interleukin-1 beta converting enzyme inhibitor, preferably prainacasan or a pro-drug or an active metabolite thereof, or a pharmaceutically acceptable salt thereof, as a combined preparation for simultaneous, separate or sequential use for treating the underlying emotion dysregulation of a pain disorder, 48: Combination Therapy with a Levodopa/Decarboylase Inhibitor Compound The mental disorder which can be treated using compounds having a high selective affinity for the 5-HT2A and D4 receptor, for instance pipamperon, in a combination therapy with a levodopa/decarboylase inhibitor compound, is Parkinson Disease.

The present invention thus relates to the use of pipamperon or a pharmaceutically acceptable salt thereof for the preparation of a medicament for treating the underlying emotion dysregulation of Parkinson Disease, characterized in that pipamperon or said pharmaceutically acceptable salt thereof is administered simultaneously with, separate from or prior to the administration of a levodopa/decarboylase inhibitor compound to augment the therapeutic effect or to provide a faster onset of the therapeutic effect of said levodopa/decarboylase inhibitor compound, further characterized in that pipamperon is to be administered to a patient in a daily dose ranging between 5 and 15 mg of the active ingredient.

According to a preferred embodiment, the invention relates to the use as described above, wherein said levodopa/decarboylase inhibitor compound is chosen from the group consisting of levodopa/carbidopa, levodopa benserazide, etilevodopa/carbidopa or etilevodopa/benserazide, or a pro-drug or an active metabolite thereof, or a pharmaceutically acceptable salt thereof. Preferably, levodopa/carbidopa is to be administered in a daily dose between 250 to 600 mg/25 to 150 mg of the active ingredients. Preferably, levodopa/benserazide is to be administered in a daily dose between 100 to 600 mg/25 to 150 mg of the active ingredients.

According to a further preferred embodiment, the invention relates to the use as described above, wherein said levodopa/decarboylase inhibitor compound is (eti)levodopa/carbidopa, or a pro-drug or an active metabolite thereof, or a pharmaceutically acceptable salt thereof in combination with entacapone, which is an inhibitor of catechol-O-methyltransferase (COMT), or a pro-drug or an active metabolite thereof, or a pharmaceutically acceptable salt thereof. Preferably, said levodopa/decarboylase inhibitor compound is levodopa/carbidopa and is to be administered in a dose ranging between 2000 mg/50 mg and 100 mg/10 mg of the active ingredients. Preferably said entacapone is to be administered in a dose ranging between 1000 mg/50 mg, more preferably between 500 mg/100 mg, and most preferably 200 mg of the active ingredients per day.

The invention also relates to a pharmaceutical composition comprising (a) pipamperon, and (b) a levodopa/decarboylase inhibitor compound, preferably levodopa/carbidopa, levodopa/benserazide, etilevodopa/carbidopa or etilevodopa/benserazide, or a pro-drug or an active metabolite thereof, or a pharmaceutically acceptable salt thereof, as a combined preparation for simultaneous, separate or sequential use for treating the underlying emotion dysregulation of Parkinson Disease. The invention also relates to a pharmaceutical composition comprising (a) pipamperon, and (b) a levodopa/decarboylase inhibitor compound, preferably is (eti)levodopa/carbidopa, or a pro-drug or an active metabolite thereof, or a pharmaceutically acceptable salt thereof in combination with entacapone, which is an inhibitor of catechol-O-methyltransferase (COMT), or a pro-drug or an active metabolite thereof, or a pharmaceutically acceptable salt thereof, as a combined preparation for simultaneous, separate or sequential use for treating the underlying emotion dysregulation of Parkinson Disease.

The invention also relates to a pharmaceutical composition as described above wherein pipamperon is provided in a unitary dose of between 5 and 15 mg of the active ingredient and wherein said levodopa/decarboylase inhibitor compound is levodopa/carbidopa, preferably provided in a unitary dose of between 250 to 600 mg and 25 to 150 mg of the active ingredients.

The invention also relates to a pharmaceutical composition as described above wherein pipamperon is provided in a unitary dose of between 5 and 15 mg of the active ingredient and wherein said levodopa/decarboylase inhibitor compound is levodopa/benserazide, preferably provided in a unitary dose of between 100 to 600 mg and 25 to 150 mg of the active ingredients.

The invention also relates to a pharmaceutical composition as described above wherein pipamperon is provided in a unitary dose of between 5 and 15 mg of the active ingredient and wherein said levodopa/decarboylase inhibitor compound is levodopa/carbidopa or etilevodopa/carbidopa in combination with entacapone, of which the latter is preferably provided in a unitary dose of between 500 mg and 100 mg of the active ingredient.

49: Combination Therapy with a Lipid-DNA Complex

The mental disorder which can be treated using compounds having a high selective affinity for the 5-HT2A and D4 receptor, for instance pipamperon, in a combination therapy with a lipid-DNA complex, is Parkinson Disease.

The present invention thus relates to the use of pipamperon or a pharmaceutically acceptable salt thereof for the preparation of a medicament for treating the underlying emotion dysregulation of Parkinson Disease, characterized in that pipamperon or said pharmaceutically acceptable salt thereof is administered simultaneously with, separate from or prior to the administration of lipid-DNA complex to augment the therapeutic effect or to provide a faster onset of the therapeutic effect of said lipid-DNA complex, further characterized in that pipamperon is to be administered to a patient in a daily dose ranging between 5 and 15 mg of the active ingredient.

According to a preferred embodiment, the invention relates to the use as described above, wherein said lipid-DNA complex is GR213487B or a pro-drug or an active metabolite thereof, or a pharmaceutically acceptable salt thereof.

The invention also relates to a pharmaceutical composition comprising (a) pipamperon, and (b) a lipid-DNA complex, preferably GR213487B or a pro-drug or an active metabolite thereof, or a pharmaceutically acceptable salt thereof, as a combined preparation for simultaneous, separate or sequential use for treating the underlying emotion dysregulation of Parkinson Disease.

50: Combination Therapy with a Monoamine Oxidase (MAO) Reuptake Inhibitor

The mental disorders which can be treated using compounds having a high selective affinity for the 5-HT2A and D4 receptor, for instance pipamperon, in a combination therapy with a monoamine oxidase (MAO) reuptake inhibitor, are chosen from the group of diseases or disorders consisting of substance related disorders and attention-deficit disorders (ADHD).

The present invention thus relates to the use of pipamperon or a pharmaceutically acceptable salt thereof for the preparation of a medicament for treating the underlying emotion dysregulation of non-cognitive mental disease or disorder which are substance related disorders, characterized in that pipamperon or said pharmaceutically acceptable salt thereof is administered simultaneously with, separate from or prior to the administration of a monoamine oxidase (MAO) reuptake inhibitor compound to augment the therapeutic effect or to provide a faster onset of the therapeutic effect of said monoamine oxidase (MAO) reuptake inhibitor compound, further characterized in that pipamperon is to be administered to a patient in a daily dose ranging between 5 and 15 mg of the active ingredient.

The present invention thus relates to the use of pipamperon or a pharmaceutically acceptable salt thereof for the preparation of a medicament for treating the underlying emotion dysregulation of attention-deficit disorders (ADHD), characterized in that pipamperon or said pharmaceutically acceptable salt thereof is administered simultaneously with, separate from or prior to the administration of a monoamine oxidase (MAO) reuptake inhibitor compound to augment the therapeutic effect or to provide a faster onset of the therapeutic effect of said monoamine oxidase (MAO) reuptake inhibitor compound, further characterized in that pipamperon is to be administered to a patient in a daily dose ranging between 5 and 15 mg of the active ingredient.

According to a preferred embodiment, the invention relates to the uses as described above, wherein said monoamine oxidase (MAO) reuptake inhibitor compound is NS 2359 or a pro-drug or an active metabolite thereof, or a pharmaceutically acceptable salt thereof.

The invention also relates to a pharmaceutical composition comprising (a) pipamperon, and (b) a monoamine oxidase (MAO) reuptake inhibitor, preferably NS 2359 or a pro-drug or an active metabolite thereof, or a pharmaceutically acceptable salt thereof, as a combined preparation for simultaneous, separate or sequential use for treating the underlying emotion dysregulation of a mental disease or disorder which is chosen from the group consisting of substance related disorders and attention-deficit disorders (ADHD).

51: Combination Therapy with a MAO-A and a MAO-B Reuptake Inhibitor

The mental disorders which can be treated using compounds having a high selective affinity for the 5-HT2A and D4 receptor, for instance pipamperon, in a combination therapy with a monoamine oxidase A (MAO-A) and a monoamine oxidase B (MAO-B) reuptake inhibitor, wherein said disorders are attention-deficit disorders.

The present invention thus relates to the use of pipamperon or a pharmaceutically acceptable salt thereof for the preparation of a medicament for treating the underlying emotion dysregulation of attention-deficit disorders, characterized in that pipamperon or said pharmaceutically acceptable salt thereof is administered simultaneously with, separate from or prior to the administration of a monoamine oxidase A (MAO-A) and a monoamine oxidase B (MAO-B) reuptake inhibitor compound to augment the therapeutic effect or to provide a faster onset of the therapeutic effect of said monoamine oxidase A (MAO-A) and a monoamine oxidase B (MAO-B) reuptake inhibitor compound, further characterized in that pipamperon is to be administered to a patient in a daily dose ranging between 5 and 15 mg of the active ingredient.

According to a preferred embodiment, the invention relates to the uses as described above, wherein said monoamine oxidase A (MAO-A) and a monoamine oxidase B (MAO-B) reuptake inhibitor compound is SPD473 or a pro-drug or an active metabolite thereof, or a pharmaceutically acceptable salt thereof.

The invention also relates to a pharmaceutical composition comprising (a) pipamperon, and (b) a monoamine oxidase A (MAO-A) and a monoamine oxidase B (MAO-B) reuptake inhibitor, preferably SPD473 or a pharmaceutically acceptable salt thereof, as a combined preparation for simultaneous, separate or sequential use for treating the underlying emotion dysregulation of attention-deficit disorders.

52: Combination Therapy with a Monoamine Oxidase B (MAO-B) Inhibitor

The mental disorders which can be treated using compounds having a high selective affinity for the 5-HT2A and D4 receptor, for instance pipamperon, in a combination therapy with a monoamine oxidase B (MAO-B) inhibitor, are chosen from the group of diseases or disorders consisting of mood disorders, anxiety disorders, eating disorders, premenstrual syndrome, somatoform disorders (excluding pain disorders), factitious disorders, dissociative disorders, adjustment disorders, impulse control disorders, attention-deficit disorders, substance-related disorders, personality disorders, problems related to abuse or neglect, pain disorder and Parkinson Disease.

The present invention thus relates to the use of pipamperon or a pharmaceutically acceptable salt thereof for the preparation of a medicament for treating the underlying emotion dysregulation of a non-cognitive mental disease or disorder selected from the group of diseases and disorders consisting of mood disorders, anxiety disorders, eating disorders, premenstrual syndrome, somatoform disorders (excluding pain disorders), factitious disorders, dissociative disorders, adjustment disorders, impulse control disorders, attention-deficit disorders, substance-related disorders, personality disorders, problems related to abuse or neglect, characterized in that pipamperon or said pharmaceutically acceptable salt thereof is administered simultaneously with, separate from or prior to the administration of a monoamine oxidase B (MAO-B) inhibitor compound to augment the therapeutic effect or to provide a faster onset of the therapeutic effect of said monoamine oxidase B (MAO-B) inhibitor compound, further characterized in that pipamperon is to be administered to a patient in a daily dose ranging between 5 and 15 mg of the active ingredient.

The present invention thus relates to the use of pipamperon or a pharmaceutically acceptable salt thereof for the preparation of a medicament for treating the underlying emotion dysregulation of pain disorders, characterized in that pipamperon or said pharmaceutically acceptable salt thereof is administered simultaneously with, separate from or prior to the administration of a monoamine oxidase B (MAO-B) inhibitor compound to augment the therapeutic effect or to provide a faster onset of the therapeutic effect of said monoamine oxidase B (MAO-B) inhibitor compound, further characterized in that pipamperon is to be administered to a patient in a daily dose ranging between 5 and 15 mg of the active ingredient.

The present invention thus relates to the use of pipamperon or a pharmaceutically acceptable salt thereof for the preparation of a medicament for treating the underlying emotion dysregulation of Parkinson Disease, characterized in that pipamperon or said pharmaceutically acceptable salt thereof is administered simultaneously with, separate from or prior to the administration of a monoamine oxidase B (MAO-B) inhibitor compound to augment the therapeutic effect or to provide a faster onset of the therapeutic effect of said monoamine oxidase B (MAO-B) inhibitor compound, further characterized in that pipamperon is to be administered to a patient in a daily dose ranging between 5 and 15 mg of the active ingredient.

According to a preferred embodiment, the invention relates to the uses as described above, wherein said monoamine oxidase B (MAO-B) inhibitor compound is chosen from the group consisting of selegiline, rasagiline (TVP-1012) and EmSam (transdermal selegiline), or a pro-drug or an active metabolite thereof, or a pharmaceutically acceptable salt thereof. More preferably, said monoamine oxidase B (MAO-B) inhibitor is selegiline and is to be administered in a daily dose ranging between 5 and 60 mg or possibly between 5 and 10 mg of the active ingredient. In a further preferred embodiment, selegiline is to be administered in a transdermal application in a daily dose ranging between 5 and 60 mg of the active ingredient. In another preferred embodiment, selegiline is to be administered orally in a daily dose ranging between 5 and 10 mg of the active ingredient. More preferably, said monoamine oxidase B (MAO-B) inhibitor is rasagiline (TVP-1012) and is to be administered in a daily dose ranging between 1 and 2 mg of the active ingredient.

The invention also relates to a pharmaceutical composition comprising (a) pipamperon, and (b) a monoamine oxidase B (MAO-B) inhibitor, preferably chosen from the group consisting of selegiline, rasagiline (TVP-1012) and EmSam (transdermal selegiline), or a pro-drug or an active metabolite thereof, or a pharmaceutically acceptable salt thereof, as a combined preparation for simultaneous, separate or sequential use for treating the underlying emotion dysregulation of a mental disease or disorder which is chosen from the group consisting of mood disorders, anxiety disorders, eating disorders, premenstrual syndrome, somatoform disorders (excluding pain disorders), factitious disorders, dissociative disorders, adjustment disorders, impulse control disorders, attention-deficit disorders, substance-related disorders, personality disorders, problems related to abuse or neglect, pain disorder and Parkinson Disease.

The invention also relates to a pharmaceutical composition as described above wherein pipamperon is provided in a unitary dose of between 5 and 15 mg of the active ingredient and wherein said monoamine oxidase B (MAO-B) inhibitor is selegiline, preferably provided in a unitary dose of between 5 and 10 mg or between 5 and 60 mg of the active ingredient.

The invention also relates to a pharmaceutical composition as described above wherein pipamperon is provided in a unitary dose of between 5 and 15 mg of the active ingredient and wherein said monoamine oxidase B (MAO-B) inhibitor is rasagiline (TVP-1012), preferably provided in a unitary dose of between 1 and 2 mg of the active ingredient.

53: Combination Therapy with a Monoamine Oxidase B (MAO-B) Reuptake Inhibitor

The mental disorder which can be treated using compounds having a high selective affinity for the 5-HT2A and D4 receptor, for instance pipamperon, in a combination therapy with a monoamine oxidase B (MAO-B) reuptake inhibitor, is Parkinson Disease.

The present invention thus relates to the use of pipamperon or a pharmaceutically acceptable salt thereof for the preparation of a medicament for treating the underlying emotion dysregulation of Parkinson Disease, characterized in that pipamperon or said pharmaceutically acceptable salt thereof is administered simultaneously with, separate from or prior to the administration of a monoamine oxidase B (MAO-B) reuptake inhibitor to augment the therapeutic effect or to provide a faster onset of the therapeutic effect of said monoamine oxidase B (MAO-B) reuptake inhibitor, further characterized in that pipamperon is to be administered to a patient in a daily dose ranging between 5 and 15 mg of the active ingredient.

According to a preferred embodiment, the invention relates to the use as described above, wherein said monoamine oxidase B (MAO-B) reuptake inhibitor is safinamide or a pro-drug or an active metabolite thereof, or a pharmaceutically acceptable salt thereof.

The invention also relates to a pharmaceutical composition comprising (a) pipamperon, and (b) a monoamine oxidase B (MAO-B) reuptake inhibitor, preferably safinamide or a pro-drug or an active metabolite thereof, or a pharmaceutically acceptable salt thereof, as a combined preparation for simultaneous, separate or sequential use for treating the underlying emotion dysregulation of Parkinson Disease.

54: Combination Therapy with a Melanocortin-4 (MC4) Receptor Antagonist Compound The mental disorders which can be treated using compounds having a high selective affinity for the 5-HT2A and D4 receptor, for instance pipamperon, in a combination therapy with a melanocortin-4 (MC4) receptor antagonist compound, are chosen from the group of diseases or disorders consisting of mood disorders, anxiety disorders, eating disorders, premenstrual syndrome, somatoform disorders (excluding pain disorders), factitious disorders, dissociative disorders, sexual and gender identity disorders, sleep disorders, adjustment disorders, impulse control disorders, substance-related disorders, personality disorders, bereavement, occupational problem, problems related to abuse or neglect and pain disorders.

The present invention thus relates to the use of pipamperon or a pharmaceutically acceptable salt thereof for the preparation of a medicament for treating the underlying emotion dysregulation of a non-cognitive mental disease or disorder selected from the group of diseases and disorders consisting of mood disorders, anxiety disorders, eating disorders, premenstrual syndrome, somatoform disorders (excluding pain disorders), factitious disorders, dissociative disorders, sexual and gender identity disorders, sleep disorders, adjustment disorders, impulse control disorders, substance-related disorders, personality disorders, bereavement, occupational problem and problems related to abuse or neglect, characterized in that pipamperon or said pharmaceutically acceptable salt thereof is administered simultaneously with, separate from or prior to the administration of a melanocortin-4 (MC4) receptor antagonist compound to augment the therapeutic effect or to provide a faster onset of the therapeutic effect of said melanocortin-4 (MC4) receptor antagonist compound, further characterized in that pipamperon is to be administered to a patient in a daily dose ranging between 5 and 15 mg of the active ingredient.

The present invention thus relates to the use of pipamperon or a pharmaceutically acceptable salt thereof for the preparation of a medicament for treating the underlying emotion dysregulation of pain disorders, characterized in that pipamperon or said pharmaceutically acceptable salt thereof is administered simultaneously with, separate from or prior to the administration of a melanocortin-4 (MC4) receptor antagonist compound to augment the therapeutic effect or to provide a faster onset of the therapeutic effect of said melanocortin-4 (MC4) receptor antagonist compound, further characterized in that pipamperon is to be administered to a patient in a daily dose ranging between 5 and 15 mg of the active ingredient.

According to a preferred embodiment, the invention relates to the uses as described above, wherein said melanocortin-4 (MC4) receptor antagonist compound is MCL0129, or a pro-drug or an active metabolite thereof, or a pharmaceutically acceptable salt thereof.

The invention also relates to a pharmaceutical composition comprising (a) pipamperon, and (b) a melanocortin-4 (MC4) receptor antagonist compound, preferably MCL0129 or a pro-drug or an active metabolite thereof, or a pharmaceutically acceptable salt thereof, as a combined preparation for simultaneous, separate or sequential use for treating the underlying emotion dysregulation of a mental disease or disorder which is chosen from the group consisting of mood disorders, anxiety disorders, eating disorders, premenstrual syndrome, somatoform disorders (excluding pain disorders), factitious disorders, dissociative disorders, sexual and gender identity disorders, sleep disorders, adjustment disorders, impulse control disorders, substance-related disorders, personality disorders, bereavement, occupational problem, problems related to abuse or neglect and pain disorders.

55: Combination Therapy with a MCH Receptor Antagonist Compound

The mental disorders which can be treated using compounds having a high selective affinity for the 5-HT2A and D4 receptor, for instance pipamperon, in a combination therapy with a melanin concentrating hormone (MCH) receptor antagonist compound, are chosen from the group of diseases or disorders consisting of mood disorders, anxiety disorders, eating disorders, premenstrual syndrome, somatoform disorders (excluding pain disorders), factitious disorders, dissociative disorders, sexual and gender identity disorders, sleep disorders, adjustment disorders, impulse control disorders, substance-related disorders, personality disorders, bereavement, occupational problem, problems related to abuse or neglect and pain disorders.

The present invention thus relates to the use of pipamperon or a pharmaceutically acceptable salt thereof for the preparation of a medicament for treating the underlying emotion dysregulation of a non-cognitive mental disease or disorder selected from the group of diseases and disorders consisting of mood disorders, anxiety disorders, eating disorders, premenstrual syndrome, somatoform disorders (excluding pain disorders), factitious disorders, dissociative disorders, sexual and gender identity disorders, sleep disorders, adjustment disorders, impulse control disorders, substance-related disorders, personality disorders, bereavement, occupational problem and problems related to abuse or neglect, characterized in that pipamperon or said pharmaceutically acceptable salt thereof is administered simultaneously with, separate from or prior to the administration of a melanin concentrating hormone (MCH) receptor antagonist compound to augment the therapeutic effect or to provide a faster onset of the therapeutic effect of said melanin concentrating hormone (MCH) receptor antagonist compound, further characterized in that pipamperon is to be administered to a patient in a daily dose ranging between 5 and 15 mg of the active ingredient.

The present invention thus relates to the use of pipamperon or a pharmaceutically acceptable salt thereof for the preparation of a medicament for treating the underlying emotion dysregulation of pain disorders, characterized in that pipamperon or said pharmaceutically acceptable salt thereof is administered simultaneously with, separate from or prior to the administration of a melanin concentrating hormone (MCH) receptor antagonist compound to augment the therapeutic effect or to provide a faster onset of the therapeutic effect of said melanin concentrating hormone (MCH) receptor antagonist compound, further characterized in that pipamperon is to be administered to a patient in a daily dose ranging between 5 and 15 mg of the active ingredient.

According to a preferred embodiment, the invention relates to the uses as described above, wherein said melanin concentrating hormone (MCH) receptor antagonist compound is SNAP-7941 or a pro-drug or an active metabolite thereof, or a pharmaceutically acceptable salt thereof.

The invention also relates to a pharmaceutical composition comprising (a) pipamperon, and (b) a melanin concentrating hormone (MCH) receptor antagonist compound, preferably SNAP-7941 or a pro-drug or an active metabolite thereof, or a pharmaceutically acceptable salt thereof, as a combined preparation for simultaneous, separate or sequential use for treating the underlying emotion dysregulation of a mental disease or disorder which is chosen from the group consisting of mood disorders, anxiety disorders, eating disorders, premenstrual syndrome, somatoform disorders (excluding pain disorders), factitious disorders, dissociative disorders, sexual and gender identity disorders, sleep disorders, adjustment disorders, impulse control disorders, substance-related disorders, personality disorders, bereavement, occupational problem, problems related to abuse or neglect and pain disorders.

56: Combination Therapy with a Melatonin Receptor (MT) Agonist Compound

The mental disorders which can be treated using compounds having a high selective affinity for the 5-HT2A and D4 receptor, for instance pipamperon, in a combination therapy with a melatonin receptor (MT) agonist compound, are chosen from the group of diseases or disorders consisting of mood disorders, anxiety disorders, eating disorders, premenstrual syndrome, somatoform disorders (excluding pain disorders), factitious disorders, dissociative disorders, sexual and gender identity disorders, sleep disorders, adjustment disorders, impulse control disorders, substance-related disorders, personality disorders, bereavement, occupational problem, problems related to abuse or neglect and pain disorders.

The present invention thus relates to the use of pipamperon or a pharmaceutically acceptable salt thereof for the preparation of a medicament for treating the underlying emotion dysregulation of a non-cognitive mental disease or disorder selected from the group of diseases and disorders consisting of mood disorders, anxiety disorders, eating disorders, premenstrual syndrome, somatoform disorders (excluding pain disorders), factitious disorders, dissociative disorders, sexual and gender identity disorders, sleep disorders, adjustment disorders, impulse control disorders, substance-related disorders, personality disorders, bereavement, occupational problem and problems related to abuse or neglect, characterized in that pipamperon or said pharmaceutically acceptable salt thereof is administered simultaneously with, separate from or prior to the administration of a melatonin receptor (MT) agonist compound to augment the therapeutic effect or to provide a faster onset of the therapeutic effect of said melatonin receptor (MT) agonist compound, further characterized in that pipamperon is to be administered to a patient in a daily dose ranging between 5 and 15 mg of the active ingredient.

The present invention thus relates to the use of pipamperon or a pharmaceutically acceptable salt thereof for the preparation of a medicament for treating the underlying emotion dysregulation of pain disorders, characterized in that pipamperon or said pharmaceutically acceptable salt thereof is administered simultaneously with, separate from or prior to the administration of a melatonin receptor (MT) agonist compound to augment the therapeutic effect or to provide a faster onset of the therapeutic effect of said melatonin receptor (MT) agonist compound, further characterized in that pipamperon is to be administered to a patient in a daily dose ranging between 5 and 15 mg of the active ingredient.

According to a preferred embodiment, the invention relates to the uses as described above, wherein said melatonin receptor (MT) agonist compound is chosen from the group consisting of ramelteon and agomelatine, or a pro-drug or an active metabolite thereof, or a pharmaceutically acceptable salt thereof. More preferably, said melatonin receptor (MT) agonist compound is agomelatine and is to be administered in a daily dose ranging between 25 and 50 mg of the active ingredient.

The invention also relates to a pharmaceutical composition comprising (a) pipamperon, and (b) a melatonin receptor (MT) agonist compound, preferably ramelteon or agomelatine or a pro-drug or an active metabolite thereof, or a pharmaceutically acceptable salt thereof, as a combined preparation for simultaneous, separate or sequential use for treating the underlying emotion dysregulation of a mental disease or disorder which is chosen from the group consisting of mood disorders, anxiety disorders, eating disorders, premenstrual syndrome, somatoform disorders (excluding pain disorders), factitious disorders, dissociative disorders, sexual and gender identity disorders, sleep disorders, adjustment disorders, impulse control disorders, substance-related disorders, personality disorders, bereavement, occupational problem, problems related to abuse or neglect and pain disorders.

The invention also relates to a pharmaceutical composition as described above wherein pipamperon is provided in a unitary dose of between 5 and 15 mg of the active ingredient and wherein said melatonin receptor (MT) agonist compound is agomelatine, preferably provided in a unitary dose of between 25 and 50 mg of the active ingredient.

57: Combination Therapy with a Metabotropic Glutamate Receptor (MgluR) Agonist Compound The mental disorders which can be treated using compounds having a high selective affinity for the 5-HT2A and D4 receptor, for instance pipamperon, in a combination therapy with a metabotropic glutamate receptor (MgluR) agonist compound, are chosen from the group of diseases or disorders consisting of anxiety disorders, somatoform disorders (excluding pain disorders), factitious disorders, dissociative disorders, adjustment disorders, impulse control disorders, substance-related disorders, personality disorders, bereavement, occupational problem, problems related to abuse or neglect and pain disorders.

The present invention thus relates to the use of pipamperon or a pharmaceutically acceptable salt thereof for the preparation of a medicament for treating the underlying emotion dysregulation of a non-cognitive mental disease or disorder selected from the group of diseases and disorders consisting of anxiety disorders, somatoform disorders (excluding pain disorders), factitious disorders, dissociative disorders, adjustment disorders, impulse control disorders, substance-related disorders, personality disorders, bereavement, occupational problem and problems related to abuse or neglect, characterized in that pipamperon or said pharmaceutically acceptable salt thereof is administered simultaneously with, separate from or prior to the administration of a metabotropic glutamate receptor (MgluR) agonist compound to augment the therapeutic effect or to provide a faster onset of the therapeutic effect of said metabotropic glutamate receptor (MgluR) agonist compound, further characterized in that pipamperon is to be administered to a patient in a daily dose ranging between 5 and 15 mg of the active ingredient.

The present invention thus relates to the use of pipamperon or a pharmaceutically acceptable salt thereof for the preparation of a medicament for treating the underlying emotion dysregulation of pain disorders, characterized in that pipamperon or said pharmaceutically acceptable salt thereof is administered simultaneously with, separate from or prior to the administration of a metabotropic glutamate receptor (MgluR) agonist compound to augment the therapeutic effect or to provide a faster onset of the therapeutic effect of said metabotropic glutamate receptor (MgluR) agonist compound, further characterized in that pipamperon is to be administered to a patient in a daily dose ranging between 5 and 15 mg of the active ingredient.

According to a preferred embodiment, the invention relates to the uses as described above, wherein said metabotropic glutamate receptor (MgluR) agonist compound is PRE703 or a pro-drug or an active metabolite thereof, or a pharmaceutically acceptable salt thereof.

The invention also relates to a pharmaceutical composition comprising (a) pipamperon, and (b) a metabotropic glutamate receptor (MgluR) agonist, preferably PRE703 or a pro-drug or an active metabolite thereof, or a pharmaceutically acceptable salt thereof, as a combined preparation for simultaneous, separate or sequential use for treating the underlying emotion dysregulation of a mental disease or disorder which is chosen from the group consisting of anxiety disorders, somatoform disorders (excluding pain disorders), factitious disorders, dissociative disorders, adjustment disorders, impulse control disorders, substance-related disorders, personality disorders, bereavement, occupational problem, problems related to abuse or neglect and pain disorders.

58: Combination Therapy with a Compound Mimicking the Effect of Nerve Growth Factor (NGF)

The mental disorders which can be treated using compounds having a high selective affinity for the 5-HT2A and D4 receptor, for instance pipamperon, in a combination therapy with a compound which mimics the effect of nerve growth factor (NGF), are chosen from the group of diseases or disorders consisting of Alzheimer Disease, substance-induced persisting dementia, vascular dementia, dementia due to HIV disease, dementia due to head trauma, dementia due to Parkinson Disease, dementia due to Huntington Disease, dementia due to Pick Disease, dementia due to Creutzfeldt-Jacob Disease, amnestic disorders due to a general medical condition, substance-induced persisting amnestic disorder, mild cognitive impairment disorder, other cognitive disorders and Parkinson Disease.

The present invention thus relates to the use of pipamperon or a pharmaceutically acceptable salt thereof for the preparation of a medicament for treating the underlying emotion dysregulation of a cognitive mental disease or disorder selected from the group of diseases and disorders consisting of Alzheimer Disease, substance-induced persisting dementia, vascular dementia, dementia due to HIV disease, dementia due to head trauma, dementia due to Parkinson Disease, dementia due to Huntington Disease, dementia due to Pick Disease, dementia due to Creutzfeldt-Jacob Disease, amnestic disorders due to a general medical condition, substance-induced persisting amnestic disorder, mild cognitive impairment disorder and other cognitive disorders, characterized in that pipamperon or said pharmaceutically acceptable salt thereof is administered simultaneously with, separate from or prior to the administration of a compound which mimics the effect of nerve growth factor (NGF) to augment the therapeutic effect or to provide a faster onset of the therapeutic effect of said compound which mimics the effect of nerve growth factor (NGF), further characterized in that pipamperon is to be administered to a patient in a daily dose ranging between 5 and 15 mg of the active ingredient.

The present invention thus relates to the use of pipamperon or a pharmaceutically acceptable salt thereof for the preparation of a medicament for treating the underlying emotion dysregulation of Parkinson Disease, characterized in that pipamperon or said pharmaceutically acceptable salt thereof is administered simultaneously with, separate from or prior to the administration of a compound which mimics the effect of nerve growth factor (NGF) to augment the therapeutic effect or to provide a faster onset of the therapeutic effect of said compound which mimics the effect of nerve growth factor (NGF), further characterized in that pipamperon is to be administered to a patient in a daily dose ranging between 5 and 15 mg of the active ingredient.

According to a preferred embodiment, the invention relates to the uses as described above, wherein said compound which mimics the effect of nerve growth factor (NGF) is xaliproden or a pro-drug or an active metabolite thereof, or a pharmaceutically acceptable salt thereof. More preferably, said compound which mimics the effect of nerve growth factor (NGF) is xaliproden and is to be administered in a daily dose ranging between 1 and 2 mg of the active ingredient.

The invention also relates to a pharmaceutical composition comprising (a) pipamperon, and (b) a compound which mimics the effect of nerve growth factor (NGF), preferably xaliproden or a pro-drug or an active metabolite thereof, or a pharmaceutically acceptable salt thereof, as a combined preparation for simultaneous, separate or sequential use for treating the underlying emotion dysregulation of a mental disease or disorder which is chosen from the group consisting of Alzheimer Disease, substance-induced persisting dementia, vascular dementia, dementia due to HIV disease, dementia due to head trauma, dementia due to Parkinson Disease, dementia due to Huntington Disease, dementia due to Pick Disease, dementia due to Creutzfeldt-Jacob Disease, amnestic disorders due to a general medical condition, substance-induced persisting amnestic disorder, mild cognitive impairment disorder, other cognitive disorders and Parkinson Disease.

The invention also relates to a pharmaceutical composition as described above wherein pipamperon is provided in a unitary dose of between 5 and 15 mg of the active ingredient and wherein said compound which mimics the effect of nerve growth factor (NGF) is xaliproden, preferably provided in a unitary dose of between 1 and 2 mg of the active ingredient.

59: Combination Therapy with a Muscarinic Receptor Partial Agonist Compound

The mental disorders which can be treated using compounds having a high selective affinity for the 5-HT2A and D4 receptor, for instance pipamperon, in a combination therapy with a muscarinic receptor partial agonist compound, are chosen from the group of diseases or disorders consisting of Alzheimer Disease, substance-induced persisting dementia, vascular dementia, dementia due to HIV disease, dementia due to head trauma, dementia due to Parkinson Disease, dementia due to Huntington Disease, dementia due to Pick Disease, dementia due to Creutzfeldt-Jacob Disease, amnestic disorders due to a general medical condition, substance-induced persisting amnestic disorder, mild cognitive impairment disorder and other cognitive disorders.

The present invention thus relates to the use of pipamperon or a pharmaceutically acceptable salt thereof for the preparation of a medicament for treating the underlying emotion dysregulation of a cognitive mental disease or disorder selected from the group of diseases and disorders consisting of Alzheimer Disease, substance-induced persisting dementia, vascular dementia, dementia due to HIV disease, dementia due to head trauma, dementia due to Parkinson Disease, dementia due to Huntington Disease, dementia due to Pick Disease, dementia due to Creutzfeldt-Jacob Disease, amnestic disorders due to a general medical condition, substance-induced persisting amnestic disorder, mild cognitive impairment disorder and other cognitive disorders, characterized in that pipamperon or said pharmaceutically acceptable salt thereof is administered simultaneously with, separate from or prior to the administration of a muscarinic receptor partial agonist compound to augment the therapeutic effect or to provide a faster onset of the therapeutic effect of said muscarinic receptor partial agonist compound, further characterized in that pipamperon is to be administered to a patient in a daily dose ranging between 5 and 15 mg of the active ingredient.

According to a preferred embodiment, the invention relates to the use as described above, wherein said muscarinic receptor partial agonist compound is sevimeline or a pro-drug or an active metabolite thereof, or a pharmaceutically acceptable salt thereof.

The invention also relates to a pharmaceutical composition comprising (a) pipamperon, and (b) a muscarinic receptor partial agonist compound, preferably sevimeline or a pro-drug or an active metabolite thereof, or a pharmaceutically acceptable salt thereof, as a combined preparation for simultaneous, separate or sequential use for treating the underlying emotion dysregulation of a mental disease or disorder which is chosen from the group consisting of Alzheimer Disease, substance-induced persisting dementia, vascular dementia, dementia due to HIV disease, dementia due to head trauma, dementia due to Parkinson Disease, dementia due to Huntington Disease, dementia due to Pick Disease, dementia due to Creutzfeldt-Jacob Disease, amnestic disorders due to a general medical condition, substance-induced persisting amnestic disorder, mild cognitive impairment disorder and other cognitive disorders.

60: Combination Therapy with a Selective Nor-Adrenaline Re-Uptake Inhibitor (NARI) Compound The mental disorders which can be treated using compounds having a high selective affinity for the 5-HT2A and D4 receptor, for instance pipamperon, in a combination therapy with a selective nor-adrenaline re-uptake inhibitor (NARI) compound, are chosen from the group of diseases or disorders consisting of mood disorders, anxiety disorders, adjustment disorders, attention-deficit disorders, personality disorders, antisocial behaviour, bereavement, occupational problem, problems related to abuse or neglect and pain disorders.

The present invention thus relates to the use of pipamperon or a pharmaceutically acceptable salt thereof for the preparation of a medicament for treating the underlying emotion dysregulation of a non-cognitive mental disease or disorder selected from the group of diseases and disorders consisting of mood disorders, anxiety disorders, adjustment disorders, attention-deficit disorders, personality disorders, antisocial behaviour, bereavement, occupational problem and problems related to abuse or neglect, characterized in that pipamperon or said pharmaceutically acceptable salt thereof is administered simultaneously with, separate from or prior to the administration of a selective nor-adrenaline re-uptake inhibitor (NARI) compound to augment the therapeutic effect or to provide a faster onset of the therapeutic effect of said selective nor-adrenaline re-uptake inhibitor (NARI) compound, further characterized in that pipamperon is to be administered to a patient in a daily dose ranging between 5 and 15 mg of the active ingredient.

The present invention thus relates to the use of pipamperon or a pharmaceutically acceptable salt thereof for the preparation of a medicament for treating the underlying emotion dysregulation of pain disorders, characterized in that pipamperon or said pharmaceutically acceptable salt thereof is administered simultaneously with, separate from or prior to the administration of a selective nor-adrenaline re-uptake inhibitor (NARI) compound to augment the therapeutic effect or to provide a faster onset of the therapeutic effect of said selective nor-adrenaline re-uptake inhibitor (NARI) compound, further characterized in that pipamperon is to be administered to a patient in a daily dose ranging between 5 and 15 mg of the active ingredient.

According to a preferred embodiment, the invention relates to the uses as described above, wherein said selective nor-adrenaline re-uptake inhibitor (NARI) compound is chosen from the group consisting of reboxetine, atomoxetine hydrochloride, A 75200, 155U88, (S)-A 75200, or a pro-drug or an active metabolite thereof, or a pharmaceutically acceptable salt thereof. More preferably, said selective nor-adrenaline re-uptake inhibitor (NARI) compound is reboxetine and is to be administered in a daily dose ranging between 8 and 12 mg of the active ingredient. More preferably, said selective nor-adrenaline re-uptake inhibitor (NARI) compound is atomoxetine hydrochloride and is to be administered in a daily dose ranging between 40 and 100 mg of the active ingredient.

The invention also relates to a pharmaceutical composition comprising (a) pipamperon, and (b) a selective nor-adrenaline re-uptake inhibitor (NARI) compound, preferably chosen from the group consisting of reboxetine, atomoxetine hydrochloride, A 75200, 155U88, (S)-A 75200, or a pro-drug or an active metabolite thereof, or a pharmaceutically acceptable salt thereof, as a combined preparation for simultaneous, separate or sequential use for treating the underlying emotion dysregulation of mental disease or disorder which is chosen from the group consisting of mood disorders, anxiety disorders, adjustment disorders, attention-deficit disorders, personality disorders, antisocial behaviour, bereavement, occupational problem, problems related to abuse or neglect and pain disorders.

The invention also relates to a pharmaceutical composition as described above wherein pipamperon is provided in a unitary dose of between 5 and 15 mg of the active ingredient and wherein said selective nor-adrenaline re-uptake inhibitor (NARI) compound is reboxetine, preferably provided in a unitary dose of between 8 and 12 mg of the active ingredient.

The invention also relates to a pharmaceutical composition as described above wherein pipamperon is provided in a unitary dose of between 5 and 15 mg of the active ingredient and wherein said selective nor-adrenaline re-uptake inhibitor (NARI) compound is atomoxetine hydrochloride, preferably provided in a unitary dose of between 40 and 100 mg of the active ingredient.

61. Combination Therapy with a NaSSA Compound

The mental disorders which can be treated using compounds having a high selective affinity for the 5-HT2A and D4 receptor, for instance pipamperon, in a combination therapy with a noradrenergic/specific serotonergic antidepressant (NaSSA) compound, are chosen from the group of diseases or disorders consisting of mood disorders, anxiety disorders, eating disorders, premenstrual syndrome, somatoform disorders (excluding pain disorders), factitious disorders, dissociative disorders, sexual and gender identity disorders, sleep disorders, adjustment disorders, impulse control disorders, personality disorders, antisocial behaviour, bereavement, occupational problem, problems related to abuse or neglect and pain disorders.

The present invention thus relates to the use of pipamperon or a pharmaceutically acceptable salt thereof for the preparation of a medicament for treating the underlying emotion dysregulation of a non-cognitive mental disease or disorder selected from the group of diseases and disorders consisting of mood disorders, anxiety disorders, eating disorders, premenstrual syndrome, somatoform disorders (excluding pain disorders), factitious disorders, dissociative disorders, sexual and gender identity disorders, sleep disorders, adjustment disorders, impulse control disorders, personality disorders, antisocial behaviour, bereavement, occupational problem and problems related to abuse or neglect, characterized in that pipamperon or said pharmaceutically acceptable salt thereof is administered simultaneously with, separate from or prior to the administration of a noradrenergic/specific serotonergic antidepressant (NaSSA) compound to augment the therapeutic effect or to provide a faster onset of the therapeutic effect of said noradrenergic/specific serotonergic antidepressant (NaSSA) compound, further characterized in that pipamperon is to be administered to a patient in a daily dose ranging between 5 and 15 mg of the active ingredient.

The present invention thus relates to the use of pipamperon or a pharmaceutically acceptable salt thereof for the preparation of a medicament for treating the underlying emotion dysregulation of pain disorders, characterized in that pipamperon or said pharmaceutically acceptable salt thereof is administered simultaneous y with, separate from or prior to the administration of a noradrenergic/specific serotonergic antidepressant (NaSSA) compound to augment the therapeutic effect or to provide a faster onset of the therapeutic effect of said noradrenergic/specific serotonergic antidepressant (NaSSA) compound, further characterized in that pipamperon is to be administered to a patient in a daily dose ranging between 5 and 15 mg of the active ingredient.

According to a preferred embodiment, the invention relates to the uses as described above, wherein said noradrenergic/specific serotonergic antidepressant (NaSSA) compound is ORG 4420 or a pro-drug or an active metabolite thereof, or a pharmaceutically acceptable salt thereof.

The invention also relates to a pharmaceutical composition comprising (a) pipamperon, and (b) a noradrenergic/specific serotonergic antidepressant (NaSSA) compound, preferably ORG 4420 or a pro-drug or an active metabolite thereof, or a pharmaceutically acceptable salt thereof, as a combined preparation for simultaneous, separate or sequential use for treating the underlying emotion dysregulation of mental disease or disorder which is chosen from the group consisting of mood disorders, anxiety disorders, eating disorders, premenstrual syndrome, somatoform disorders (excluding pain disorders), factitious disorders, dissociative disorders, sexual and gender identity disorders, sleep disorders, adjustment disorders, impulse control disorders, personality disorders, antisocial behaviour, bereavement, occupational problem, problems related to abuse or neglect and pain disorders.

62: Combination Therapy with a Selective NDRI Compound

The mental disorders which can be treated using compounds having a high selective affinity for the 5-HT2A and D4 receptor, for instance pipamperon, in a combination therapy with a selective nor-adrenaline and dopamine re-uptake inhibitor (NDRI) compound, are chosen from the group of diseases or disorders consisting of mood disorders, anxiety disorders, adjustment disorders, attention-deficit disorders, personality disorders, antisocial behaviour, bereavement, occupational problem, problems related to abuse or neglect, pain disorders, delirium, Alzheimer Disease, substance-induced persisting dementia, vascular dementia, dementia due to HIV disease, dementia due to head trauma, dementia due to Parkinson Disease, dementia due to Huntington Disease, dementia due to Pick Disease, dementia due to Creutzfeldt-Jacob Disease, amnestic disorders due to a general medical condition, substance-induced persisting amnestic disorder, mild cognitive impairment disorder and other cognitive disorders.

The present invention thus relates to the use of pipamperon or a pharmaceutically acceptable salt thereof for the preparation of a medicament for treating the underlying emotion dysregulation of a non-cognitive mental disease or disorder selected from the group of diseases and disorders consisting of mood disorders, anxiety disorders, adjustment disorders, attention-deficit disorders, personality disorders, antisocial behaviour, bereavement, occupational problem and problems related to abuse or neglect, characterized in that pipamperon or said pharmaceutically acceptable salt thereof is administered simultaneously with, separate from or prior to the administration of a selective nor-adrenaline and dopamine re-uptake inhibitor (NDRI) compound to augment the therapeutic effect or to provide a faster onset of the therapeutic effect of said selective nor-adrenaline and dopamine re-uptake inhibitor (NDRI) compound, further characterized in that pipamperon is to be administered to a patient in a daily dose ranging between 5 and 15 mg of the active ingredient.

The present invention thus relates to the use of pipamperon or a pharmaceutically acceptable salt thereof for the preparation of a medicament for treating the underlying emotion dysregulation of pain disorders, characterized in that pipamperon or said pharmaceutically acceptable salt thereof is administered simultaneously with, separate from or prior to the administration of a selective nor-adrenaline and dopamine re-uptake inhibitor (NDRI) compound to augment the therapeutic effect or to provide a faster onset of the therapeutic effect of said selective nor-adrenaline and dopamine re-uptake inhibitor (NDRI) compound, further characterized in that pipamperon is to be administered to a patient in a daily dose ranging between 5 and 15 mg of the active ingredient.

The present invention thus relates to the use of pipamperon or a pharmaceutically acceptable salt thereof for the preparation of a medicament for treating the underlying emotion dysregulation of a cognitive mental disease or disorder selected from the group of diseases and disorders consisting of delirium, Alzheimer Disease, substance-induced persisting dementia, vascular dementia, dementia due to HIV disease, dementia due to head trauma, dementia due to Parkinson Disease, dementia due to Huntington Disease, dementia due to Pick Disease, dementia due to Creutzfeldt-Jacob Disease, amnestic disorders due to a general medical condition, substance-induced persisting amnestic disorder, mild cognitive impairment disorder and other cognitive disorders, characterized in that pipamperon or said pharmaceutically acceptable salt thereof is administered simultaneously with, separate from or prior to the administration of a selective nor-adrenaline and dopamine re-uptake inhibitor (NDRI) compound to augment the therapeutic effect or to provide a faster onset of the therapeutic effect of said selective nor-adrenaline and dopamine re-uptake inhibitor (NDRI) compound, further characterized in that pipamperon is to be administered to a patient in a daily dose ranging between 5 and 15 mg of the active ingredient.

According to a preferred embodiment, the invention relates to the uses as described above, wherein said selective nor-adrenaline and dopamine re-uptake inhibitor (NDRI) compound is GW353162 or a pro-drug or an active metabolite thereof, or a pharmaceutically acceptable salt thereof. More preferably, said selective nor-adrenaline and dopamine re-uptake inhibitor (NDRI) compound is GW353162 and is to be administered in a daily dose ranging between 20 and 60 mg of the active ingredient.

The invention also relates to a pharmaceutical composition comprising (a) pipamperon, and (b) a selective nor-adrenaline and dopamine re-uptake inhibitor (NDRI) compound, preferably GW353162 or a pro-drug or an active metabolite thereof, or a pharmaceutically acceptable salt thereof, as a combined preparation for simultaneous, separate or sequential use for treating the underlying emotion dysregulation of mental disease or disorder which is chosen from the group consisting of mood disorders, anxiety disorders, adjustment disorders, attention-deficit disorders, personality disorders, antisocial behaviour, bereavement, occupational problem, problems related to abuse or neglect, pain disorders, delirium, Alzheimer Disease, substance-induced persisting dementia, vascular dementia, dementia due to HIV disease, dementia due to head trauma, dementia due to Parkinson Disease, dementia due to Huntington Disease, dementia due to Pick Disease, dementia due to Creutzfeldt-Jacob Disease, amnestic disorders due to a general medical condition, substance-induced persisting amnestic disorder, mild cognitive impairment disorder and other cognitive disorders.

The invention also relates to a pharmaceutical composition as described above wherein pipamperon is provided in a unitary dose of between 5 and 15 mg of the active ingredient and wherein said selective nor-adrenaline and dopamine re-uptake inhibitor (NDRI) compound is GW353162, preferably provided in a unitary dose of between 20 and 60 mg of the active ingredient.

63: Combination Therapy with a Compound which is a Neuroimmunophilin Ligand

The mental disorder which can be treated using compounds having a high selective affinity for the 5-HT2A and D4 receptor, for instance pipamperon, in a combination therapy with a compound which is a neuroimmunophilin ligand, is Parkinson Disease.

The present invention thus relates to the use of pipamperon or a pharmaceutically acceptable salt thereof for the preparation of a medicament for treating the underlying emotion dysregulation of Parkinson Disease, characterized in that pipamperon or said pharmaceutically acceptable salt thereof is administered simultaneously with, separate from or prior to the administration of a compound which is a neuroimmunophilin ligand to augment the therapeutic effect or to provide a faster onset of the therapeutic effect of said compound which is a neuroimmunophilin ligand, further characterized in that pipamperon is to be administered to a patient in a daily dose ranging between 5 and 15 mg of the active ingredient.

According to a preferred embodiment, the invention relates to the use as described above, wherein said a compound which is a neuroimmunophilin ligand is GPI 1485 or a pro-drug or an active metabolite thereof, or a pharmaceutically acceptable salt thereof. More preferably, said a compound which is a neuroimmunophilin ligand is GPI 1485 and is to be administered in a daily dose ranging between 200 and 1000 mg of the active ingredient.

The invention also relates to a pharmaceutical composition comprising (a) pipamperon, and (b) a compound which is a neuroimmunophilin ligand, preferably GPI 1485 or a pro-drug or an active metabolite thereof, or a pharmaceutically acceptable salt thereof, as a combined preparation for simultaneous, separate or sequential use for treating the underlying emotion dysregulation of Parkinson Disease.

The invention also relates to a pharmaceutical composition as described above wherein pipamperon is provided in a unitary dose of between 5 and 15 mg of the active ingredient and wherein said a compound which is a neuroimmunophilin ligand is GPI 1485, preferably provided in a unitary dose of between 200 and 1000 mg of the active ingredient.

64: Combination Therapy with a Neuromodulator Compound

The mental disorder which can be treated using compounds having a high selective affinity for the 5-HT2A and D4 receptor, for instance pipamperon, in a combination therapy with a neuromodulator compound, is Parkinson Disease.

The present invention thus relates to the use of pipamperon or a pharmaceutically acceptable salt thereof for the preparation of a medicament for treating the underlying emotion dysregulation of Parkinson Disease, characterized in that pipamperon or said pharmaceutically acceptable salt thereof is administered simultaneously with, separate from or prior to the administration of a neuromodulator compound to augment the therapeutic effect or to provide a faster onset of the therapeutic effect of said neuromodulator compound, further characterized in that pipamperon is to be administered to a patient in a daily dose ranging between 5 and 15 mg of the active ingredient.

According to a preferred embodiment, the invention relates to the use as described above, wherein said neuromodulator compound is adenosine or a pro-drug or an active metabolite thereof, or a pharmaceutically acceptable salt thereof.

The invention also relates to a pharmaceutical composition comprising (a) pipamperon, and (b) a neuromodulator compound, preferably adenosine or a pro-drug or an active metabolite thereof, or a pharmaceutically acceptable salt thereof, as a combined preparation for simultaneous, separate or sequential use for treating the underlying emotion dysregulation of Parkinson Disease.

65: Combination Therapy with a Neurotensin Receptor Antagonist Compound

The mental disorders which can be treated using compounds having a high selective affinity for the 5-HT2A and D4 receptor, for instance pipamperon, in a combination therapy with a neurotensin receptor antagonist compound, are chosen from the group of diseases or disorders consisting of mood disorders, anxiety disorders, psychotic disorders, somatoform disorders (excluding pain disorders), factitious disorders, dissociative disorders, sleep disorders, adjustment disorders, impulse control disorders, pervasive development disorders, disruptive behaviour disorders, substance-related disorders, personality disorders, psychological factors affecting medical conditions, malingering, antisocial behaviour, bereavement, occupational problem, identity problem, problems related to abuse or neglect, pain disorders and delirium.

The present invention thus relates to the use of pipamperon or a pharmaceutically acceptable salt thereof for the preparation of a medicament for treating the underlying emotion dysregulation of a non-cognitive mental disease or disorder selected from the group of diseases and disorders consisting of mood disorders, anxiety disorders, psychotic disorders, somatoform disorders (excluding pain disorders), factitious disorders, dissociative disorders, sleep disorders, adjustment disorders, impulse control disorders, pervasive development disorders, disruptive behaviour disorders, substance-related disorders, personality disorders, psychological factors affecting medical conditions, malingering, antisocial behaviour, bereavement, occupational problem, identity problem and problems related to abuse or neglect, characterized in that pipamperon or said pharmaceutically acceptable salt thereof is administered simultaneously with, separate from or prior to the administration of a neurotensin receptor antagonist compound to augment the therapeutic effect or to provide a faster onset of the therapeutic effect of said neurotensin receptor antagonist compound, further characterized in that pipamperon is to be administered to a patient in a daily dose ranging between 5 and 15 mg of the active ingredient.

The present invention thus relates to the use of pipamperon or a pharmaceutically acceptable salt thereof for the preparation of a medicament for treating the underlying emotion dysregulation of pain disorders, characterized in that pipamperon or said pharmaceutically acceptable sat thereof is administered simultaneously with, separate from or prior to the administration of a neurotensin receptor antagonist compound to augment the therapeutic effect or to provide a faster onset of the therapeutic effect of said neurotensin receptor antagonist compound, further characterized in that pipamperon is to be administered to a patient in a daily dose ranging between 5 and 15 mg of the active ingredient.

The present invention thus relates to the use of pipamperon or a pharmaceutically acceptable salt thereof for the preparation of a medicament for treating the underlying emotion dysregulation of a cognitive mental disease or disorder which is delirium, characterized in that pipamperon or said pharmaceutically acceptable salt thereof is administered simultaneously with, separate from or prior to the administration of a neurotensin receptor antagonist compound to augment the therapeutic effect or to provide a faster onset of the therapeutic effect of said neurotensin receptor antagonist compound, further characterized in that pipamperon is to be administered to a patient in a daily dose ranging between 5 and 15 mg of the active ingredient.

According to a preferred embodiment, the invention relates to the use as described above, wherein said neurotensin receptor antagonist compound is SR 48692 or a pro-drug or an active metabolite thereof, or a pharmaceutically acceptable salt thereof. More preferably, said neurotensin receptor antagonist compound is SR 48692 and is to be administered in a daily dose ranging between 90 and 300 mg of the active ingredient.

The invention also relates to a pharmaceutical composition comprising (a) pipamperon, and (b) a neurotensin receptor antagonist compound, preferably SR 48692 or a pro-drug or an active metabolite thereof, or a pharmaceutically acceptable salt thereof, as a combined preparation for simultaneous, separate or sequential use for treating the underlying emotion dysregulation of a mental disease or disorder which is chosen from the group consisting mood disorders, anxiety disorders, psychotic disorders, somatoform disorders (excluding pain disorders), factitious disorders, dissociative disorders, sleep disorders, adjustment disorders, impulse control disorders, pervasive development disorders, disruptive behaviour disorders, substance-related disorders, personality disorders, psychological factors affecting medical conditions, malingering, antisocial behaviour, bereavement, occupational problem, identity problem, problems related to abuse or neglect, pain disorders and delirium.

The invention also relates to a pharmaceutical composition as described above wherein pipamperon is provided in a unitary dose of between 5 and 15 mg of the active ingredient and wherein said neurotensin receptor antagonist compound is SR 48692, preferably provided in a unitary dose of between 90 and 300 mg of the active ingredient.

66: Combination Therapy with Nerve Growth Factor (NGF) Gene Therapy

The mental disorders which can be treated using compounds having a high selective affinity for the 5-HT2A and D4 receptor, for instance pipamperon, in a combination therapy with nerve growth factor (NGF) gene therapy, are chosen from the group of diseases or disorders consisting of Alzheimer Disease, substance-induced persisting dementia, vascular dementia, dementia due to HIV disease, dementia due to head trauma, dementia due to Parkinson Disease, dementia due to Huntington Disease, dementia due to Pick Disease, dementia due to Creutzfeldt-Jacob Disease, amnestic disorders due to a general medical condition, substance-induced persisting amnestic disorder, mild cognitive impairment disorder, other cognitive disorders and Parkinson Disease.

The present invention thus relates to the use of pipamperon or a pharmaceutically acceptable salt thereof for the preparation of a medicament for treating the underlying emotion dysregulation of a cognitive mental disease or disorder selected from the group of diseases and disorders consisting of Alzheimer Disease, substance-induced persisting dementia, vascular dementia, dementia due to HIV disease, dementia due to head trauma, dementia due to Parkinson Disease, dementia due to Huntington Disease, dementia due to Pick Disease, dementia due to Creutzfeldt-Jacob Disease, amnestic disorders due to a general medical condition, substance-induced persisting amnestic disorder, mild cognitive impairment disorder and other cognitive disorders, characterized in that pipamperon or said pharmaceutically acceptable salt thereof is administered simultaneously with, separate from nerve growth factor (NGF) gene therapy, to augment the therapeutic effect or to provide a faster onset of the therapeutic effect of said nerve growth factor (NGF) gene therapy, further characterized in that pipamperon is to be administered to a patient in a daily dose ranging between 5 and 15 mg of the active ingredient.

The present invention thus relates to the use of pipamperon or a pharmaceutically acceptable salt thereof for the preparation of a medicament for treating the underlying emotion dysregulation of Parkinson Disease, characterized in that pipamperon or said pharmaceutically acceptable salt thereof is administered simultaneously with, separate from or prior to nerve growth factor (NGF) gene therapy, to augment the therapeutic effect or to provide a faster onset of nerve growth factor (NGF) gene therapy, further characterized in that pipamperon is to be administered to a patient in a daily dose ranging between 5 and 15 mg of the active ingredient.

The invention also relates to a pharmaceutical composition comprising (a) pipamperon, and (b) a compound useful in nerve growth factor (NGF) gene therapy, preferably xaliproden or a pro-drug or an active metabolite thereof, or a pharmaceutically acceptable salt thereof, as a combined preparation for simultaneous, separate or sequential use for treating the underlying emotion dysregulation of a mental disease or disorder which is chosen from the group consisting of Alzheimer Disease, substance-induced persisting dementia, vascular dementia, dementia due to HIV disease, dementia due to head trauma, dementia due to Parkinson Disease, dementia due to Huntington Disease, dementia due to Pick Disease, dementia due to Creutzfeldt-Jacob Disease, amnestic disorders due to a general medical condition, substance-induced persisting amnestic disorder, mild cognitive impairment disorder, other cognitive disorders and Parkinson Disease.

It should be understood that "nerve growth factor gene therapy" is well known in the art, and the compounds, for instance nucleic acids used in nerve growth factor gene therapy are well described (see e.g. Tuszynski et al., (2002) Journal of Molecular Neuroscience Volume 19, Issue 1-2, pps. 207-208).

67: Combination Therapy with a Nicotinic Acetylcholine Receptor Antagonist Compound The mental disorders which can be treated using compounds having a high selective affinity for the 5-HT2A and D4 receptor, for instance pipamperon, in a combination therapy with a nicotinic acetylcholine receptor antagonist compound, are chosen from the group of diseases or disorders consisting of anxiety disorders, somatoform disorders (excluding pain disorders), factitious disorders, dissociative disorders, adjustment disorders, impulse control disorders, substance-related disorders, personality disorders, bereavement, occupational problem, problems related to abuse or neglect and pain disorders.

The present invention thus relates to the use of pipamperon or a pharmaceutically acceptable salt thereof for the preparation of a medicament for treating the underlying emotion dysregulation of a non-cognitive mental disease or disorder selected from the group of diseases and disorders consisting of anxiety disorders, somatoform disorders (excluding pain disorders), factitious disorders, dissociative disorders, adjustment disorders, impulse control disorders, substance-related disorders, personality disorders, bereavement, occupational problem and problems related to abuse or neglect, characterized in that pipamperon or said pharmaceutically acceptable salt thereof is administered simultaneously with, separate from or prior to the administration of a nicotinic acetylcholine receptor antagonist compound to augment the therapeutic effect or to provide a faster onset of the therapeutic effect of said nicotinic acetylcholine receptor antagonist compound, further characterized in that pipamperon is to be administered to a patient in a daily dose ranging between 5 and 15 mg of the active ingredient.

The present invention thus relates to the use of pipamperon or a pharmaceutically acceptable salt thereof for the preparation of a medicament for treating the underlying emotion dysregulation of pain disorders, characterized in that pipamperon or said pharmaceutically acceptable salt thereof is administered simultaneously with, separate from or prior to the administration of a nicotinic acetylcholine receptor antagonist compound to augment the therapeutic effect or to provide a faster onset of the therapeutic effect of said nicotinic acetylcholine receptor antagonist compound, further characterized in that pipamperon is to be administered to a patient in a daily dose ranging between 5 and 15 mg of the active ingredient.

According to a preferred embodiment, the invention relates to the uses as described above, wherein said nicotinic acetylcholine receptor antagonist compound is SEP174559 or a pro-drug or an active metabolite thereof, or a pharmaceutically acceptable salt thereof.

The invention also relates to a pharmaceutical composition comprising (a) pipamperon, and (b) a nicotinic acetylcholine receptor antagonist compound, preferably SEP174559 or a pro-drug or an active metabolite thereof, or a pharmaceutically acceptable salt thereof, as a combined preparation for simultaneous, separate or sequential use for treating the underlying emotion dysregulation of a mental disease or disorder which is chosen from the group consisting of anxiety disorders, somatoform disorders (excluding pain disorders), factitious disorders, dissociative disorders, adjustment disorders, impulse control disorders, substance-related disorders, personality disorders, bereavement, occupational problem, problems related to abuse or neglect and pain disorders.

68: Combination Therapy with a Nicotinic Receptor Agonist Compound

The mental disorders which can be treated using compounds having a high selective affinity for the 5-HT2A and D4 receptor, for instance pipamperon, in a combination therapy with a nicotinic receptor agonist compound, are chosen from the group of diseases or disorders consisting of Alzheimer Disease, substance-induced persisting dementia, vascular dementia, dementia due to HIV disease, dementia due to head trauma, dementia due to Parkinson Disease, dementia due to Huntington Disease, dementia due to Pick Disease, dementia due to Creutzfeldt-Jacob Disease, amnestic disorders due to a general medical condition, substance-induced persisting amnestic disorder, mild cognitive impairment disorder and other cognitive disorders.

The present invention thus relates to the use of pipamperon or a pharmaceutically acceptable salt thereof for the preparation of a medicament for treating the underlying emotion dysregulation of a cognitive mental disease or disorder selected from the group of diseases and disorders consisting of Alzheimer Disease, substance-induced persisting dementia, vascular dementia, dementia due to HIV disease, dementia due to head trauma, dementia due to Parkinson Disease, dementia due to Huntington Disease, dementia due to Pick Disease, dementia due to Creutzfeldt-Jacob Disease, amnestic disorders due to a general medical condition, substance-induced persisting amnestic disorder, mild cognitive impairment disorder and other cognitive disorders, characterized in that pipamperon or said pharmaceutically acceptable salt thereof is administered simultaneously with, separate from or prior to the administration of a nicotinic receptor agonist compound to augment the therapeutic effect or to provide a faster onset of the therapeutic effect of said nicotinic receptor agonist compound, further characterized in that pipamperon is to be administered to a patient in a daily dose ranging between 5 and 15 mg of the active ingredient.

According to a preferred embodiment, the invention relates to the use as described above, wherein said nicotinic receptor agonist compound is ABT-089, or a pro-drug or an active metabolite thereof, or a pharmaceutically acceptable salt thereof. More preferably, said nicotinic receptor agonist compound is ABT-089 and is to be administered in a daily dose ranging between 4 and 40 mg of the active ingredient.

The invention also relates to a pharmaceutical composition comprising (a) pipamperon, and (b) a nicotinic receptor agonist compound, preferably ABT-089 or a pro-drug or an active metabolite thereof, or a pharmaceutically acceptable salt thereof, as a combined preparation for simultaneous, separate or sequential use for treating the underlying emotion dysregulation of a cognitive mental disease or disorder which is chosen from the group consisting of Alzheimer Disease, substance-induced persisting dementia, vascular dementia, dementia due to HIV disease, dementia due to head trauma, dementia due to Parkinson Disease, dementia due to Huntington Disease, dementia due to Pick Disease, dementia due to Creutzfeldt-Jacob Disease, amnestic disorders due to a general medical condition, substance-induced persisting amnestic disorder, mild cognitive impairment disorder and other cognitive disorders.

The invention also relates to a pharmaceutical composition as described above, wherein pipamperon is provided in a unitary dose of between 5 and 15 mg of the active ingredient and wherein said nicotinic receptor agonist compound is ABT-089, preferably provided in a unitary dose of between 4 and 40 mg of the active ingredient.

69: Combination Therapy with a Neurokinin 2 Receptor (NK2) Antagonist Compound The mental disorders which can be treated using compounds having a high selective affinity for the 5-HT2A and D4 receptor, for instance pipamperon, in a combination therapy with a neurokinin 2 receptor (NK2) antagonist compound, are chosen from the group of diseases or disorders consisting of mood disorders, anxiety disorders, eating disorders, premenstrual syndrome, somatoform disorders (excluding pain disorders), factitious disorders, dissociative disorders, sexual and gender identity disorders, sleep disorders, adjustment disorders, impulse control disorders, substance-related disorders, personality disorders, bereavement, occupational problem, problems related to abuse or neglect and pain disorders.

The present invention thus relates to the use of pipamperon or a pharmaceutically acceptable salt thereof for the preparation of a medicament for treating the underlying emotion dysregulation of a non-cognitive mental disease or disorder selected from the group of diseases and disorders consisting of mood disorders, anxiety disorders, eating disorders, premenstrual syndrome, somatoform disorders (excluding pain disorders), factitious disorders, dissociative disorders, sexual and gender identity disorders, sleep disorders, adjustment disorders, impulse control disorders, substance-related disorders, personality disorders, bereavement, occupational problem and problems related to abuse or neglect, characterized in that pipamperon or said pharmaceutically acceptable salt thereof is administered simultaneously with, separate from or prior to the administration of a neurokinin 2 receptor (NK2) antagonist compound to augment the therapeutic effect or to provide a faster onset of the therapeutic effect of said neurokinin 2 receptor (NK2) antagonist compound, further characterized in that pipamperon is to be administered to a patient in a daily dose ranging between 5 and 15 mg of the active ingredient.

The present invention thus relates to the use of pipamperon or a pharmaceutically acceptable salt thereof for the preparation of a medicament for treating the underlying emotion dysregulation of pain disorders, characterized in that pipamperon or said pharmaceutically acceptable salt thereof is administered simultaneously with, separate from or prior to the administration of a neurokinin 2 receptor (NK2) antagonist compound to augment the therapeutic effect or to provide a faster onset of the therapeutic effect of said neurokinin 2 receptor (NK2) antagonist compound, further characterized in that pipamperon is to be administered to a patient in a daily dose ranging between 5 and 15 mg of the active ingredient.

According to a preferred embodiment, the invention relates to the uses as described above, wherein said neurokinin 2 receptor (NK2) antagonist compound is saredutant or a pro-drug or an active metabolite thereof, or a pharmaceutically acceptable salt thereof. More preferably, said neurokinin 2 receptor (NK2) antagonist compound is saredutant and is to be administered in a daily dose ranging between 25 and 200 mg of the active ingredient.

The invention also relates to a pharmaceutical composition comprising (a) pipamperon, and (b) a neurokinin 2 receptor (NK2) antagonist compound, preferably saredutant or a pro-drug or an active metabolite thereof, or a pharmaceutically acceptable salt thereof, as a combined preparation for simultaneous, separate or sequential use for treating the underlying emotion dysregulation of a mental disease or disorder which is chosen from the group consisting of mood disorders, anxiety disorders, eating disorders, premenstrual syndrome, somatoform disorders (excluding pain disorders), factitious disorders, dissociative disorders, sexual and gender identity disorders, sleep disorders, adjustment disorders, impulse control disorders, substance-related disorders, personality disorders, bereavement, occupational problem, problems related to abuse or neglect and pain disorders.

The invention also relates to a pharmaceutical composition as described above wherein pipamperon is provided in a unitary dose of between 5 and 15 mg of the active ingredient and wherein said neurokinin 2 receptor (NK2) antagonist compound is saredutant, preferably provided in a unitary dose of between 25 and 200 mg of the active ingredient.

70: Combination Therapy with a Neurokinin 3 Receptor (NK3) Antagonist Compound

The mental disorders which can be treated using compounds having a high selective affinity for the 5-HT2A and D4 receptor, for instance pipamperon, in a combination therapy with a neurokinin 3 receptor (NK3) antagonist compound, are chosen from the group of diseases or disorders consisting of mood disorders, anxiety disorders, psychotic disorders, somatoform disorders (excluding pain disorders), factitious disorders, dissociative disorders, sleep disorders, adjustment disorders, impulse control disorders, pervasive development disorders, disruptive behaviour disorders, substance-related disorders, personality disorders, psychological factors affecting medical conditions, malingering, antisocial behaviour, bereavement, occupational problem, identity problem, problems related to abuse or neglect, pain disorders and delirium.

The present invention thus relates to the use of pipamperon or a pharmaceutically acceptable salt thereof for the preparation of a medicament for treating the underlying emotion dysregulation of a non-cognitive mental disease or disorder selected from the group of diseases and disorders consisting of mood disorders, anxiety disorders, psychotic disorders, somatoform disorders (excluding pain disorders), factitious disorders, dissociative disorders, sleep disorders, adjustment disorders, impulse control disorders, pervasive development disorders, disruptive behaviour disorders, substance-related disorders, personality disorders, psychological factors affecting medical conditions, malingering, antisocial behaviour, bereavement, occupational problem, identity problem and problems related to abuse or neglect, characterized in that pipamperon or said pharmaceutically acceptable salt thereof is administered simultaneously with, separate from or prior to the administration of a neurokinin 3 receptor (NK3) antagonist compound to augment the therapeutic effect or to provide a faster onset of the therapeutic effect of said neurokinin 3 receptor (NK3) antagonist compound, further characterized in that pipamperon is to be administered to a patient in a daily dose ranging between 5 and 15 mg of the active ingredient.

The present invention thus relates to the use of pipamperon or a pharmaceutically acceptable salt thereof for the preparation of a medicament for treating the underlying emotion dysregulation of pain disorders, characterized in that pipamperon or said pharmaceutically acceptable salt thereof is administered simultaneously with, separate from or prior to the administration of a neurokinin 3 receptor (NK3) antagonist compound to augment the therapeutic effect or to provide a faster onset of the therapeutic effect of said neurokinin 3 receptor (NK3) antagonist compound, further characterized in that pipamperon is to be administered to a patient in a daily dose ranging between 5 and 15 mg of the active ingredient.

The present invention thus relates to the use of pipamperon or a pharmaceutically acceptable salt thereof for the preparation of a medicament for treating the underlying emotion dysregulation of a cognitive mental disease or disorder which is delirium, characterized in that pipamperon or said pharmaceutically acceptable salt thereof is administered simultaneously with, separate from or prior to the administration of a neurokinin 3 receptor (NK3) antagonist compound to augment the therapeutic effect or to provide a faster onset of the therapeutic effect of said neurokinin 3 receptor (NK3) antagonist compound, further characterized in that pipamperon is to be administered to a patient in a daily dose ranging between 5 and 15 mg of the active ingredient.

According to a preferred embodiment, the invention relates to the uses as described above, wherein said neurokinin 3 receptor (NK3) antagonist compound is talnetant or osanetant, or a pro-drug or an active metabolite thereof, or a pharmaceutically acceptable salt thereof. More preferably, said neurokinin 3 receptor (NK3) antagonist compound is talnetant and is to be administered in a daily dose ranging between 1.5 and 12 mg of the active ingredient.

The invention also relates to a pharmaceutical composition comprising (a) pipamperon, and (b) a neurokinin 3 receptor (NK3) antagonist compound, preferably talnetant or osanetant, or a pro-drug or an active metabolite thereof, or a pharmaceutically acceptable salt thereof, as a combined preparation for simultaneous, separate or sequential use for treating the underlying emotion dysregulation of a mental disease or disorder which is chosen from the group consisting mood disorders, anxiety disorders, psychotic disorders, somatoform disorders (excluding pain disorders), factitious disorders, dissociative disorders, sleep disorders, adjustment disorders, impulse control disorders, pervasive development disorders, disruptive behaviour disorders, substance-related disorders, personality disorders, psychological factors affecting medical conditions, malingering, antisocial behaviour, bereavement, occupational problem, identity problem, problems related to abuse or neglect, pain disorders and delirium.

The invention also relates to a pharmaceutical composition as described above wherein pipamperon is provided in a unitary dose of between 5 and 15 mg of the active ingredient and wherein said neurokinin 3 receptor (NK3) antagonist compound is talnetant, preferably provided in a unitary dose of between 1.5 and 12 mg of the active ingredient.

71: Combination Therapy with an N-Methyl-D-aspartate (NMDA) Antagonist Compound

The mental disorders which can be treated using compounds having a high selective affinity for the 5-HT2A and D4 receptor, for instance pipamperon, in a combination therapy with an N-Methyl-D-aspartate (NMDA) antagonist compound, are chosen from the group of diseases or disorders consisting of mood disorders, anxiety disorders, eating disorders, premenstrual syndrome, somatoform disorders (excluding pain disorders), factitious disorders, dissociative disorders, sexual and gender identity disorders, adjustment disorders, impulse control disorders, personality disorders, bereavement, occupational problem, problems related to abuse or neglect, pain disorders, Alzheimer Disease, substance-related persisting dementia, vascular dementia, dementia due to HIV disease, dementia due to head trauma, dementia due to Parkinson Disease, dementia due to Huntington Disease, dementia due to Pick Disease, dementia due to Creutzfeldt-Jacob Disease, amnestic disorders due to a general medical condition, substance-induced persisting amnestic disorder, mild cognitive impairment disorder and other cognitive disorders.

The present invention thus relates to the use of pipamperon or a pharmaceutically acceptable salt thereof for the preparation of a medicament for treating the underlying emotion dysregulation of a non-cognitive mental disease or disorder selected from the group of diseases and disorders consisting of mood disorders, anxiety disorders, eating disorders, premenstrual syndrome, somatoform disorders (excluding pain disorders), factitious disorders, dissociative disorders, sexual and gender identity disorders, adjustment disorders, impulse control disorders, personality disorders, bereavement, occupational problem and problems related to abuse or neglect, characterized in that pipamperon or said pharmaceutically acceptable salt thereof is administered simultaneously with, separate from or prior to the administration of an N-Methyl-D-aspartate (NMDA) antagonist compound to augment the therapeutic effect or to provide a faster onset of the therapeutic effect of said N-Methyl-D-aspartate (NMDA) antagonist compound, further characterized in that pipamperon is to be administered to a patient in a daily dose ranging between 5 and 15 mg of the active ingredient.

The present invention thus relates to the use of pipamperon or a pharmaceutically acceptable salt thereof for the preparation of a medicament for treating the underlying emotion dysregulation of pain disorders, characterized in that pipamperon or said pharmaceutically acceptable salt thereof is administered simultaneously with, separate from or prior to the administration of an N-Methyl-D-aspartate (NMDA) antagonist compound to augment the therapeutic effect or to provide a faster onset of the therapeutic effect of said N-Methyl-D-aspartate (NMDA) antagonist compound, further characterized in that pipamperon is to be administered to a patient in a daily dose ranging between 5 and 15 mg of the active ingredient.

The present invention thus relates to the use of pipamperon or a pharmaceutically acceptable salt thereof for the preparation of a medicament for treating the underlying emotion dysregulation of a cognitive mental disease or disorder selected from the group of diseases and disorders consisting of Alzheimer Disease, substance-related persisting dementia, vascular dementia, dementia due to HIV disease, dementia due to head trauma, dementia due to Parkinson Disease, dementia due to Huntington Disease, dementia due to Pick Disease, dementia due to Creutzfeldt-Jacob Disease, amnestic disorders due to a general medical condition, substance-induced persisting amnestic disorder, mild cognitive impairment disorder and other cognitive disorders, characterized in that pipamperon or said pharmaceutically acceptable salt thereof is administered simultaneously with, separate from or prior to the administration of an N-Methyl-D-aspartate (NMDA) antagonist compound to augment the therapeutic effect or to provide a faster onset of the therapeutic effect of said N-Methyl-D-aspartate (NMDA) antagonist compound, further characterized in that pipamperon is to be administered to a patient in a daily dose ranging between 5 and 15 mg of the active ingredient.

According to a preferred embodiment, the invention relates to the uses as described above, wherein said N-Methyl-D-aspartate (NMDA) antagonist compound is chosen from the group consisting of SEP174559, memantine, delucemine, or a pro-drug or an active metabolite thereof, or a pharmaceutically acceptable salt thereof. More preferably, said N-Methyl-D-aspartate (NMDA) antagonist compound is memantine and is to be administered in a daily dose ranging between 5 and 40 mg of the active ingredient.

The invention also relates to a pharmaceutical composition comprising (a) pipamperon, and (b) an N-Methyl-D-aspartate (NMDA) antagonist compound, preferably chosen from the group consisting of SEP174559, memantine, delucemine or a pro-drug or an active metabolite thereof, or a pharmaceutically acceptable salt thereof, as a combined preparation for simultaneous, separate or sequential use for treating the underlying emotion dysregulation of mental disease or disorder which is chosen from the group consisting of mood disorders, anxiety disorders, eating disorders, premenstrual syndrome, somatoform disorders (excluding pain disorders), factitious disorders, dissociative disorders, sexual and gender identity disorders, adjustment disorders, impulse control disorders, personality disorders, bereavement, occupational problem, problems related to abuse or neglect, pain disorders, Alzheimer Disease, substance-related persisting dementia, vascular dementia, dementia due to HIV disease, dementia due to head trauma, dementia due to Parkinson Disease, dementia due to Huntington Disease, dementia due to Pick Disease, dementia due to Creutzfeldt-Jacob Disease, amnestic disorders due to a general medical condition, substance-induced persisting amnestic disorder, mild cognitive impairment disorder and other cognitive disorders.

The invention also relates to a pharmaceutical composition as described above wherein pipamperon is provided in a unitary dose of between 5 and 15 mg of the active ingredient and wherein said N-Methyl-D-aspartate (NMDA) antagonist compound is memantine, preferably provided in a unitary dose of between 5 and 40 mg of the active ingredient.

72: Combination Therapy with a Non-Steroidal Anti-Inflammatory Drug

The mental disorder which can be treated using compounds having a high selective affinity for the 5-HT2A and D4 receptor, for instance pipamperon, in a combination therapy with a non-steroidal anti-inflammatory drug, is a pain disorder or Alzheimer Disease.

The present invention thus relates to the use of pipamperon or a pharmaceutically acceptable salt thereof for the preparation of a medicament for treating the underlying emotion dysregulation of a pain disorder, characterized in that pipamperon or said pharmaceutically acceptable salt thereof is administered simultaneously with, separate from or prior to the administration of a non-steroidal anti-inflammatory drug to augment the therapeutic effect or to provide a faster onset of the therapeutic effect of said a non-steroidal anti-inflammatory drug, further characterized in that pipamperon is to be administered to a patient in a daily dose ranging between 5 and 15 mg of the active ingredient.

The present invention thus relates to the use of pipamperon or a pharmaceutically acceptable salt thereof for the preparation of a medicament for treating the underlying emotion dysregulation of a cognitive disease, such as Alzheimer Disease, characterized in that pipamperon or said pharmaceutically acceptable salt thereof is administered simultaneously with, separate from or prior to the administration of a non-steroidal anti-inflammatory drug to augment the therapeutic effect or to provide a faster onset of the therapeutic effect of said a non-steroidal anti-inflammatory drug, further characterized in that pipamperon is to be administered to a patient in a daily dose ranging between 5 and 15 mg of the active ingredient.

According to a preferred embodiment, the invention relates to the uses as described above, wherein said a non-steroidal anti-inflammatory drug is chosen from the group consisting of piroxicam, MX-1094, meloxicam and flurizan (pure R-enantiomer form of flurbiprofen), or a pro-drug or an active metabolite thereof, or a pharmaceutically acceptable salt thereof.

The invention also relates to a pharmaceutical composition comprising (a) pipamperon, and (b) a non-steroidal anti-inflammatory drug, preferably chosen from the group consisting of piroxicam, MX-1094, meloxicam and flurizan (pure R-enantiomer form of flurbiprofen), or a pro-drug or an active metabolite thereof, or a pharmaceutically acceptable salt thereof, as a combined preparation for simultaneous, separate or sequential use for treating the underlying emotion dysregulation of a pain disorder or Alzheimer Disease.

73: Combination Therapy with an Opoid Receptor Antagonist Compound

The mental disorders which can be treated using compounds having a high selective affinity for the 5-HT2A and D4 receptor, for instance pipamperon, in a combination therapy with an opoid receptor antagonist compound, are substance related disorders.

It will be appreciated that the terms "opoid" and "opioid" may be used interchangeably.

The present invention thus relates to the use of pipamperon or a pharmaceutically acceptable salt thereof for the preparation of a medicament for treating the underlying emotion dysregulation of substance related disorders, characterized in that pipamperon or said pharmaceutically acceptable salt thereof is administered simultaneously with, separate from or prior to the administration of a opoid receptor antagonist compound to augment the therapeutic effect or to provide a faster onset of the therapeutic effect of said opoid receptor antagonist compound, further characterized in that pipamperon is to be administered to a patient in a daily dose ranging between 5 and 15 mg of the active ingredient.

According to a preferred embodiment, the invention relates to the use as described above, wherein said opoid receptor antagonist compound is naltrexone, preferably as a depot formulation, more preferably in the form of microcapsules, or a pro-drug or an active metabolite thereof, or a pharmaceutically acceptable salt thereof. Preferably, said naltrexone is to be administered in the form of a depot, preferably a depot of microcapsules comprising a daily dose of between 192 and 384 mg.

The invention also relates to a pharmaceutical composition comprising (a) pipamperon, and (b) an opoid receptor antagonist, preferably naltrexone, or a pro-drug or an active metabolite thereof, or a pharmaceutically acceptable salt thereof, as a combined preparation for simultaneous, separate or sequential use for treating the underlying emotion dysregulation of substance related disorders.

The invention also relates to a pharmaceutical composition as described above wherein pipamperon is provided in a unitary dose of between 5 and 15 mg of the active ingredient and wherein said opoid receptor antagonist compound is naltrexone, preferably provided in a unitary dose of between 192 and 384 mg of the active ingredient.

74: Combination Therapy with an Opoid Agonist Compound

The mental disorders which can be treated using compounds having a high selective affinity for the 5-HT2A and D4 receptor, for instance pipamperon, in a combination therapy with an opoid agonist compound, are chosen from the group of diseases or disorders consisting of anxiety disorders, psychotic disorders, eating disorders, premenstrual syndrome, somatoform disorders (excluding pain disorders), factitious disorders, dissociative disorders, sexual and gender identity disorders, sleep disorders, adjustment disorders, impulse control disorders, substance-related disorders, personality disorders, bereavement, occupational problem and problems related to abuse or neglect.

The present invention thus relates to the use of pipamperon or a pharmaceutically acceptable salt thereof for the preparation of a medicament for treating the underlying emotion dysregulation of a non-cognitive mental disease or disorder selected from the group of diseases and disorders consisting of anxiety disorders, psychotic disorders, eating disorders, premenstrual syndrome, somatoform disorders (excluding pain disorders), factitious disorders, dissociative disorders, sexual and gender identity disorders, sleep disorders, adjustment disorders, impulse control disorders, substance-related disorders, personality disorders, bereavement, occupational problem and problems related to abuse or neglect, characterized in that pipamperon or said pharmaceutically acceptable salt thereof is administered simultaneously with, separate from or prior to the administration of an opoid agonist compound to augment the therapeutic effect or to provide a faster onset of the therapeutic effect of said opoid agonist compound, further characterized in that pipamperon is to be administered to a patient in a daily dose ranging between 5 and 15 mg of the active ingredient.

According to a preferred embodiment, the invention relates to the use as described above, wherein said opoid agonist compound is chosen from the group consisting of siramesine, E-5842 and cyclazocine, preferably siramesine, or a pro-drug or an active metabolite thereof, or a pharmaceutically acceptable salt thereof.

The invention also relates to a pharmaceutical composition comprising (a) pipamperon, and (b) an opoid agonist compound, preferably chosen from the group consisting of siramesine, E-5842 and cyclazocine, preferably siramesine, or a pro-drug or an active metabolite thereof, or a pharmaceutically acceptable salt thereof, as a combined preparation for simultaneous, separate or sequential use for treating the underlying emotion dysregulation of a non-cognitive mental disease or disorder which is chosen from the group consisting of anxiety disorders, psychotic disorders, eating disorders, premenstrual syndrome, somatoform disorders (excluding pain disorders), factitious disorders, dissociative disorders, sexual and gender identity disorders, sleep disorders, adjustment disorders, impulse control disorders, substance-related disorders, personality disorders, bereavement, occupational problem and problems related to abuse or neglect.

75: Combination Therapy with a Phosphodiesterase-4 (PDE4) Inhibitor Compound The mental disorders which can be treated using compounds having a high selective affinity for the 5-HT2A and D4 receptor, for instance pipamperon, in a combination therapy with a phosphodiesterase-4 (PDE4) inhibitor compound, are chosen from the group of diseases or disorders consisting of mood disorders, anxiety disorders, eating disorders, premenstrual syndrome, somatoform disorders (excluding pain disorders), factitious disorders, dissociative disorders, sexual and gender identity disorders, adjustment disorders, impulse control disorders, personality disorders, bereavement, occupational problem, problems related to abuse or neglect, pain disorders, Alzheimer Disease, substance-related persisting dementia, vascular dementia, dementia due to HIV disease, dementia due to head trauma, dementia due to Parkinson Disease, dementia due to Huntington Disease, dementia due to Pick Disease, dementia due to Creutzfeldt-Jacob Disease, amnestic disorders due to a general medical condition, substance-induced persisting amnestic disorder, mild cognitive impairment disorder and other cognitive disorders.

The present invention thus relates to the use of pipamperon or a pharmaceutically acceptable salt thereof for the preparation of a medicament for treating the underlying emotion dysregulation of a non-cognitive mental disease or disorder selected from the group of diseases and disorders consisting of mood disorders, anxiety disorders, eating disorders, premenstrual syndrome, somatoform disorders (excluding pain disorders), factitious disorders, dissociative disorders, sexual and gender identity disorders, adjustment disorders, impulse control disorders, personality disorders, bereavement, occupational problem and problems related to abuse or neglect, characterized in that pipamperon or said pharmaceutically acceptable salt thereof is administered simultaneously with, separate from or prior to the administration of phosphodiesterase-4 (PDE4) inhibitor compound to augment the therapeutic effect or to provide a faster onset of the therapeutic effect of said phosphodiesterase-4 (PDE4) inhibitor compound, further characterized in that pipamperon is to be administered to a patient in a dally dose ranging between 5 and 15 mg of the active ingredient.

The present invention thus relates to the use of pipamperon or a pharmaceutically acceptable salt thereof for the preparation of a medicament for treating the underlying emotion dysregulation of pain disorders, characterized in that pipamperon or said pharmaceutically acceptable salt thereof is administered simultaneously with, separate from or prior to the administration of a phosphodiesterase-4 (PDE4) inhibitor compound d to augment the therapeutic effect or to provide a faster onset of the therapeutic effect of said phosphodiesterase-4 (PDE4) inhibitor compound, further characterized in that pipamperon is to be administered to a patient in a daily dose ranging between 5 and 15 mg of the active ingredient.

The present invention thus relates to the use of pipamperon or a pharmaceutically acceptable salt thereof for the preparation of a medicament for treating the underlying emotion dysregulation of a cognitive mental disease or disorder selected from the group of diseases and disorders consisting of Alzheimer Disease, substance-related persisting dementia, vascular dementia, dementia due to HIV disease, dementia due to head trauma, dementia due to Parkinson Disease, dementia due to Huntington Disease, dementia due to Pick Disease, dementia due to Creutzfeldt-Jacob Disease, amnestic disorders due to a general medical condition, substance-induced persisting amnestic disorder, mild cognitive impairment disorder and other cognitive disorders, characterized in that pipamperon or said pharmaceutically acceptable salt thereof is administered simultaneously with, separate from or prior to the administration of a phosphodiesterase-4 (PDE4) inhibitor compound to augment the therapeutic effect or to provide a faster onset of the therapeutic effect of said phosphodiesterase-4 (PDE4) inhibitor compound, further characterized in that pipamperon is to be administered to a patient in a daily dose ranging between 5 and 15 mg of the active ingredient.

According to a preferred embodiment, the invention relates to the uses as described above, wherein said phosphodiesterase-4 (PDE4) inhibitor compound is chosen from the group consisting of ND1251 and MEM 1917 (R1497), or a pro-drug or an active metabolite thereof, or a pharmaceutically acceptable salt thereof.

The invention also relates to a pharmaceutical composition comprising (a) pipamperon, and (b) a phosphodiesterase-4 (PDE4) inhibitor antagonist compound, preferably chosen from the group consisting of ND1251 and MEM 1917 (R1497), or a pro-drug or an active metabolite thereof, or a pharmaceutically acceptable salt thereof, as a combined preparation for simultaneous, separate or sequential use for treating the underlying emotion dysregulation of mental disease or disorder which is chosen from the group consisting of mood disorders, anxiety disorders, eating disorders, premenstrual syndrome, somatoform disorders (excluding pain disorders), factitious disorders, dissociative disorders, sexual and gender identity disorders, adjustment disorders, impulse control disorders, personality disorders, bereavement, occupational problem, problems related to abuse or neglect, pain disorders, Alzheimer Disease, substance-related persisting dementia, vascular dementia, dementia due to HIV disease, dementia due to head trauma, dementia due to Parkinson Disease, dementia due to Huntington Disease, dementia due to Pick Disease, dementia due to Creutzfeldt-Jacob Disease, amnestic disorders due to a general medical condition, substance-induced persisting amnestic disorder, mild cognitive impairment disorder and other cognitive disorders.

76: Combination Therapy with a Peptidic Compound

The mental disorders which can be treated using compounds having a high selective affinity for the 5-HT2A and D4 receptor, for instance pipamperon, in a combination therapy with a peptidic compound, are chosen from the group of diseases or disorders consisting of mood disorders, anxiety disorders, eating disorders, premenstrual syndrome, somatoform disorders (excluding pain disorders), factitious disorders, dissociative disorders, sexual and gender identity disorders, sleep disorders, adjustment disorders, impulse control disorders, pervasive development disorders, disruptive behaviour disorders, substance related disorders, personality disorders, bereavement, occupational problem, problems related to abuse or neglect, pain disorders, Alzheimer Disease, substance-induced persisting dementia, vascular dementia, dementia due to HIV disease, dementia due to head trauma, dementia due to Parkinson Disease, dementia due to Huntington Disease, dementia due to Pick Disease, dementia due to Creutzfeldt-Jacob Disease, amnestic disorders due to a general medical condition, substance-induced persisting amnestic disorder, mild cognitive impairment disorder and other cognitive disorders.

The present invention thus relates to the use of pipamperon or a pharmaceutically acceptable salt thereof for the preparation of a medicament for treating the underlying emotion dysregulation of a non-cognitive mental disease or disorder selected from the group of diseases and disorders consisting of mood disorders, anxiety disorders, eating disorders, premenstrual syndrome, somatoform disorders (excluding pain disorders), factitious disorders, dissociative disorders, sexual and gender identity disorders, sleep disorders, adjustment disorders, impulse control disorders, pervasive development disorders, disruptive behaviour disorders, substance related disorders, personality disorders, bereavement, occupational problem and problems related to abuse or neglect, characterized in that pipamperon or said pharmaceutically acceptable salt thereof is administered simultaneously with, separate from or prior to the administration of a peptidic compound to augment the therapeutic effect or to provide a faster onset of the therapeutic effect of said peptidic compound, further characterized in that pipamperon is to be administered to a patient in a daily dose ranging between 5 and 15 mg of the active ingredient.

The present invention thus relates to the use of pipamperon or a pharmaceutically acceptable salt thereof for the preparation of a medicament for treating the underlying emotion dysregulation of pain disorders, characterized in that pipamperon or said pharmaceutically acceptable salt thereof is administered simultaneously with, separate from or prior to the administration of a peptidic compound to augment the therapeutic effect or to provide a faster onset of the therapeutic effect of said peptidic compound, further characterized in that pipamperon is to be administered to a patient in a daily dose ranging between 5 and 15 mg of the active ingredient.

The present invention thus relates to the use of pipamperon or a pharmaceutically acceptable salt thereof for the preparation of a medicament for treating the underlying emotion dysregulation of a cognitive mental disease or disorder selected from the group of diseases and disorders consisting of Alzheimer Disease, substance-induced persisting dementia, vascular dementia, dementia due to HIV disease, dementia due to head trauma, dementia due to Parkinson Disease, dementia due to Huntington Disease, dementia due to Pick Disease, dementia due to Creutzfeldt-Jacob Disease, amnestic disorders due to a general medical condition, substance-induced persisting amnestic disorder, mild cognitive impairment disorder and other cognitive disorders, characterized in that pipamperon or said pharmaceutically acceptable salt thereof is administered simultaneously with, separate from or prior to the administration of a peptidic compound to augment the therapeutic effect or to provide a faster onset of the therapeutic effect of said peptidic compound, further characterized in that pipamperon is to be administered to a patient in a daily dose ranging between 5 and 15 mg of the active ingredient.

According to a preferred embodiment, the invention relates to the uses as described above, wherein said peptidic compound is chosen from the group consisting of secretin, PT-141, INN 00835 and beta sheet breaker peptide, or a pro-drug or an active metabolite thereof, or a pharmaceutically acceptable salt thereof. More preferably, said peptidic compound is secretin and is to be administered in a daily dose ranging between 0.2 and 0.4 mg/kg of the active ingredient. More preferably, said peptidic compound is INN 00835 and is to be administered in a daily dose ranging between 18 and 160 mg of the active ingredient.

The invention also relates to a pharmaceutical composition comprising (a) pipamperon, and (b) a peptidic compound, preferably chosen from the group consisting of secretin, PT-141, INN 00835 and beta sheet breaker peptide, or a pro-drug or an active metabolite thereof, or a pharmaceutically acceptable salt thereof, as a combined preparation for simultaneous, separate or sequential use for treating the underlying emotion dysregulation of mental disease or disorder which is chosen from the group consisting of mood disorders, anxiety disorders, eating disorders, premenstrual syndrome, somatoform disorders (excluding pain disorders), factitious disorders, dissociative disorders, sexual and gender identity disorders, sleep disorders, adjustment disorders, impulse control disorders, pervasive development disorders, disruptive behaviour disorders, substance related disorders, personality disorders, bereavement, occupational problem, problems related to abuse or neglect, pain disorders, Alzheimer Disease, substance-induced persisting dementia, vascular dementia, dementia due to HIV disease, dementia due to head trauma, dementia due to Parkinson Disease, dementia due to Huntington Disease, dementia due to Pick Disease, dementia due to Creutzfeldt-Jacob Disease, amnestic disorders due to a general medical condition, substance-induced persisting amnestic disorder, mild cognitive impairment disorder and other cognitive disorders.

The invention also relates to a pharmaceutical composition as described above wherein pipamperon is provided in a unitary dose of between 5 and 15 mg of the active ingredient and wherein said peptidic compound is secretin, preferably provided in a unitary dose of 0.2 and 0.4 mg/kg of the active ingredient.

The invention also relates to a pharmaceutical composition as described above wherein pipamperon is provided in a unitary dose of between 5 and 15 mg of the active ingredient and wherein said peptidic compound is INN 00835, preferably provided in a unitary dose of 18 and 160 mg of the active ingredient.

77: Combination Therapy with a Phospholipase A2 Inhibitor Compound

The mental disorders which can be treated using compounds having a high selective affinity for the 5-HT2A and D4 receptor, for instance pipamperon, in a combination therapy with a phospholipase A2 inhibitor compound which has caspase inhibitor activity, are chosen from the group of diseases or disorders consisting of mood disorders, anxiety disorders, psychotic disorders, eating disorders, premenstrual syndrome, somatoform disorders (excluding pain disorders), factitious disorders, dissociative disorders, sexual and gender identity disorders, sleep disorders, adjustment disorders, impulse control disorders, pervasive development disorders, disruptive behaviour disorders, substance-related disorders, personality disorders, bereavement, occupational problem, problems related to abuse or neglect, pain disorders and delirium.

The present invention thus relates to the use of pipamperon or a pharmaceutically acceptable salt thereof for the preparation of a medicament for treating the underlying emotion dysregulation of a non-cognitive mental disease or disorder selected from the group of diseases and disorders consisting of mood disorders, anxiety disorders, psychotic disorders, eating disorders, premenstrual syndrome, somatoform disorders (excluding pain disorders), factitious disorders, dissociative disorders, sexual and gender identity disorders, sleep disorders, adjustment disorders, impulse control disorders, pervasive development disorders, disruptive behaviour disorders, substance-related disorders, personality disorders, bereavement, occupational problem and problems related to abuse or neglect, characterized in that pipamperon or said pharmaceutically acceptable salt thereof is administered simultaneously with, separate from or prior to the administration of a phospholipase A2 inhibitor compound which has caspase inhibitor activity to augment the therapeutic effect or to provide a faster onset of the therapeutic effect of said phospholipase A2 inhibitor compound which has caspase inhibitor activity, further characterized in that pipamperon is to be administered to a patient in a daily dose ranging between 5 and 15 mg of the active ingredient.

The present invention thus relates to the use of pipamperon or a pharmaceutically acceptable salt thereof for the preparation of a medicament for treating the underlying emotion dysregulation of pain disorders, characterized in that pipamperon or said pharmaceutically acceptable salt thereof is administered simultaneously with, separate from or prior to the administration of a phospholipase A2 inhibitor compound which has caspase inhibitor activity to augment the therapeutic effect or to provide a faster onset of the therapeutic effect of said phospholipase A2 inhibitor compound which has caspase inhibitor activity, further characterized in that pipamperon is to be administered to a patient in a daily dose ranging between 5 and 15 mg of the active ingredient.

The present invention thus relates to the use of pipamperon or a pharmaceutically acceptable salt thereof for the preparation of a medicament for treating the underlying emotion dysregulation of a cognitive mental disease or disorder which is delirium, characterized in that pipamperon or said pharmaceutically acceptable salt thereof is administered simultaneously with, separate from or prior to the administration of a phospholipase A2 inhibitor compound which has caspase inhibitor activity to augment the therapeutic effect or to provide a faster onset of the therapeutic effect of said phospholipase A2 inhibitor compound which has caspase inhibitor activity, further characterized in that pipamperon is to be administered to a patient in a daily dose ranging between 5 and 15 mg of the active ingredient.

According to a preferred embodiment, the invention relates to the uses as described above, wherein said phospholipase A2 inhibitor compound which has caspase inhibitor activity is chosen from the group consisting of LAX-101a, LAX-101b and LAX-101c, preferably LAX-101c, or a pro-drug or an active metabolite thereof, or a pharmaceutically acceptable salt thereof.

The invention also relates to a pharmaceutical composition comprising (a) pipamperon, and (b) a phospholipase A2 inhibitor compound which has caspase inhibitor activity, preferably chosen from the group consisting of LAX-101a, LAX-101b and LAX-101c, more preferably LAX-101c, or a pro-drug or an active metabolite thereof, or a pharmaceutically acceptable salt thereof, as a combined preparation for simultaneous, separate or sequential use for treating the underlying emotion dysregulation of a mental disease or disorder which is chosen from the group consisting mood disorders, anxiety disorders, psychotic disorders, eating disorders, premenstrual syndrome, somatoform disorders (excluding pain disorders), factitious disorders, dissociative disorders, sexual and gender identity disorders, sleep disorders, adjustment disorders, impulse control disorders, pervasive development disorders, disruptive behaviour disorders, substance-related disorders, personality disorders, bereavement, occupational problem, problems related to abuse or neglect, pain disorders and delirium.

78: Combination Therapy with a Compound which is a Prodrug of Uridine

The mental disorders which can be treated using compounds having a high selective affinity for the 5-HT2A and D4 receptor, for instance pipamperon, in a combination therapy with a compound which is a prodrug of uridine, are chosen from the group of diseases or disorders consisting of mood disorders, anxiety disorders, eating disorders, premenstrual syndrome, somatoform disorders (excluding pain disorders), factitious disorders, dissociative disorders, sexual and gender identity disorders, sleep disorders, adjustment disorders, impulse control disorders, personality disorders, bereavement, occupational problem, problems related to abuse or neglect and pain disorders.

The present invention thus relates to the use of pipamperon or a pharmaceutically acceptable salt thereof for the preparation of a medicament for treating the underlying emotion dysregulation of a non-cognitive mental disease or disorder selected from the group of diseases and disorders consisting of mood disorders, anxiety disorders, eating disorders, premenstrual syndrome, somatoform disorders (excluding pain disorders), factitious disorders, dissociative disorders, sexual and gender identity disorders, sleep disorders, adjustment disorders, impulse control disorders, personality disorders, bereavement, occupational problem and problems related to abuse or neglect, characterized in that pipamperon or said pharmaceutically acceptable salt thereof is administered simultaneously with, separate from or prior to the administration of a compound which is a prodrug of uridine to augment the therapeutic effect or to provide a faster onset of the therapeutic effect of said compound which is a prodrug of uridine, further characterized in that pipamperon is to be administered to a patient in a daily dose ranging between 5 and 15 mg of the active ingredient.

The present invention thus relates to the use of pipamperon or a pharmaceutically acceptable salt thereof for the preparation of a medicament for treating the underlying emotion dysregulation of pain disorders, characterized in that pipamperon or said pharmaceutically acceptable salt thereof is administered simultaneously with, separate from or prior to the administration of a compound which is a prodrug of uridine to augment the therapeutic effect or to provide a faster onset of the therapeutic effect of said compound which is a prodrug of uridine, further characterized in that pipamperon is to be administered to a patient in a daily dose ranging between 5 and 15 mg of the active ingredient.

According to a preferred embodiment, the invention relates to the uses as described above, wherein said compound which is a prodrug of uridine is RG2133 (triacetyluridine) or a pro-drug or an active metabolite thereof, or a pharmaceutically acceptable salt thereof.

The invention also relates to a pharmaceutical composition comprising (a) pipamperon, and (b) a compound which is a prodrug of uridine, preferably RG2133 (triacetyluridine) or a pro-drug or an active metabolite thereof, or a pharmaceutically acceptable salt thereof, as a combined preparation for simultaneous, separate or sequential use for treating the underlying emotion dysregulation of a mental disease or disorder which is chosen from the group consisting of mood disorders, anxiety disorders, eating disorders, premenstrual syndrome, somatoform disorders (excluding pain disorders), factitious disorders, dissociative disorders, sexual and gender identity disorders, sleep disorders, adjustment disorders, impulse control disorders, personality disorders, bereavement, occupational problem, problems related to abuse or neglect and pain disorders.

79: Combination Therapy with Prostaglandin E1 Compound

The mental disorders which can be treated using compounds having a high selective affinity for the 5-HT2A and D4 receptor, for instance pipamperon, in a combination therapy with prostaglandin E1 compound, are sexual and gender identity disorders.

The present invention thus relates to the use of pipamperon or a pharmaceutically acceptable salt thereof for the preparation of a medicament for treating the underlying emotion dysregulation of a non-cognitive mental disease or disorder selected from the group of sexual and gender identity disorders, characterized in that pipamperon or said pharmaceutically acceptable salt thereof is administered simultaneously with, separate from or prior to the administration of a prostaglandin E1 compound to augment the therapeutic effect or to provide a faster onset of the therapeutic effect of said prostaglandin E1 compound, further characterized in that pipamperon is to be administered to a patient in a daily dose ranging between 5 and 15 mg of the active ingredient.

According to a preferred embodiment, the invention relates to the use as described above, wherein said prostaglandin E1 is alprostadil or a pro-drug or an active metabolite thereof, or a pharmaceutically acceptable salt thereof. More preferably, said prostaglandin E1 compound is alprostadil, preferably in the form of cream or gel, preferably a topical gel, and is to be administered in a daily dose ranging between 50 and 300 microgram per application of the active ingredient.

The invention also relates to a pharmaceutical composition comprising (a) pipamperon, and (b) a prostaglandin E1 compound, preferably alprostadil or a pro-drug or an active metabolite thereof, or a pharmaceutically acceptable salt thereof, as a combined preparation for simultaneous, separate or sequential use for treating the underlying emotion dysregulation of a mental disease or disorder which is chosen from the group of sexual and gender identity disorders.

The invention also relates to a pharmaceutical composition as described above wherein pipamperon is provided in a unitary dose of between 5 and 15 mg of the active ingredient and wherein said prostaglandin E1 compound is alprostadil, preferably provided in the form of a cream or gel, preferably a topical gel, wherein a unitary dose comprises between 50 and 300 microgram of the active ingredient per application.

80: Combination Therapy with a Compound Protecting Dopaminergic and Cholinergic Neurons The mental disorders which can be treated using compounds having a high selective affinity for the 5-HT2A and D4 receptor, for instance pipamperon, in a combination therapy with a compound which protects dopaminergic and cholinergic neurons, are chosen from the group of diseases or disorders consisting of Alzheimer Disease, substance-induced persisting dementia, vascular dementia, dementia due to HIV disease, dementia due to head trauma, dementia due to Parkinson Disease, dementia due to Huntington Disease, dementia due to Pick Disease, dementia due to Creutzfeldt-Jacob Disease, amnestic disorders due to a general medical condition, substance-induced persisting amnestic disorder, mild cognitive impairment disorder, other cognitive disorders and Parkinson Disease.

The present invention thus relates to the use of pipamperon or a pharmaceutically acceptable salt thereof for the preparation of a medicament for treating the underlying emotion dysregulation of a cognitive mental disease or disorder selected from the group of diseases and disorders consisting of Alzheimer Disease, substance-induced persisting dementia, vascular dementia, dementia due to HIV disease, dementia due to head trauma, dementia due to Parkinson Disease, dementia due to Huntington Disease, dementia due to Pick Disease, dementia due to Creutzfeldt-Jacob Disease, amnestic disorders due to a general medical condition, substance-induced persisting amnestic disorder, mild cognitive impairment disorder and other cognitive disorders, characterized in that pipamperon or said pharmaceutically acceptable salt thereof is administered simultaneously with, separate from or prior to the administration of a compound which protects dopaminergic and cholinergic neurons to augment the therapeutic effect or to provide a faster onset of the therapeutic effect of said compound which protects dopaminergic and cholinergic neurons, further characterized in that pipamperon is to be administered to a patient in a daily dose ranging between 5 and 15 mg of the active ingredient.

The present invention thus relates to the use of pipamperon or a pharmaceutically acceptable salt thereof for the preparation of a medicament for treating the underlying emotion dysregulation of Parkinson Disease, characterized in that pipamperon or said pharmaceutically acceptable salt thereof is administered simultaneously with, separate from or prior to the administration of a compound which protects dopaminergic and cholinergic neurons to augment the therapeutic effect or to provide a faster onset of the therapeutic effect of said compound which protects dopaminergic and cholinergic neurons, further characterized in that pipamperon is to be administered to a patient in a daily dose ranging between 5 and 15 mg of the active ingredient.

According to a preferred embodiment, the invention relates to the uses as described above, wherein said compound which protects dopaminergic and cholinergic neurons is SR 57667 or a pro-drug or an active metabolite thereof, or a pharmaceutically acceptable salt thereof.

The invention also relates to a pharmaceutical composition comprising (a) pipamperon, and (b) a compound which protects dopaminergic and cholinergic neurons, preferably SR 57667 or a pro-drug or an active metabolite thereof, or a pharmaceutically acceptable salt thereof, as a combined preparation for simultaneous, separate or sequential use for treating the underlying emotion dysregulation of a mental disease or disorder which is chosen from the group consisting of Alzheimer Disease, substance-induced persisting dementia, vascular dementia, dementia due to HIV disease, dementia due to head trauma, dementia due to Parkinson Disease, dementia due to Huntington Disease, dementia due to Pick Disease, dementia due to Creutzfeldt-Jacob Disease, amnestic disorders due to a general medical condition, substance-induced persisting amnestic disorder, mild cognitive impairment disorder, other cognitive disorders and Parkinson Disease.

81: Combination Therapy with a Psycho Stimulant

The mental disorders which can be treated using compounds having a high selective affinity for the 5-HT2A and D4 receptor, for instance pipamperon, in a combination therapy with a psycho stimulant, are chosen from the group of diseases or disorders consisting of sleep disorders, attention-deficit disorders and substance-related disorders.

The present invention thus relates to the use of pipamperon or a pharmaceutically acceptable salt thereof for the preparation of a medicament for treating the underlying emotion dysregulation of a non-cognitive mental disease or disorder selected from the group of diseases and disorders consisting of sleep disorders, attention-deficit disorders and substance-related disorders, characterized in that pipamperon or said pharmaceutically acceptable salt thereof is administered simultaneously with, separate from or prior to the administration of a psycho stimulant to augment the therapeutic effect or to provide a faster onset of the therapeutic effect of said psycho stimulant, further characterized in that pipamperon is to be administered to a patient in a daily dose ranging between 5 and 15 mg of the active ingredient.

According to a preferred embodiment, the invention relates to the uses as described above, wherein said psycho stimulant is chosen from the group consisting of SPD 503, r-modafinil and modafinil, or a pro-drug or an active metabolite thereof, or a pharmaceutically acceptable salt thereof. More preferably, said psycho stimulant is SPE 503, more preferably said psycho stimulant is modafinil and is to be administered in a daily dose ranging between 200 and 600 mg of the active ingredient.

The invention also relates to a pharmaceutical composition comprising (a) pipamperon, and (b) a psycho stimulant, preferably chosen from the group consisting of SPD 503, r-modafinil and modafinil, more preferably said SPC 503 or modafinil or a pro-drug or an active metabolite thereof, or a pharmaceutically acceptable salt thereof, as a combined preparation for simultaneous, separate or sequential use for treating the underlying emotion dysregulation of a non-cognitive mental disease or disorder which is chosen from the group consisting of sleep disorders, attention-deficit disorders and substance-related disorders.

The invention also relates to a pharmaceutical composition as described above wherein pipamperon is provided in a unitary dose of between 5 and 15 mg of the active ingredient and wherein said psycho stimulant is modafinil, preferably provided in a unitary dose of between 200 and 600 mg of the active ingredient.

82: Combination Therapy with a Compound which is a Reversible Inhibitor of Mono-Amine Oxydase A (RIMA)

The mental disorders which can be treated using compounds having a high selective affinity for the 5-HT2A and D4 receptor, for instance pipamperon, in a combination therapy with a compound which is a reversible inhibitor of mono-amine oxydase A (RIMA), are chosen from the group of diseases or disorders consisting of mood disorders, anxiety disorders, eating disorders, premenstrual syndrome, somatoform disorders (excluding pain disorders), factitious disorders, dissociative disorders, sexual and gender identity disorders, adjustment disorders, impulse control disorders, personality disorders, antisocial behaviour, bereavement, occupational problem, problems related to abuse or neglect and pain disorders.

The present invention thus relates to the use of pipamperon or a pharmaceutically acceptable salt thereof for the preparation of a medicament for treating the underlying emotion dysregulation of a non-cognitive mental disease or disorder selected from the group of diseases and disorders consisting of mood disorders, anxiety disorders, eating disorders, premenstrual syndrome, somatoform disorders (excluding pain disorders), factitious disorders, dissociative disorders, sexual and gender identity disorders, adjustment disorders, impulse control disorders, personality disorders, antisocial behaviour, bereavement, occupational problem and problems related to abuse or neglect, characterized in that pipamperon or said pharmaceutically acceptable salt thereof is administered simultaneously with, separate from or prior to the administration of a compound which is a reversible inhibitor of mono-amine oxydase A (RIMA) to augment the therapeutic effect or to provide a faster onset of the therapeutic effect of said compound which is a reversible inhibitor of mono-amine oxydase A (RIMA), further characterized in that pipamperon is to be administered to a patient in a daily dose ranging between 5 and 15 mg of the active ingredient.

The present invention thus relates to the use of pipamperon or a pharmaceutically acceptable salt thereof for the preparation of a medicament for treating the underlying emotion dysregulation of pain disorders, characterized in that pipamperon or said pharmaceutically acceptable salt thereof is administered simultaneously with, separate from or prior to the administration of a compound which is a reversible inhibitor of mono-amine oxydase A (RIMA) to augment the therapeutic effect or to provide a faster onset of the therapeutic effect of said compound which is a reversible inhibitor of mono-amine oxydase A (RIMA), further characterized in that pipamperon is to be administered to a patient in a daily dose ranging between 5 and 15 mg of the active ingredient.

According to a preferred embodiment, the invention relates to the uses as described above, wherein said compound which is a reversible inhibitor of mono-amine oxydase A (RIMA) is chosen from the group consisting of toloxatone, RS 8359, moclobemide, cimoxatone, caroxazone (FJ 6654) and befloxatone, or a pro-drug or an active metabolite thereof, or a pharmaceutically acceptable salt thereof. More preferably, said compound which is a reversible inhibitor of mono-amine oxydase A (RIMA) is befloxatone and is to be administered in a daily dose ranging between 2.5 and 20 mg of the active ingredient.

The invention also relates to a pharmaceutical composition comprising (a) pipamperon, and (b) a compound which is a reversible inhibitor of mono-amine oxydase A (RIMA), preferably chosen from the group consisting of toloxatone, RS 8359, moclobemide, cimoxatone, caroxazone (FJ 6654) and befloxatone, or a pro-drug or an active metabolite thereof, or a pharmaceutically acceptable salt thereof, as a combined preparation for simultaneous, separate or sequential use for treating the underlying emotion dysregulation of mental disease or disorder which is chosen from the group consisting of mood disorders, anxiety disorders, eating disorders, premenstrual syndrome, somatoform disorders (excluding pain disorders), factitious disorders, dissociative disorders, sexual and gender identity disorders, adjustment disorders, impulse control disorders, personality disorders, antisocial behaviour, bereavement, occupational problem, problems related to abuse or neglect and pain disorders.

The invention also relates to a pharmaceutical composition as described above wherein pipamperon is provided in a unitary dose of between 5 and 15 mg of the active ingredient and wherein said compound which is a reversible inhibitor of mono-amine oxydase A (RIMA) is befloxatone, preferably provided in a unitary dose of between 2.5 and 20 mg of the active ingredient.

83: Combination Therapy with a Compound which Modulates SCT-11

The mental disorders which can be treated using compounds having a high selective affinity for the 5-HT2A and D4 receptor, for instance pipamperon, in a combination therapy with a compound which modulates SCT-11 (i.e. SCT-11 is a G protein-coupled receptor), are chosen from the group of diseases or disorders consisting of mood disorders, anxiety disorders, eating disorders, premenstrual syndrome, somatoform disorders (excluding pain disorders), factitious disorders, dissociative disorders, sexual and gender identity disorders, sleep disorders, adjustment disorders, impulse control disorders, personality disorders, bereavement, occupational problem, problems related to abuse or neglect and pain disorders.

The present invention thus relates to the use of pipamperon or a pharmaceutically acceptable salt thereof for the preparation of a medicament for treating the underlying emotion dysregulation of a non-cognitive mental disease or disorder selected from the group of diseases and disorders consisting of mood disorders, anxiety disorders, eating disorders, premenstrual syndrome, somatoform disorders (excluding pain disorders), factitious disorders, dissociative disorders, sexual and gender identity disorders, sleep disorders adjustment disorders, impulse control disorders, personality disorders, bereavement, occupational problem and problems related to abuse or neglect, characterized in that pipamperon or said pharmaceutically acceptable salt thereof is administered simultaneously with, separate from or prior to the administration of a compound which modulates SCT-11 to augment the therapeutic effect or to provide a faster onset of the therapeutic effect of said compound which modulates SCT-11, further characterized in that pipamperon is to be administered to a patient in a daily dose ranging between 5 and 15 mg of the active ingredient.

The present invention thus relates to the use of pipamperon or a pharmaceutically acceptable salt thereof for the preparation of a medicament for treating the underlying emotion dysregulation of pain disorders, characterized in that pipamperon or said pharmaceutically acceptable salt thereof is administered simultaneously with, separate from or prior to the administration of a compound which modulates SCT-11 to augment the therapeutic effect or to provide a faster onset of the therapeutic effect of said compound which modulates SCT-11, further characterized in that pipamperon is to be administered to a patient in a daily dose ranging between 5 and 15 mg of the active ingredient.

According to a preferred embodiment, the invention relates to the use as described above, wherein said compound which modulates SCT-11 is SNEC-2 or a pro-drug or an active metabolite thereof, or a pharmaceutically acceptable salt thereof.

The invention also relates to a pharmaceutical composition comprising (a) pipamperon, and (b) a compound which modulates SCT-11, preferably SNE-2 or a pro-drug or an active metabolite thereof, or a pharmaceutically acceptable salt thereof, as a combined preparation for simultaneous, separate or sequential use for treating the underlying emotion dysregulation of a mental disease or disorder which is chosen from the group consisting of mood disorders, anxiety disorders, eating disorders, premenstrual syndrome, somatoform disorders (excluding pain disorders), factitious disorders, dissociative disorders, sexual and gender identity disorders, sleep disorders, adjustment disorders, impulse control disorders, personality disorders, bereavement, occupational problem, problems related to abuse or neglect and pain disorders.

84: Combination Therapy with a Serotonin/Dopamine Antagonist Compound (SDA)

The mental disorders which can be treated using compounds having a high selective affinity for the 5-HT2A and D4 receptor, for instance pipamperon, in a combination therapy with a serotonin/dopamine antagonist compound (SDA), are chosen from the group of diseases or disorders consisting of mood disorders, anxiety disorders, psychotic disorders, somatoform disorders (excluding pain disorders), factitious disorders, dissociative disorders, sleep disorders, adjustment disorders, impulse control disorders, pervasive development disorders, disruptive behaviour disorders, substance-related disorders, personality disorders, psychological factors affecting medical conditions, malingering, antisocial behaviour, bereavement, occupational problem, identity problem, problems related to abuse or neglect, pain disorders and delirium.

The present invention thus relates to the use of pipamperon or a pharmaceutically acceptable salt thereof for the preparation of a medicament for treating the underlying emotion dysregulation of a non-cognitive mental disease or disorder selected from the group of diseases and disorders consisting of mood disorders, anxiety disorders, psychotic disorders, somatoform disorders (excluding pain disorders), factitious disorders, dissociative disorders, sleep disorders, adjustment disorders, impulse control disorders, pervasive development disorders, disruptive behaviour disorders, substance-related disorders, personality disorders, psychological factors affecting medical conditions, malingering, antisocial behaviour, bereavement, occupational problem, identity problem and problems related to abuse or neglect, characterized in that pipamperon or said pharmaceutically acceptable salt thereof is administered simultaneously with, separate from or prior to the administration of a serotonin/dopamine antagonist compound to augment the therapeutic effect or to provide a faster onset of the therapeutic effect of said serotonin/dopamine antagonist compound, further characterized in that pipamperon is to be administered to a patient in a daily dose ranging between 5 and 15 mg of the active ingredient.

The present invention thus relates to the use of pipamperon or a pharmaceutically acceptable salt thereof for the preparation of a medicament for treating the underlying emotion dysregulation of pain disorders, characterized in that pipamperon or said pharmaceutically acceptable salt thereof is administered simultaneously with, separate from or prior to the administration of a serotonin/dopamine antagonist compound to augment the therapeutic effect or to provide a faster onset of the therapeutic effect of said serotonin/dopamine antagonist compound, further characterized in that pipamperon is to be administered to a patient in a daily dose ranging between 5 and 15 mg of the active ingredient.

The present invention thus relates to the use of pipamperon or a pharmaceutically acceptable salt thereof for the preparation of a medicament for treating the underlying emotion dysregulation of a cognitive mental disease or disorder which is delirium, characterized in that pipamperon or said pharmaceutically acceptable salt thereof is administered simultaneously with, separate from or prior to the administration of a serotonin/dopamine antagonist compound to augment the therapeutic effect or to provide a faster onset of the therapeutic effect of said serotonin/dopamine antagonist compound, further characterized in that pipamperon is to be administered to a patient in a daily dose ranging between 5 and 15 mg of the active ingredient.

According to a preferred embodiment, the invention relates to the uses as described above, wherein said serotonin/dopamine antagonist compound is chosen from the group consisting of zotepine, ziprasidone, SM-13496, SL 91.0177, sertindole, S-18327, risperidone, quetiapine fumarate (preferably sustained release formulation), quetiapine fumarate (preferably granules), quetiapine, perospirone, paliperidone, olanzapine, ocaperidone, LU 31-131, iloperidone, clozapine, BSF-190555, blonanserin, bifeprunox, asenapine and aripiprazole, or a pro-drug or an active metabolite thereof, or a pharmaceutically acceptable salt thereof. Even more preferably, said serotonin/dopamine antagonist compound is chosen from the group consisting of SL 91.0177, sertindole, perospirone, paliperidone, blonanserin, bifeprunox and asenapine, or a pro-drug or an active metabolite thereof, or a pharmaceutically acceptable salt thereof. More preferably, said serotonin/dopamine antagonist compound is sertindole and is to be administered in a daily dose ranging between 12 and 24 mg of the active ingredient. More preferably, said serotonin/dopamine antagonist compound is paliperidone and is to be administered in a daily dose ranging between 3 and 15 mg of the active ingredient. More preferably, said serotonin/dopamine antagonist compound is asenapine and is to be administered in a daily dose ranging between 2.5 and 20 mg of the active ingredient.

The invention also relates to a pharmaceutical composition comprising (a) pipamperon, and (b) a serotonin/dopamine antagonist compound, preferably chosen from the group consisting of SL 91.0177, sertindole, perospirone, paliperidone, blonanserin, bifeprunox and asenapine, or a pro-drug or an active metabolite thereof, or a pharmaceutically acceptable salt thereof, as a combined preparation for simultaneous, separate or sequential use for treating the underlying emotion dysregulation of a mental disease or disorder which is chosen from the group consisting mood disorders, anxiety disorders, psychotic disorders, somatoform disorders (excluding pain disorders), factitious disorders, dissociative disorders, sleep disorders, adjustment disorders, impulse control disorders, pervasive development disorders, disruptive behaviour disorders, substance-related disorders, personality disorders, psychological factors affecting medical conditions, malingering, antisocial behaviour, bereavement, occupational problem, identity problem, problems related to abuse or neglect, pain disorders and delirium.

The invention also relates to a pharmaceutical composition as described above wherein pipamperon is provided in a unitary dose of between 5 and 15 mg of the active ingredient and wherein said serotonin/dopamine antagonist compound is sertindole, preferably provided in a unitary dose of between 12 and 24 mg of the active ingredient.

The invention also relates to a pharmaceutical composition as described above wherein pipamperon is provided in a unitary dose of between 5 and 15 mg of the active ingredient and wherein said serotonin/dopamine antagonist compound is paliperidone, preferably provided in a unitary dose of between 3 and 15 mg of the active ingredient.

The invention also relates to a pharmaceutical composition as described above wherein pipamperon is provided in a unitary dose of between 5 and 15 mg of the active ingredient and wherein said serotonin/dopamine antagonist compound is asenapine, preferably provided in a unitary dose of between 2.5 and 20 mg of the active ingredient.

85: Combination Therapy with a Selective SDRI Compound

The mental disorders which can be treated using compounds having a high selective affinity for the 5-HT2A and D4 receptor, for instance pipamperon, in a combination therapy with a selective serotonin and dopamine re-uptake inhibitor (SDRI) compound, are chosen from the group of diseases or disorders consisting of mood disorders, anxiety disorders, eating disorders, premenstrual syndrome, somatoform disorders (excluding pain disorders), factitious disorders, dissociative disorders, sleep disorders, adjustment disorders, impulse control disorders, substance-related disorders, personality disorders, antisocial behaviour, bereavement, occupational problem, problems related to abuse or neglect, pain disorders, delirium, Alzheimer Disease, substance-induced persisting dementia, vascular dementia, dementia due to HIV disease, dementia due to head trauma, dementia due to Parkinson Disease, dementia due to Huntington Disease, dementia due to Pick Disease, dementia due to Creutzfeldt-Jacob Disease, amnestic disorders due to a general medical condition, substance-induced persisting amnestic disorder, mild cognitive impairment disorder and other cognitive disorders.

The present invention thus relates to the use of pipamperon or a pharmaceutically acceptable salt thereof for the preparation of a medicament for treating the underlying emotion dysregulation of a non-cognitive mental disease or disorder selected from the group of diseases and disorders consisting of mood disorders, anxiety disorders, eating disorders, premenstrual syndrome, somatoform disorders (excluding pain disorders), factitious disorders, dissociative disorders, sleep disorders, adjustment disorders, impulse control disorders, substance-related disorders, personality disorders, antisocial behaviour, bereavement, occupational problem and problems related to abuse or neglect, characterized in that pipamperon or said pharmaceutically acceptable salt thereof is administered simultaneously with, separate from or prior to the administration of a selective serotonin and dopamine reuptake inhibitor (SDRI) compound to augment the therapeutic effect or to provide a faster onset of the therapeutic effect of said selective serotonin and dopamine reuptake inhibitor (SDRI) compound, further characterized in that pipamperon is to be administered to a patient in a daily dose ranging between 5 and 15 mg of the active ingredient.

The present invention thus relates to the use of pipamperon or a pharmaceutically acceptable salt thereof for the preparation of a medicament for treating the underlying emotion dysregulation of pain disorders, characterized in that pipamperon or said pharmaceutically acceptable salt thereof is administered simultaneously with, separate from or prior to the administration of a selective serotonin and dopamine reuptake inhibitor (SDRI) compound to augment the therapeutic effect or to provide a faster onset of the therapeutic effect of said selective serotonin and dopamine reuptake inhibitor (SDRI) compound, further characterized in that pipamperon is to be administered to a patient in a daily dose ranging between 5 and 15 mg of the active ingredient.

The present invention thus relates to the use of pipamperon or a pharmaceutically acceptable salt thereof for the preparation of a medicament for treating the underlying emotion dysregulation of a cognitive mental disease or disorder selected from the group of diseases and disorders consisting of delirium, Alzheimer Disease, substance-induced persisting dementia, vascular dementia, dementia due to HIV disease, dementia due to head trauma, dementia due to Parkinson Disease, dementia due to Huntington Disease, dementia due to Pick Disease, dementia due to Creutzfeldt-Jacob Disease, amnestic disorders due to a general medical condition, substance-induced persisting amnestic disorder, mild cognitive impairment disorder and other cognitive disorders, characterized in that pipamperon or said pharmaceutically acceptable salt thereof is administered simultaneously with, separate from or prior to the administration of a selective serotonin and dopamine reuptake inhibitor (SDRI) compound to augment the therapeutic effect or to provide a faster onset of the therapeutic effect of said selective serotonin and dopamine reuptake inhibitor (SDRI) compound, further characterized in that pipamperon is to be administered to a patient in a daily dose ranging between 5 and 15 mg of the active ingredient.

According to a preferred embodiment, the invention relates to the uses as described above, wherein said selective serotonin and dopamine reuptake inhibitor (SDRI) compound is bazinaprine, or a pro-drug or an active metabolite thereof, or a pharmaceutically acceptable salt thereof.

The invention also relates to a pharmaceutical composition comprising (a) pipamperon, and (b) a selective serotonin and dopamine reuptake inhibitor (SDRI) compound, preferably bazinaprine or a pro-drug or an active metabolite thereof, or a pharmaceutically acceptable salt thereof, as a combined preparation for simultaneous, separate or sequential use for treating the underlying emotion dysregulation of mental disease or disorder which is chosen from the group consisting of mood disorders, anxiety disorders, eating disorders, premenstrual syndrome, somatoform disorders (excluding pain disorders), factitious disorders, dissociative disorders, sleep disorders, adjustment disorders, impulse control disorders, substance-related disorders, personality disorders, antisocial behaviour, bereavement, occupational problem, problems related to abuse or neglect, pain disorders, delirium, Alzheimer Disease, substance-induced persisting dementia, vascular dementia, dementia due to HIV disease, dementia due to head trauma, dementia due to Parkinson Disease, dementia due to Huntington Disease, dementia due to Pick Disease, dementia due to Creutzfeldt-Jacob Disease, amnestic disorders due to a general medical condition, substance-induced persisting amnestic disorder, mild cognitive impairment disorder and other cognitive disorders.

86: Combination Therapy with a Second Messenger Beta Agonist Compound

The mental disorders which can be treated using compounds having a high selective affinity for the 5-HT2A and D4 receptor, for instance pipamperon, in a combination therapy with a second messenger beta agonist compound, are chosen from the group of diseases or disorders consisting of mood disorders, anxiety disorders, eating disorders, premenstrual syndrome, somatoform disorders (excluding pain disorders), factitious disorders, dissociative disorders, sexual and gender identity disorders, sleep disorders, adjustment disorders, impulse control disorders, personality disorders, bereavement, occupational problem, problems related to abuse or neglect and pain disorders.

The present invention thus relates to the use of pipamperon or a pharmaceutically acceptable salt thereof for the preparation of a medicament for treating the underlying emotion dysregulation of a non-cognitive mental disease or disorder selected from the group of diseases and disorders consisting of mood disorders, anxiety disorders, eating disorders, premenstrual syndrome, somatoform disorders (excluding pain disorders), factitious disorders, dissociative disorders, sexual and gender identity disorders, sleep disorders, adjustment disorders, impulse control disorders, personality disorders, bereavement, occupational problem and problems related to abuse or neglect, characterized in that pipamperon or said pharmaceutically acceptable salt thereof is administered simultaneously with, separate from or prior to the administration of a second messenger beta agonist compound to augment the therapeutic effect or to provide a faster onset of the therapeutic effect of said second messenger beta agonist compound, further characterized in that pipamperon is to be administered to a patient in a daily dose ranging between 5 and 15 mg of the active ingredient.

The present invention thus relates to the use of pipamperon or a pharmaceutically acceptable salt thereof for the preparation of a medicament for treating the underlying emotion dysregulation of pain disorders, characterized in that pipamperon or said pharmaceutically acceptable salt thereof is administered simultaneously with, separate from or prior to the administration of a second messenger beta agonist compound to augment the therapeutic effect or to provide a faster onset of the therapeutic effect of said second messenger beta agonist compound, further characterized in that pipamperon is to be administered to a patient in a daily dose ranging between 5 and 15 mg of the active ingredient.

According to a preferred embodiment, the invention relates to the uses as described above, wherein said second messenger beta agonist compound is chosen from the group consisting of SR 57227, rolipram and eplivanserin, or a pro-drug or an active metabolite thereof, or a pharmaceutically acceptable salt thereof. More preferably, said second messenger beta agonist compound is rolipram and is to be administered in a daily dose ranging between 1.5 and 3 mg of the active ingredient.

The invention also relates to a pharmaceutical composition comprising (a) pipamperon, and (b) a second messenger beta agonist compound, preferably chosen from the group consisting of SR 57227, rolipram and eplivanserin or a pro-drug or an active metabolite thereof, or a pharmaceutically acceptable salt thereof, as a combined preparation for simultaneous, separate or sequential use for treating the underlying emotion dysregulation of a mental disease or disorder which is chosen from the group consisting of mood disorders, anxiety disorders, eating disorders, premenstrual syndrome, somatoform disorders (excluding pain disorders), factitious disorders, dissociative disorders, sexual and gender identity disorders, sleep disorders, adjustment disorders, impulse control disorders, personality disorders, bereavement, occupational problem, problems related to abuse or neglect and pain disorders.

The invention also relates to a pharmaceutical composition as described above wherein pipamperon is provided in a unitary dose of between 5 and 15 mg of the active ingredient and wherein said second messenger beta agonist compound is rolipram, preferably provided in a unitary dose of between 1.5 and 3 mg of the active ingredient.

87: Combination Therapy with a Secretin Pancreatic Hormone

The mental disorders which can be treated using compounds having a high selective affinity for the 5-HT2A and D4 receptor, for instance pipamperon, in a combination therapy with a secretin pancreatic hormone, are chosen from the group of diseases or disorders consisting of anxiety disorders, psychotic disorders, somatoform disorders (excluding pain disorders), factitious disorders, dissociative disorders, sleep disorders, adjustment disorders, impulse control disorders, pervasive development disorders, disruptive behaviour disorders, substance-related disorders, personality disorders, psychological factors affecting medical conditions, malingering, antisocial behaviour, bereavement, occupational problem, identity problem, problems related to abuse or neglect, pain disorders and delirium.

The present invention thus relates to the use of pipamperon or a pharmaceutically acceptable salt thereof for the preparation of a medicament for treating the underlying emotion dysregulation of a non-cognitive mental disease or disorder selected from the group of diseases and disorders consisting of anxiety disorders, psychotic disorders, somatoform disorders (excluding pain disorders), factitious disorders, dissociative disorders, sleep disorders, adjustment disorders, impulse control disorders, pervasive development disorders, disruptive behaviour disorders, substance-related disorders, personality disorders, psychological factors affecting medical conditions, malingering, antisocial behaviour, bereavement, occupational problem, identity problem and problems related to abuse or neglect, characterized in that pipamperon or said pharmaceutically acceptable salt thereof is administered simultaneously with, separate from or prior to the administration of a secretin pancreatic hormone to augment the therapeutic effect or to provide a faster onset of the therapeutic effect of said secretin pancreatic hormone, further characterized in that pipamperon is to be administered to a patient in a daily dose ranging between 5 and 15 mg of the active ingredient.

The present invention thus relates to the use of pipamperon or a pharmaceutically acceptable salt thereof for the preparation of a medicament for treating the underlying emotion dysregulation of pain disorders, characterized in that pipamperon or said pharmaceutically acceptable salt thereof is administered simultaneously with, separate from or prior to the administration of a secretin pancreatic hormone to augment the therapeutic effect or to provide a faster onset of the therapeutic effect of said secretin pancreatic hormone, further characterized in that pipamperon is to be administered to a patient in a daily dose ranging between 5 and 15 mg of the active ingredient.

The present invention thus relates to the use of pipamperon or a pharmaceutically acceptable salt thereof for the preparation of a medicament for treating the underlying emotion dysregulation of a cognitive mental disease or disorder which is delirium, characterized in that pipamperon or said pharmaceutically acceptable salt thereof is administered simultaneously with, separate from or prior to the administration of a secretin pancreatic hormone to augment the therapeutic effect or to provide a faster onset of the therapeutic effect of said secretin pancreatic hormone, further characterized in that pipamperon is to be administered to a patient in a daily dose ranging between 5 and 15 mg of the active ingredient.

According to a preferred embodiment, the invention relates to the uses as described above, wherein said secretin pancreatic hormone is RG1068 or a pro-drug or an active metabolite thereof, or a pharmaceutically acceptable salt thereof.

The invention also relates to a pharmaceutical composition comprising (a) pipamperon, and (b) a secretin pancreatic hormone, preferably RG1068, or a pro-drug or an active metabolite thereof, or a pharmaceutically acceptable salt thereof, as a combined preparation for simultaneous, separate or sequential use for treating the underlying emotion dysregulation of a mental disease or disorder which is chosen from the group consisting of anxiety disorders, psychotic disorders, somatoform disorders (excluding pain disorders), factitious disorders, dissociative disorders, sleep disorders, adjustment disorders, impulse control disorders, pervasive development disorders, disruptive behaviour disorders, substance-related disorders, personality disorders, psychological factors affecting medical conditions, malingering, antisocial behaviour, bereavement, occupational problem, identity problem, problems related to abuse or neglect, pain disorders and delirium.

88: Combination Therapy with a Sigma Receptor Agonist Compound

The mental disorders which can be treated using compounds having a high selective affinity for the 5-HT2A and D4 receptor, for instance pipamperon, in a combination therapy with a sigma receptor agonist compound, are chosen from the group of diseases or disorders consisting of mood disorders, anxiety disorders, eating disorders, premenstrual syndrome, somatoform disorders (excluding pain disorders), factitious disorders, dissociative disorders, sexual and gender identity disorders, sleep disorders, adjustment disorders, impulse control disorders, attention-deficit disorders, personality disorders, bereavement, occupational problem, problems related to abuse or neglect and pain disorders.

The present invention thus relates to the use of pipamperon or a pharmaceutically acceptable salt thereof for the preparation of a medicament for treating the underlying emotion dysregulation of a non-cognitive mental disease or disorder selected from the group of diseases and disorders consisting of mood disorders, anxiety disorders, eating disorders, premenstrual syndrome, somatoform disorders (excluding pain disorders), factitious disorders, dissociative disorders, sexual and gender identity disorders, sleep disorders, adjustment disorders, impulse control disorders, attention-deficit disorders, personality disorders, bereavement, occupational problem and problems related to abuse or neglect, characterized in that pipamperon or said pharmaceutically acceptable salt thereof is administered simultaneously with, separate from or prior to the administration of a sigma receptor agonist compound to augment the therapeutic effect or to provide a faster onset of the therapeutic effect of said sigma receptor agonist compound, further characterized in that pipamperon is to be administered to a patient in a daily dose ranging between 5 and 15 mg of the active ingredient.

The present invention thus relates to the use of pipamperon or a pharmaceutically acceptable salt thereof for the preparation of a medicament for treating the underlying emotion dysregulation of pain disorders, characterized in that pipamperon or said pharmaceutically acceptable salt thereof is administered simultaneously with, separate from or prior to the administration of a sigma receptor agonist compound to augment the therapeutic effect or to provide a faster onset of the therapeutic effect of said sigma receptor agonist compound, further characterized in that pipamperon is to be administered to a patient in a daily dose ranging between 5 and 15 mg of the active ingredient.

According to a preferred embodiment, the invention relates to the uses as described above, wherein said sigma receptor agonist compound is VPI-013 (also known as OPC-14523) or PRX-00023, preferably VPI-013 (also known as OPC-14523), or a pro-drug or an active metabolite thereof, or a pharmaceutically acceptable salt thereof.

The invention also relates to a pharmaceutical composition comprising (a) pipamperon, and (b) a sigma receptor agonist compound, preferably VPI-013 (also known as OPC-14523) or PRX-00023, preferably VPI-013 (also known as OPC-14523), or a pro-drug or an active metabolite thereof, or a pharmaceutically acceptable salt thereof, as a combined preparation for simultaneous, separate or sequential use for treating the underlying emotion dysregulation of a mental disease or disorder which is chosen from the group consisting of mood disorders, anxiety disorders, eating disorders, premenstrual syndrome, somatoform disorders (excluding pain disorders), factitious disorders, dissociative disorders, sexual and gender identity disorders, sleep disorders, adjustment disorders, impulse control disorders, attention-deficit disorders, personality disorders, bereavement, occupational problem, problems related to abuse or neglect and pain disorders.

89: Combination Therapy with a Sigma Receptor Antagonist Compound

The mental disorders which can be treated using compounds having a high selective affinity for the 5-HT2A and D4 receptor, for instance pipamperon, in a combination therapy with a sigma receptor antagonist compound, are chosen from the group of diseases or disorders consisting of mood disorders, anxiety disorders, psychotic disorders, eating disorders, premenstrual syndrome, somatoform disorders (excluding pain disorders), factitious disorders, dissociative disorders, sexual and gender identity disorders, sleep disorders, adjustment disorders, impulse control disorders, pervasive development disorders, disruptive behaviour disorders, substance-related disorders, personality disorders, bereavement, occupational problem, problems related to abuse or neglect, pain disorders and delirium.

The present invention thus relates to the use of pipamperon or a pharmaceutically acceptable salt thereof for the preparation of a medicament for treating the underlying emotion dysregulation of a non-cognitive mental disease or disorder selected from the group of diseases and disorders consisting of mood disorders, anxiety disorders, psychotic disorders, eating disorders, premenstrual syndrome, somatoform disorders (excluding pain disorders), factitious disorders, dissociative disorders, sexual and gender identity disorders, sleep disorders, adjustment disorders, impulse control disorders, pervasive development disorders, disruptive behaviour disorders, substance-related disorders, personality disorders, bereavement, occupational problem and problems related to abuse or neglect, characterized in that pipamperon or said pharmaceutically acceptable salt thereof is administered simultaneously with, separate from or prior to the administration of a sigma receptor antagonist compound to augment the therapeutic effect or to provide a faster onset of the therapeutic effect of said sigma receptor antagonist compound, further characterized in that pipamperon is to be administered to a patient in a daily dose ranging between 5 and 15 mg of the active ingredient.

The present invention thus relates to the use of pipamperon or a pharmaceutically acceptable salt thereof for the preparation of a medicament for treating the underlying emotion dysregulation of pain disorders, characterized in that pipamperon or said pharmaceutically acceptable salt thereof is administered simultaneously with, separate from or prior to the administration of a sigma receptor antagonist compound to augment the therapeutic effect or to provide a faster onset of the therapeutic effect of said sigma receptor antagonist compound, further characterized in that pipamperon is to be administered to a patient in a daily dose ranging between 5 and 15 mg of the active ingredient.

The present invention thus relates to the use of pipamperon or a pharmaceutically acceptable salt thereof for the preparation of a medicament for treating the underlying emotion dysregulation of a cognitive mental disease or disorder which is delirium, characterized in that pipamperon or said pharmaceutically acceptable salt thereof is administered simultaneously with, separate from or prior to the administration of a sigma receptor antagonist compound to augment the therapeutic effect or to provide a faster onset of the therapeutic effect of said sigma receptor antagonist compound, further characterized in that pipamperon is to be administered to a patient in a daily dose ranging between 5 and 15 mg of the active ingredient.

According to a preferred embodiment, the invention relates to the uses as described above, wherein said sigma receptor antagonist compound is chosen from the group consisting of SR 31742 and EMD 68843, or a pro-drug or an active metabolite thereof, or a pharmaceutically acceptable salt thereof. More preferably, said sigma receptor antagonist compound is EMD 68843 and is to be administered in a daily dose ranging between 5 and 40 mg of the active ingredient.

The invention also relates to a pharmaceutical composition comprising (a) pipamperon, and (b) a sigma receptor antagonist compound, preferably chosen from the group consisting of SR 31742 and EMD 68843, or a pro-drug or an active metabolite thereof, or a pharmaceutically acceptable salt thereof, as a combined preparation for simultaneous, separate or sequential use for treating the underlying emotion dysregulation of a mental disease or disorder which is chosen from the group consisting mood disorders, anxiety disorders, psychotic disorders, eating disorders, premenstrual syndrome, somatoform disorders (excluding pain disorders), factitious disorders, dissociative disorders, sexual and gender identity disorders, sleep disorders, adjustment disorders, impulse control disorders, pervasive development disorders, disruptive behaviour disorders, substance-related disorders, personality disorders, bereavement, occupational problem, problems related to abuse or neglect, pain disorders and delirium.

The invention also relates to a pharmaceutical composition as described above wherein pipamperon is provided in a unitary dose of between 5 and 15 mg of the active ingredient and wherein said sigma receptor antagonist compound is EMD 68843, preferably provided in a unitary dose of between 5 and 40 mg of the active ingredient.

90: Combination Therapy with a Selective SNDRI Compound

The mental disorders which can be treated using compounds having a high selective affinity for the 5-HT2A and D4 receptor, for instance pipamperon, in a combination therapy with a selective serotonin, nor-adrenaline and dopamine re-uptake inhibitor (SNDRI) compound, are chosen from the group of diseases or disorders consisting of mood disorders, anxiety disorders, eating disorders, premenstrual syndrome, somatoform disorders (excluding pain disorders), factitious disorders, dissociative disorders, sleep disorders, adjustment disorders, impulse control disorders, attention-deficit disorders, substance-related disorders, personality disorders, antisocial behaviour, bereavement, occupational problem, problems related to abuse or neglect, pain disorders, delirium, Alzheimer Disease, substance-induced persisting dementia, vascular dementia, dementia due to HIV disease, dementia due to head trauma, dementia due to Parkinson Disease, dementia due to Huntington Disease, dementia due to Pick Disease, dementia due to Creutzfeldt-Jacob Disease, amnestic disorders due to a general medical condition, substance-induced persisting amnestic disorder, mild cognitive impairment disorder and other cognitive disorders.

The present invention thus relates to the use of pipamperon or a pharmaceutically acceptable salt thereof for the preparation of a medicament for treating the underlying emotion dysregulation of a non-cognitive mental disease or disorder selected from the group of diseases and disorders consisting of mood disorders, anxiety disorders, eating disorders, premenstrual syndrome, somatoform disorders (excluding pain disorders), factitious disorders, dissociative disorders, sleep disorders, adjustment disorders, impulse control disorders, attention-deficit disorders, substance-related disorders, personality disorders, antisocial behaviour, bereavement, occupational problem and problems related to abuse or neglect, characterized in that pipamperon or said pharmaceutically acceptable salt thereof is administered simultaneously with, separate from or prior to the administration of a selective serotonin, nor-adrenaline and dopamine re-uptake inhibitor (SNDRI) compound to augment the therapeutic effect or to provide a faster onset of the therapeutic effect of said selective serotonin, nor-adrenaline and dopamine re-uptake inhibitor (SNDRI) compound, further characterized in that pipamperon is to be administered to a patient in a daily dose ranging between 5 and 15 mg of the active ingredient.

The present invention thus relates to the use of pipamperon or a pharmaceutically acceptable salt thereof for the preparation of a medicament for treating the underlying emotion dysregulation of pain disorders, characterized in that pipamperon or said pharmaceutically acceptable salt thereof is administered simultaneously with, separate from or prior to the administration of a selective serotonin, nor-adrenaline and dopamine re-uptake inhibitor (SNDRI) compound to augment the therapeutic effect or to provide a faster onset of the therapeutic effect of said se ective serotonin, nor-adrenaline and dopamine re-uptake inhibitor (SNDRI) compound, further characterized in that pipamperon is to be administered to a patient in a daily dose ranging between 5 and 15 mg of the active ingredient.

The present invention thus relates to the use of pipamperon or a pharmaceutically acceptable salt thereof for the preparation of a medicament for treating the underlying emotion dysregulation of a cognitive mental disease or disorder selected from the group of diseases and disorders consisting of delirium, Alzheimer Disease, substance-induced persisting dementia, vascular dementia, dementia due to HIV disease, dementia due to head trauma, dementia due to Parkinson Disease, dementia due to Huntington Disease, dementia due to Pick Disease, dementia due to Creutzfeldt-Jacob Disease, amnestic disorders due to a general medical condition, substance-induced persisting amnestic disorder, mild cognitive impairment disorder and other cognitive disorders, characterized in that pipamperon or said pharmaceutically acceptable salt thereof is administered simultaneously with, separate from or prior to the administration of a selective serotonin, nor-adrenaline and dopamine re-uptake inhibitor (SNDRI) compound to augment the therapeutic effect or to provide a faster onset of the therapeutic effect of said selective serotonin, nor-adrenaline and dopamine re-uptake inhibitor (SNDRI) compound, further characterized in that pipamperon is to be administered to a patient in a daily dose ranging between 5 and 15 mg of the active ingredient.

According to a preferred embodiment, the invention relates to the uses as described above, wherein said selective serotonin, nor-adrenaline and dopamine re-uptake inhibitor (SNDRI) compound is selected from the group consisting of NS 2330; McN 5652; DOV 216,303 and DOV 21,947; more preferably NS 2330 or DOV 216.303; or a pro-drug or an active metabolite thereof; or a pharmaceutically acceptable salt thereof.

The invention also relates to a pharmaceutical composition comprising (a) pipamperon, and (b) a selective serotonin, nor-adrenaline and dopamine re-uptake inhibitor (SNDRI) compound, preferably selected from the group consisting of NS 2330; McN 5652; DOV 216,303 and DOV 21,947, more preferably NS 2330 or DOV 216,303, or a pro-drug or an active metabolite thereof, or a pharmaceutically acceptable salt thereof, as a combined preparation for simultaneous, separate or sequential use for treating the underlying emotion dysregulation of mental disease or disorder which is chosen from the group consisting of mood disorders, anxiety disorders, eating disorders, premenstrual syndrome, somatoform disorders (excluding pain disorders), factitious disorders, dissociative disorders, sleep disorders, adjustment disorders, impulse control disorders, attention-deficit disorders, substance-related disorders, personality disorders, antisocial behaviour, bereavement, occupational problem, problems related to abuse or neglect, pain disorders, delirium, Alzheimer Disease, substance-induced persisting dementia, vascular dementia, dementia due to HIV disease, dementia due to head trauma, dementia due to Parkinson Disease, dementia due to Huntington Disease, dementia due to Pick Disease, dementia due to Creutzfeldt-Jacob Disease, amnestic disorders due to a general medical condition, substance-induced persisting amnestic disorder, mild cognitive impairment disorder and other cognitive disorders.

91: Combination Therapy with a Selective SNRI Compound

The mental disorders which can be treated using compounds having a high selective affinity for the 5-HT2A and D4 receptor, for instance pipamperon, in a combination therapy with a selective serotonin and nor-adrenaline re-uptake inhibitor (SNRI) compound, are chosen from the group of diseases or disorders consisting of mood disorders, anxiety disorders, eating disorders, premenstrual syndrome, somatoform disorders (excluding pain disorders), factitious disorders, dissociative disorders, sleep disorders, adjustment disorders, impulse control disorders, attention-deficit disorders, substance-related disorders, personality disorders, antisocial behaviour, bereavement, occupational problem, problems related to abuse or neglect and pain disorders.

The present invention thus relates to the use of pipamperon or a pharmaceutically acceptable salt thereof for the preparation of a medicament for treating the underlying emotion dysregulation of a non-cognitive mental disease or disorder selected from the group of diseases and disorders consisting of mood disorders, anxiety disorders, eating disorders, premenstrual syndrome, somatoform disorders (excluding pain disorders), factitious disorders, dissociative disorders, sleep disorders, adjustment disorders, impulse control disorders, attention-deficit disorders, substance-related disorders, personality disorders, antisocial behaviour, bereavement, occupational problem and problems related to abuse or neglect, characterized in that pipamperon or said pharmaceutically acceptable salt thereof is administered simultaneously with, separate from or prior to the administration of a selective serotonin and nor-adrenaline re-uptake inhibitor (SNRI) compound to augment the therapeutic effect or to provide a faster onset of the therapeutic effect of said selective serotonin and nor-adrenaline re-uptake inhibitor (SNRI) compound, further characterized in that pipamperon is to be administered to a patient in a daily dose ranging between 5 and 15 mg of the active ingredient.

The present invention thus relates to the use of pipamperon or a pharmaceutically acceptable salt thereof for the preparation of a medicament for treating the underlying emotion dysregulation of pain disorders, characterized in that pipamperon or said pharmaceutically acceptable salt thereof is administered simultaneously with, separate from or prior to the administration of a selective serotonin and nor-adrenaline re-uptake inhibitor (SNRI) compound to augment the therapeutic effect or to provide a faster onset of the therapeutic effect of said selective serotonin and nor-adrenaline re-uptake inhibitor (SNRI) compound, further characterized in that pipamperon is to be administered to a patient in a daily dose ranging between 5 and 15 mg of the active ingredient.

According to a preferred embodiment, the invention relates to the uses as described above, wherein said selective serotonin and nor-adrenaline re-uptake inhibitor (SNRI) compound is selected from the group consisting of venlafaxine, tomoxetine, tandamine, talsupram, talopram, nefazodone, milnacipran, LY 113.821, duloxetine, desvenlafaxine and amoxapine, or a pro-drug or an active metabolite thereof, or a pharmaceutically acceptable salt thereof. Even more preferably, said selective serotonin and nor-adrenaline re-uptake inhibitor (SNRI) compound is chosen from the group consisting of venlafaxine, tomoxetine, milnacipran, duloxetine and desvenlafaxine, or a pro-drug or an active metabolite thereof, or a pharmaceutically acceptable salt thereof. More preferably, said selective serotonin and nor-adrenaline re-uptake inhibitor (SNRI) compound is venlafaxine and is to be administered in a daily dose ranging between 75 and 300 mg of the active ingredient. More preferably, said selective serotonin and nor-adrenaline re-uptake inhibitor (SNRI) compound is tomoxetine and is to be administered in a daily dose ranging between 0.475 and 3.8 mg/kg of the active ingredient. More preferably, said selective serotonin and nor-adrenaline re-uptake inhibitor (SNRI) compound is milnacipran and is to be administered in a daily dose ranging between 50 and 200 mg of the active ingredient. More preferably, said selective serotonin and nor-adrenaline re-uptake inhibitor (SNRI) compound is duloxetine and is to be administered in a daily dose ranging between 40 and 60 mg of the active ingredient.

The invention also relates to a pharmaceutical composition comprising (a) pipamperon, and (b) a selective serotonin and nor-adrenaline re-uptake inhibitor (SNRI) compound, preferably selected from the group consisting of venlafaxine, tomoxetine, tandamine, talsupram, talopram, nefazodone, milnacipran, LY 113.821, duloxetine, desvenlafaxine and amoxapine, or a pro-drug or an active metabolite thereof, or a pharmaceutically acceptable salt thereof, as a combined preparation for simultaneous, separate or sequential use for treating the underlying emotion dysregulation of mental disease or disorder which is chosen from the group consisting of mood disorders, anxiety disorders, eating disorders, premenstrual syndrome, somatoform disorders (excluding pain disorders), factitious disorders, dissociative disorders, sleep disorders, adjustment disorders, impulse control disorders, attention-deficit disorders, substance-related disorders, personality disorders, antisocial behaviour, bereavement, occupational problem, problems related to abuse or neglect and pain disorders.

The invention also relates to a pharmaceutical composition as described above wherein pipamperon is provided in a unitary dose of between 5 and 15 mg of the active ingredient and wherein said selective serotonin and nor-adrenaline re-uptake inhibitor (SNRI) compound is venlafaxine, preferably provided in a unitary dose of between 75 and 300 mg of the active ingredient.

The invention also relates to a pharmaceutical composition as described above wherein pipamperon is provided in a unitary dose of between 5 and 15 mg of the active ingredient and wherein said selective serotonin and nor-adrenaline re-uptake inhibitor (SNRI) compound is tomoxetine, preferably provided in a unitary dose of between 0.475 and 3.8 mg/kg of the active ingredient.

The invention also relates to a pharmaceutical composition as described above wherein pipamperon is provided in a unitary dose of between 5 and 15 mg of the active ingredient and wherein said selective serotonin and nor-adrenaline re-uptake inhibitor (SNRI) compound is milnacipran, preferably provided in a unitary dose of between 50 and 200 mg of the active ingredient.

The invention also relates to a pharmaceutical composition as described above wherein pipamperon is provided in a unitary dose of between 5 and 15 mg of the active ingredient and wherein said selective serotonin and nor-adrenaline re-uptake inhibitor (SNRI) compound is duloxetine, preferably provided in a unitary dose of between 40 and 60 mg of the active ingredient.

92: Combination Therapy with a Selective Serotonin Re-Uptake Inhibitor (SSRI) Compound The mental disorders which can be treated using compounds having a high selective affinity for the 5-HT2A and D4 receptor, for instance pipamperon, in a combination therapy with a selective serotonin re-uptake inhibitor (SSRI) compound, are chosen from the group of diseases or disorders consisting of mood disorders, anxiety disorders, eating disorders, premenstrual syndrome, somatoform disorders (excluding pain disorders), factitious disorders, dissociative disorders, sleep disorders, adjustment disorders, impulse control disorders, substance-related disorders, personality disorders, antisocial behaviour, bereavement, occupational problem, problems related to abuse or neglect and pain disorders.

The present invention thus relates to the use of pipamperon or a pharmaceutically acceptable salt thereof for the preparation of a medicament for treating the underlying emotion dysregulation of a non-cognitive mental disease or disorder selected from the group of diseases and disorders consisting of mood disorders, anxiety disorders, eating disorders, premenstrual syndrome, somatoform disorders (excluding pain disorders), factitious disorders, dissociative disorders, sleep disorders, adjustment disorders, impulse control disorders, substance-related disorders, personality disorders, antisocial behaviour, bereavement, occupational problem and problems related to abuse or neglect, characterized in that pipamperon or said pharmaceutically acceptable salt thereof is administered simultaneously with, separate from or prior to the administration of a selective serotonin re-uptake inhibitor (SSRI) compound to augment the therapeutic effect or to provide a faster onset of the therapeutic effect of said selective serotonin re-uptake inhibitor (SSRI) compound, further characterized in that pipamperon is to be administered to a patient in a daily dose ranging between 5 and 15 mg of the active ingredient.

The present invention thus relates to the use of pipamperon or a pharmaceutically acceptable salt thereof for the preparation of a medicament for treating the underlying emotion dysregulation of pain disorders, characterized in that pipamperon or said pharmaceutically acceptable salt thereof is administered simultaneously with, separate from or prior to the administration of a selective serotonin re-uptake inhibitor (SSRI) compound to augment the therapeutic effect or to provide a faster onset of the therapeutic effect of said selective serotonin re-uptake inhibitor (SSRI) compound, further characterized in that pipamperon is to be administered to a patient in a daily dose ranging between 5 and 15 mg of the active ingredient.

According to a preferred embodiment, the invention relates to the uses as described above, wherein said selective serotonin re-uptake inhibitor (SSRI) compound is selected from the group consisting of YM 992, VPI-013 (also known as OPC-14523), sertra line, paroxetine, LY 214.281, LU AA 21-004, Lu 35-138, litoxetine, ifoxetine, fluvoxamine (controlled release formulation), fluvoxamine, fluoxetine, femoxetine, escitalopram, EMD 68843, cyanodothepine, citalopram, cericlamine and ademethionine (preferably s-adenosylmethionine), or a pro-drug or an active metabolite thereof, or a pharmaceutically acceptable salt thereof. Even more preferably, said selective serotonin re-uptake inhibitor (SSRI) compound is chosen from the group consisting of litoxetine, fluvoxamine (controlled release formulation), citalopram and escitalopram, or a pro-drug or an active metabolite thereof, or a pharmaceutically acceptable salt thereof. More preferably, said selective serotonin re-uptake inhibitor (SSRI) compound is fluvoxamine (controlled release formulation) and is to be administered in a daily dose ranging between 100 and 300 mg of the active ingredient. More preferably, said selective serotonin re-uptake inhibitor (SSRI) compound is escitalopram and is to be administered in a daily dose ranging between 10 and 20 mg of the active ingredient. More preferably, said selective serotonin re-uptake inhibitor (SSRI) compound is citalopram and is to be administered in a daily dose ranging between 10 and 40 mg of the active ingredient.

The invention also relates to a pharmaceutical composition comprising (a) pipamperon, and (b) a selective serotonin re-uptake inhibitor (SSRI) compound, preferably selected from the group consisting of YM 992, VPI-013 (also known as OPC-14523), sertraline, paroxetine, LY 214.281, LU AA 21-004, Lu 35-138, litoxetine, ifoxetine, fluvoxamine (controlled release formulation), fluvoxamine, fluoxetine, femoxetine, escitalopram, EMD 68843, cyanodothepine, citalopram, venlafaxine, milnacipran, duloxetine, cericlamine and ademethionine (preferably s-adenosylmethionine), or a pro-drug or an active metabolite thereof, or a pharmaceutically acceptable salt thereof, as a combined preparation for simultaneous, separate or sequential use for treating the underlying emotion dysregulation of mental disease or disorder which is chosen from the group consisting of mood disorders, anxiety disorders, eating disorders, premenstrual syndrome, somatoform disorders (excluding pain disorders), factitious disorders, dissociative disorders, sleep disorders, adjustment disorders, impulse control disorders, substance-related disorders, personality disorders, antisocial behaviour, bereavement, occupational problem, problems related to abuse or neglect and pain disorders.

The invention also relates to a pharmaceutical composition as described above wherein pipamperon is provided in a unitary dose of between 5 and 15 mg of the active ingredient and wherein said selective serotonin re-uptake inhibitor (SSRI) compound is fluvoxamine (controlled release formulation), preferably provided in a unitary dose of between 100 and 300 mg of the active ingredient.

The invention also relates to a pharmaceutical composition as described above wherein pipamperon is provided in a unitary dose of between 5 and 15 mg of the active ingredient and wherein said selective serotonin re-uptake inhibitor (SSRI) compound is escitalopram, preferably provided in a unitary dose of between 10 and 20 mg of the active ingredient.

The invention also relates to a pharmaceutical composition as described above wherein pipamperon is provided in a unitary dose of between 5 and 15 mg of the active ingredient and wherein said selective serotonin re-uptake inhibitor (SSRI) compound is citalopram, preferably provided in a unitary dose of between 10 and 40 mg of the active ingredient.

Citalopram or citalopram hydrobromide is a selective serotonin (5-hydroxytryptamine/5-HT) re-uptake inhibitor (SSRI) and is the conventional name given for the compound of the formula (RS)-1-[3-(dimethylamino)propyl]-1-(p-fluorophenyl)-5-phthalancarbonitrile-hydro-bromide. According to an embodiment, a daily doses of active ingredient of SSRI, preferably citalopram, ranges between 10 and 40 mg per day. Preferably, daily doses of active ingredient ranging between 20 and 30 mg per day are administered. More preferably, a daily dose of 10, 15, 20, 25, 30, 35 or 40 mg per day is administered.

Fluvoxamine or fluvoxamine maleate (luvox, fevarin) is a selective serotonin (5-HT) re-uptake inhibitor (SSRI) belonging to a new chemical series, the 2-aminoethyl oxime ethers of aralkylketones. It is chemically unrelated to other SSRIs and clomipramine. It is chemically designated as 5-methoxy-4'-(trifluoromethyl)valerophenone (E)-O-(2-aminoethyl) oxime maleate (1:1).

According to an embodiment, a daily dose of active ingredient of fluvoxamine in a controlled release mode ranges between 100 and 300 mg per day. Preferably, daily doses of active ingredient ranging between 150 and 200 mg per day are administered in a controlled release mode. More preferably, a daily dose of 100, 150, 200, 250 or 300 mg per day is administered by controlled release.

93: Combination Therapy with a Substance P Receptor (NK1) Antagonist Compound

The mental disorders which can be treated using compounds having a high selective affinity for the 5-HT2A and D4 receptor, for instance pipamperon, in a combination therapy with a substance P receptor (NK1) antagonist compound, are chosen from the group of diseases or disorders consisting of mood disorders, anxiety disorders, eating disorders, premenstrual syndrome, somatoform disorders (excluding pain disorders), factitious disorders, dissociative disorders, sexual and gender identity disorders, sleep disorders, adjustment disorders, impulse control disorders, substance-related disorders, personality disorders, bereavement, occupational problem, problems related to abuse or neglect and pain disorders.

The present invention thus relates to the use of pipamperon or a pharmaceutically acceptable salt thereof for the preparation of a medicament for treating the underlying emotion dysregulation of a non-cognitive mental disease or disorder selected from the group of diseases and disorders consisting of mood disorders, anxiety disorders, eating disorders, premenstrual syndrome, somatoform disorders (excluding pain disorders), factitious disorders, dissociative disorders, sexual and gender identity disorders, sleep disorders, adjustment disorders, impulse control disorders, substance-related disorders, personality disorders, bereavement, occupational problem and problems related to abuse or neglect, characterized in that pipamperon or said pharmaceutically acceptable salt thereof is administered simultaneously with, separate from or prior to the administration of a substance P receptor (NK1) antagonist compound to augment the therapeutic effect or to provide a faster onset of the therapeutic effect of said substance P receptor (NK1) antagonist compound, further characterized in that pipamperon is to be administered to a patient in a daily dose ranging between 5 and 15 mg of the active ingredient.

The present invention thus relates to the use of pipamperon or a pharmaceutically acceptable salt thereof for the preparation of a medicament for treating the underlying emotion dysregulation of pain, characterized in that pipamperon or said pharmaceutically acceptable salt thereof is administered simultaneously with, separate from or prior to the administration of a substance P receptor (NK1) antagonist compound to augment the therapeutic effect or to provide a faster onset of the therapeutic effect of said substance P receptor (NK1) antagonist compound, further characterized in that pipamperon is to be administered to a patient in a daily dose ranging between 5 and 15 mg of the active ingredient.

According to a preferred embodiment, the invention relates to the uses as described above, wherein said substance P receptor (NK1) antagonist compound is chosen from the group consisting of vestipitant, TAK-637, 8673, GW823296, GW679769, GW597599, CP-122.721, aprepitant, 823296 and 679769, or a pro-drug or an active metabolite thereof, or a pharmaceutically acceptable salt thereof. More preferably, said substance P receptor (NK1) antagonist compound is aprepitant and is to be administered in a daily dose ranging between 40 and 160 mg of the active ingredient.

The invention also relates to a pharmaceutical composition comprising (a) pipamperon, and (b) a substance P receptor (NK1) antagonist compound, preferably chosen from the group consisting of vestipitant, TAK-637, R673, GW823296, GW679769, GW597599, CP-122.721, aprepitant, 823296 and 679769, or a pro-drug or an active metabolite thereof, or a pharmaceutically acceptable salt thereof, as a combined preparation for simultaneous, separate or sequential use for treating the underlying emotion dysregulation of a mental disease or disorder which is chosen from the group of diseases and disorders consisting of mood disorders, anxiety disorders, eating disorders, premenstrual syndrome, somatoform disorders (excluding pain disorders), factitious disorders, dissociative disorders, sexual and gender identity disorders, sleep disorders, adjustment disorders, impulse control disorders, substance-related disorders, personality disorders, bereavement, occupational problem, problems related to abuse or neglect and pain disorders.

The invention also relates to a pharmaceutical composition as described above wherein pipamperon is provided in a unitary dose of between 5 and 15 mg of the active ingredient and wherein said substance P receptor (NK1) antagonist compound is aprepitant, preferably provided in a unitary dose of between 40 and 160 mg of the active ingredient.

94: Combination Therapy with a Sulfonamide Compound

The mental disorders which can be treated using compounds having a high selective affinity for the 5-HT2A and D4 receptor, for instance pipamperon, in a combination therapy with a sulfonamide compound, are chosen from the group of diseases or disorders consisting of mood disorders, psychotic disorders, somatoform disorders (excluding pain disorders), factitious disorders, dissociative disorders, sleep disorders, adjustment disorders, impulse control disorders, pervasive development disorders, disruptive behaviour disorders, substance-related disorders, personality disorders, psychological factors affecting medical conditions, malingering, antisocial behaviour, bereavement, occupational problem, identity problem, problems related to abuse or neglect, pain disorders and delirium.

The present invention thus relates to the use of pipamperon or a pharmaceutically acceptable salt thereof for the preparation of a medicament for treating the underlying emotion dysregulation of a non-cognitive mental disease or disorder selected from the group of diseases and disorders consisting of mood disorders, psychotic disorders, somatoform disorders (excluding pain disorders), factitious disorders, dissociative disorders, sleep disorders, adjustment disorders, impulse control disorders, pervasive development disorders, disruptive behaviour disorders, substance-related disorders, personality disorders, psychological factors affecting medical conditions, malingering, antisocial behaviour, bereavement, occupational problem, identity problem and problems related to abuse or neglect, characterized in that pipamperon or said pharmaceutically acceptable salt thereof is administered simultaneously with, separate from or prior to the administration of a sulfonamide compound to augment the therapeutic effect or to provide a faster onset of the therapeutic effect of said sulfonamide compound, further characterized in that pipamperon is to be administered to a patient in a daily dose ranging between 5 and 15 mg of the active ingredient.

The present invention thus relates to the use of pipamperon or a pharmaceutically acceptable salt thereof for the preparation of a medicament for treating the underlying emotion dysregulation of pain disorders, characterized in that pipamperon or said pharmaceutically acceptable salt thereof is administered simultaneously with, separate from or prior to the administration of a sulfonamide compound to augment the therapeutic effect or to provide a faster onset of the therapeutic effect of said sulfonamide compound, further characterized in that pipamperon is to be administered to a patient in a daily dose ranging between 5 and 15 mg of the active ingredient.

The present invention thus relates to the use of pipamperon or a pharmaceutically acceptable salt thereof for the preparation of a medicament for treating the underlying emotion dysregulation of a cognitive mental disease or disorder which is delirium, characterized in that pipamperon or said pharmaceutically acceptable salt thereof is administered simultaneously with, separate from or prior to the administration of a sulfonamide compound to augment the therapeutic effect or to provide a faster onset of the therapeutic effect of said sulfonamide compound, further characterized in that pipamperon is to be administered to a patient in a daily dose ranging between 5 and 15 mg of the active ingredient.

According to a preferred embodiment, the invention relates to the uses as described above, wherein said sulfonamide compound is zonisamide or a pro-drug or an active metabolite thereof, or a pharmaceutically acceptable salt thereof. More preferably, said sulfonamide compound is zonisamide and is to be administered in a daily dose ranging between 100 and 600 mg of the active ingredient.

The invention also relates to a pharmaceutical composition comprising (a) pipamperon, and (b) a sulfonamide compound, preferably zonisamide, or a pro-drug or an active metabolite thereof, or a pharmaceutically acceptable salt thereof, as a combined preparation for simultaneous, separate or sequential use for treating the underlying emotion dysregulation of a mental disease or disorder which is chosen from the group consisting mood disorders, psychotic disorders, somatoform disorders (excluding pain disorders), factitious disorders, dissociative disorders, sleep disorders, adjustment disorders, impulse control disorders, pervasive development disorders, disruptive behaviour disorders, substance-related disorders, personality disorders, psychological factors affecting medical conditions, malingering, antisocial behaviour, bereavement, occupational problem, identity problem, problems related to abuse or neglect, pain disorders and delirium.

The invention also relates to a pharmaceutical composition as described above wherein pipamperon is provided in a unitary dose of between 5 and 15 mg of the active ingredient and wherein said sulfonamide compound is zonisamide, preferably provided in a unitary dose of between 100 and 600 mg of the active ingredient.

95: Combination Therapy with a Tachykinin Antagonist Compound

The mental disorders which can be treated using compounds having a high selective affinity for the 5-HT2A and D4 receptor, for instance pipamperon, in a combination therapy with a tachykinin antagonist compound, are chosen from the group of diseases or disorders consisting of mood disorders, anxiety disorders, eating disorders, premenstrual syndrome, somatoform disorders (excluding pain disorders), factitious disorders, dissociative disorders, sexual and gender identity disorders, sleep disorders, adjustment disorders, impulse control disorders, substance-related disorders, personality disorders, bereavement, occupational problem, problems related to abuse or neglect and pain disorders.

The present invention thus relates to the use of pipamperon or a pharmaceutically acceptable salt thereof for the preparation of a medicament for treating the underlying emotion dysregulation of a non-cognitive mental disease or disorder selected from the group of diseases and disorders consisting of mood disorders, anxiety disorders, eating disorders, premenstrual syndrome, somatoform disorders (excluding pain disorders), factitious disorders, dissociative disorders, sexual and gender identity disorders, sleep disorders, adjustment disorders, impulse control disorders, substance-related disorders, personality disorders, bereavement, occupational problem and problems related to abuse or neglect, characterized in that pipamperon or said pharmaceutically acceptable salt thereof is administered simultaneously with, separate from or prior to the administration of a tachykinin antagonist compound to augment the therapeutic effect or to provide a faster onset of the therapeutic effect of said tachykinin antagonist compound, further characterized in that pipamperon is to be administered to a patient in a daily dose ranging between 5 and 15 mg of the active ingredient.

The present invention thus relates to the use of pipamperon or a pharmaceutically acceptable salt thereof for the preparation of a medicament for treating the underlying emotion dysregulation of pain disorders, characterized in that pipamperon or said pharmaceutically acceptable salt thereof is administered simultaneously with, separate from or prior to the administration of a tachykinin antagonist compound to augment the therapeutic effect or to provide a faster onset of the therapeutic effect of said tachykinin antagonist compound, further characterized in that pipamperon is to be administered to a patient in a daily dose ranging between 5 and 15 mg of the active ingredient.

According to a preferred embodiment, the invention relates to the use as described above, wherein said tachykinin antagonist compound is SR 48968 or a pro-drug or an active metabolite thereof, or a pharmaceutically acceptable salt thereof.

The invention also relates to a pharmaceutical composition comprising (a) pipamperon, and (b) a tachykinin antagonist compound, preferably SR 48968 or a pro-drug or an active metabolite thereof, or a pharmaceutically acceptable salt thereof, as a combined preparation for simultaneous, separate or sequential use for treating the underlying emotion dysregulation of a mental disease or disorder which is chosen from the group consisting of mood disorders, anxiety disorders, eating disorders, premenstrual syndrome, somatoform disorders (excluding pain disorders), factitious disorders, dissociative disorders, sexual and gender identity disorders, sleep disorders, adjustment disorders, impulse control disorders, substance-related disorders, personality disorders, bereavement, occupational problem, problems related to abuse or neglect and pain disorders.

96: Combination Therapy with a Compound Selected from the Group Consisting of R228060 (YKP-10A), Palanpanel, ORG 39479/PH80, ORG 34167, DP 543 and CJ-017.493

The mental disorders which can be treated using compounds having a high selective affinity for the 5-HT2A and D4 receptor, for instance pipamperon, in a combination therapy with a compound selected from the group consisting of R228060 (YKP-10A), palanpanel, ORG 39479/PH80, ORG 34167, DP 543 and CJ-017.493, are chosen from the group of diseases or disorders consisting of mood disorders, anxiety disorders, psychotic disorders, eating disorders, premenstrual syndrome, somatoform disorders (excluding pain disorders), factitious disorders, dissociative disorders, sexual and gender identity disorders, sleep disorders, adjustment disorders, impulse control disorders, pervasive development disorders, attention-deficit disorders, disruptive behaviour disorders, substance-related disorders, personality disorders, psychological factors affecting medical conditions, malingering, antisocial behaviour, bereavement, occupational problem, identity problem, phase of life problem, academic problem, problems related to abuse or neglect, pain disorders, delirium, Alzheimer Disease, substance-induced persisting dementia, vascular dementia, dementia due to REV disease, dementia due to head trauma, dementia due to Parkinson Disease, dementia due to Huntington Disease, dementia due to Pick Disease, dementia due to Creutzfeldt-Jacob Disease, amnestic disorders due to a general medical condition, substance-induced persisting amnestic disorder, mild cognitive impairment disorder, other cognitive disorders and Parkinson Disease.

The present invention thus relates to the use of pipamperon or a pharmaceutically acceptable salt thereof for the preparation of a medicament for treating the underlying emotion dysregulation of a non-cognitive mental disease or disorder selected from the group of diseases and disorders consisting of mood disorders, anxiety disorders, psychotic disorders, eating disorders, premenstrual syndrome, somatoform disorders (excluding pain disorders), factitious disorders, dissociative disorders, sexual and gender identity disorders, sleep disorders, adjustment disorders, impulse control disorders, pervasive development disorders, attention-deficit disorders, disruptive behaviour disorders, substance-related disorders, personality disorders, psychological factors affecting medical conditions, malingering, antisocial behaviour, bereavement, occupational problem, identity problem, phase of life problem, academic problem and problems related to abuse or neglect, characterized in that pipamperon or said pharmaceutically acceptable salt thereof is administered simultaneously with, separate from or prior to the administration of a compound selected from the group consisting of R228060 (YKP-10A), palanpanel, ORG 39479/PH80, ORG 34167, DP 543 and CJ-017.493, to augment the therapeutic effect or to provide a faster onset of the therapeutic effect of said compound selected from the group consisting of R228060 (YKP-10A), palanpanel, ORG 39479/PH80, ORG 34167, DP 543 and CJ-017.493, further characterized in that pipamperon is to be administered to a patient in a daily dose ranging between 5 and 15 mg of the active ingredient.

The present invention thus relates to the use of pipamperon or a pharmaceutically acceptable salt thereof for the preparation of a medicament for treating the underlying emotion dysregulation of pain disorders, characterized in that pipamperon or said pharmaceutically acceptable salt thereof is administered simultaneously with, separate from or prior to the administration of a compound selected from the group consisting of R228060 (YKP-10A), palanpanel, ORG 39479/PH80, ORG 34167, DP 543 and CJ-017.493, to augment the therapeutic effect or to provide a faster onset of the therapeutic effect of said compound selected from the group consisting of R228060 (YKP-10A), palanpanel, ORG 39479/PH80, ORG 34167, DP 543 and CJ-017.493, further characterized in that pipamperon is to be administered to a patient in a daily dose ranging between 5 and 15 mg of the active ingredient.

The present invention thus relates to the use of pipamperon or a pharmaceutically acceptable salt thereof for the preparation of a medicament for treating the underlying emotion dysregulation of a non-cognitive mental disease or disorder selected from the group of diseases and disorders consisting of delirium, Alzheimer Disease, substance-induced persisting dementia, vascular dementia, dementia due to HIV disease, dementia due to head trauma, dementia due to Parkinson Disease, dementia due to Huntington Disease, dementia due to Pick Disease, dementia due to Creutzfeldt-Jacob Disease, amnestic disorders due to a general medical condition, substance-induced persisting amnestic disorder, mild cognitive impairment disorder and other cognitive disorders, characterized in that pipamperon or said pharmaceutically acceptable salt thereof is administered simultaneously with, separate from or prior to the administration of a compound selected from the group consisting of R228060 (YKP-10A), palanpanel, ORG 39479/PH80, ORG 34167, DP 543 and CJ-017.493, to augment the therapeutic effect or to provide a faster onset of the therapeutic effect of said compound selected from the group consisting of R228060 (YKP-10A), palanpanel, ORG 39479/PH80, ORG 34167, DP 543 and CJ-017.493, further characterized in that pipamperon is to be administered to a patient in a daily dose ranging between 5 and 15 mg of the active ingredient.

The present invention thus relates to the use of pipamperon or a pharmaceutically acceptable salt thereof for the preparation of a medicament for treating the underlying emotion dysregulation of Parkinson Disease, characterized in that pipamperon or said pharmaceutically acceptable salt thereof is administered simultaneously with, separate from or prior to the administration of a compound selected from the group consisting of R228060 (YKP-10A), palanpanel, ORG 39479/PH80, ORG 34167, DP 543 and CJ-017.493, to augment the therapeutic effect or to provide a faster onset of the therapeutic effect of said compound selected from the group consisting of R228060 (YKP-10A), palanpanel, ORG 39479/PH80, ORG 34167, DP 543 and CJ-017.493, further characterized in that pipamperon is to be administered to a patient in a daily dose ranging between 5 and 15 mg of the active ingredient.

The invention also relates to a pharmaceutical composition comprising (a) pipamperon, and (b) a compound selected from the group consisting of R228060 (YKP-10A), palanpanel, ORG 39479/PH80, ORG 34167, DP 543 and CJ-017.493, or a pro-drug or an active metabolite thereof, or a pharmaceutically acceptable salt thereof, as a combined preparation for simultaneous, separate or sequential use for treating the underlying emotion dysregulation of mental disease or disorder which is chosen from the group consisting of mood disorders, anxiety disorders, psychotic disorders, eating disorders, premenstrual syndrome, somatoform disorders (excluding pain disorders), factitious disorders, dissociative disorders, sexual and gender identity disorders, sleep disorders, adjustment disorders, impulse control disorders, pervasive development disorders, attention-deficit disorders, disruptive behaviour disorders, substance-related disorders, personality disorders, psychological factors affecting medical conditions, malingering, antisocial behaviour, bereavement, occupational problem, identity problem, phase of life problem, academic problem, problems related to abuse or neglect, pain disorders, delirium, Alzheimer Disease, substance-induced persisting dementia, vascular dementia, dementia due to HIV disease, dementia due to head trauma, dementia due to Parkinson Disease, dementia due to Huntington Disease, dementia due to Pick Disease, dementia due to Creutzfeldt-Jacob Disease, amnestic disorders due to a general medical condition, substance-induced persisting amnestic disorder, mild cognitive impairment disorder, other cognitive disorders and Parkinson Disease.

97: Combination Therapy with a Vasopressin 1B Receptor (V1B) Antagonist Compound The mental disorders which can be treated using compounds having a high selective affinity for the 5-HT2A and D4 receptor, for instance pipamperon, in a combination therapy with a vasopressin 1B receptor (V1B) antagonist compound, are chosen from the group of diseases or disorders consisting of mood disorders, anxiety disorders, eating disorders, premenstrual syndrome, somatoform disorders (excluding pain disorders), factitious disorders, dissociative disorders, sexual and gender identity disorders, sleep disorders, adjustment disorders, impulse control disorders, substance-related disorders, personality disorders, bereavement, occupational problem, problems related to abuse or neglect and pain disorders.

The present invention thus relates to the use of pipamperon or a pharmaceutically acceptable salt thereof for the preparation of a medicament for treating the underlying emotion dysregulation of a non-cognitive mental disease or disorder selected from the group of diseases and disorders consisting of mood disorders, anxiety disorders, eating disorders, premenstrual syndrome, somatoform disorders (excluding pain disorders), factitious disorders, dissociative disorders, sexual and gender identity disorders, sleep disorders, adjustment disorders, impulse control disorders, substance-related disorders, personality disorders, bereavement, occupational problem and problems related to abuse or neglect, characterized in that pipamperon or said pharmaceutically acceptable salt thereof is administered simultaneously with, separate from or prior to the administration of a vasopressin 1B receptor (V1B) antagonist compound to augment the therapeutic effect or to provide a faster onset of the therapeutic effect of said vasopressin 1B receptor (V1B) antagonist compound, further characterized in that pipamperon is to be administered to a patient in a daily dose ranging between 5 and 15 mg of the active ingredient.

The present invention thus relates to the use of pipamperon or a pharmaceutically acceptable salt thereof for the preparation of a medicament for treating the underlying emotion dysregulation of pain disorders, characterized in that pipamperon or said pharmaceutically acceptable salt thereof is administered simultaneously with, separate from or prior to the administration of a vasopressin 1B receptor (V1B) antagonist compound to augment the therapeutic effect or to provide a faster onset of the therapeutic effect of said vasopressin 1B receptor (V1B) antagonist compound, further characterized in that pipamperon is to be administered to a patient in a daily dose ranging between 5 and 15 mg of the active ingredient.

According to a preferred embodiment, the invention relates to the uses as described above, wherein said vasopressin 1B receptor (V1B) antagonist compound is SSR149415 or a pro-drug or an active metabolite thereof, or a pharmaceutically acceptable salt thereof.

The invention also relates to a pharmaceutical composition comprising (a) pipamperon, and (b) a vasopressin 1B receptor (V1B) antagonist compound, preferably SSR149415 or a pro-drug or an active metabolite thereof, or a pharmaceutically acceptable salt thereof, as a combined preparation for simultaneous, separate or sequential use for treating the underlying emotion dysregulation of a mental disease or disorder which is chosen from the group consisting of mood disorders, anxiety disorders, eating disorders, premenstrual syndrome, somatoform disorders (excluding pain disorders), factitious disorders, dissociative disorders, sexual and gender identity disorders, sleep disorders, adjustment disorders, impulse control disorders, substance-related disorders, personality disorders, bereavement, occupational problem, problems related to abuse or neglect and pain disorders.

98: Combination Therapy with a Voltage-Gated Calcium Channel α(2)δ Subunit Modulator Compound The mental disorders which can be treated using compounds having a high selective affinity for the 5-HT2A and D4 receptor, for instance pipamperon, in a combination therapy with a voltage-gated calcium channel alpha(2)delta subunit modulator compound, are chosen from the group of diseases or disorders consisting of mood disorders, anxiety disorders, eating disorders, premenstrual syndrome, somatoform disorders (excluding pain disorders), factitious disorders, dissociative disorders, sexual and gender identity disorders, sleep disorders, adjustment disorders, impulse control disorders, substance-related disorders, personalty disorders, bereavement, occupational problem, problems related to abuse or neglect and pain disorders.

The present invention thus relates to the use of pipamperon or a pharmaceutically acceptable sat thereof for the preparation of a medicament for treating the underlying emotion dysregulation of a non-cognitive mental disease or disorder selected from the group of diseases and disorders consisting of mood disorders, anxiety disorders, eating disorders, premenstrual syndrome, somatoform disorders (excluding pain disorders), factitious disorders, dissociative disorders, sexual and gender identity disorders, sleep disorders, adjustment disorders, impulse control disorders, substance-related disorders, personality disorders, bereavement, occupational problem and problems related to abuse or neglect, characterized in that pipamperon or said pharmaceutically acceptable salt thereof is administered simultaneously with, separate from or prior to the administration of a voltage-gated calcium channel alpha(2)delta subunit modulator compound to augment the therapeutic effect or to provide a faster onset of the therapeutic effect of said voltage-gated calcium channel alpha(2)delta subunit modulator compound, further characterized in that pipamperon is to be administered to a patient in a daily dose ranging between 5 and 15 mg of the active ingredient.

The present invention thus relates to the use of pipamperon or a pharmaceutically acceptable salt thereof for the preparation of a medicament for treating the underlying emotion dysregulation of pain disorders, characterized in that pipamperon or said pharmaceutically acceptable salt thereof is administered simultaneously with, separate from or prior to the administration of a voltage-gated calcium channel alpha(2)delta subunit modulator compound to augment the therapeutic effect or to provide a faster onset of the therapeutic effect of said voltage-gated calcium channel alpha(2)delta subunit modulator compound, further characterized in that pipamperon is to be administered to a patient in a daily dose ranging between 5 and 15 mg of the active ingredient.

According to a preferred embodiment, the invention relates to the uses as described above, wherein said voltage-gated calcium channel alpha(2)delta subunit modulator compound is pregabalin or PD-200,390; or a pro-drug or an active metabolite thereof, or a pharmaceutically acceptable salt thereof. More preferably, said voltage-gated calcium channel alpha(2)delta subunit modulator compound is pregabalin, and is to be administered in a daily dose ranging between 50 and 600 mg of the active ingredient.

The invention also relates to a pharmaceutical composition comprising (a) pipamperon, and (b) a voltage-gated calcium channel alpha(2)delta subunit modulator compound, preferably pregabalin or PD-200,390; or a pro-drug or an active metabolite thereof, or a pharmaceutically acceptable salt thereof, as a combined preparation for simultaneous, separate or sequential use for treating the underlying emotion dysregulation of a mental disease or disorder which is chosen from the group consisting of mood disorders, anxiety disorders, eating disorders, premenstrual syndrome, somatoform disorders (excluding pain disorders), factitious disorders, dissociative disorders, sexual and gender identity disorders, sleep disorders, adjustment disorders, impulse control disorders, substance-related disorders, personality disorders, bereavement, occupational problem, problems related to abuse or neglect and pain disorders.

The invention also relates to a pharmaceutical composition as described above wherein pipamperon is provided in a unitary dose of between 5 and 15 mg of the active ingredient and wherein said voltage-gated calcium channel alpha(2)delta subunit modulator compound is pregabalin, preferably provided in a unitary dose of between 50 and 600 mg of the active ingredient.

99: Combination Therapy with a Vomeropherin Compound

The mental disorders which can be treated using compounds having a high selective affinity for the 5-HT2A and D4 receptor, for instance pipamperon, in a combination therapy with a vomeropherin compound, are chosen from the group of diseases or disorders consisting of anxiety disorders, eating disorders, premenstrual syndrome, somatoform disorders (excluding pain disorders), factitious disorders, dissociative disorders, sexual and gender identity disorders, sleep disorders, adjustment disorders, impulse control disorders, personality disorders, bereavement, occupational problem and problems related to abuse or neglect.

The present invention thus relates to the use of pipamperon or a pharmaceutically acceptable salt thereof for the preparation of a medicament for treating the underlying emotion dysregulation of a non-cognitive mental disease or disorder selected from the group of diseases and disorders consisting of anxiety disorders, eating disorders, premenstrual syndrome, somatoform disorders (excluding pain disorders), factitious disorders, dissociative disorders, sexual and gender identity disorders, sleep disorders, adjustment disorders, impulse control disorders, personality disorders, bereavement, occupational problem and problems related to abuse or neglect, characterized in that pipamperon or said pharmaceutically acceptable salt thereof is administered simultaneously with, separate from or prior to the administration of vomeropherin compound to augment the therapeutic effect or to provide a faster onset of the therapeutic effect of said vomeropherin compound, further characterized in that pipamperon is to be administered to a patient in a daily dose ranging between 5 and 15 mg of the active ingredient.

According to a preferred embodiment, the invention relates to the use as described above, wherein said vomeropherin compound is PH94B or a pro-drug or an active metabolite thereof, or a pharmaceutically acceptable salt thereof.

The invention also relates to a pharmaceutical composition comprising (a) pipamperon, and (b) vomeropherin compound, preferably PH94B or a pro-drug or an active metabolite thereof, or a pharmaceutically acceptable salt thereof, as a combined preparation for simultaneous, separate or sequential use for treating the underlying emotion dysregulation of a non-cognitive mental disease or disorder which is chosen from the group consisting of anxiety disorders, eating disorders, premenstrual syndrome, somatoform disorders (excluding pain disorders), factitious disorders, dissociative disorders, sexual and gender identity disorders, sleep disorders, adjustment disorders, impulse control disorders, personality disorders, bereavement, occupational problem and problems related to abuse or neglect.

Also, the invention relates in particular to the use as described before, wherein said second compound is chosen from the group consisting of fluvoxamine controlled release, phenserine tartrate, atomoxetine hydrochloride, bupropion (controlled-release formulation), ropinirole HCL (controlled-release formulation), INN 00835, galantamine (extended release formulation), paliperidone, tomoxetine, aprepitant, rivastigmine tartrate, ORG 34517/34850, sunepitron, sumanirole, milnacipran, idazoxan, xaliproden, SR 58611, befioxatone, litoxetine, tianeptine, agomelatine, SPD 503, flesinoxan, bifeprunox, ramelteon, etilevodopa, rasagiline (TVP-1012) and desvenlafaxine.

Also, the invention relates in particular to the use as described before, wherein said second compound is chosen from the group consisting of galantamine (extended release formulation), R121919, risperidone, paliperidone and R228060 (YKP-10A).

100: Combination Therapy with a Dopamine Releaser

The mental disorders which can be treated using compounds having a high selective affinity for the 5-HT2A and D4 receptor, for instance pipamperon, in a combination therapy with a dopamine releaser, are chosen from the group of diseases or disorders consisting of mood disorders, anxiety disorders, eating disorders, premenstrual syndrome, somatoform disorders (excluding pain disorders), factitious disorders, dissociative disorders, adjustment disorders, impulse control disorders, attention-deficit disorders, substance-related disorders, personality disorders, problems related to abuse or neglect, pain disorders and Parkinson disease.

The present invention thus relates to the use of pipamperon or a pharmaceutically acceptable salt thereof for the preparation of a medicament for treating the underlying emotion dysregulation of a non-cognitive mental disease or disorder selected from the group of diseases and disorders consisting mood disorders, anxiety disorders, eating disorders, premenstrual syndrome, somatoform disorders (excluding pain disorders), factitious disorders, dissociative disorders, adjustment disorders, impulse control disorders, attention-deficit disorders, substance-related disorders, personality disorders and problems related to abuse or neglect, characterized in that pipamperon or said pharmaceutically acceptable salt thereof is administered simultaneously with, separate from or prior to the administration of a dopamine releaser compound to augment the therapeutic effect or to provide a faster onset of the therapeutic effect of said dopamine releaser compound, further characterized in that pipamperon is to be administered to a patient in a daily dose ranging between 5 and 15 mg of the active ingredient.

The present invention thus relates to the use of pipamperon or a pharmaceutically acceptable salt thereof for the preparation of a medicament for treating the underlying emotion dysregulation of pain disorders, characterized in that pipamperon or said pharmaceutically acceptable salt thereof is administered simultaneously with, separate from or prior to the administration of a dopamine releaser compound to augment the therapeutic effect or to provide a faster onset of the therapeutic effect of said dopamine releaser compound, further characterized in that pipamperon is to be administered to a patient in a daily dose ranging between 5 and 15 mg of the active ingredient.

The present invention thus relates to the use of pipamperon or a pharmaceutically acceptable salt thereof for the preparation of a medicament for treating the underlying emotion dysregulation of Parkinson disease, characterized in that pipamperon or said pharmaceutically acceptable salt thereof is administered simultaneously with, separate from or prior to the administration of a dopamine releaser compound to augment the therapeutic effect or to provide a faster onset of the therapeutic effect of said dopamine releaser compound, further characterized in that pipamperon is to be administered to a patient in a daily dose ranging between 5 and 15 mg of the active ingredient.

According to a preferred embodiment, the invention relates to the uses as described above, wherein said dopamine (receptor) agonist compound is amantadine, or a pro-drug or an active metabolite thereof, or a pharmaceutically acceptable salt thereof. Preferably, amantadine is to be administered in a daily dose of between 100 and 300 mg of the active ingredient.

The invention a so relates to a pharmaceutical composition comprising (a) pipamperon, and (b) a dopamine (receptor) agonist, preferably amantadine, or a pro-drug or an active metabolite thereof, or a pharmaceutically acceptable salt thereof, as a combined preparation for simultaneous, separate or sequential use for treating the underlying emotion dysregulation of a mental disease or disorder which is chosen from the group of diseases or disorders consisting of mood disorders, anxiety disorders, eating disorders, premenstrual syndrome, somatoform disorders (excluding pain disorders), factitious disorders, dissociative disorders, adjustment disorders, impulse control disorders, attention-deficit disorders, substance-related disorders, personality disorders, problems related to abuse or neglect, pain disorders and Parkinson disease.

The invention also relates to a pharmaceutical composition as described above wherein pipamperon is provided in a unitary dose of between 5 and 15 mg of the active ingredient and wherein said dopamine (receptor) agonist is amantadine, preferably provided in a unitary dose of between 100 and 300 mg of the active ingredient.

From the above it will be apparent that the numbering of the grouping according to the action on the pathway or system corresponds to the numbering of the columns in Table 5 and the numbering of the pharmalogical profile in Table 6.

The disclosure of all patents, publications (including published patent publications), and database accession numbers and depository accession numbers referenced in this specification are specifically incorporated herein by reference in their entirety to the same extent as if each such individual patent, publication, and database accession number, and depository accession number were specifically and individually indicated to be incorporated by reference.

The invention, now being generally described, will be more readily understood by reference to the following tables and examples, which are included merely for purposes of illustration of certain aspects and embodiments of the present invention and are not intended to limit the invention.

SHORT DESCRIPTION OF THE TABLES AND FIGURES

Table 1: In Table 1, the pKi values of test compounds are given for each of the dopamine receptors, 5HT receptors, adrenergic receptors and the histamine1 receptor.

Table 2: Set-up of a clinical trial comprising for treatment groups.

Table 3: Overview of a placebo, active and period controlled clinical trial in a fore-going pipamperon-citalopram treatment in Major Depressive Disorder.

Table 4: POC process for major depressive disorder.

Table 5: Summary of diseases and disorders relative to known psycho-tropics.

Table 6: Overview of Pharmacological grouping, indicating pharmacological profile numbering (column 2), pharmacological profile (column 3), main indication(s) (column 4), name of the compound (column 4), the dose range (column 5), and the company producing or selling said compound (column 6). Compounds indicated by hatching are preferred.

FIG. 1: Add-on treatment with pipamperon after treatment with citalopram.

Figure 2:
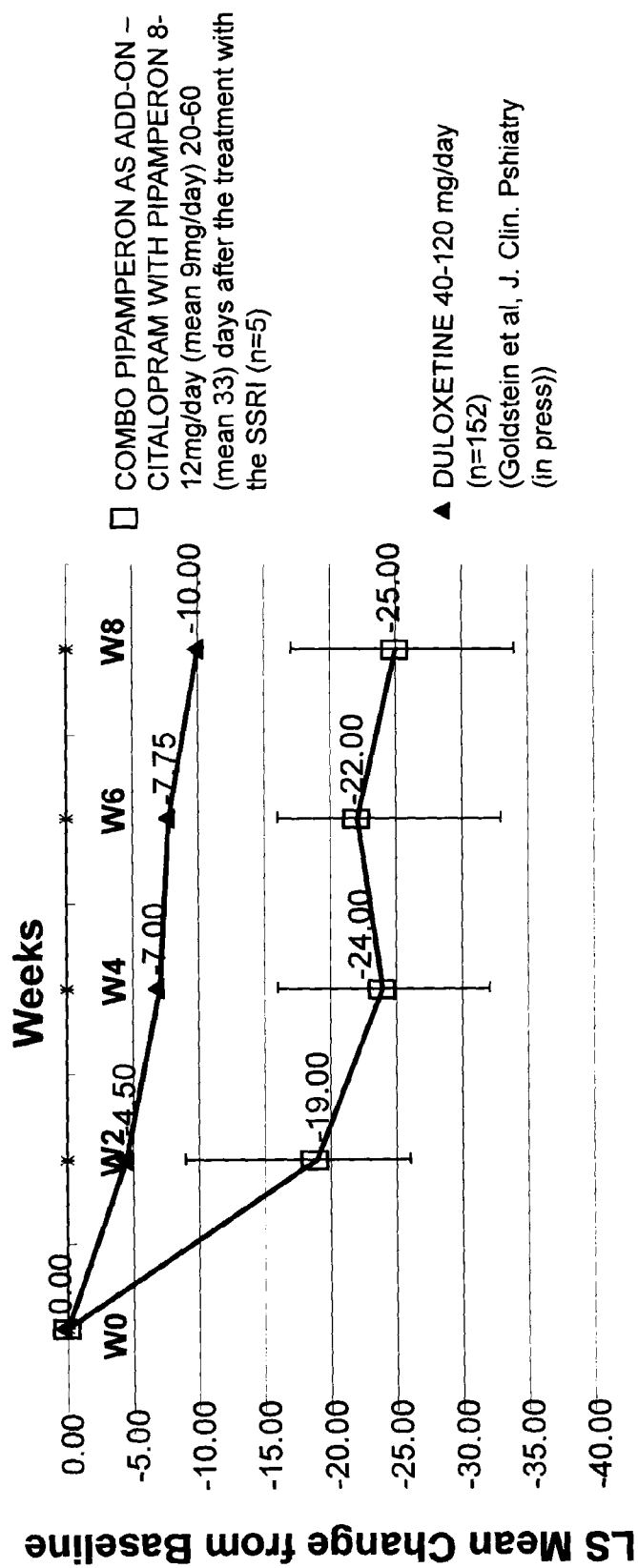

FIG. 2: HDRS-17 change from baseline: combo treatment pipamperon as add-on—citalopram vs SNRI (duloxetine) in Major Depression.

Figure 3:
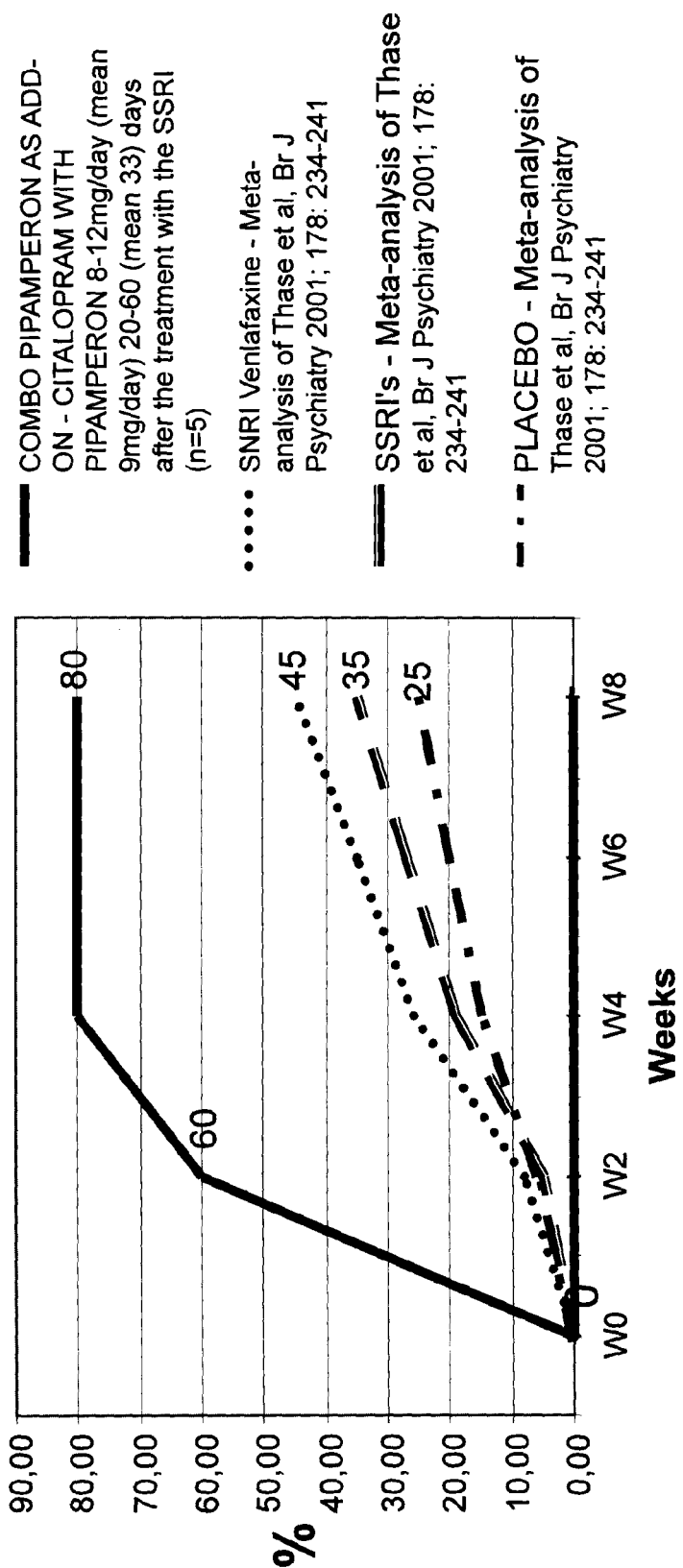

FIG. 3: Remission rates (HDRS-17<=7): combo treatment pipamperon as add-on—citalopram vs SNRI (veniafaxine) vs SSRIs vs placebo in Major Depression.

FIG. 4: Fore-going treatment during 1-5 days with pipamperon followed with the combination treatment of pipamperon and citalopram.

Figure 5:
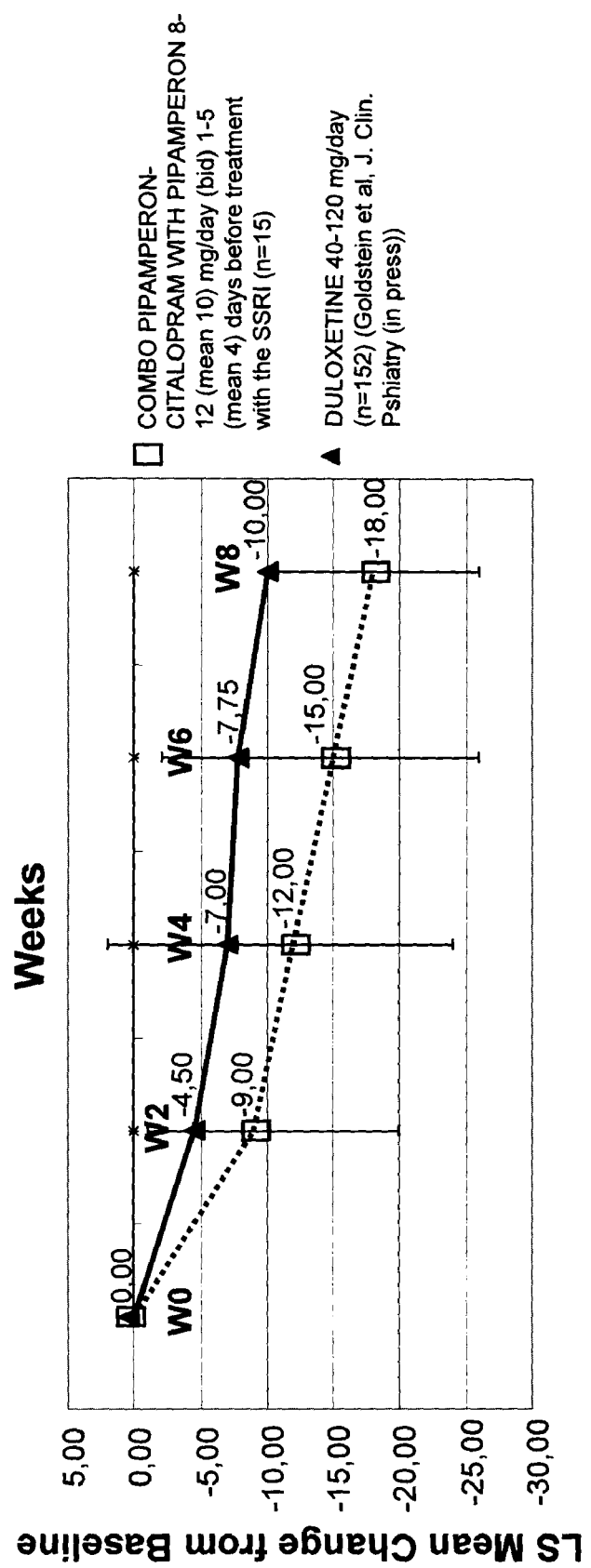

FIG. 5: HDRS-17 change from baseline: combo treatment pipamperon-citalopram with a fore-going treatment of 4 days with pipamperon vs SNRI (duloxetine) in Major Depression.

FIG. 6: Remission rates (HDRS-17<=7): combo pipamperon-citalopram with a fore-going treatment of 4 days with pipamperon vs SNRI (venlafaxine) in Major Depression.

Figure 7:
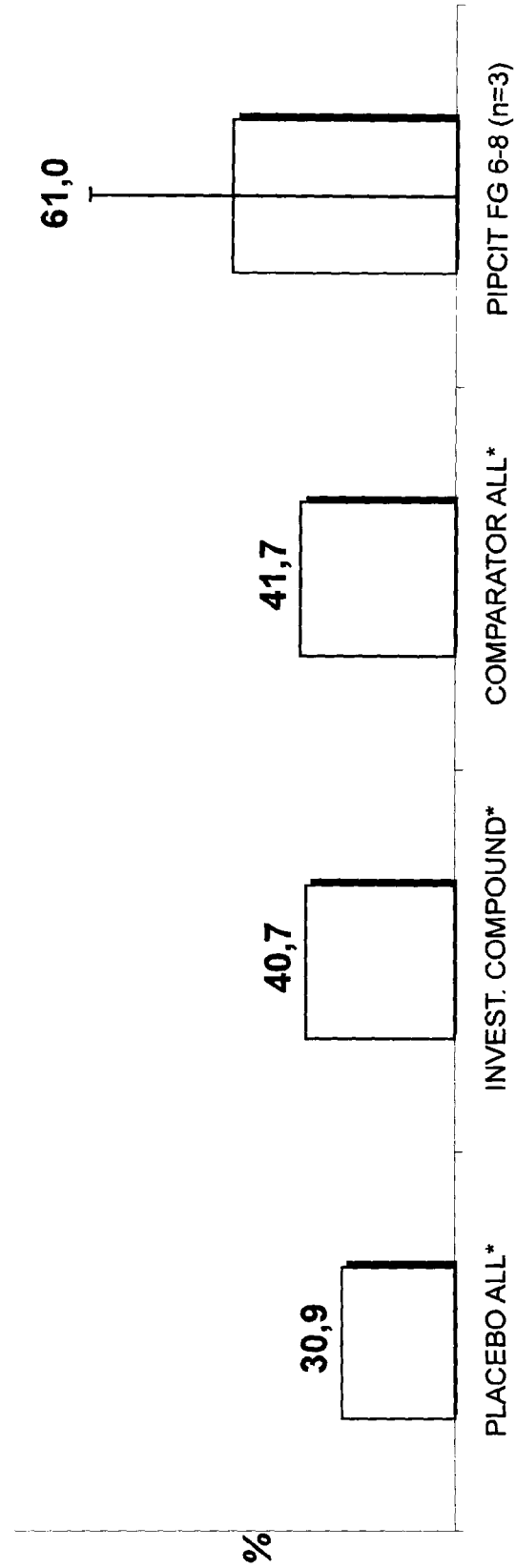

FIG. 7: Fore-going treatment during 6-8 days with pipamperon followed with the combination treatment of pipamperon and citalopram.

Figure 8:
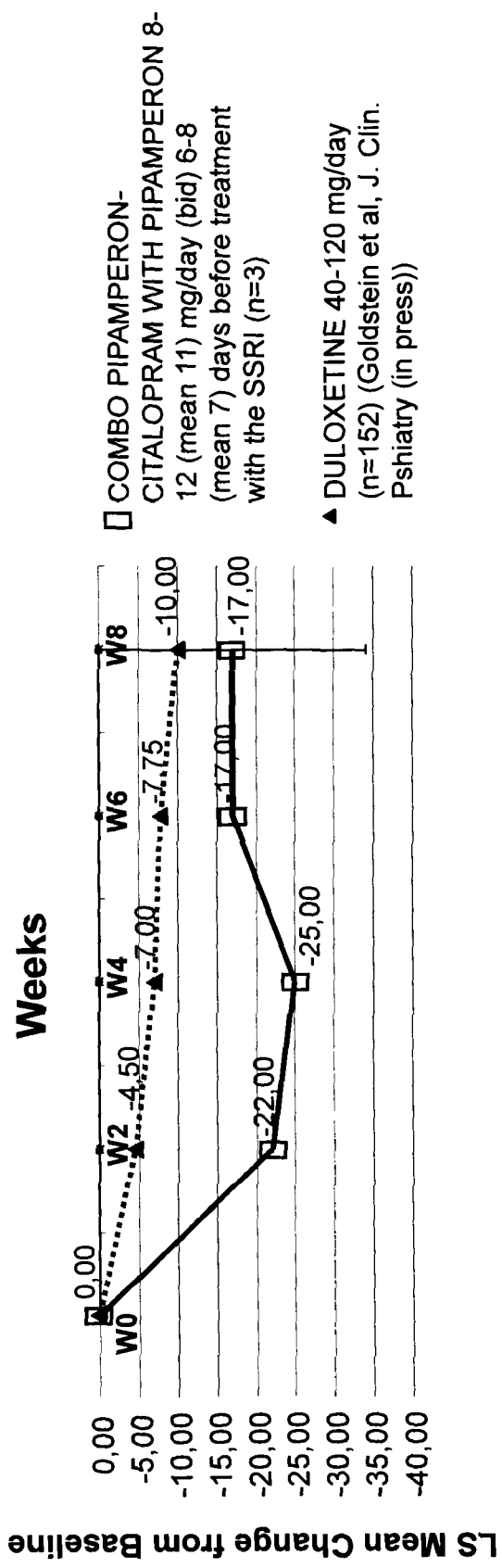

FIG. 8: HDRS-17 change from baseline: combo treatment pipamperon-citalopram with a fore-going treatment of 7 days with pipamperon vs SNRI (duloxetine) in Major Depression.

Figure 9:
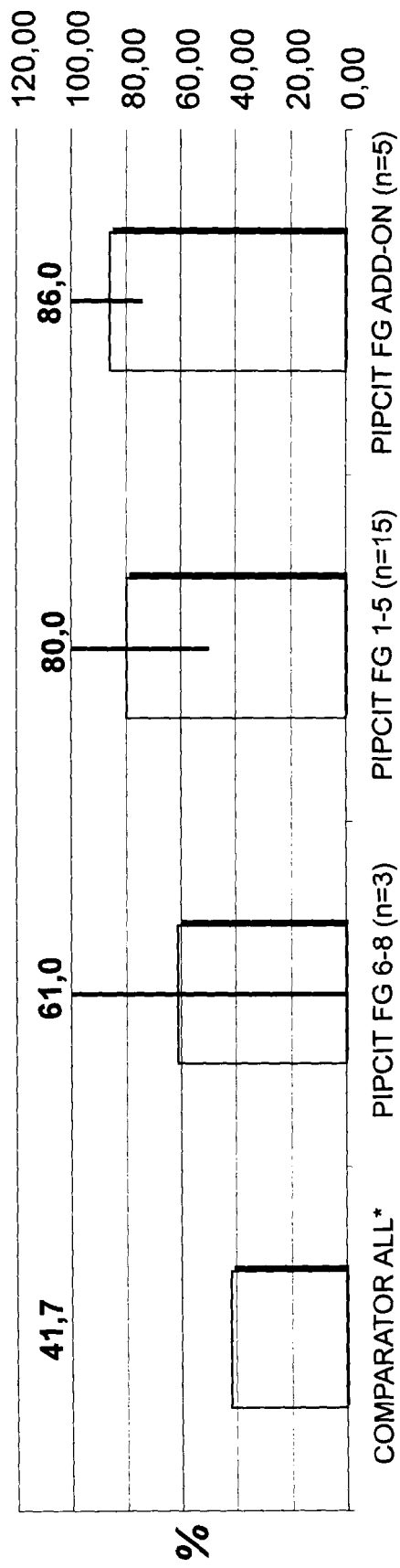

FIG. 9: Fore-going and add-on treatment with pipamperon in MDD.

Figure 10:
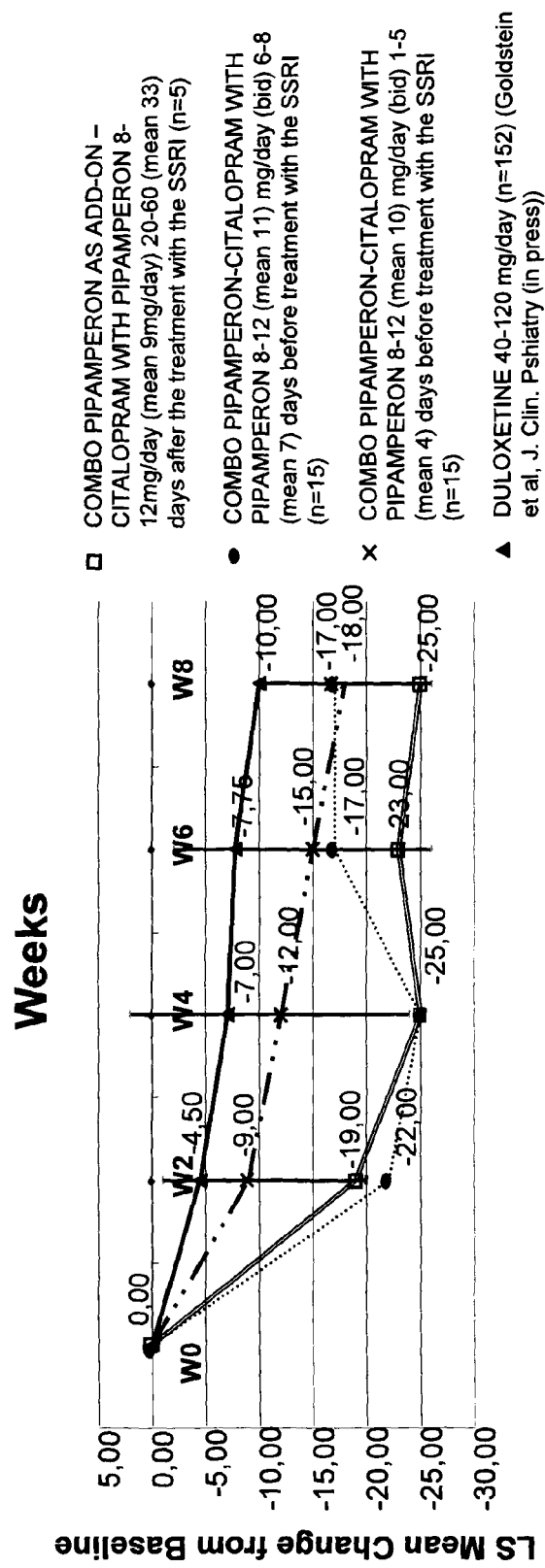

FIG. 10: HDRS-17 change from baseline: fore-going and add-on treatment with pipamperon and citalopram in comparison with the SNRI duloxetine in Major Depression.

Figure 11:
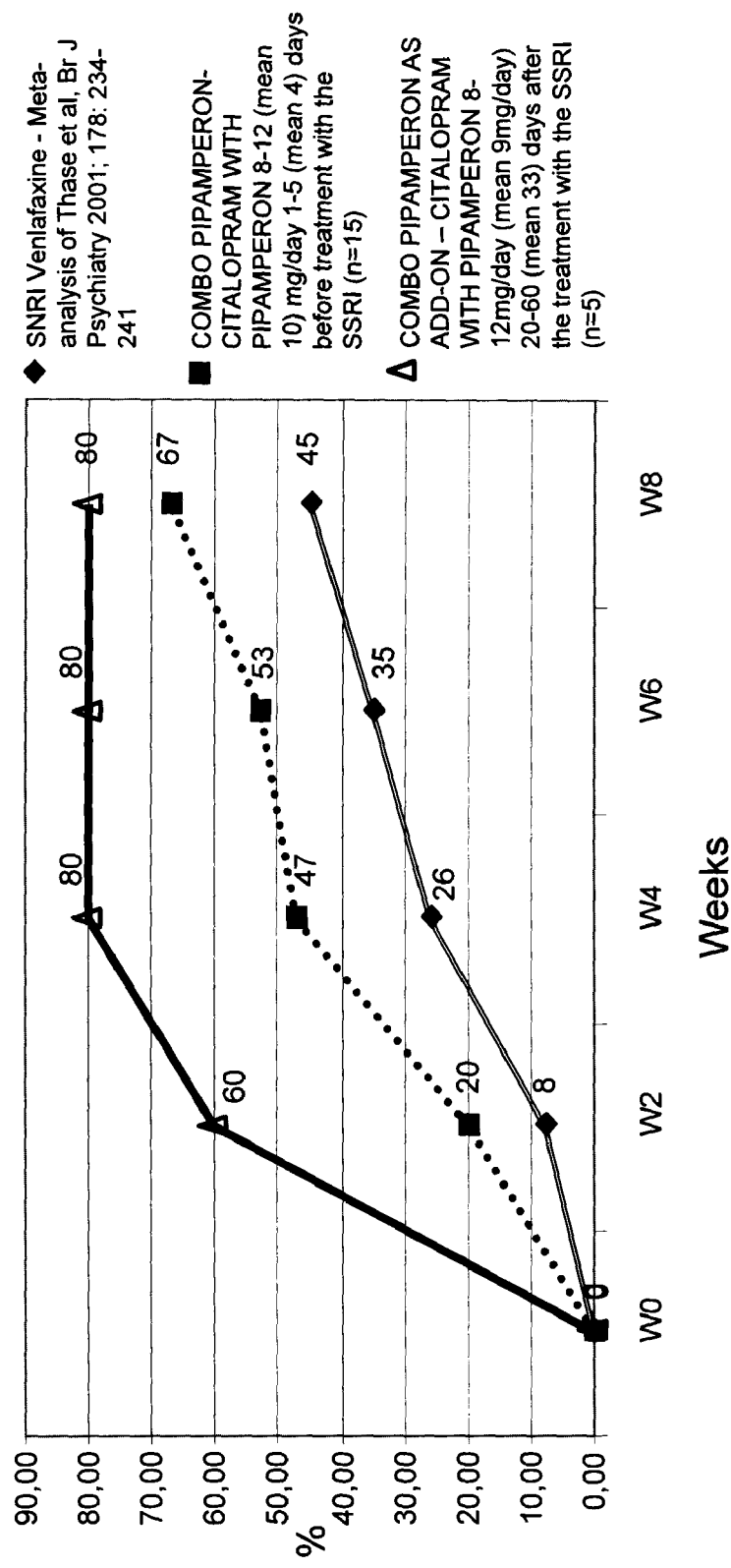

FIG. 11: Remission rates (HDRS-17<=7): fore-going and add-on treatment with pipamperon and citalopram in comparison with the SNRI venlafaxine in Major Depression.

FIG. 12: Y-BOCS total score: fore-going and add-on treatment with pipamperon and citalopram in comparison with the SSRI fluvoxamine in OCD.

Figure 13:
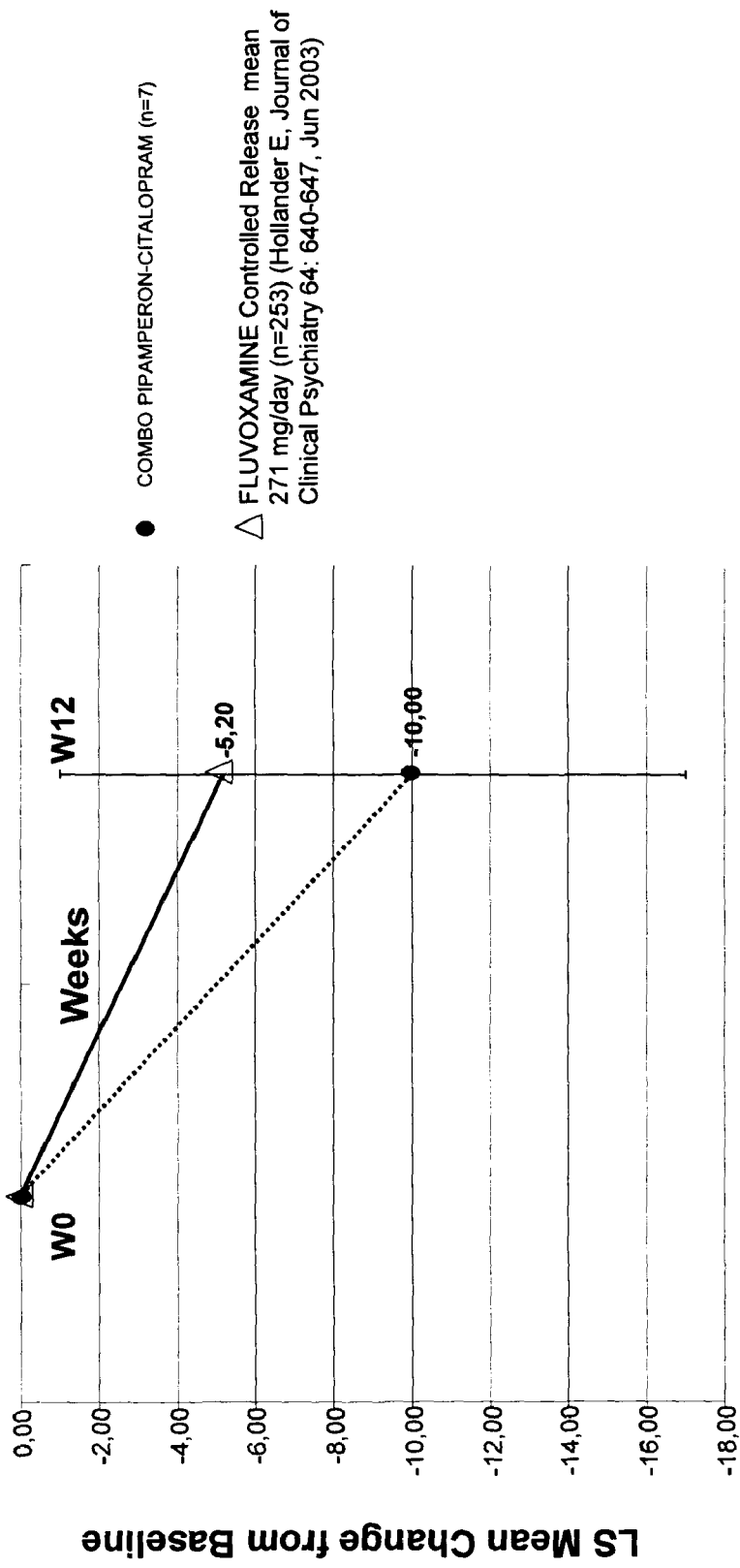

FIG. 13: Y-BOCS obsession score: fore-going and add-on treatment with pipamperon and citalopram in comparison with the SSRI fluvoxamine in OCD.

FIG. 14: Y-BOOS compulsion score: fore-going and add-on treatment with pipamperon and citalopram in comparison with the SSR fluvoxamine in OCD.

FIG. 15: CGI-severity score: fore-going and add-on treatment with pipamperon and citalopram in comparison with the SSRI in panic disorder.

TABLE 1

| | D1 | D2 | D3 | D4 | $5HT_{1A}$ | $5HT_{1B}$ | $5HT_{1D}$ | $5HT_{1E}$ | $5HT_{1F}$ | $5HT_{2A}$ | $5HT_{2B}$ |
|---|---|---|---|---|---|---|---|---|---|---|---|
| ORG5222 | 8-9 | 8-9 | 8-9 | 8-9 | 8-9 | 8-9 | 8-9 | 7-8 | 0 | >9 | >9 |
| Zotepine | 0 | 8-9 | 8-9 | 7-8 | 6-7 | 7-8 | 7-8 | 6-7 | 0 | 8-9 | 0 |
| Fluparoxan | 0 | <6 | <6 | 0 | 6-7 | <6 | <6 | 0 | 0 | <6 | 0 |
| Olanzapine | 7-8 | 7-8 | 7-8 | 7-8 | <6 | 6-7 | 6-7 | <6 | 6-7 | 8-9 | 8-9 |
| Clozapine | 7-8 | 6-7 | 6-7 | 7-8 | 6-7 | 6-7 | 6-7 | 6-7 | 6-7 | 8-9 | 8-9 |
| S16924 | 0 | 7-8 | 7-8 | 7-8 | 8-9 | 0 | 0 | 0 | 0 | >9 | 8-9 |
| S18327 | 7-8 | 7-8 | 6-7 | 8-9 | 7-8 | 0 | 0 | 0 | 0 | 8-9 | 0 |
| Amperozide | 6-7 | 6-7 | 6-7 | <6 | <6 | 0 | 0 | 0 | 0 | 8-9 | 0 |
| GGR218231 | <6 | 7-8 | >9 | <6 | 6-7 | <6 | <6 | 0 | 0 | <6 | <6 |
| Sertindole | 7-8 | 8-9 | 8-9 | 7-8 | 6-7 | 7-8 | 7-8 | 6-7 | 6-7 | >9 | 0 |
| MDL100,907 | 6-7 | <6 | <6 | 6-7 | <6 | 0 | 0 | 0 | 0 | >9 | 0 |
| Haloperidol | 8-9 | >9 | 8-9 | 8-9 | <6 | 6-7 | <6 | <6 | <6 | 6-7 | <6 |
| Tiospirone | 7-8 | 8-9 | 8-9 | 8-9 | 8-9 | 0 | 0 | 0 | 0 | >9 | 0 |
| Raciopride | <6 | 8-9 | 8-9 | <6 | <6 | 0 | 0 | 0 | 0 | 6-7 | 0 |
| Fluspirilene | 0 | >9 | 8-9 | 8-9 | 7-8 | <6 | <6 | <6 | 0 | <6 | 0 |
| Ocaperidone | 7-8 | >9 | 8-9 | 8-9 | 7-8 | 0 | 0 | 0 | 0 | >9 | 0 |
| Risperidone | 7-8 | 8-9 | 7-8 | 8-9 | 6-7 | 8-9 | 6-7 | <6 | <6 | >9 | 0 |
| S33084 | 6-7 | 7-8 | >9 | <6 | <6 | 6-7 | 6-7 | 0 | 0 | 6-7 | 6-7 |
| L741626 | 6-7 | 8-9 | 7-8 | 6-7 | <6 | <6 | <6 | 0 | 0 | 6-7 | 6-7 |
| Seroquel | 6-7 | 6-7 | 6-7 | <6 | 6-7 | <6 | <6 | <6 | <6 | 6-7 | 6-7 |
| Yohimbine | 0 | 6-7 | <6 | 0 | 7-8 | 6-7 | 7-8 | 0 | 0 | <6 | 0 |
| Ziprasidone | 8-9 | 8-9 | 7-8 | 7-8 | 8-9 | >9 | 8-9 | 6-7 | 0 | >9 | 8-9 |
| Pipamperon | 0 | 6-7 | 6-7 | 8-9 | <6 | 6-7 | 6-7 | <6 | <6 | 8-9 | 0 |

TABLE 1-continued

|  | 5HT$_{2C}$ | 5HT$_6$rat | 5HT$_7$rat | Alpha1 | Alpha2 | Alpha2 | Alpha2 | Beta1 | Beta2 | H1 |
|---|---|---|---|---|---|---|---|---|---|---|
| ORG5222 | >9 | >9 | >9 | >9 | 8-9 | >9 | 7-8 | <6 | <6 | >9 |
| Zotepine | 0 | 0 | 0 | 0 | 6-7 | 8-9 | 6-7 | <6 | <6 | >9 |
| Fluparoxan | <6 | 0 | 0 | 6-7 | 8-9 | 8-9 | 8-9 | 0 | 0 | 0 |
| Olanzapine | 8-9 | 7-8 | 6-7 | 7-8 | 6-7 | 6-7 | 6-7 | <6 | <6 | >9 |
| Clozapine | 7-8 | 7-8 | 7-8 | 8-9 | 7-8 | 7-8 | 7-8 | <6 | <6 | >9 |
| S16924 | 7-8 | 7-8 | 7-8 | 8-9 | 6-7 | 7-8 | 6-7 | <6 | <6 | 0 |
| S18327 | 6-7 | 0 | 0 | >9 | 6-7 | 0 | 0 | 0 | 0 | 0 |
| Amperozide | <6 | 0 | 0 | 7-8 | <6 | 0 | 0 | 0 | 0 | 0 |
| GGR218231 | <6 | 0 | 0 | <6 | <6 | 0 | 0 | 0 | 0 | 0 |
| Sertindole | 8-9 | 0 | 0 | >9 | 6-7 | 6-7 | 6-7 | <6 | <6 | 6-7 |
| MDL100,907 | 7-8 | 0 | 0 | <6 | <6 | 0 | 0 | 0 | 0 | 0 |
| Haloperidol | <6 | <6 | 6-7 | 8-9 | <6 | 6-7 | <6 | <6 | <6 | 6-7 |
| Tiospirone | 8-9 | 0 | 0 | >9 | 6-7 | 0 | 0 | 0 | 0 | 0 |
| Raciopride | <6 | 0 | 0 | <6 | <6 | 0 | 0 | 0 | 0 | 0 |
| Fluspirilene | 0 | 0 | 0 | 0 | 6-7 | 7-8 | 7-8 | 6-7 | 6-7 | 7-8 |
| Ocaperidone | 7-8 | 0 | 0 | >9 | 0 | 0 | 0 | 0 | 0 | 0 |
| Risperidone | 7-8 | 0 | 0 | >9 | 7-8 | 8-9 | 8-9 | <6 | <6 | 7-8 |
| S33084 | 7-8 | 0 | 0 | 6-7 | <6 | 0 | 0 | 0 | 0 | 0 |
| L741626 | <6 | 0 | 0 | 6-7 | <6 | 0 | 0 | 0 | 0 | 0 |
| Seroquel | 6-7 | 0 | 6-7 | 7-8 | <6 | 7-8 | 6-7 | <6 | <6 | 8-9 |
| Yohimbine | <6 | 0 | 0 | 6-7 | 8-9 | 8-9 | >9 | <6 | <6 | 0 |
| Ziprasidone | 8-9 | 7-8 | 8-9 | 8-9 | 6-7 | 7-8 | 7-8 | <6 | <6 | 7-8 |
| Pipamperon | 0 | 0 | 0 | 0 | 6-7 | 7-8 | 6-7 | <6 | <6 | <6 |

TABLE 2

| | ACUTE PHASE** | | | | | | | EXTENSION PHASE*** | | | | | | | FOLLOW-UP PHASE | | | | |
|---|---|---|---|---|---|---|---|---|---|---|---|---|---|---|---|---|---|---|---|
| | VISITS | | | | | | | | | | | | | | | | | | |
| | V1 | V2 | V3 | V4 | V5 | V6 | V7 | V8 | V9 | V10 | V11 | V12 | V13 | V14 | V15 | V16 | V17 | V18 | V19 |
| | | | | | | | | | | Day/Week/Month | | | | | | | | | |
| | Screen minus D7 | Baseline D0 | D4 | D7 | W2 | W3 | W4 | W6 | W8 | W10 | W12 | W16 | W20 | W24 | M8 | M10 | M12 | W1 | W2 |
| TREATMENT GROUP | | | | | | | | | | | | | | | | | | | |
| Group Pip-Active/D7 | A | B | B | C | | | | | | | | | | | | | | A | A |
| Group Pip-Active/D4 | A | B | C | | | | | | | | | | | | | | | A | A |
| Group Pip-Active/D0 | A | C | | | | | | | | | | | | | | | | A | A |
| Group Plc-Active/D0 | A | D | | | | | | | | | | | | | | | | A | A |
| Informed Consent | x | | | | | | | | | | | | | | | | | | |
| NECT* | x | x | x | x | x | x | x | x | x | x | x | x | x | x | x | x | x | x | x |
| Vital Signs/Weight | x | | | | | | | | | | | | | x | | x | | x | x |
| LAB | x | | | | | | | | | | | | | x | | x | | x | x |
| ECG | x | | | | | | | | | | | | | x | | x | | x | x |
| Phys Exam | x | | | | | | | | | | | | | | | | | | |
| Alc/Drugs Screen | x | | | | | | | | | | | | | x | | x | | x | x |
| CGI-S**** | x | x | x | x | x | x | x | x | x | x | x | x | x | x | x | x | x | x | x |

TABLE 2-continued

|  | ACUTE PHASE** | | | | | | | EXTENSION PHASE*** | | | | | | | | FOLLOW-UP PHASE | | | |
|---|---|---|---|---|---|---|---|---|---|---|---|---|---|---|---|---|---|---|---|
|  | VISITS | | | | | | | | | | | | | | | | | | |
|  | V1 | V2 | V3 | V4 | V5 | V6 | V7 | V8 | V9 | V10 | V11 | V12 | V13 | V14 | V15 | V16 | V17 | V18 | V19 |
|  | | | | | | | | | | Day/Week/Month | | | | | | | | | |
|  | Screen minus D7 | Baseline D0 | D4 | D7 | W2 | W3 | W4 | W6 | W8 | W10 | W12 | W16 | W20 | W24 | M8 | M10 | M12 | W1 | W2 |
| Q-LES-Q***** | | | | | | | | | | | | | | | | | | | |

Treatment regimen:
A: PLC + PLC
B: 2 × (PLC + PIP (4 mg))/d
C: 2 × (CIT (10 mg) + PIP (4 mg))/d
D: 2 × (CIT (10 mg) + PLC)/d
*Neuronal E-Clinical Trial = Vesalius Expert Development for this Trial which includes the bottom-up measurement of:
**Entering Acute Phase: only NON-placebo responders as defined by the DSM-IV criteria of efficacy
***Entering Extension Phase: only remittors as defined by the DSM-IV criteria of efficacy
****CGI-S: Clinical Global Impressions-Improvement Scale
*****Q-LES-Q: Quality of Life, Enjoyment and Satisfaction Questionnaire

TABLE 3

FOREGOING PIPAMPERON-CITALOPRAM TREATMENT IN MAJOR DEPRESSIVE DISORDER A PLACEBO, ACTIVE AND PERIODE CONTROLLED CLINICAL TRIAL

|  | ACUTE PHASE** | | | | | | | | | | | | EXTENSION PHASE*** | | | | FOLLOW-UP PHASE | | |
|---|---|---|---|---|---|---|---|---|---|---|---|---|---|---|---|---|---|---|---|
|  | VISITS | | | | | | | | | | | | | | | | | | |
|  | V1 | V2 | V3 | V4 | V5 | V6 | V7 | V8 | V9 | V10 | V11 | V12 | V13 | V14 | V15 | V16 | V17 | V18 | V19 |
|  | | | | | | | | | | DAY/WEEK/MONTH | | | | | | | | | |
|  | SCREEN minus D7 | BASELINE D0 | D4 | D7 | W2 | W3 | W4 | W6 | W8 | W10 | W12 | W16 | W20 | W24 | M8 | M10 | M12 | W1 | W2 |
| TREATMENT GROUP | | | | | | | | | | | | | | | | | | | |
| Group Pip - Active/ Day 4 | PLC + PLC | 2 × (PLC + PIP (4 mg))/d | 2 × (CIT (10 mg) + PIP (4 mg))/d | | | | | | | | | | | | | | | PLC + PLC | PLC + PLC |
| Group Pip - Active/ Day 0 | PLC + PLC | 2 × (CIT (10 mg) + PIP (4 mg))/d | | | | | | | | | | | | | | | | PLC + PLC | PLC + PLC |
| Group Plc - Active/ Day 0 | PLC + PLC | 2 × (CIT (10 mg) + PLC)/d | | | | | | | | | | | | | | | | PLC + PLC | PLC + PLC |
| Group Placebo Informed Consent | PLC + PLC x | | | | | | | | | | | | | | | | | PLC + PLC | PLC + PLC |
| NECT* | x | x | x | x | x | x | x | x | x | x | x | x | x | x | x | x | x | x | x |
| Vital Signs/ Weight | x | x | x | x | x | x | x | x | x | x | x | x | x | x | x | x | x | x | x |
| LAB | x | x | | | | | | | | | x | | x | | x | | x | | |

TABLE 3-continued

FOREGOING PIPAMPERON-CITALOPRAM TREATMENT IN MAJOR
DEPRESSIVE DISORDER A PLACEBO, ACTIVE AND PERIODE
CONTROLLED CLINICAL TRIAL

| | ACUTE PHASE** | | | | | | | | | EXTENSION PHASE*** | | | | | FOLLOW-UP PHASE | | | | |
|---|---|---|---|---|---|---|---|---|---|---|---|---|---|---|---|---|---|---|---|
| | VISITS | | | | | | | | | | | | | | | | | | |
| | V1 | V2 | V3 | V4 | V5 | V6 | V7 | V8 | V9 | V10 | V11 | V12 | V13 | V14 | V15 | V16 | V17 | V18 | V19 |
| | | | | | | | | | | DAY/WEEK/MONTH | | | | | | | | | |
| | SCREEN minus D7 | BASE-LINE D0 | D4 | D7 | W2 | W3 | W4 | W6 | W8 | W10 | W12 | W16 | W20 | W24 | M8 | M10 | M12 | W1 | W2 |
| ECG | x | | | | | | | | | x | | x | | x | | | x | | |
| Phys Exam | x | | | | | | x | | | x | | x | | x | | | x | | |
| Alc/Drugs Screen | x | | | | | | | | | x | | x | | x | | | x | | |
| CGI-S | x | x | x | x | x | x | x | x | x | x | x | x | x | x | x | x | x | x | x |
| ****Q-LES-Q | x | x | x | x | x | | x | x | x | x | x | x | x | x | x | x | x | | x |

*Neuronal E-Clinical Trial = Vesalius Expert Development for this Trial which includes the bottom-up measurement of:
In- and exclusion criteria
Functional status evaluation
Medical history
(Pre-)treatment signs & symptoms
DSM-IV rules for diagnosis & efficacy
Rating Scales: HDRS-28, MADRS, HAMA
Medical resource utulisation
Pre-trial & Concomittant medication
Drug administration
(Serious) Adverse events
Admission to the acute and extension phase of treatment
Right flow of the trial
**Entering Acute Phase: only NON-placebo responders as defined by the DSM-IV criteria of efficacy
***Entering Extension Phase: only remittors as defined by the DSM-IV criteria of efficacy
****Q-LES-Q: Quality of Life, Enjoyment and Satisfaction Questionnaire

TABLE 4

| DAY | minus D7 | D0 | =>D4 |
|---|---|---|---|
| TREATMENTGROUP | | | |
| Placebo (PLC) | PLC + PLC | 2 × (PLC + PLC) | 2 × (PLC + PC) |
| PIP - Active/Day 4 | PLC + PLC | 2 × (PLC + PIP (4 mg))/d | 2 × (CIT (10 mg) + PIP (4 mg))/d |
| PIP - Active/Day 0 | PLC + PLC | 2 × (CIT (10 mg) + PIP (4 mg))/d | 2 × (CIT (10 mg) + PIP (4 mg))/d |
| PLC - Active/Day 0 | PLC + PLC | 2 × (CIT (10 mg) + PLC)/d | 2 × (CIT (10 mg) + PLC)/d |

TABLE 5

*SEE GLOSSARY HEREUNDER

| | | MEDICAMENT | | | | | | | | |
|---|---|---|---|---|---|---|---|---|---|---|
| | | 92 | 91 | 90 | 85 | 60 | 62 | 61 | 82 | 51 |
| | MONO | | | | | COMBO's | | | | |
| | 5- | | | | 5-HT2A/D4*-Antagonist + CNS Compound | | | | | |
| MEDICAL INDICATION | HT2A/D4* Antagonist | SSRI* | SNRI* | SNDRI* | SDRI* | NARI* | NDRI* | NaSSA* | RIMA* | MAO-A* & MAO-B* reuptake inhibitor |
| DISORDER WITH AN UNDERLYING EMOTION DYSREGULATION NON-COGNITIVE | X | X | X | X | X | X | X | X | X | X |

TABLE 5-continued

*SEE GLOSSARY HEREUNDER

| | 1 | 2 | 3 | 4 | 5 | 6 | 7 | 8 | 9 | 10 |
|---|---|---|---|---|---|---|---|---|---|---|
| MENTAL DISORDERS (excl. Pain Disorder) | | | | | | | | | | |
| mood disorders | | X | X | X | X | X | X | X | X | |
| anxiety disorders | X | X | X | X | X | X | X | X | X | |
| psychotic disorders | | | | | | | | | | |
| eating disorders | X | X | X | X | X | | | X | X | |
| premenstrual syndrome | X | X | X | X | X | | | X | X | |
| somatoform disorders (excluding Pain Disorder) | X | X | X | X | X | | | X | X | |
| factitious disorders | X | X | X | X | X | | | X | X | |
| dissociative disorders | X | X | X | X | X | | | X | X | |
| sexual and gender identity disorders | X | | | | | | | X | X | |
| sleep disorders | X | X | X | X | X | | | X | | |
| adjustment disorders | X | X | X | X | X | X | X | X | X | |
| impulse control disorders | X | X | X | X | X | | | X | X | |
| pervasive development disorders | X | | | | | | | | | |
| attention-deficit disorders | X | | X | X | | X | X | | | X |
| disruptive behaviour disorders | X | | | | | | | | | |
| substance-related disorders | X | X | X | X | X | | | | | |
| personality disorders | X | X | X | X | X | X | X | X | X | |
| psychological factors affecting medical conditions | X | | | | | | | | | |
| malingering | X | | | | | | | | | |
| antisocial behaviour | X | X | X | X | X | X | X | X | X | |
| bereavement | X | X | X | X | X | X | X | X | X | |
| occupational problem | X | X | X | X | X | X | X | X | X | |
| identity problem | X | | | | | | | | | |
| phase of life problem | X | | | | | | | | | |
| academic problem | X | | | | | | | | | |
| problems related to abuse or neglect | X | X | X | X | X | X | X | X | X | |
| PAIN DISORDER | | X | X | X | X | X | X | X | X | |
| COGNITIVE DISORDERS | | | | | | | | | | |
| delirium | | | | X | X | | X | | | |
| Alzheimer Disease | | | | X | X | | X | | | |
| substance-induced persisting dementia | | | | X | X | | X | | | |
| vascular dementia | | | | X | X | | X | | | |
| dementia due to HIV disease | | | | X | X | | X | | | |
| dementia due to head trauma | | | | X | X | | X | | | |
| dementia due to Parkinson Disease | | | | X | X | | X | | | |
| dementia due to Huntington Disease | | | | X | X | | X | | | |
| dementia due to Pick Disease | | | | X | X | | X | | | |
| dementia due to Creutzfeldt-Jacob Disease | | | | X | X | | X | | | |
| amnestic disorders due to a general medical condition | X | | | X | X | | X | | | |
| substance-induced persisting amnestic disorder | X | | | X | X | | X | | | |
| mild cognitive impairment disorder | X | | | X | X | | X | | | |
| other cognitive disorders | X | | | X | X | | X | | | |

TABLE 5-continued

*SEE GLOSSARY HEREUNDER

PARKINSON DISEASE

| MEDICAL INDICATION | MONO 5-HT2A/D4* Antagonist | 3 5-HTA1* agonist | 4 5-HTA1* antagonist | 5 5-HT1B* antagonist | 6 COMBO's 5-HT2A/D4*-Antagonist + CNS Compound 5-HT2B* antagonist | 7 5-HT2C* antagonist | 8 5HT3* antagonist | 9 5HT6* antagonist | 2 5-HT1* auto-receptor agonist |
|---|---|---|---|---|---|---|---|---|---|
| DISORDER WITH AN UNDERLYING EMOTION DYSREGULATION NON-COGNITIVE MENTAL DISORDERS (excl. Pain Disorder) | X | X | X | X | X | X | X | X | X |
| mood disorders | | X | X | X | X | X | | | X |
| anxiety disorders | X | X | X | X | X | X | | | X |
| psychotic disorders | | | | | | | | | |
| eating disorders | X | X | X | X | X | X | | | X |
| premenstrual syndrome | X | X | X | X | X | X | | | X |
| somatoform disorders (excluding Pain Disorder) | X | X | X | X | X | X | | | X |
| factitious disorders | X | X | X | X | X | X | | | X |
| dissociative disorders | X | X | X | X | X | X | | | X |
| sexual and gender identity disorders | X | X | X | X | X | X | | | X |
| sleep disorders | X | X | | X | X | X | | | X |
| adjustment disorders | X | X | X | X | X | X | | | X |
| impulse control disorders | X | X | X | X | X | X | | | X |
| pervasive development disorders | X | | | | | | | | |
| attention-deficit disorders | X | X | | | | | | | |
| disruptive behaviour disorders | X | | | | | | | | |
| substance-related disorders | X | X | X | X | X | X | X | | X |
| personality disorders | X | X | X | X | X | X | | | X |
| psychological factors affecting medical conditions | X | | | | | | | | |
| malingering | X | | | | | | | | |
| antisocial behaviour | X | X | X | X | X | X | | | X |
| bereavement | X | X | X | X | X | X | | | X |
| occupational problem | X | X | X | X | X | X | | | X |
| identity problem | X | | | | | | | | |
| phase of life problem | X | | | | | | | | |
| academic problem | X | | | | | | | | |
| problems related to abuse or neglect | X | X | X | X | X | X | | | X |
| PAIN DISORDER | | X | | | X | X | | | X |
| COGNITIVE DISORDERS | | | | | | | | | |
| delirium | | | | | | | | | |
| Alzheimer Disease | | | | | | | | X | |
| substance-induced persisting dementia | | | | | | | | X | |
| vascular dementia | | | | | | | | X | |
| dementia due to HIV disease | | | | | | | | X | |
| dementia due to head trauma | | | | | | | | X | |
| dementia due to Parkinson Disease | | | | | | | | X | |
| dementia due to Huntington Disease | | | | | | | | X | |

TABLE 5-continued

*SEE GLOSSARY HEREUNDER

| | | | | | | | | |
|---|---|---|---|---|---|---|---|---|
| dementia due to Pick Disease | | | | | | | X | |
| dementia due to Creutzfeldt-Jacob Disease | | | | | | | X | |
| amnestic disorders due to a general medical condition | X | | | | | | X | |
| substance-induced persisting amnestic disorder | X | | | | | | X | |
| mild cognitive impairment disorder | X | | | | | | X | |
| other cognitive disorders | X | | | | | | X | |

PARKINSON DISEASE

| | | MEDICAMENT | | | | | | |
|---|---|---|---|---|---|---|---|---|
| | | 1 | 44 | 93 | 69 | 95 | 76 | 55 |
| | MONO | | | | COMBO's | | | |
| | 5- | | | 5-HT2A/D4*-Antagonist + CNS compound | | | | |
| MEDICAL INDICATION | HT2A/ D4* Antag- onist | 5-HT* reuptake enhancer | Increase brain concentrations of 5-HT* | Substance P Antagonist | NK2* Antagonist | tachykinin antagonist | peptide | MCH*-receptor antagonist |
| DISORDER WITH AN UNDERLYING EMOTION DYSREGULATION NON-COGNITIVE MENTAL DISORDERS (excl. Pain Disorder) | X | X | X | X | X | X | X | X |
| mood disorders | | X | X | X | X | X | X | X |
| anxiety disorders | X | X | X | X | X | X | X | X |
| psychotic disorders | | | | | | | | |
| eating disorders | X | X | X | X | X | X | X | X |
| premenstrual syndrome | X | X | X | X | X | X | X | X |
| somatoform disorders (excluding Pain Disorder) | X | X | X | X | X | X | X | X |
| factitious disorders | X | X | X | X | X | X | X | X |
| dissociative disorders | X | X | X | X | X | X | X | X |
| sexual and gender identity disorders | X | X | X | X | X | X | X | X |
| sleep disorders | X | X | X | X | X | X | X | X |
| adjustment disorders | X | X | X | X | X | X | X | X |
| impulse control disorders | X | X | X | X | X | X | X | X |
| pervasive development disorders | X | | | | | | X | |
| attention-deficit disorders | X | | | | | | | |
| disruptive behaviour disorders | X | | | | | | X | |
| substance-related disorders | X | X | X | X | X | X | X | X |
| personality disorders | X | X | X | X | X | X | X | X |
| psychological factors affecting medical conditions | X | | | | | | | |
| malingering | X | | | | | | | |
| antisocial behaviour | X | X | | | | | | |
| bereavement | X | X | X | X | X | X | X | X |
| occupational problem | X | X | X | X | X | X | X | X |
| identity problem | X | | | | | | | |
| phase of life problem | X | | | | | | | |
| academic problem | X | | | | | | | |
| problems related to abuse or neglect | X | X | X | X | X | X | X | X |

TABLE 5-continued

*SEE GLOSSARY HEREUNDER

| MEDICAL INDICATION | MONO 5-HT2A/D4* Antagonist | MT* agonist | GR* antagonist | CRF-1* antagonist | GPCR* modulator | MC4* antagonists | beta-3-adrenoceptor agonist | alpha 2 antagonists |
|---|---|---|---|---|---|---|---|---|
| PAIN DISORDER | X | X | X | X | X | X | X |  |
| COGNITIVE DISORDERS |  |  |  |  |  |  |  |  |
| delirium |  |  |  |  |  |  |  |  |
| Alzheimer Disease |  |  |  |  |  |  | X |  |
| substance-induced persisting dementia |  |  |  |  |  |  | X |  |
| vascular dementia |  |  |  |  |  |  | X |  |
| dementia due to HIV disease |  |  |  |  |  |  | X |  |
| dementia due to head trauma |  |  |  |  |  |  | X |  |
| dementia due to Parkinson Disease |  |  |  |  |  |  | X |  |
| dementia due to Huntington Disease |  |  |  |  |  |  | X |  |
| dementia due to Pick Disease |  |  |  |  |  |  | X |  |
| dementia due to Creutzfeldt-Jacob Disease |  |  |  |  |  |  | X |  |
| amnestic disorders due to a general medical condition | X |  |  |  |  |  | X |  |
| substance-induced persisting amnestic disorder | X |  |  |  |  |  | X |  |
| mild cognitive impairment disorder | X |  |  |  |  |  | X |  |
| other cognitive disorders | X |  |  |  |  |  | X |  |
| PARKINSON DISEASE |  |  |  |  |  |  |  |  |

| | MEDICAMENT | | | | | | | |
|---|---|---|---|---|---|---|---|---|
| | MONO 5-HT2A/D4* | 56 | 41 | 26 | 40 | 54 | 19 | 14 |
| | | COMBO's 5-HT2A/D4*-Antagonist + CNS compound | | | | | | |
| MEDICAL INDICATION | Antagonist | MT* agonist | GR* antagonist | CRF-1* antagonist | GPCR* modulator | MC4* antagonists | beta-3-adrenoceptor agonist | alpha 2 antagonists |
| DISORDER WITH AN UNDERLYING EMOTION DYSREGULATION NON-COGNITIVE MENTAL DISORDERS (excl. Pain Disorder) | X | X | X | X | X | X | X | X |
| mood disorders |  | X | X | X | X | X | X | X |
| anxiety disorders | X | X | X | X | X | X | X | X |
| psychotic disorders |  |  |  |  |  |  |  | X |
| eating disorders | X | X | X | X | X | X | X | X |
| premenstrual syndrome | X | X | X | X | X | X | X | X |
| somatoform disorders (excluding Pain Disorder) | X | X | X | X | X | X | X | X |
| factitious disorders | X | X | X | X | X | X | X | X |
| dissociative disorders | X | X | X | X | X | X | X | X |
| sexual and gender identity disorders | X | X | X | X | X | X | X | X |
| sleep disorders | X | X | X | X | X | X | X | X |
| adjustment disorders | X | X | X | X | X | X | X | X |
| impulse control disorders | X | X | X | X | X | X | X | X |
| pervasive development disorders | X |  |  |  |  |  |  |  |
| attention-deficit disorders | X |  |  |  |  |  |  |  |
| disruptive behaviour disorders | X |  |  |  |  |  |  |  |
| substance-related disorders | X | X | X | X | X | X | X | X |

TABLE 5-continued

*SEE GLOSSARY HEREUNDER

| | | | | | | | | |
|---|---|---|---|---|---|---|---|---|
| personality disorders | X | X | X | X | X | X | X | X |
| psychological factors affecting medical conditions | X | | | | | | | |
| malingering | X | | | | | | | |
| antisocial behaviour | X | | | | | | | |
| bereavement | X | X | X | X | X | X | X | X |
| occupational problem | X | X | X | X | X | X | X | X |
| identity problem | X | | | | | | | |
| phase of life problem | X | | | | | | | |
| academic problem | X | | | | | | | |
| problems related to abuse or neglect | X | X | X | X | X | X | X | X |
| PAIN DISORDER | | X | X | X | X | X | X | X |
| COGNITIVE DISORDERS | | | | | | | | |
| delirium | | | | | | | | |
| Alzheimer Disease | | | | | | | | |
| substance-induced persisting dementia | | | | | | | | |
| vascular dementia | | | | | | | | |
| dementia due to HIV disease | | | | | | | | |
| dementia due to head trauma | | | | | | | | |
| dementia due to Parkinson Disease | | | | | | | | |
| dementia due to Huntington Disease | | | | | | | | |
| dementia due to Pick Disease | | | | | | | | |
| dementia due to Creutzfeldt-Jacob Disease | | | | | | | | |
| amnestic disorders due to a general medical condition | X | | | | | | | |
| substance-induced persisting amnestic disorder | X | | | | | | | |
| mild cognitive impairment disorder | X | | | | | | | |
| other cognitive disorders | X | | | | | | | |
| PARKINSON DISEASE | | | | | | | | |

| | | MEDICAMENT | | | | | | |
|---|---|---|---|---|---|---|---|---|
| | | 13 | 86 | 97 | 12 | 71 | 75 | 98 |
| | MONO | | | | COMBO's | | | |
| | 5- | | | 5-HT2A/D4*-Antagonist + CNS compound | | | | |
| MEDICAL INDICATION | HT2A/ D4* Antag- onist | alpha 1 antagonists | Second messenger beta agonist | V1B* antagonist | X Adrenergic transmitter releaser | NMDA* antagonist | PDE4* inhibitor | Voltage-gated calcium channel alpha(2)delta subunit modulator |
| DISORDER WITH AN UNDERLYING EMOTION DYSREGULATION | X | X | X | X | X | X | X | X |
| NON-COGNITIVE MENTAL DISORDERS (excl. Pain Disorder) | | | | | | | | |
| mood disorders | | X | X | X | X | X | X | X |
| anxiety disorders | X | X | X | X | X | X | X | X |
| psychotic disorders | | | | | | | | |
| eating disorders | X | X | X | X | X | X | X | X |
| premenstrual syndrome | X | X | X | X | X | X | X | X |
| somatoform disorders (excluding Pain Disorder) | X | X | X | X | X | X | X | X |
| factitious disorders | X | X | X | X | X | X | X | X |
| dissociative disorders | X | X | X | X | X | X | X | X |

TABLE 5-continued

*SEE GLOSSARY HEREUNDER

| | | | | | | | | |
|---|---|---|---|---|---|---|---|---|
| sexual and gender identity disorders | X | X | X | X | X | X | X | X |
| sleep disorders | X | X | X | X | | | | X |
| adjustment disorders | X | X | X | X | X | X | X | X |
| impulse control disorders | X | X | X | X | X | X | X | X |
| pervasive development disorders | X | | | | | | | |
| attention-deficit disorders | X | | | | | | | |
| disruptive behaviour disorders | X | | | | | | | |
| substance-related disorders | X | | | X | | | | X |
| personality disorders | X | X | X | X | X | X | X | X |
| psychological factors affecting medical conditions | X | | | | | | | |
| malingering | X | | | | | | | |
| antisocial behaviour | X | | | | | | | |
| bereavement | X | X | X | X | X | X | X | X |
| occupational problem | X | X | X | X | X | X | X | X |
| identity problem | X | | | | | | | |
| phase of life problem | X | | | | | | | |
| academic problem | X | | | | | | | |
| problems related to abuse or neglect | X | X | X | X | X | X | X | X |
| PAIN DISORDER | | X | X | X | X | X | X | X |
| COGNITIVE DISORDERS | | | | | | | | |
| delirium | | | | | | | | |
| Alzheimer Disease | | | | | | X | X | |
| substance-induced persisting dementia | | | | | | X | X | |
| vascular dementia | | | | | | X | X | |
| dementia due to HIV disease | | | | | | X | X | |
| dementia due to head trauma | | | | | | X | X | |
| dementia due to Parkinson Disease | | | | | | X | X | |
| dementia due to Huntington Disease | | | | | | X | X | |
| dementia due to Pick Disease | | | | | | X | X | |
| dementia due to Creutzfeldt-Jacob Disease | | | | | | X | X | |
| amnestic disorders due to a general medical condition | X | | | | | X | X | |
| substance-induced persisting amnestic disorder | X | | | | | X | X | |
| mild cognitive impairment disorder | X | | | | | X | X | |
| other cognitive disorders | X | | | | | X | X | |
| PARKINSON DISEASE | | X | | | | | | |

| | | MEDICAMENT | | | | | | |
|---|---|---|---|---|---|---|---|---|
| | | 83 | 78 | 88 | 39 | 57 | 67 | 35 |
| | MONO | | | | COMBO's | | | |
| | 5- | | | 5-HT2A/D4*-Antagonist + CNS compound | | | | |
| MEDICAL INDICATION | HT2A/ D4* Antagonist | SCT-11* modulation | Prodrug of uridine | sigma receptor agonist | Glutamate receptor antagonist | mGluR* agonist | nicotinic acetylcholine receptor antagonist | GABA-A* modulator |
| DISORDER WITH AN UNDERLYING EMOTION | X | X | X | X | X | X | X | X |

TABLE 5-continued

*SEE GLOSSARY HEREUNDER

| | | | | | | | | |
|---|---|---|---|---|---|---|---|---|
| DYSREGULATION NON-COGNITIVE MENTAL DISORDERS (excl. Pain Disorder) | | | | | | | | |
| mood disorders | | X | X | X | | | | |
| anxiety disorders | X | X | X | X | X | X | X | X |
| psychotic disorders | | | | | | | | |
| eating disorders | X | X | X | X | | | | X |
| premenstrual syndrome | X | X | X | X | | | | X |
| somatoform disorders (excluding Pain Disorder) | X | X | X | X | X | X | X | X |
| factitious disorders | X | X | X | X | X | X | X | X |
| dissociative disorders | X | X | X | X | X | X | X | X |
| sexual and gender identity disorders | X | X | X | X | | | | X |
| sleep disorders | X | X | X | X | | | | X |
| adjustment disorders | X | X | X | X | X | X | X | X |
| impulse control disorders | X | X | X | X | X | X | X | X |
| pervasive development disorders | X | | | | | | | |
| attention-deficit disorders | X | | | X | | | | |
| disruptive behaviour disorders | X | | | | | | | |
| substance-related disorders | X | | | | X | X | X | |
| personality disorders | X | X | X | X | X | X | X | X |
| psychological factors affecting medical conditions | X | | | | | | | |
| malingering | X | | | | | | | |
| antisocial behaviour | X | | | | | | | |
| bereavement | X | X | X | X | X | X | X | X |
| occupational problem | X | X | X | X | X | X | X | X |
| identity problem | X | | | | | | | |
| phase of life problem | X | | | | | | | |
| academic problem | X | | | | | | | |
| problems related to abuse or neglect | X | X | X | X | X | X | X | X |
| PAIN DISORDER | | X | X | X | X | X | X | X |
| COGNITIVE DISORDERS | | | | | | | | |
| delirium | | | | | | | | |
| Alzheimer Disease | | | | | | | | |
| substance-induced persisting dementia | | | | | | | | |
| vascular dementia | | | | | | | | |
| dementia due to HIV disease | | | | | | | | |
| dementia due to head trauma | | | | | | | | |
| dementia due to Parkinson Disease | | | | | | | | |
| dementia due to Huntington Disease | | | | | | | | |
| dementia due to Pick Disease | | | | | | | | |
| dementia due to Creutzfeldt-Jacob Disease | | | | | | | | |
| amnestic disorders due to a general medical condition | X | | | | | | | |
| substance-induced persisting amnestic disorder | X | | | | | | | |
| mild cognitive impairment disorder | X | | | | | | | |
| other cognitive disorders | X | | | | | | | |
| PARKINSON DISEASE | | | | | | | | |

TABLE 5-continued

*SEE GLOSSARY HEREUNDER

| | | MEDICAMENT | | | | | | |
|---|---|---|---|---|---|---|---|---|
| | | 36 | 99 | 74 | 77 | 89 | 94 | 87 |
| | MONO | | | | COMBO's | | | |
| | 5- | | | 5-HT2A/D4*-Antagonist + CNS compound | | | | |
| MEDICAL INDICATION | HT2A/D4* Antagonist | GABA-B* antagonist | vomeropherin | opoid agonist | Phospholipase A2 inhibitor with caspase inhibitor activity | sigma receptor antagonist | sulfonamide | Secretin pancreatic hormone |
| DISORDER WITH AN UNDERLYING EMOTION DYSREGULATION NON-COGNITIVE MENTAL DISORDERS (excl. Pain Disorder) | X | X | X | X | X | X | X | X |
| mood disorders | | | | | X | X | X | |
| anxiety disorders | X | X | X | X | X | X | | X |
| psychotic disorders | | | | X | X | X | X | X |
| eating disorders | X | X | X | X | X | X | | |
| premenstrual syndrome | X | X | X | X | X | X | | |
| somatoform disorders (excluding Pain Disorder) | X | X | X | X | X | X | X | X |
| factitious disorders | X | X | X | X | X | X | X | X |
| dissociative disorders | X | X | X | X | X | X | X | X |
| sexual and gender identity disorders | X | X | X | X | X | X | | |
| sleep disorders | X | X | X | X | X | X | X | X |
| adjustment disorders | X | X | X | X | X | X | X | X |
| impulse control disorders | X | X | X | X | X | X | X | X |
| pervasive development disorders | X | | | | X | X | X | X |
| attention-deficit disorders | X | | | | | | | |
| disruptive behaviour disorders | X | | | | X | X | X | X |
| substance-related disorders | X | | | X | X | X | X | X |
| personality disorders | X | X | X | X | X | X | X | X |
| psychological factors affecting medical conditions | X | | | | | | X | X |
| malingering | X | | | | | | X | X |
| antisocial behaviour | X | | | | | | X | X |
| bereavement | X | X | X | X | X | X | X | X |
| occupational problem | X | X | X | X | X | X | X | X |
| identity problem | X | | | | | | X | X |
| phase of life problem | X | | | | | | | |
| academic problem | X | | | | | | | |
| problems related to abuse or neglect | X | X | X | X | X | X | X | X |
| PAIN DISORDER COGNITIVE DISORDERS | | | | | X | X | X | X |
| delirium | | | | | X | X | X | X |
| Alzheimer Disease | | | | | | | | |
| substance-induced persisting dementia | | | | | | | | |
| vascular dementia | | | | | | | | |
| dementia due to HIV disease | | | | | | | | |
| dementia due to head trauma | | | | | | | | |
| dementia due to Parkinson Disease | | | | | | | | |
| dementia due to Huntington Disease | | | | | | | | |
| dementia due to Pick Disease | | | | | | | | |
| dementia due to Creutzfeldt-Jacob | | | | | | | | |

TABLE 5-continued

*SEE GLOSSARY HEREUNDER

| Disease | | | | | | | |
|---|---|---|---|---|---|---|---|
| amnestic disorders due to a general medical condition | X | | | | | | |
| substance-induced persisting amnestic disorder | X | | | | | | |
| mild cognitive impairment disorder | X | | | | | | |
| other cognitive disorders | X | | | | | | |
| PARKINSON DISEASE | | | | | | | |

| | | | | MEDICAMENT | | | |
|---|---|---|---|---|---|---|---|
| | MONO 5-HT2A/ | 84 | 28 | 29 | 70 | 65 | 21 |
| | | | | COMBO's 5-HT2A/D4*-Antagonist + CNS compound | | | |
| MEDICAL INDICATION | D4* Antagonist | SDA* | D2*-antagonist | D3*-antagonist | NK3* antagonist | neurotensin receptor antagonist | CB1* antagonist |
| DISORDER WITH AN UNDERLYING EMOTION DYSREGULATION NON-COGNITIVE MENTAL DISORDERS (excl. Pain Disorder) | X | X | X | X | X | X | X |
| mood disorders | | X | X | | X | X | X |
| anxiety disorders | X | X | | | X | X | X |
| psychotic disorders | | X | X | X | X | X | X |
| eating disorders | X | | | | | | |
| premenstrual syndrome | X | | | | | | |
| somatoform disorders (excluding Pain Disorder) | X | X | X | X | X | X | X |
| factitious disorders | X | X | X | X | X | X | X |
| dissociative disorders | X | X | X | X | X | X | X |
| sexual and gender identity disorders | X | | | | | | |
| sleep disorders | X | X | X | X | X | X | X |
| adjustment disorders | X | X | X | X | X | X | X |
| impulse control disorders | X | X | X | X | X | X | X |
| pervasive development disorders | X | X | X | X | X | X | X |
| attention-deficit disorders | X | | | | | | |
| disruptive behaviour disorders | X | X | X | X | X | X | X |
| substance-related disorders | X | X | X | X | X | X | X |
| personality disorders | X | X | X | X | X | X | X |
| psychological factors affecting medical conditions | X | X | X | X | X | X | X |
| malingering | X | X | X | X | X | X | X |
| antisocial behaviour | X | X | X | X | X | X | X |
| bereavement | X | X | X | X | X | X | X |
| occupational problem | X | X | X | X | X | X | X |
| identity problem | X | X | X | X | X | X | X |
| phase of life problem | X | | | | | | |
| academic problem | X | | | | | | |
| problems related to abuse or neglect | X | X | X | X | X | X | X |
| PAIN DISORDER | | X | X | X | X | X | X |
| COGNITIVE DISORDERS | | | | | | | |
| delirium | | X | X | X | X | X | X |
| Alzheimer Disease | | | | | | | |
| substance-induced persisting dementia | | | | | | | |

TABLE 5-continued

*SEE GLOSSARY HEREUNDER vascular dementia
dementia due to HIV disease
dementia due to head trauma
dementia due to Parkinson Disease
dementia due to Huntington Disease
dementia due to Pick Disease
dementia due to Creutzfeldt-Jacob Disease

| MEDICAL INDICATION | MONO 5-HT2A/D4* Antagonist |
|---|---|
| amnestic disorders due to a general medical condition | X |
| substance-induced persisting amnestic disorder | X |
| mild cognitive impairment disorder | X |
| other cognitive disorders | X |
| PARKINSON DISEASE | (X in prostaglandin E 1 column) |

|  | MEDICAMENT | | | | | | | | |
|---|---|---|---|---|---|---|---|---|---|
|  | MONO 5-HT2A/ D4* | 15 | 34 | 18 | 79 | 81 | 16 | 73 | 27 |
|  |  | COMBO's 5-HT2A/D4*-Antagonist + CNS compound | | | | | | | |
| MEDICAL INDICATION | D4* Antag-onist | AMPA* receptor mediator | GABA-A* agonist | androgen receptor modulator | prosta-glandin E 1 | Psycho-stimulant | ampheta-mine | opioid receptor inhibitor | D1* receptor agonist |
| DISORDER WITH AN UNDERLYING EMOTION DYSREGULATION NON-COGNITIVE MENTAL DISORDERS (excl. Pain Disorder) | X | X | X | X | X | X | X | X | X |
| mood disorders |  | X | | | | | | | |
| anxiety disorders | X | X | | | | | | | |
| psychotic disorders |  | X | | | | | | | |
| eating disorders | X | X | | | | | | | |
| premenstrual syndrome | X | X | | | | | | | |
| somatoform disorders (excluding Pain Disorder) | X | X | | | | | | | |
| factitious disorders | X | X | | | | | | | |
| dissociative disorders | X | X | | | | | | | |
| sexual and gender identity disorders | X | | | X | X | | | | |
| sleep disorders | X | X | X | | | X | | | |
| adjustment disorders | X | X | | | | | | | |
| impulse control disorders | X | X | | | | | | | |
| pervasive development disorders | X | X | | | | | | | |
| attention-deficit disorders | X | | | | | X | X | | |
| disruptive behaviour disorders | X | X | | | | | | | |
| substance-related disorders | X | X | | | | X | | X | X |
| personality disorders | X | X | | | | | | | |
| psychological factors affecting medical conditions | X | X | | | | | | | |
| malingering | X | X | | | | | | | |
| antisocial behaviour | X | X | | | | | | | |
| bereavement | X | X | | | | | | | |
| occupational problem | X | X | | | | | | | |

TABLE 5-continued

*SEE GLOSSARY HEREUNDER

| | | |
|---|---|---|
| identity problem | X | X |
| phase of life problem | X | |
| academic problem | X | |
| problems related to abuse or neglect | X | X |
| PAIN DISORDER | | X |
| COGNITIVE DISORDERS | | |
| delirium | | X |
| Alzheimer Disease | | X |
| substance-induced persisting dementia | | X |
| vascular dementia | | X |
| dementia due to HIV disease | | X |
| dementia due to head trauma | | X |
| dementia due to Parkinson Disease | | X |
| dementia due to Huntington Disease | | X |
| dementia due to Pick Disease | | X |
| dementia due to Creutzfeldt-Jacob Disease | | X |
| amnestic disorders due to a general medical condition | X | X |
| substance-induced persisting amnestic disorder | X | X |
| mild cognitive impairment disorder | X | X |
| other cognitive disorders | X | X |
| PARKINSON DISEASE | | |

Last column (rightmost) of PARKINSON DISEASE row: X

| | | MEDICAMENT | | | | | | |
|---|---|---|---|---|---|---|---|---|
| | MONO | 38 | 50 | 43 | 10 | 23 | 66 | 58 |
| | 5-HT2A/ | | | | COMBO's | | | |
| | | | | | 5-HT2A/D4*-Antagonist + CNS compound | | | |
| MEDICAL INDICATION | D4* Antagonist | glucocorticoid synthesis inhibitor | MAO* reuptake inhibitor | Hormonal Substance | acetylholin estrase-Inhibitor | choline uptake enhancer | NGF* | mimics the effects of NGF* |
| DISORDER WITH AN UNDERLYING EMOTION DYSREGULATION NON-COGNITIVE MENTAL DISORDERS (excl. Pain Disorder) | X | X | X | X | X | X | X | X |
| mood disorders | | | | | | | | |
| anxiety disorders | X | | | | | | | |
| psychotic disorders | | | | | | | | |
| eating disorders | X | | | | | | | |
| premenstrual syndrome | X | | | X | | | | |
| somatoform disorders (excluding Pain Disorder) | X | | | | | | | |
| factitious disorders | X | | | | | | | |
| dissociative disorders | X | | | | | | | |
| sexual and gender identity disorders | X | | | X | | | | |
| sleep disorders | X | | | | | | | |
| adjustment disorders | X | | | | | | | |
| impulse control disorders | X | | | | | | | |
| pervasive development disorders | X | | | | | | | |

TABLE 5-continued

*SEE GLOSSARY HEREUNDER

| | | | | | | | | |
|---|---|---|---|---|---|---|---|---|
| attention-deficit disorders | X | | X | | | | | |
| disruptive behaviour disorders | X | | | | | | | |
| substance-related disorders | X | X | X | | | | | |
| personality disorders | X | | | | | | | |
| psychological factors affecting medical conditions | X | | | | | | | |
| malingering | X | | | | | | | |
| antisocial behaviour | X | | | | | | | |
| bereavement | X | | | | | | | |
| occupational problem | X | | | | | | | |
| identity problem | X | | | | | | | |
| phase of life problem | X | | | | | | | |
| academic problem | X | | | | | | | |
| problems related to abuse or neglect | X | | | | | | | |
| PAIN DISORDER | | | | | | | | |
| COGNITIVE DISORDERS | | | | | | | | |
| delirium | | | | | | | | |
| Alzheimer Disease | | | | X | X | X | X | |
| substance-induced persisting dementia | | | | X | X | X | X | |
| vascular dementia | | | | X | X | X | X | |
| dementia due to HIV disease | | | | X | X | X | X | |
| dementia due to head trauma | | | | X | X | X | X | |
| dementia due to Parkinson Disease | | | | X | X | X | X | |
| dementia due to Huntington Disease | | | | X | X | X | X | |
| dementia due to Pick Disease | | | | X | X | X | X | |
| dementia due to Creutzfeldt-Jacob Disease | | | | X | X | X | X | |
| amnestic disorders due to a general medical condition | X | | | X | X | X | X | |
| substance-induced persisting amnestic disorder | X | | | X | X | X | X | |
| mild cognitive impairment disorder | X | | | X | X | X | X | |
| other cognitive disorders | X | | | X | X | X | X | |
| PARKINSON DISEASE | | X | | | | X | X | |

| | MEDICAMENT | | | | | | | |
|---|---|---|---|---|---|---|---|---|
| | MONO | 59 | 17 | 80 | 45 | 68 | 33 | 32 |
| | 5- | COMBO's 5-HT2A/D4*-Antagonist + CNS compound | | | | | | |
| MEDICAL INDICATION | HT2A/D4* Antagonist | Muscarinic receptor partial agonist | amyloid aggregation inhibitor | protect dopaminergic and cholinergic neurons | increasing insulin sensitivity | nicotinic receptor agonists | GABA* agonist | ERK* activation |
| DISORDER WITH AN UNDERLYING EMOTION DYSREGULATION NON-COGNITIVE MENTAL DISORDERS (excl. Pain Disorder) | X | X | X | X | X | X | X | X |
| mood disorders | | | | | | | | |
| anxiety disorders | X | | | | | | | |
| psychotic disorders | | | | | | | | |
| eating disorders | X | | | | | | | |

TABLE 5-continued

*SEE GLOSSARY HEREUNDER

| | | | | | | | | |
|---|---|---|---|---|---|---|---|---|
| premenstrual syndrome | X | | | | | | | |
| somatoform disorders (excluding Pain Disorder) | X | | | | | | | |
| factitious disorders | X | | | | | | | |
| dissociative disorders | X | | | | | | | |
| sexual and gender identity disorders | X | | | | | | | |
| sleep disorders | X | | | | | | | |
| adjustment disorders | X | | | | | | | |
| impulse control disorders | X | | | | | | | |
| pervasive development disorders | X | | | | | | | |
| attention-deficit disorders | X | | | | | | | |
| disruptive behaviour disorders | X | | | | | | | |
| substance-related disorders | X | | | | | | | |
| personality disorders | X | | | | | | | |
| psychological factors affecting medical conditions | X | | | | | | | |
| malingering | X | | | | | | | |
| antisocial behaviour | X | | | | | | | |
| bereavement | X | | | | | | | |
| occupational problem | X | | | | | | | |
| identity problem | X | | | | | | | |
| phase of life problem | X | | | | | | | |
| academic problem | X | | | | | | | |
| problems related to abuse or neglect | X | | | | | | | |
| PAIN DISORDER | | | | | | | | |
| COGNITIVE DISORDERS | | | | | | | | |
| delirium | | | | | | | | |
| Alzheimer Disease | | X | X | X | X | X | X | X |
| substance-induced persisting dementia | | X | X | X | X | X | X | X |
| vascular dementia | | X | X | X | X | X | X | X |
| dementia due to HIV disease | | X | X | X | X | X | X | X |
| dementia due to head trauma | | X | X | X | X | X | X | X |
| dementia due to Parkinson Disease | | X | X | X | X | X | X | X |
| dementia due to Huntington Disease | | X | X | X | X | X | X | X |
| dementia due to Pick Disease | | X | X | X | X | X | X | X |
| dementia due to Creutzfeldt-Jacob Disease | | X | X | X | X | X | X | X |
| amnestic disorders due to a general medical condition | X | X | X | X | X | X | X | X |
| substance-induced persisting amnestic disorder | X | X | X | X | X | X | X | X |
| mild cognitive impairment disorder | X | X | X | X | X | X | X | X |
| other cognitive disorders | X | X | X | X | X | X | X | X |

TABLE 5-continued

*SEE GLOSSARY HEREUNDER

| | | | | | | | | |
|---|---|---|---|---|---|---|---|---|
| PARKINSON DISEASE | | | | | X | | | |

| | MEDICAMENT | | | | | | | |
|---|---|---|---|---|---|---|---|---|
| | MONO | 42 | 20 | 48 | 31 | 100 | 52 | 30 |
| | 5-HT2A/ | | | | COMBO's | | | |
| | | | | | 5-HT2A/D4*-Antagonist + CNS compound | | | |
| MEDICAL INDICATION | D4* Antagonist | H3* Antagonist | Calcium Channel Modulator | Levodopa | Dopamine-agonist | Dopamine releaser | MAO-B*-inhibitor | DA* uptake inhibitor |
| DISORDER WITH AN UNDERLYING EMOTION DYSREGULATION NON-COGNITIVE MENTAL DISORDERS (excl. Pain Disorder) | X | X | X | X | X | X | X | X |
| mood disorders | | | | | X | X | X | |
| anxiety disorders | X | | | | X | X | X | |
| psychotic disorders | | | | | | | | |
| eating disorders | X | | | | X | X | X | |
| premenstrual syndrome | X | | | | X | X | X | |
| somatoform disorders (excluding Pain Disorder) | X | | | | X | X | X | |
| factitious disorders | X | | | | X | X | X | |
| dissociative disorders | X | | | | X | X | X | |
| sexual and gender identity disorders | X | | | | | | | |
| sleep disorders | X | | | | | | | |
| adjustment disorders | X | | | | X | X | X | |
| impulse control disorders | X | | | | X | X | X | |
| pervasive development disorders | X | | | | | | | |
| attention-deficit disorders | X | | | | X | X | X | |
| disruptive behaviour disorders | X | | | | | | | |
| substance-related disorders | X | | | | X | X | X | X |
| personality disorders | X | | | | X | X | X | |
| psychological factors affecting medical conditions | X | | | | | | | |
| malingering | X | | | | | | | |
| antisocial behaviour | X | | | | | | | |
| bereavement | X | | | | | | | |
| occupational problem | X | | | | | | | |
| identity problem | X | | | | | | | |
| phase of life problem | X | | | | | | | |
| academic problem | X | | | | | | | |
| problems related to abuse or neglect | X | | | | X | X | X | |
| PAIN DISORDER | | | | | X | X | X | |
| COGNITIVE DISORDERS | | | | | | | | |
| delirium | | | | | | | | |
| Alzheimer Disease | | X | X | | | | | |
| substance-induced persisting dementia | | X | X | | | | | |
| vascular dementia | | X | X | | | | | |
| dementia due to HIV disease | | X | X | | | | | |
| dementia due to head trauma | | X | X | | | | | |
| dementia due to Parkinson Disease | | X | X | | | | | |
| dementia due to Huntington Disease | | X | X | | | | | |
| dementia due to Pick Disease | | X | X | | | | | |

TABLE 5-continued

*SEE GLOSSARY HEREUNDER

| | | | | | | | | |
|---|---|---|---|---|---|---|---|---|
| dementia due to Creutzfeldt-Jacob Disease | | X | X | | | | | |
| amnestic disorders due to a general medical condition | X | X | X | | | | | |
| substance-induced persisting amnestic disorder | X | X | X | | | | | |
| mild cognitive impairment disorder | X | X | X | | | | | |
| other cognitive disorders | X | X | X | | | | | |
| PARKINSON DISEASE | | X | | X | X | X | X | X | X |

| | MEDICAMENT | | | | | | | | |
|---|---|---|---|---|---|---|---|---|---|
| | | 49 | 63 | 64 | 37 | 46 | 11 | 24 | 25 |
| | MONO | | | | COMBO's 5-HT2A/D4*-Antagonist + CNS compound | | | | | |
| MEDICAL INDICATION | 5-HT2A/D4* Antagonist | Lipid-DNA Complex | neuro-immuno-philin ligands | neuro-modulator | Glial-cell Line Derived Neurotrophic Factor | inhibitor of the mixed lineage kinase family | adenosine A2a receptor antagonist | COX-2* Inhibitor | COX*-inhibiting nitric. oxide donators |
| DISORDER WITH AN UNDERLYING EMOTION DYSREGULATION NON-COGNITIVE MENTAL DISORDERS (excl. Pain Disorder) | X | X | X | X | X | X | X | X | X |
| mood disorders | | | | | | | | | |
| anxiety disorders | X | | | | | | | | |
| psychotic disorders | | | | | | | | | |
| eating disorders | X | | | | | | | | |
| premenstrual syndrome | X | | | | | | | | |
| somatoform disorders (excluding Pain Disorder) | X | | | | | | | | |
| factitious disorders | X | | | | | | | | |
| dissociative disorders | X | | | | | | | | |
| sexual and gender identity disorders | X | | | | | | | | |
| sleep disorders | X | | | | | | | | |
| adjustment disorders | X | | | | | | | | |
| impulse control disorders | X | | | | | | | | |
| pervasive development disorders | X | | | | | | | | |
| attention-deficit disorders | X | | | | | | | | |
| disruptive behaviour disorders | X | | | | | | | | |
| substance-related disorders | X | | | | | | | | |
| personality disorders | X | | | | | | | | |
| psychological factors affecting medical conditions | X | | | | | | | | |
| malingering | X | | | | | | | | |
| antisocial behaviour | X | | | | | | | | |
| bereavement | X | | | | | | | | |
| occupational problem | X | | | | | | | | |
| identity problem | X | | | | | | | | |
| phase of life problem | X | | | | | | | | |
| academic problem | X | | | | | | | | |
| problems related to abuse or neglect | X | | | | | | | | |

TABLE 5-continued

*SEE GLOSSARY HEREUNDER

| MEDICAL INDICATION | | | | | | | | |
|---|---|---|---|---|---|---|---|---|
| PAIN DISORDER | | | | | | | X | X |
| COGNITIVE DISORDERS | | | | | | | | |
| delirium | | | | | | | | |
| Alzheimer Disease | | | | | | | | |
| substance-induced persisting dementia | | | | | | | | |
| vascular dementia | | | | | | | | |
| dementia due to HIV disease | | | | | | | | |
| dementia due to head trauma | | | | | | | | |
| dementia due to Parkinson Disease | | | | | | | | |
| dementia due to Huntington Disease | | | | | | | | |
| dementia due to Pick Disease | | | | | | | | |
| dementia due to Creutzfeldt-Jacob Disease | | | | | | | | |
| amnestic disorders due to a general medical condition | X | | | | | | | |
| substance-induced persisting amnestic disorder | X | | | | | | | |
| mild cognitive impairment disorder | X | | | | | | | |
| other cognitive disorders | X | | | | | | | |
| PARKINSON DISEASE | | X | X | X | X | X | X | |

| | MEDICAMENT | | | | | | | |
|---|---|---|---|---|---|---|---|---|
| | | 72 | 47 | 22 | 96 | 53 | | |
| | | | | COMBO's | | | | |
| | MONO | 5-HT2A/D4*-Antagonist + CNS compound | | | | | | |
| MEDICAL INDICATION | 5-HT2A/D4* Antagonist | (nitric oxide) NSAID* | interleukin-1 beta converting enzyme inhibitor | cathepsin K inhibitor | unknown | MAO-B* re-uptake inhibition | 5-HT2A Antagonist + D4-Antagonist + CNS Compound | 5-HT2A Antagonist + D4-Antagonist |
| DISORDER WITH AN UNDERLYING EMOTION DYSREGULATION NON-COGNITIVE MENTAL DISORDERS (excl. Pain Disorder) | X | X | X | X | X | X | | |
| mood disorders | | | | | | X | | |
| anxiety disorders | X | | | | | X | | |
| psychotic disorders | | | | | | X | | |
| eating disorders | X | | | | | X | | |
| premenstrual syndrome | X | | | | | X | | |
| somatoform disorders (excluding Pain Disorder) | X | | | | | X | | |
| factitious disorders | X | | | | | X | | |
| dissociative disorders | X | | | | | X | | |
| sexual and gender identity disorders | X | | | | | X | | |
| sleep disorders | X | | | | | X | | |
| adjustment disorders | X | | | | | X | | |
| impulse control disorders | X | | | | | X | | |

TABLE 5-continued

*SEE GLOSSARY HEREUNDER

| | | | | | |
|---|---|---|---|---|---|
| pervasive development disorders | X | | | | X |
| attention-deficit disorders | X | | | | X |
| disruptive behaviour disorders | X | | | | X |
| substance-related disorders | X | | | | X |
| personality disorders | X | | | | X |
| psychological factors affecting medical conditions | X | | | | X |
| malingering | X | | | | X |
| antisocial behaviour | X | | | | X |
| bereavement | X | | | | X |
| occupational problem | X | | | | X |
| identity problem | X | | | | X |
| phase of life problem | X | | | | X |
| academic problem | X | | | | X |
| problems related to abuse or neglect | X | | | | X |
| PAIN DISORDER | | X | X | X | X |

COGNITIVE DISORDERS

| | | | | | |
|---|---|---|---|---|---|
| delirium | | | | | X |
| Alzheimer Disease | | X | | | X |
| substance-induced persisting dementia | | | | | X |
| vascular dementia | | | | | X |
| dementia due to HIV disease | | | | | X |
| dementia due to head trauma | | | | | X |
| dementia due to Parkinson Disease | | | | | X |
| dementia due to Huntington Disease | | | | | X |
| dementia due to Pick Disease | | | | | X |
| dementia due to Creutzfeldt-Jacob Disease | | | | | X |
| amnestic disorders due to a general medical condition | X | | | | X |
| substance-induced persisting amnestic disorder | X | | | | X |
| mild cognitive impairment disorder | X | | | | X |
| other cognitive disorders | X | | | | X |

TABLE 5-continued

*SEE GLOSSARY HEREUNDER

| | | | | |
|---|---|---|---|---|
| PARKINSON DISEASE | | | X | X |

GLOSSARY
5-HT = serotonin
5-HT1 = serotonin 1 receptor
5-HT1A = serotonin 1A receptor
5-HT1B = serotonin 1B receptor
5-HT2A/D4 = serotonin 2A en dopamine D4 receptor
5-HT2B = serotonin 2B receptor
5-HT2C = serotonin 2C receptor
5HT3 = serotonin 3 receptor
5HT6 = serotonin 6 receptor
AMPA = alpha-amino-3-hydroxy-5-methyl-4-isoxazole propionate
CB1 = cannabioid receptor 1
CINODs = COX-inhibiting nitric oxide donators
COX = cyclooxigenase
COX-2 = cyclooxigenase 2
CRF-1 = Corticotropin-Releasing Factor Receptor 1
D1 = Dopamine 1
D2 = Dopamine 2
D2 = Dopamine 3
DA = Dopamine
ERK = extracellular signal-related kinase
GABA = gamma-aminobutyric acid
GABA-A = gamma-aminobutyric acid A receptor
GABA-B = gamma-aminobutyric acid B receptor
GPCR = G-Protein-Coupled Receptor
GR = glucocorticoid receptor
H3 = histamine H3-receptor
MAO = mono-amine oxydase
MAO-A = mono-amine oxydase A
MAO-B = mono-amine oxydase B
MC4 = melanocortin-4 receptor
MCH = Melanin concentrating hormone
MgluR = metabotropic glutamate receptor
MT = melatonin receptor
NARI = selective nor-adrenaline re-uptake inhibitor
NaSSA = noradrenergic/specific serotonergic antidepressant
NDRI = selective nor-adrenaline and dopamine re-uptake inhibitor
NGF = Nerve Growth Factor
NGF = nerve growth factor
NK1 = neurokinin 1 receptor
NK2 = neurokinin 2 receptor
ND3 = neurokinin 3 receptor
NMDA = N-Methyl-D-aspartate
NSAID = Non-steroidal anti-inflammatory drugs
PDE4 = phosphodiesterase-4
RIMA = reversible inhibitor of mono-amine oxydase A
SCT-11 = G protein-coupled receptor
SDA = Serotonin/Dopamine Antagonist
SDRI = selective serotonin and dopamine reuptake inhibitor
SNDRI = selective serotonin, nor-adrenaline and dopamine reuptake inhibitor
SNRI = selective serotonin and nor-adrenaline reuptake inhibitor
SSRI = selective serotonin reuptake inhibitor
V1B = vasopressin 1B receptor

TABLE 6

| PHARMAC. GROUP (see overview hereunder) | nr. PH. PROF. | PHARMA- COLOGICAL PROFILE | MAIN INDICATIONS | COMPOUND | DOSE RANGE | COMPANY |
|---|---|---|---|---|---|---|
| Monoaminergic Transmitter Systems | 1 | 5-HT reuptake enhancer | Depression/Anxiety | Tianeptine | 25 to 50 mg daily | Servier |
| Monoaminergic Transmitter Systems | 2 | 5-HT1 autoreceptor agonist | Depression/Anxiety | SUNEPITRON | unknown | Pfizer |
| Monoaminergic Transmitter Systems | 3 | 5HT1A agonist | Anxiety | MN-305 | | MediciNova |
| | | 5-HT1A agonist | Depression/Anxiety | Buspirone | | Briston-Myers Squibb |
| | | 5-HT1A agonist | Depression | bupropion (controlled-release formulation, once-day | 150 mg to 450 mg | GlaxoSmithKline |
| | | 5-HT1A agonist | Depression | gepirone | 20 mg to 80 mg daily | Organon |

TABLE 6-continued

| PHARMAC. GROUP (see overview hereunder) | nr. PH. PROF. | PHARMA-COLOGICAL PROFILE | MAIN INDICATIONS | COMPOUND | DOSE RANGE | COMPANY |
|---|---|---|---|---|---|---|
| | | 5-HT1A agonist | Alzheimer's Disease | Xaliproden | 1 to 2 mg daily | Sanofi-Synthelabo |
| | | 5-HT1A agonist | Depression/Anxiety | Flesinoxan | unknown | Solvay |
| | | 5-HT1A agonist | Anxiety | lesopitron | | Esteve |
| | | 5-HT1A agonist | Depression | VPI-013 (also known as OPC-14523) | | Vela, Otsuka |
| | | 5-HT1A agonist | Depression/Anxiety | metanospirone | | ? |
| | | 5-HT1A agonist | Depression/Anxiety | EMD 68843 | | EMD Pharmaceuticals |
| | | 5-HT1A agonist | Depression/Anxiety | alnespirone | | Servier |
| | | 5-HT1A agonist | Depression/Anxiety | tandospirone | | Sumitomo |
| | | 5-HT1A agonist | Depression/Anxiety | zalospirone | | Weyth |
| | | 5-HT1A agonist | Parkinson's Disease | sarizotan | unknown | EMD Pharmaceuticals |
| | | 5-HT1A agonist | ADHD | PRX-00023 | | Predix |
| | | 5-HT1A agonist | Anxiety | PRX-00023 | | Predix |
| Monoaminergic Transmitter Systems | 4 | 5-HT1A antagonist | Depression | robalzotan tartrate hydrate | unknown | AstraZeneca |
| | | 5-HT1A antagonist | Depression | NAD299 | | AstraZeneca |
| Monoaminergic Transmitter Systems | 5 | 5-HT1B antagonist | Depression/Anxiety | AR-A2 | | AstraZeneca |
| | | 5-HT1B antagonist | Depression/Anxiety | elzasonan | unknown | Pfizer |
| | | 5-HT1B antagonist | Depression/Anxiety | AZD1134 | | AstraZeneca |
| Monoaminergic Transmitter Systems | 6 | 5-HT2B antagonist | Depression/Anxiety | Agomelatine | 25 to 50 mg daily | Servier |
| Monoaminergic Transmitter Systems | 7 | 5-HT2C antagonist | Depression/Anxiety | Agomelatine | 25 to 50 mg daily | Servier |
| | | 5-HT2C antagonist | Depression/Anxiety | SB 243213 | | GlaxoSmithKline |
| Monoaminergic Transmitter Systems | 8 | 5-HT3 antagonist | Cocaine Dependence | ondansetron | 8 to 32 mg daily | National Institute on Drug Abuse |
| Monoaminergic Transmitter Systems | 9 | 5-HT6 antagonist | Alzheimer's Disease | SB-271046 | | GlaxoSmithKline |
| | | 5-HT6 antagonist | Alzheimer's Disease | 271046 | | GlaxoSmithKline |
| | | 5-HT6 antagonist | Alzheimer's Disease | 742457 | | GlaxoSmithKline |
| Excitatory Amino Acid System | 10 | acetylcholinesterase inhibitor | Alzheimer's Disease | dichlorvos | | Bayer |
| | | acetylcholinesterase inhibitor | Alzheimer's Disease | metrifonate | | Bayer |
| | | acetylcholinesterase inhibitor | Alzheimer's Disease | physostigmine | | Lundbeck/Forest Laboratories |
| | | acetylcholinesterase inhibitor | Alzheimer's Disease | rivastigmine | | Novartis Pharmaceuticals |
| | | acetylcholinesterase inhibitor | Alzheimer's Disease | tacrine | | Parke Davis |
| | | acetylcholinesterase inhibitor | Alzheimer's Disease | donezepil | | Pfizer |
| | | acetylcholinesterase inhibitor | Alzheimer's Disease | galantamine (extended release formulation) | 8 to 24 mg daily | Johnson & Johnson Pharmaceutical |
| | | acetylcholinesterase inhibitor | Alzheimer's Disease | phenserine tartrate | 20 to 30 mg daily | Axonyx |
| | | acetylcholinesterase inhibitor | Alzheimer's Disease | huperzine A | | Interneuron |
| | | acetylcholinesterase inhibitor | Alzheimer's Disease | rivastigmine tartrate | 3 to 12 mg daily | Novartis Pharmaceuticals |
| | | acetylcholinesterase inhibitor | Alzheimer's Disease | anseculin hydrochloride | | Schwabe |
| Adenosine Transmitter System | 11 | adenosine A2a receptor antagonist | Parkinson's Disease | KW-6002 | 40 to 80 mg daily | Kyowa Pharmaceutical |
| Monoaminergic Transmitter Systems | 12 | Adrenergic transmitter releaser | Depression | Pipoxazole | 30 to 60 mg daily | Sarget |
| Monoaminergic Transmitter Systems | 13 | alpha 1 adrenoreceptor antagonist | Depression/Anxiety | Flesinoxan | unknown | Solvay |
| | | alpha 1 adrenoreceptor antagonist | Parkinson's Disease | SDZ NVI 085 | unknown | Sandoz |
| Monoaminergic Transmitter Systems | 14 | alpha 2 adrenoreceptor antagonist | Depression | Mirtazapine | | Organon |
| | | alpha 2 adrenoreceptor antagonist | Depression | Idazoxan | 20 mg daily | Reckitt and Colman |
| | | alpha 2 adrenoreceptor antagonist | Schizophrenia | Idazoxan | 20 mg daily | Reckitt and Colman |
| | | alpha 2 adrenoreceptor antagonist | Depression/Anxiety | SUNEPITRON | unknown | Pfizer |
| | | alpha 2 adrenoreceptor antagonist | Depression | fluparoxan | | GlaxoSmithKline |
| | | alpha 2 adrenoreceptor antagonist | Depression/Anxiety | (R)-A 75200 | | Abbott |
| | | alpha 2 adrenoreceptor antagonist | Depression/Anxiety | A 75200 | | Abbott |
| | | alpha 2 adrenoreceptor antagonist | Insomnia | Mirtazepine | | Organon |

TABLE 6-continued

| PHARMAC. GROUP (see overview hereunder) | nr. PH. PROF. | PHARMACOLOGICAL PROFILE | MAIN INDICATIONS | COMPOUND | DOSE RANGE | COMPANY |
|---|---|---|---|---|---|---|
| | | alpha 2 adrenoreceptor antagonist | Depression | UK-14304 | | ? |
| Excitatory Amino Acid System | 15 | AMPA receptor mediator | Alzheimer's Disease | ampakine CX-516 | | Cortex Pharmaceuticals/Organon |
| | | AMPA receptor mediator | Alzheimer's Disease | ampakine CX-717 | unknown | Cortex Pharmaceuticals/Organon |
| | | AMPA receptor mediator | Schizophrenia | ampakine ORG 24448/CX-619 | unknown | Organon |
| | | AMPA receptor mediator | Depression | Ampakine CX-691 | unknown | Cortex Pharmaceuticals/Organon |
| Excitatory Amino Acid System | 16 | amphetamine | ADHD | methylphenidate transdermal system | | Noven Pharmaceuticals |
| Pathogenic Mechanisms of Dementia of the Alzheimer Type | 17 | amyloid aggregation-inhibitor | Alzheimer's Disease | Alzhemed | 200 to 300 mg daily | Neurochem |
| | | amyloid aggregation-inhibitor | Alzheimer's Disease | APAN | | Praecis Pharmaceutical |
| Endocrine System | 18 | androgen receptor modulator | Female Sexual Dysfunction | LGD2226 | | Ligand Pharmaceutical |
| Monoaminergic Transmitter Systems | 19 | beta 3 adrenoreceptor agonist | Depression/Anxiety | SR 58611 | unknown | Sanofi-Synthelabo |
| Other/Unknown | 20 | Calcium Channel Modulator | Alzheimer's Disease | MEM 1003 | | Memory Pharmaceuticals |
| | | Calcium Channel Modulator | Parkinson's Disease | safinamide | | Newron Pharmaceuticals |
| Monoaminergic Transmitter Systems | 21 | cannabioid receptor antagonist | Schizophrenia | SR 141716 | unknown | Sanofi-Synthelabo |
| Enzymatic System | 22 | cathepsin K inhibitor | Pain | 462795 | | GlaxoSmithKline |
| Excitatory Amino Acid System | 23 | choline uptake enhancer | Alzheimer's Disease | MKC-231 | 20 to 160 mg daily | Mitsubishi Pharma |
| Enzymatic System | 24 | COX-2 inhibitor | Pain | celecoxib | | Pfizer |
| | | COX-2 inhibitor | Pain | rofecoxib | | Pfizer |
| | | COX-2 inhibitor | Pain | valdecoxib | | Pfizer |
| | | COX-2 inhibitor | Pain | etoricoxib | 20 to 120 mg daily | Merck |
| | | COX-2 inhibitor | Pain | COX 189 | 100 to 800 mg daily | Novartis Pharmaceuticals |
| | | COX-2 inhibitor | Pain | parecoxib | 20 to 80 mg daily | Pfizer |
| | | COX-2 inhibitor | Pain | ABT-963 | | Abbott |
| Enzymatic System | 25 | COX-inhibiting nitric oxide donators (CINODs) | Pain | AZD3582 | 375 mg daily | AstraZeneca |
| | | COX-inhibiting nitric oxide donators (CINODs) | Pain | AZD4717 | | AstraZeneca |
| Endocrine System | 26 | CRF1 antagonist | Depression | AAG 561 | unknown | Novartis Pharmaceuticals |
| | | CRF1 antagonist | Depression/Anxiety | R121919 | 5 to 80 mg daily | Johnson & Johnson Pharmaceutical |
| | | CRF1 antagonist | Depression/Anxiety | elzasonan | unknown | Pfizer |
| | | CRF1 antagonist | Depression | 723620 | | GlaxoSmithKline |
| | | CRF1 antagonist | Depression/Anxiety | NBI-34041 | | Neurocrine Biosciences |
| | | CRF1 antagonist | Depression/Anxiety | CP-154-526 | | Pfizer |
| | | CRF1 antagonist | Depression/Anxiety | CP-448,187 | | Pfizer |
| Monoaminergic Transmitter Systems | 27 | D1 receptor agonist | Cocaine Dependence | DAS-431 | unknown | Drug Abuse Sciences |
| Monoaminergic Transmitter Systems | 28 | D2 receptor antagonist | Schizophrenia | amisulpride | | off patent |
| | | D2 receptor antagonist | Schizophrenia | bifeprunox | unknown | Solvay |
| Monoaminergic Transmitter Systems | 29 | D3 antagonist | Cocaine Dependence | BSF-201640 | | ? |
| | | D3 antagonist | Cocaine Dependence | PD 58491 | | ? |
| | | D3 antagonist | Parkinson's Disease | BSF-201640 | | ? |
| | | D3 antagonist | Parkinson's Disease | PD 58491 | | ? |
| | | D3 antagonist | schizophrenia | BSF-201640 | | ? |
| | | D3 antagonist | schizophrenia | PD 58491 | | ? |
| Monoaminergic Transmitter Systems | 30 | DA uptake inhibitor | Cocaine Dependence | GBR 12909 | | National Institute on Drug Abuse |
| | | DA uptake inhibitor | Parkinson's Disease | safinamide | | Newron Pharmaceuticals |
| Monoaminergic Transmitter Systems | 31 | dopamine agonist | Parkinson's Disease | sumanirole | 4 to 16 mg daily | Pfizer |
| | | dopamine agonist | Parkinson's Disease, Early and Advanced | rotigotine CDS (Once-a-Day Transdermal Patch) | 4.5 to 13.5 mg daily | Schwarz Pharma |
| | | dopamine agonist | Parkinson's Disease Restless Leg | ropinirole HCL (controlled-release formulation) | 0.75 to 24 mg daily | GlaxoSmithKline |
| | | dopamine agonist | Cocaine Dependence | cabergoline | | Abbott |
| | | dopamine agonist | Parkinson's Disease | sarizotan | | EMD Pharmaceuticals |
| | | dopamine agonist | Parkinson's Disease | pramipexole | | Pfizer |

TABLE 6-continued

| PHARMAC. GROUP (see overview hereunder) | nr. PH. PROF. | PHARMA- COLOGICAL PROFILE | MAIN INDICATIONS | COMPOUND | DOSE RANGE | COMPANY |
|---|---|---|---|---|---|---|
| | | dopamine agonist | Parkinson's Disease | DAB452 | | Weyth |
| | | dopamine agonist | Parkinson's Disease, Comorbid | SLV 308 | | Solvay |
| | | dopamine agonist | Depression/Anxiety | S32504 | | Servier |
| | | dopamine agonist | Parkinson's Disease | S32504 | | Servier |
| | | dopamine agonist | Parkinson's Disease | bromocriptine | | Novartis Pharmaceuticals |
| | | dopamine agonist | Parkinson's Disease | alaptide | | VU-Res. Inst. Pharm. Biochem (CZ) |
| | | dopamine agonist | Parkinson's Disease | cabergoline | 1 to 4 mg daily | Pharmacia |
| | | dopamine agonist | Parkinson's Disease | lisuride | 0.6 to 5 mg daily | Shering |
| | | dopamine agonist | Parkinson's Disease | pergolide | 2 to 3 mg daily | Lilly |
| Enzymatic System | 32 | ERK activation | Alzheimer's Disease | CPI-1189 | 50 to 100 mg daily | Centaur Pharmaceuticals |
| Inhibitory Amino Acid System | 33 | GABA agonist | Alzheimer's Disease | Nefiracetam | unknown | Daiichi Seiyaku, JPN Nattermann, BRD |
| Inhibitory Amino Acid System | 34 | GABA-A agonist | Insomnia | Gaboxadol | 5 to 20 mg daily | Lundbeck |
| Inhibitory Amino Acid System | 35 | GABA-A modulator | Insomnia | eszopiclone | 2 to 3 mg daily | Sepracor |
| | | GABA-A modulator | Insomnia | Zolpidem MR sustained-release version | 10 to 20 mg daily | Sanofi-Synthelabo |
| | | GABA-A modulator | Insomnia | Indiplon | 10 to 20 mg daily | DOV/Neurocrine |
| | | GABA-A modulator | Anxiety | Pagoclone | 30 mg daily | Indevus |
| | | GABA-A modulator | Insomnia | Zaleplon extended-release | 10 mg daily | King Pharmaceuticals |
| | | GABA-A modulator | Anxiety | SEP174559 | | Sepracor |
| | | GABA-A modulator | Anxiety, muscular contractions | SL 65.1498 | | Sanofi-Synthelabo |
| | | GABA-A modulator | Insomnia | CP-730,330 (NGD 96-3) | | Neurogen |
| | | GABA-A modulator | Insomnia | NGD 96-3 | | Neurogen |
| | | GABA-A modulator | Anxiety | Ocinaplon | 10 to 60 mg daily | DOV |
| Inhibitory Amino Acid System | 36 | GABA-B antagonist | Depression/Anxiety | AVE 7398 | unknown | Aventis |
| Neurotrophic System | 37 | Glial-cell Line Derived Neurotrophic Factor | Parkinson's Disease | GDNF | 15 mg daily | Amgen |
| Endocrine System | 38 | glucocorticoid synthesis inhibitor | Cocaine Dependence | metyrapone | | National Institute on Drug Abuse |
| Excitatory Amino Acid System | 39 | Glutamate receptor antagonist | Anxiety | LY354740 | | Eli Lilly |
| Other/Unknown | 40 | GPCR modulator | Depression/Anxiety | R1204 | | Roche |
| Endocrine System | 41 | GR antagonist | depression (psychotic) | Mifepristone | 600 to 1200 mg daily | Corcept |
| | | GR antagonist | Depression | ORG 34517/ 34850 | unknown | Organon |
| Monoaminergic Transmitter Systems | 42 | H3 Antagonist | Alzheimer's Disease | ABT-239 | | Abbott |
| | | H3 Antagonist | Alzheimer's Disease | ABT-834 | | Abbott |
| Endocrine System | 43 | Hormonal Substance | Premenstrual Syndrome | drospirenone 3 mg/ethinyl estradiol 0.020 mg tablets | see formula | Berlex Laboratories |
| | | Hormonal Substance | Female Sexual Dysfunction | female testosterone patch | | Procter & Gamble Pharmaceuticals |
| | | Hormonal Substance | Premenstrual Syndrome | synthetic conjugated estrogen A | 0.3 mg daily | Barr Laboratories |
| | | Hormonal Substance | Female Sexual Dysfunction | testosterone gel | | Bio Sante Pharmaceuticals |
| | | Hormonal Substance | Female Sexual Dysfunction | testosterone gel | | Cellegy Pharmaceuticals |
| | | Hormonal Substance | Female Sexual Dysfunction | methyl- testosterone | | Noven Pharmaceuticals |
| | | Hormonal Substance | Female Sexual Dysfunction | estrogens/ methyl- testosterone | | Solvay |
| | | Hormonal Substance | Female Sexual Dysfunction | testosterone transdermal spray | | VIVUS |
| Monoaminergic Transmitter Systems | 44 | Increase brain concentrations of 5-HT | Depression/Anxiety | KW 6055 | | ? |
| | | Increase brain concentrations of 5-HT | Depression/Anxiety | PMD 145 | | ? |
| | | Increase brain concentrations of 5-HT | Depression/Anxiety | SP 186 | | ? |
| | | Increase brain concentrations of 5-HT | Depression/Anxiety | Triptosine | | ? |

TABLE 6-continued

| PHARMAC. GROUP (see overview hereunder) | nr. PH. PROF. | PHARMA-COLOGICAL PROFILE | MAIN INDICATIONS | COMPOUND | DOSE RANGE | COMPANY |
|---|---|---|---|---|---|---|
| Endocrine System | 45 | increasing insulin sensitivity | Alzheimer's Disease | rosiglitazone maleate | | GlaxoSmithKline |
| Enzymatic System | 46 | inhibitor of the mixed lineage kinase family | Parkinson's Disease | CEP-1347 | unknown | Cephalon |
| Enzymatic System | 47 | interleukin-1 beta converting enzyme inhibitor | Pain | prainacasan | | Aventis |
| Monoaminergic Transmitter Systems | 48 | levodopa/decarboxylase inhibitor | Parkinson's Disease | levadopa/carbidopa | 250 to 600/ 25 to 150 mg daily | Merck |
| | 48 | levodopa/decarboxylase inhibitor | Parkinson's Disease | levadopa/benserazide | 100 to 600/ 25 to 150 mg daily | Roche |
| | 48 | levodopa/decarboxylase inhibitor | Parkinson's Disease | etilevodopa/carbidopa | unknown | TEVA Pharmaceuticals USA |
| | 48 | levodopa/decarboxylase inhibitor | Parkinson's Disease | etilevodopa/benserazide | unknown | TEVA Pharmaceuticals USA |
| Other/Unknown | 49 | Lipid-DNA Complex | Parkinson's Disease | GR213487B | | Valentis |
| Monoaminergic Transmitter Systems | 50 | MAO reuptake inhibitor | Cocaine Dependence | NS 2359 | | National Institute on Drug Abuse |
| Monoaminergic Transmitter Systems | | MAO reuptake inhibitor | ADHD | NS 2359 | | NeuroSearch |
| Monoaminergic Transmitter Systems | 51 | MAO-A & MAO-B reuptake inhibitor | ADHD | SPD473 | unknown | Shire Pharmaceutical Development |
| Monoaminergic Transmitter Systems | 52 | MAO-B inhibitor | Depression | EmSam (transdermal selegiline) | | Somerset |
| | | MAO-B inhibitor | Parkinson's Disease | selegiline | 5 to 10 mg daily | Amarin Pharmaceuticals |
| | | MAO-B inhibitor | Parkinson's Disease | rasagiline (TVP-1012) | 1 to 2 mg daily | TEVA Pharmaceuticals USA/ Lundbeck |
| Monoaminergic Transmitter Systems | 53 | MAO-B re-uptake inhibition | Parkinson's Disease | safinamide | | Newron Pharmaceuticals |
| Peptidergic Transmitter System | 54 | MC4 antagonists | Depression/Anxiety | MCL0129 | | Taisho |
| Peptidergic Transmitter System | 55 | MCH receptor antagonist | Depression | SNAP-7941 | | Synaptic |
| Endocrine System | 56 | melatonin receptor agonist | Insomnia | Ramelteon | unknown | Takeda |
| | | melatonin receptor agonist | Depression/Anxiety | Agomelatine | 25 to 50 mg daily | Servier |
| Excitatory Amino Acid System | 57 | MgluR agonist | Anxiety | PRE703 | | Prescient |
| Neurotrophic System | 58 | mimics the effects of NGF | Alzheimer's Disease | Xaliproden | 1 to 2 mg daily | Sanofi-Synthelabo |
| Excitatory Amino Acid System | 59 | Muscarinic receptor partial agonist | Alzheimer (JP)/ Sjogren (US) | Sevimeline | unknown | Daiichi Seiyaku |
| Monoaminergic Transmitter Systems | 60 | NARI | Depression/Anxiety | reboxetine | | Pfizer |
| | | NARI | ADHD | atomoxetine hydrochloride | 40 to 100 mg daily | Eli Lilly |
| | | NARI | Depression | reboxetine | 8 to 12 mg daily | Pfizer |
| Monoaminergic Transmitter Systems | 61 | NaSSA | Insomnia | ORG 4420 | unknown | Organon |
| Monoaminergic Transmitter Systems | 62 | NDRI | Depression (bipolar disorder) | GW353162 | 20 to 60 mg daily | GlaxoSmithKline |
| Neuroimmunophilin System | 63 | neuroimmunophilin ligands | Parkinson's Disease | GPI 1485 | 200 to 1000 mg daily | Guilford Pharmaceuticals |
| Adenosine Transmitter System | 64 | neuromodulator | Parkinson's Disease | adenosine | | Schering-Plough |
| Peptidergic Transmitter System | 65 | neurotensin receptor antagonist | Schizophrenia | SR 48692 | 90 to 300 mg daily | Sanofi-Synthelabo |
| Neurotrophic System | 66 | NGF (nerve growth factor) | Alzheimer's Disease | nerve growth factor (NGF) gene therapy | | Ceregene |
| Excitatory Amino Acid System | 67 | nicotinic acetylcholine receptor antagonist | Anxiety | SEP174559 | unknown | Sepracor |
| Excitatory Amino Acid System | 68 | nicotinic receptor agonists | Alzheimer's Disease | ABT-089 | 4 to 40 mg daily | Abbott |
| Peptidergic Transmitter System | 69 | NK2 antagonist | Depression/Anxiety | saredutant | 100 mg daily | Sanofi-Synthelabo |
| Peptidergic Transmitter System | 70 | NK3 antagonist | Schizophrenia | osanetant | | Sanofi-Synthelabo |
| | | NK3 antagonist | Schizophrenia/IBS/ Overactive bladder | talnetant | 6 mg daily | GlaxoSmithKline |
| Excitatory Amino Acid System | 71 | NMDA antagonist | Anxiety | SEP174559 | | Sepracor |
| | | NMDA antagonist | Alzheimer's Disease | memantine | 20 mg daily | Lundbeck/Forest Laboratories |
| | | NMDA antagonist | Depression | memantine | 20 mg daily | Lundbeck/Forest Laboratories |

TABLE 6-continued

| PHARMAC. GROUP (see overview hereunder) | nr. PH. PROF. | PHARMACOLOGICAL PROFILE | MAIN INDICATIONS | COMPOUND | DOSE RANGE | COMPANY |
|---|---|---|---|---|---|---|
| | | NMDA antagonist | Pain | memantine | 20 mg daily | Lundbeck/Forest Laboratories |
| | | NMDA antagonist | Depression | Delucemine | | NPS |
| Enzymatic System | 72 | NSAID | Pain | meloxicam | | Boehringer-Ingelheim Pharmaceuticals |
| | | NSAID | Pain | piroxicam | | off patent |
| | | NSAID | Alzheimer's Disease | Flurizan (pure R-enantiomer form of flurbiprofen) | unknown | Myriad Genetics |
| | | NSAID | Pain | MX-1094 | | Medinox |
| Excitatory Amino Acid System | 73 | opoid antagonist | Alcohol/Drug Dependence | naltrexone depot | 192 to 384 mg | Drug Abuse Sciences |
| | | opoid antagonist | Opiate/Alcohol Dependence | depot naltrexone microcapsules | | Biotek |
| Excitatory Amino Acid System | 74 | opoid agonist | Anxiety | Siramesine | unknown | Lundbeck/Forest |
| | | opoid agonist | Cocaine Dependence | cyclazocine | | National Institute on Drug Abuse |
| | | opoid agonist | Schizophrenia | E-5842 | | Esteve |
| Enzymatic System | 75 | PDE4 inhibitor | Depression | ND1251 | | Neuro3d |
| | | PDE4 inhibitor | Alzheimer's Disease | MEM 1917 (R1497) | | Roche/Memory Pharm |
| | | PDE4 inhibitor | Depression | MEM 1917 (R1497) | | Roche/Memory Pharm |
| Peptidergic Transmitter System | 76 | peptide | Depression | INN 00835 | 18 to 160 mg daily | Innapharma |
| | | peptide | Autism | secretin | 0.2 to 0.4 mg/kg daily | Repligen |
| | | peptide | Female Sexual Dysfunction | PT-141 | | Palatin Technologies |
| | | peptide | Alzheimer's Disease | beta-sheet breaker peptide | | Serono |
| Enzymatic System | 77 | Phospholipase A2 inhibitor with caspase inhibitor activity | Depression | LAX-101c | unknown | Laxdale |
| | | Phospholipase A2 inhibitor with caspase inhibitor activity | Depression (bipolar disorder) | LAX-101b | | Laxdale |
| | | Phospholipase A2 inhibitor with caspase inhibitor activity | Schizophrenia | LAX-101a | | Laxdale |
| Nucleosides | 78 | Prodrug of uridine | depression (bipolar disorder) | RG2133 (triacetyluridine) | unknown | Repligen |
| Endocrine System | 79 | prostaglandin E 1 | Female Sexual Dysfunction | alprostadil gel | 50 to 300 microgram/application | VIVUS |
| | | Prostaglandin E1 | Female Sexual Dysfunction | alprostadil cream | | NexMed |
| Neurotrophic System | 80 | protect dopaminergic and cholinergic neurons | Alzheimer's Disease | SR 57667 | unknown | Sanofi-Synthelabo |
| Excitatory Amino Acid System | 81 | Psychostimulant | ADHD | modafinil | 200 to 600 mg daily | Cephalon |
| | | Psychostimulant | ADHD | SPD 503 | unknown | Shire Pharmaceutical Development |
| | | Psychostimulant | Hypersomnia | r-modafinil | | Cephalon |
| | | Psychostimulant | Cocaine Dependence | modafinil | | National Institute on Drug Abuse |
| Monoaminergic Transmitter Systems | 82 | RIMA | Depression/Anxiety | moclobemide | | Roche |
| | | RIMA | Depression/Anxiety | toloxatone | | Sanofi-Synthelabo |
| | | RIMA | Depression/Anxiety | Befloxatone | 10 mg daily | Sanofi-Synthelabo |
| | | RIMA | Depression | caroxazone F.I 6654 | | Farmitalia |
| | | RIMA | Depression/Anxiety | cimoxatone | | MD |
| | | RIMA | Depression/Anxiety | RS 8359 | | Sankyo |
| Other/Unknown | 83 | SCT-11 modulation | Depression | SNEC-2 | | Synaptic |
| Monoaminergic Transmitter Systems | 84 | SDA | Schizophrenia | quetiapine | | AstraZeneca |
| | | SDA | Schizophrenia | aripiprazole | | Bristol-Myers Squibb |
| | | SDA | Schizophrenia | risperidone | | Johnson & Johnson Pharmaceutical |
| | | SDA | Schizophrenia | zotepine | | Knoll/BASF |
| | | SDA | Schizophrenia | olanzapine | | Lilly |
| | | SDA | Schizophrenia | clozapine | | Novartis Pharmaceutical |
| | | SDA | Schizophrenia | ziprisidone | | Pfizer |
| | | SDA | Depression (Bipolar Maintenance) | olanzapine | | Eli Lilly |

TABLE 6-continued

| PHARMAC. GROUP (see overview hereunder) | nr. PH. PROF. | PHARMA- COLOGICAL PROFILE | MAIN INDICATIONS | COMPOUND | DOSE RANGE | COMPANY |
|---|---|---|---|---|---|---|
| | | SDA | Schizophrenia | perospirone | unknown | Sumitomo |
| | | SDA | Schizophrenia | blonanserin | unknown | Almirall Prodesfarma |
| | | SDA | Alzheimer's Disease | olanzapine | | Eli Lilly |
| | | SDA | Alzheimer's Disease | aripiprazole | | Bristol-Myers Squibb |
| | | SDA | Schizophrenia | quetiapine fumarate (granules) | | AstraZeneca |
| | | SDA | Schizophrenia | quetiapine fumarate (sustained release) | | AstraZeneca |
| | | SDA | Schizophrenia | paliperidone | 3 to 15 mg daily | Johnson & Johnson Pharmaceutical |
| | | SDA | Schizophrenia | sertindole | 12 to 24 mg daily | Lundbeck |
| | | SDA | Schizophrenia | iloperidone | | Novartis Pharmaceuticals |
| | | SDA | Schizophrenia | asenapine | 10 mg daily | Organon |
| | | SDA | Schizophrenia | SL 91.0177 | unknown | Sanofi-Synthelabo |
| | | SDA | Schizophrenia | bifeprunox | unknown | Solvay |
| | | SDA | Schizophrenia | ocaperidone | | Neuro3d |
| | | SDA | Schizophrenia | SM-13496 | | Sumitomo |
| | | SDA | Schizophrenia | LU 31-131 | | Lundbeck |
| | | SDA | Schizophrenia | BSF-190555 | | ? |
| | | SDA | Schizophrenia | S-18327 | | Servier |
| Monoaminergic Transmitter Systems | 85 | SDRI | Depression/Anxiety | Bazinaprine | | Sanofi-Synthelabo |
| Monoaminergic Transmitter Systems | 86 | Second messenger beta agonist | Depression | rolipram | 1.5 to 3 mg daily | Shering |
| | | Second messenger beta agonist | Depression | SR 57227 | | Sanofi-Synthelabo |
| | | Second messenger beta agonist | Depression | eplivanserin | | Sanofi-Synthelabo |
| | | Second messenger beta agonist | Insomnia | eplivanserin | | Sanofi-Synthelabo |
| Endocrine System | 87 | Secretin pancreatic hormone | Anxiety | RG1068 | unknown | Repligen |
| | | Secretin pancreatic hormone | Schizophrenia | RG1068 | unknown | Repligen |
| Excitatory Amino Acid System | 88 | sigma receptor agonist | Depression | VPI-013 (also known as OPC-14523) | unknown | Vela, Otsuka |
| | | sigma receptor agonist | ADHD | PRX-00023 | | Predix |
| | | sigma receptor agonist | Anxiety | PRX-00023 | | Predix |
| Excitatory Amino Acid System | 89 | sigma receptor antagonist | Depression/Anxiety | EMD 68843 | 20 mg daily | EMD Pharmaceuticals |
| | | Sigma receptor antagonist | Schizophrenia | SR 31742 | unknown | Sanofi-Synthelabo |
| Monoaminergic Transmitter Systems | 90 | SNDRI | Alzheimer's Disease | NS 2330 | unknown | Boehringer-Ingelheim Pharmaceuticals |
| | | SNDRI | Depression/Anxiety | DOV 216,303 | unknown | DOV |
| | | SNDRI | Alzheimer's Disease | DOV 21,947 | | DOV |
| | | SNDRI | Depression | DOV 21,947 | | DOV |
| | | SNDRI | Depression | McN 5652 | | McNeil |
| Monoaminergic Transmitter Systems | 91 | SNRI | Depression | milnacipran | 50 to 200 mg daily | Pierre Fabre |
| | | SNRI | Depression/Anxiety | nefazodone | | Mead Johnson |
| | | SNRI | Depression/Anxiety | amoxapine | | Weyth |
| | | SNRI | Depression/Anxiety | venlafaxine | 75 to 300 mg daily | Wyeth |
| | | SNRI | Depression/Anxiety | duloxetine | 40 to 60 mg daily | Eli Lilly |
| | | SNRI | ADHD | tornoxetine | 1.9 mg/kg/day | Lilly |
| | | SNRI | Depression/Anxiety | desvenlafaxine | unknown | Wyeth |
| | | SNRI | Depression | talsupram | | Lundbeck |
| | | SNRI | Depression | talopram | | Lundbeck/Wyeth |
| | | SNRI | Depression | tandamine | | Wyeth |
| | | SNRI | Depression | LY 113.821 | | Lilly |
| Monoaminergic Transmitter Systems | 92 | SSRI | Depression/Anxiety | paroxetine | | GlaxoSmithKline |
| | | SSRI | Depression/Anxiety | escitalopram | 10 to 20 mg daily | Lundbeck/Forest Laboratories |
| | | SSRI | Depression/Anxiety | citalopram | 10 to 40 mg daily | off patent |
| | | SSRI | Depression/Anxiety | fluoxetine | | off patent |
| | | SSRI | Depression/Anxiety | fluvoxamine | | off patent |
| | | SSRI | Depression/Anxiety | sertraline | | Pfizer |
| | | SSRI | Anxiety (OCD/Soc Phobia) | fluvoxamine controlled release | 100 to 300 mg daily | Solvay |
| | | SSRI | Depression/Anxiety | titoxetine | unknown | Sanofi-Synthelabo |
| | | SSRI | Depression/Anxiety | femoxetine | | Ferrosan |
| | | SSRI | Depression/Anxiety | ifoxetine | | Novartis Pharmaceuticals |

TABLE 6-continued

| PHARMAC. GROUP (see overview hereunder) | nr. PH. PROF. | PHARMA-COLOGICAL PROFILE | MAIN INDICATIONS | COMPOUND | DOSE RANGE | COMPANY |
|---|---|---|---|---|---|---|
| | | SSRI | Depression | VPI-013 (also known as OPC-14523) | | Vela, Otsuka |
| | | SSRI | Depression/Anxiety | EMD 68843 | | EMD Pharmaceuticals |
| | | SSRI | Depression/Anxiety | cericlamine | | Jouveinal |
| | | SSRI | Depression | Lu 35-138 | | Lundbeck |
| | | SSRI | Depression/OCD/Pain | LY 214.281 | | Lilly |
| | | SSRI | Depression | LU AA 21-004 | | Lundbeck |
| | | SSRI | Depression/Anxiety | cyanodothepine | | ? |
| | | SSRI | Depression/Anxiety | ademethionine/ s-adenosyl-methionine | | Sampl-Gibipharma |
| | | SSRI | Depression/Anxiety | YM 992 | | Yamanouchi |
| Peptidergic Transmitter System | 93 | Substanc P receptor (NK1) antagonist | Depression/Anxiety | aprepitant | 40 to 160 mg daily | Merck |
| | | Substanc P receptor (NK1) antagonist | Depression/Anxiety | TAK-637 | | Takeda/Abbott |
| | | Substanc P receptor (NK1) antagonist | Depression/Anxiety | GW597599 | | GlaxoSmithKline |
| | | Substanc P receptor (NK1) antagonist | Depression/Anxiety | vestipitant | | GlaxoSmithKline |
| | | Substanc P receptor (NK1) antagonist | Depression/Anxiety | CP-122,721 | | Pfizer |
| | | Substanc P receptor (NK1) antagonist | Depression/Anxiety | R673 | | Roche |
| | | Substanc P receptor (NK1) antagonist | Depression/Anxiety | GW679769 | | GlaxoSmithKline |
| | | Substanc P receptor (NK1) antagonist | Depression/Anxiety | GW823296 | | GlaxoSmithKline |
| | | Substanc P receptor (NK1) antagonist | Depression/Anxiety | 679769 | | GlaxoSmithKline |
| | | Substanc P receptor (NK1) antagonist | Depression/Anxiety | 823296 | | GlaxoSmithKline |
| Other/Unknown | 94 | sulfonamide | Mania | zonisamide | 100 to 600 mg daily | Elan Pharmaceuticals |
| Peptidergic Transmitter System | 95 | tachykinin antagonists | Depression/Anxiety | SR 48968 | unknown | Sanofi-Synthelabo |
| Other/Unknown | 96 | unknown | Alzheimer's Disease | DP 543 | unknown | Bristol-Myers Squibb |
| | | unknown | Depression | R228060 (YKP-10A) | unknown | Johnson & Johnson Pharmaceuticals |
| | | unknown | Parkinson's Disease | palanpanel | unknown | IVAX |
| | | unknown | Premenstrual Syndrome | ORG 39479/PH80 | unknown | Organon |
| | | unknown | Depression | ORG 34167 | | Organon |
| | | unknown | Depression | CJ-017,493 | | Pfizer |
| Endocrine System | 97 | V1B antagonist | Depression/Anxiety | SSR149415 | | Sanofi-Synthelabo |
| Inhibitory Amino Acid System | 98 | modulator | Depression/Anxiety | Pregabalin | 50 to 600 mg daily | Pfizer |
| | | modulator | Pain | Pregabalin | 50 to 600 mg daily | Pfizer |
| | | modulator | Insomnia | PD-200,390 | | Pfizer |
| Other/Unknown | 99 | vomeropherin | Anxiety, Acute | PH94B | | Pherin Pharmaceuticals |
| Monoaminergic Transmitter Systems | 100 | dopamine release stimulation | Parkinson's Disease | amantadine | 100 to 300 mg daily | |
| | | dopamine release stimulation | Depression | amantadine | 100 to 300 mg daily | |
| Neurotrophic System | 66 | NGF (nerve growth factor) | Alzheimer's Disease | xaliproden | unknown | Sanofi |

PHARMA-COLOGICAL GROUPS: COMPOUNDS WORKING ON THE

Amino Acid Transmitter System

| | |
|---|---|
| Monoaminergic Transmitter System | 1 |
| Excitatory Amino Acid System | 2 |
| Inhibitory Amino Acid System | 3 |
| Peptidergic Transmitter System | 4 |
| Adenosine Transmitter System | 5 |
| Endocrine System | 6 |

TABLE 6-continued

| PHARMAC. GROUP (see overview hereunder) | nr. PH. PROF. | PHARMA- COLOGICAL PROFILE | MAIN INDICATIONS | COMPOUND | DOSE RANGE | COMPANY |
|---|---|---|---|---|---|---|
| Enzymatic System Nerve Cell Function System | 7 | | | | | |
| Neurotrophic System | 9 | | | | | |
| Neuroimmunophilin System | 10 | | | | | |
| Pathogenic Mechanisms of Dementia of the Alzheimer Type | 11 | | | | | |

EXAMPLES

Example 1

Measuring pKi Values of Test Compounds

In Table 1, the pKi values of test compounds are given for each of the dopamine receptors, 5HT receptors, adrenergic receptors and the histamine1 receptor. The affinity of test compounds for the respective receptors has been performed according to conventional procedures known in the art.

An indication "0" means that no affinity has been measured between the test compound and the receptor.

The columns displaying the pKi values for the D4 and the 5-HT2A receptor are filled with dark grey. pKi values between 8 and 9 and higher than 9 are represented by light grey boxes.

Example 2

Foregoing Pipamperon-Citalopram Treatment in Major Depressive Disorder: a Placebo and Active Controlled Period Finding Clinical Trial Table 2 represents the set-up of a clinical trial comprising for treatment groups:

Group Plc—Active/Day 0 represents the group receiving 10 mg citalopram, twice a day, starting the first day (Day 0) of active treatment in the clinical trial. This administration regime is also indicated as the mono therapy.

Group Pip—Active/Day 0 represents the group receiving a combination of 4 mg pipamperon and 10 mg citalopram, twice a day, starting the first day (Day 0) of active treatment in the clinical trial. This administration regime is also indicated as the non-foregoing combo therapy.

Group Pip—Active/Day 4 represents the group receiving 4 mg pipamperon, twice a day, starting the first day (Day 0) of active treatment in the clinical trial, followed by a combination of 4 mg pipamperon and 10 mg citalopram, twice a day, starting the fifth (Day 4) day of active treatment in the clinical trial. This administration regime is also indicated as the foregoing therapy with combination therapy starting after 4 days of active treatment.

Group Pip—Active/Day 7 represents the group receiving 4 mg pipamperon, twice a day, starting the first day (Day 0) of active treatment in the clinical trial, followed by a combination of 4 mg pipamperon and 10 mg citalopram, twice a day, starting the eight (Day 7) day of active treatment in the clinical trial. This administration regime is also indicated as the foregoing therapy with combination therapy starting after 7 days of active treatment.

All subjects also undergo a placebo (PLC) run-in therapy, administered during a period of about 7 days before the active treatment starts.

During daily (D), weekly (W) or monthly (M) visits, several parameters are measured.

Under NECT is to be understood: Neuronal E-clinical Trial=Vesalius Expert development for this trial which includes the bottom-up measurement of:
In- and exclusion-criteria
Functional status evaluation
Medical history
(Pre-)treatment signs & symptoms
DSM-IV rules for diagnosis & efficacy
HDRS-28 (Hamilton Depression Rating Scale-28 items)
Medical resource utilisation
Pre-trial & Concomittant medication
Drug administration
(Serious) Adverse events
Admission to the acute and extension phase of treatment
Right flow of the trial Example 3

Combo Pipamperon-Citalopram: Therapeutic Use in Major Depression

Purpose

Pipamperon (1'-[3-(p-Fluorobenzoyl)propyl]-[1,4'-bipiperidine]-4'-carboxamide), the active ingredient of Dipiperon (Janssen-Cilag B.V), administered to patients in a dose ranging between 8 and 12 mg is claimed via its specific pharmacological properties to be a booster of the antidepressant effect of the selective serotonin re-uptake inhibitor citalopram. Preferably, pipamperon is administered daily at least 4-5 days before administering said antidepressant. The mechanism of boosting of pipamperon has to deal with (i) the selective affinity for the dopamine-4 (D4) receptor with a pKi value equal to or higher than 8 towards the D4 receptor and less than 8 towards other dopamine receptors, and (ii) the selective affinity for the 5-HT2A receptor with a pKi value equal to or higher than 8 towards the 5-HT2A receptor and less than 8 towards other 5HT receptors. This semi-naturalistic open label study investigated the efficacy and tolerability of the combo pipamperon-citalopramin the treatment of patients with major depression.

Details

| Design: | Semi-naturalistic i.e. inclusion of every 'natural' patient in an outpatient practice but without concomitant use of mood enhancing drugs, open label |
|---|---|
| Control: | No |
| Phase: | Phase IIa - preliminary Proof of Concept |
| Location: | Belgium - Research Centre ANIMA, Alken |
| End Points : | Assessment scale scores, Hamilton Depression Rating Scale 17 items, Reduction, Response, Remission |
| Medication: | Exclusion of mood stabilisers, antipsychotics (typical and atypical) and other antidepressants |

Subjects

| Type | No. | Sex | Age |
|---|---|---|---|
| Patients | 23 | 10 male & 13 female | 23-80 (mean 47) years |

Characteristics: patients had a major depressive disorder according to DSM-IV criteria, with or without a chronic course and a treatment refractory state towards another SSRI then citalopram.

Treatments

PIP-CIT[1] add-on: citalopram from day minus 60-20—pipamperon from DAY 0

| Drug/Treatment | Dose | Route | Frequency | Duration |
|---|---|---|---|---|
| Pipamperon[1] | +Pip.: 8-12 mg/day – | PO | bid | 8 weeks |
| Citalopram[1] | Cit.: 20-40 mg/day | | | |

[1]Pipamperon (Pip) and citalopram (Cit) dosage was adjusted according to clinical response.

PIP-CIT[1] fore-going 1-5: pipamperon from day 0—cital from day 1-5

| Drug/Treatment | Dose | Route | Frequency | Duration |
|---|---|---|---|---|
| Pipamperon[1] | +Pip.: 8-12 mg/day – | PO | bid | 8 weeks |
| Citalopram[1] | Cit.: 20-40 mg/day | | | |

[1]Pipamperon (Pip) and citalopram (Cit) dosage was adjusted according to clinical response.

PIP-CIT[1] fore-going 6-8: pipamperon from day 0—citalopram from day 6-8

| Drug/Treatment | Dose | Route | Frequency | Duration |
|---|---|---|---|---|
| Pipamperon[1] | +Pip.: 8-12 mg/day – | PO | bid | 8 weeks |
| Citalopram[1] | Cit.: 20-40 mg/day | | | |

[1]Pipamperon (Pip) and citalopram (Cit) dosage was adjusted according to clinical response.

Results

| | PIP-CIT add-on After 29-60 DAYS (mean 33) (n = 5) | PIP-CIT foregoing 1-5 DAYS (mean 4) (n = 15) | 6-8 DAYS (mean 7) (n = 3) |
|---|---|---|---|
| Mean Used Medication | | | |
| Pipamperone | 9 mg/day | 10 mg/day | 11 mg/day |
| Citalopram | 30 mg/day | 26 mg/day | 30 mg/day |
| Depression scale scores | | | |
| HDRS 17-item total score | | | |
| baseline | 29 | 23 | 28 |
| endpoint (week 8) | 4 | 5 | 11 |
| diminishment at week 8 | −25 (+8/−9) | −18 (+8/−8) | −17 (+17/−17) |
| % reduction at week 8 | 86 (+14/−12) | 80 (+20/−30) | 61 (+39/−61) |
| response[1] at week 8 | 5 (100%) | 15 (100%) | 2 (67%) |
| remission[2] at week 8 | 4 (80%) | 10 (67%) | 1 (33%) |

[1]Response = ≧50% reduction in HDRS 17-item score;
[2]Remission = HDRS 17-item score <8

Notably, the results obtained are highly significant since the variability in every group is distributed evenly around the mean.

Add-On PIP-CIT

FIG. 1 schematically depicts the "add-on" treatment with pipamperon 8-12 (mean 9) mg (bid) after treatment with citalopram 10-20 (mean 30) mg (bid) during 20-60 (mean 33) days (PIPCIT ADD-ON) with HDRS-17. Totalscore is 29 at baseline in MDD in comparison with the standard efficacy of antidepressants in clinical trials according to Khan at al. (2000), in "Symptom Reduction and Suicide Risk in Patients Treated With Placebo in Antidepressant Clinical Trials" (Arch. of General Psychiatry, Vol. 57, April 2000).

FIG. 2 schematically depicts the HDRS-17 change from baseline in the combo pipamperon as "add-on" to citalopram vs SNRI (duloxetine) in Major Depression. Treatment with pipamperon 8-12 (mean 9 mg/day) during 20-60 (mean 33) days after treatment with SSRI (n=5). The SNRI (duloxetine) treatment was 40-120 mg/day (n=152) according to Goldstein et al., (Olin, Psychiatry, in press).

FIG. 3 schematically depicts the remission rates (HDRS-17<=7) with the combo pipamperon as "add-on" to citalopram vs SNRI (venlafaxine) vs SSRIs vs placebo in Major Depression. Treatment with pipamperon 8-12 mg/day) during 20-60 (mean 33) days after treatment with SSRI (n=5). Treatment with the SNRI venlafaxine is according to a meta-analysis of Thase et al. (Br. J. Psychiatry (2001) 178:234-241). Treatment with SSRIs is according to a meta-analysis of Thase et al. (Br. J. Psychiatry (2001) 178:234-241). Treatment with placebo is according to a meta-analysis of Thase et al. (Br. J. Psychiatry (2001) 178:234-241).

Fore-Going 1-5 PIP-CIT

FIG. 4 schematically depicts the "fore-going" treatment during 1-5 (mean 4) days with pipamperon 8-12 (mean 10) mg (bid), followed with the combination treatment of pipamperon and citalopram 20-50 (mean 26) mg/day (bid) (PIPCIT FG 1-5) in MDD (HDRS-17 at BL=23) in comparison with the standard efficacy of antidepressants in clinical trials according to Khan et al., (2000), in "Symptom Reduction and Suicide Risk in Patients Treated With Placebo in Antidepressant Clinical Trials" (Arch. of General Psychiatry, Vol. 57, April 2000).

FIG. 5 schematically depicts the HDRS-17 change from baseline in the combo pipamperon-citalopram treatment with a "fore-going" treatment of 4 days with pipamperon (10 mg/day) vs SNRI (duloxetine) in Major Depression. Treatment with the combo pipamperon-citalopram with pipamperon 8-12 (mean 10 mg/day) (bid) 1-5 (mean 4) days before treatment with SSRI (n=15). The SNRI (duloxetine) treatment was 40-120 mg/day (n=152) according to Goldstein et al., (Clin. Psychiatry, in press).

FIG. 6 schematically depicts the remission rates (HDRS-17<=7) with the combo pipamperon with a "fore-going" treatment of 4 days with pipamperon (10 mg/day) vs SNRI (venlafaxine) in Major Depression. Treatment with the combo pipamperon-citalopram was with pipamperon 8-12 (mean 10 mg/day) during 1-5 (mean 4) days before treatment with the SSRI (n=5). Treatment with the SNRI venlafaxine is according to a meta-analysis of Thase et al. (Br. J. Psychiatry (2001) 178:234-241). Treatment with SSRIs is according to a meta-analysis of Thase et al. (Br. J. Psychiatry (2001) 178: 234-241). Treatment with placebo is according to a meta-analysis of Thase et al. (Br. J. Psychiatry (2001) 178:234-241).

Fore-Going 6-8 PIP-CIT

FIG. 7 schematically depicts the "fore-going" treatment during 6-8 (mean 7) days with pipamperon 8-12 (mean 11) mg/day (bid), followed with the combination treatment of pipamperon and citalopram 20-40 (mean 30) mg/day (bid) (PIPCIT FG 6-8) in MDD (HDRS-17 at BL=28) in comparison with the standard efficacy of antidepressants in clinical trials according to Khan et al. (2000), in "Symptom Reduction and Suicide Risk in Patients Treated With Placebo in Antidepressant Clinical Trials" (Arch. of General Psychiatry, Vol. 57, April 2000).

FIG. 8 schematically depicts the HDRS-17 change from baseline in the combo pipamperon-citalopram treatment with a "fore-going" treatment of 7 days with pipamperon (11 mg/day) vs SNRI (duloxetine) in Major Depression. Treatment with the combo pipamperon-citalopram with pipamperon 8-12 (mean 11 mg/day) (bid) 6-8 (mean 7) days before treatment with SSRI (n=3). The SNRI (duloxetine) treatment was 40-120 mg/day (n=152) according to Goldstein et al., (Clin. Psychiatry, in press).

Comparison "Add-On" Vs "Fore-Going"

FIG. 9 schematically depicts a comparison between "fore-going" and "add-on" treatments with pipamperon (8-12 mg/day; bid) and citalopram (20-40 mg/day; bid) in MDD in comparison with the standard efficacy of antidepressants in clinical trials according to Khan et al. (2000), in "Symptom Reduction and Suicide Risk in Patients Treated With Placebo in Antidepressant Clinical Trials" (Arch. of General Psychiatry, Vol. 57, April 2000).

FIG. 10 schematically depicts a comparison between "fore-going" and "add-on" treatments. In particular, the HDRS-17 change from baseline between "fore-going" and "add-on" treatment with pipamperon (8-12 mg/day; bid) and citalopram (20-40 mg/day; bid) in comparison with the SNRI duloxetine in Major Depression is depicted. Treatment with the combo pipamperon as "add-on" to citalopram, with pipamperon 8-12 mg/day (mean 9 mg/day) 20-60 (mean 33) days after treatment with the SSRI (n=5). Treatment with the combo pipamperon-citalopram, with pipamperon 8-12 mg/day (mean 11 mg/day; bid) 6-8 days (mean 7 days) before treatment with the SSRI (n=15). Treatment with the combo pipamperon-citalopram, with pipamperon 8-12 mg/day (mean 10 mg/day; bid) 1-5 days (mean 4 days) before treatment with the SSRI (n=15). The SNRI (duloxetine) treatment was 40-120 mg/day (n=152) according to Goldstein et al., (Clin. Psychiatry, in press).

FIG. 11 schematically depicts the remission rates (HDRS-17<=7) in a comparison between "fore-going" and "add-on" treatment with pipamperon (8-12 mg/day; bid) and citalopram (20-40 mg/day; bid) in comparison with the SNRI venlafaxine in Major Depression. Treatment with the combo pipamperon-citalopram was with pipamperon 8-12 (mean 10 mg/day) during 1-5 (mean 4) days before treatment with the SSRI (n=15). Treatment with the SNRI venlafaxine is according to a meta-analysis of Thase et al. (Br. J. Psychiatry (2001) 178:234-241). Treatment with pipamperon as "add-on" to citalopram, with pipamperon 8-12 (mean 9 mg/day) during 20-60 (mean 33) days after treatment with SSRI (n=5).

The intention-to-treat/last-observation-carried-forward analysis showed a high therapeutic efficacy according HDRS 17-item in all the treatment groups. This was especially true for the 'add-on' group probably caused by the longer treatment with an active antidepressant (+33 days). The huge therapeutic effect observed in the 'PIP-CIT 1-5' group present for at a mean dosage of pipamperon of 10 mg per day and administered the first four days of treatment without an active antidepressant, indicates the boosting effect of pipamperon on the SSRI citalopram at an extremely and thus unconventional low dose. Only 1 patient discontinued treatment due to a lost of follow-up.

Adverse Events

| Side effects (patients) | PIP-CIT add-on After 20-60 DAYS (mean 33) (n = 5) | PIP-CIT foregoing 1-5 DAYS (mean 4) (n = 15) | 6-8 DAYS (mean 7) (n = 3) |
|---|---|---|---|
| Discontinued treatment due to adverse events | 0 | 0 | 0 |
| By system: | | | |
| body as a whole | 0 | 0 | 0 |
| central and peripheral nervous system | 1 (20%) | 4 (26.6%) | 0 |
| gastrointestinal | 1 (20%) | 5 (33%) | 2 (66.6%) |
| musculoskeletal | 1 (20%) | 3 (20%) | 0 |
| psychiatric | 0 | 0 | 0 |
| respiratory | 0 | 1 (6.6%) | 0 |
| skin and appendages | 1 (20%) | 2 (13.3%) | 1 (33.3%) |
| vascular | 0 | 1 (6.6%) | 0 |
| urinary | 0 | 1 (6.6%) | 0 |

Laboratory parameters, ECG, bodyweight and vital signs were not measured since this was a naturalistic study.

Assessment
Outcome

Efficacy: the 4-day fore-going combo pipamperon 8-12 mg/d-citalopram 20-40 mg/day is comparable to the add-on combo pipamperon-citalopram.

Efficacy: the 4-day fore-going combo pipamperon 8-12 mg/d-citalopram 20-40 mg/day is larger than the 7-day fore-going combo pipamperon 8-12 mg/d-citalopram 20-40 mg/day.

Efficacy: the combo pipamperon 8-12 mg/d-citalopram 20-40 mg/day is larger than the in the art known antidepressants SSRIs.

Tolerability

Tolerability: the 4-day fore-going treatment is comparable to the 7-day fore-going combo is comparable to add-on combo pipamperon-citalopram.

Tolerability: no discontinued treatment due to adverse events.

Study Messages

The boosting effect of pipamperon at an extremely unconventional low dose on a SSRI is indicated since the efficacy of the 'add-on' and '4-day fore-going' combo 'pipamperon 8-12 mg/d-citalopram 20-40 mg/day' is in this study as twice higher as known in the art in the treatment of patients with major depression.

The combo pipamperon-citalopram is generally well tolerated in patients with depression i.e. at least no specific added adverse events were occurring by adding pipamperon at the doses used in the study.

Example 4

Combo Pipamperon-Citalopram: Therapeutic Use in Obsessive-Compulsive Disorder (OCD)

Purpose

Pipamperon (1'-[3-(p-Fluorobenzoyl)propyl]-[1,4'-bipiperidine]-4'-carboxamide), the active ingredient of Dipiperon (Janssen-Cilag B.V.), administered to a patient in a dose ranging between 8 and 12 mg is claimed via its specific pharmacological properties to be a booster of the effect of the selective serotonin re-uptake inhibitor citalopram towards OCD. Preferably, pipamperon is administered daily at least 4-5 days before administering said antidepressant. The mechanism of boosting of pipamperon has to deal with (i) the selective affinity for the dopamine-4 (D4) receptor with a pKi value equal to or higher than 8 towards the D4 receptor and less than 8 towards other Dopamine receptors, and (ii) the selective affinity for the 5-HT2A receptor with a pKi value equal to or higher than 8 towards the 5-HT2A receptor and less than 8 towards other 5HT receptors. This semi-naturalistic open label study investigated the efficacy and tolerability of the combo pipamperon-citalopram in the treatment of patients with OCD.

Details

| Design: | Semi-naturalistic i.e. inclusion of every 'natural' patient in an outpatient practice but without concomitant use of mood enhancing drugs, open label |
|---|---|
| Control: | No |
| Phase: | Phase IIa - preliminary Proof of Concept |
| Location: | Belgium - Research Centre ANIMA, Alken |
| End Points: | Assessment scale scores, Yale-Brown Obsessive-Compulsive Scale, Reduction, Remission |

-continued

| Medication: | Exclusion of mood stabilisers, antipsychotics (typical and atypical) and other antidepressants |
|---|---|

Subjects

| Type | No. | Sex | Age |
|---|---|---|---|
| Patients | 7 | 1 male & 7 female | 20-63 (mean 33) years |

Characteristics: patients had an obsessive-compulsive disorder according to DSM-IV criteria, with or without a chronic course and a treatment refractory state towards another SSRI then citalopram.

Treatments

PIP-CIT[1] ADD-ON: citalopram from DAY minus 730-60—pipamperon from DAY 0

| Drug/Treatment | Dose | Route | Frequency | Duration |
|---|---|---|---|---|
| Pipamperone[1] | +Pip.: 8-16 mg/day – | PO | bid | 12 |
| Citalopram[1] | Cit.: 30-80 mg/day | | | weeks |

[1]Pipamperone (Pip) and Citalopram (Cit) dosage was adjusted according to clinical response.

PIP-CIT[1] FORE-GOING 4-6: pipamperon from DAY 0—citalopram from DAY 4-6

| Drug/Treatment | Dose | Route | Frequency | Duration |
|---|---|---|---|---|
| Pipamperone[1] | +Pip.: 8-16 mg/day – | PO | bid | 12 |
| Citalopram[1] | Cit.: 30-80 mg/day | | | weeks |

[1]Pipamperone (Pip) and Citalopram (Cit) dosage was adjusted according to clinical response.

Results

| | PIP-CIT add-on after 730-60 DAYS (mean 241) (n = 6) with mean Cit. 54 mg/d and Pip. 11 mg/d PIP-CIT foregoing 4-6 DAYS (mean 5) (n = 2) |
|---|---|
| Y-BOCS score | with mean Cit. 60 mg/d and Pip. 10 mg/d |
| Baseline | |
| Total | 31 |
| Obsessions | 18 |
| Compulsions | 13 |
| Endpoint (week 12) | |
| Total | 15 |
| diminishment | −16 (+16/−11) |
| % reduction Obsessions | 53 |
| total | 8 |
| diminishment | −10 (+9/−7) |
| % reduction Compulsions | 57 |
| total | 7 |
| diminishment | −6 (+7/−6) |
| % reduction | 45 |
| % Remission | |
| YBOCS score ≤8 | 29 |
| BOCS score ≤16 | 57 |

Notably, the results obtained are highly significant since the variability in every group is distributed evenly around the mean.

FIG. 12 schematically depicts the Y-BOCS total score: "fore-going" and "add-on" treatment with pipamperon (8-15 mg/day; bid) and citalopram (30-80 mg/day; bid) in comparison with the SSRI fluvoxamine in OCD. Treatment with the combo pipamperon-citalopram (n=7). Treatment with fluvoxamine (controlled release) mean 271 mg/day (n=253) is according to Hollander et al. (2003).

FIG. 13 schematically depicts the Y-BOCS obsession score: "fore-going" and "add-on" treatment with pipamperon (8-15 mg/day; bid) and citalopram (30-80 mg/day; bid) in comparison with the SSRI fluvoxamine in OCD. Treatment with the combo pipamperon-citalopram (n=7). Treatment with fluvoxamine (controlled release) mean 271 mg/day (n=253) is according to Hollander et al. (2003).

FIG. 14 schematically depicts the Y-BOCS compulsion score: "fore-going" and "add-on" treatment with pipamperon (8-16 mg/day; bid) and citalopram (30-80 mg/day; bid) in comparison with the SSRI fluvoxamine in OCD. Treatment with the combo pipamperon-citalopram (n=7). Treatment with fluvoxamine (controlled release) mean 271 mg/day (n=253) is according to Hollander et al. (2003).

The intention-to-treat/last-observation-carried-forward analysis showed a high therapeutic efficacy according Y-BOCS total score, obsession and compulsion scores. This indicates the boosting effect of pipamperon on the SSRI citalopram at an extremely and thus unconventional low dose. No patient discontinued treatment.

Assessment

Efficacy: the combo pipamperone 8-16 mg/d-citalopram 30-80 mg/day>the in the art known compounds effective towards OCD (Hollander E, Koran L M, Goodman W K, Greist J H, Ninan P T, et al. A double-blind, placebo-controlled study of the efficacy and safety of controlled-release fluvoxamine in patients with obsessive-compulsive disorder. Journal of Clinical Psychiatry 64: 640-647, June 2003 Mount Sinai School of Medicine, New York, N.Y., USA; Solvay Pharmaceuticals Inc., Marietta, Ga., USA).

Study Messages

The boosting effect of pipamperon at an extremely unconventional low dose on a SSRI is indicated since the efficacy of the 'add-on' and 'fore-going' combo 'pipamperon 8-15 mg/d-citalopram 30-80 mg/day' is in this study as twice higher as known in the art in the treatment of patients with obsessive-compulsive disorder.

Example 5

Combo Pipamperon-Citalopram: Therapeutic Use in Panic Disorder

Purpose

Preliminary examination of a "fore-going" and "add-on" treatment with pipamperon and citalopram in comparison with the SSRI in Panic Disorder.

Results

The results are indicated in FIG. 15. FIG. 15 schematically depicts the CGI-severity score: "fore-going" and "add-on" treatment with pipamperon (8 mg/day; bid) and citalopram (20-40 mg/day; bid) in comparison with the SSRI in Panic Disorder. Treatment with the combo pipamperon-citalopram (n=3). Treatment with paroxetine is according to the Journal of Clinical Psychiatry (2004) 65: 405-413. Treatment with Sertraline is according to the Journal of Clinical Psychiatry (2004) 65: 405-413.

Conclusion

Notably, although a small test group has been used (n=3), the distribution around the mean is good. It will further be apparent from FIG. 15 that the effect of the combo treatment of pipamperon and citalopram is twice as high as the standard treatments with paroxetine or sertraline.

Example 6

POC Process for Mayor Depressive Disorder

Concept:

Combo of the high selective 5-HT2A/D4 antagonist pipamperon with:
  a compound active towards the Amino Acid Transmitter, Peptidergic Transmitter, Adenosine Transmitter, Endocrine and/or Enzymatic System;
  a fore-going admission during 4 days of pipamperon;
  a dose of pipamperon of 12 mg/day Objectives:

Demonstrating that this combo therapy has:
  the potency of being a treatment standard for depression by having an added value of reducing the total score of the Hamilton Depression Rating Scale-17 items (HDRS-17) after 8 weeks of therapy with a least 20% more than reached with the conventional known antidepressants, i.e. 60% versus 40%. This stands for an added medium demission of 5 points on the total score of the HDRS-17 and by this will be very highly significant since the mean difference in all recent clinical trials between placebo and active treatment is 2.5;
  a more sustained therapeutic effect than the conventional mono therapy by preventing significant more relapses during 48 weeks following the acute treatment; and/or
  a complete neutral safety profile, e.g. there are no more adverse events in the combo therapy then in mono admission of the in the combo used antidepressant compound.

Process:

the following different steps were implemented to reach out for these objectives (see also Tables 3 and 4):

(1) an naturalistic open label study (n=>20) on a depressive population with a normal variability of medical and psychiatric history, course of depression, earlier and concomitant therapy admitting the golden standard antidepressant citalopram 20-40 mg/day and a dose of 8-12 mg/day of pipamperon in a foregoing, simultaneous or add-on use.

(2) a 16 weeks placebo controlled randomised four armed study of each 36 patients with a mayor depressive disorder admitting:
  from day 0: placebo or pipamperon (PIP) 10 mg/day or an active antidepressant compound or the combination of the last two;
  from day 4: placebo or pipamperon 10 mg/day combined with an active antidepressant compound or an active antidepressant compound without pipamperon.

By including rigorous control groups (placebo and active comparator; see Tables 3 and 4) this clinical trial is evaluated as a proof of concept of the added value of the combo and the foregoing treatment method since the inclusion/exclusion of:
  a negative trial, i.e. no significant difference between the placebo and active treatment with the comparator;
  a failed trial, i.e. no significant difference between the active and the studied treatment i.e. the combo.

(3) an active controlled randomised relapse prevention study following the POC trial during another 36 weeks with three arms of each 36 patients which is formed by:
continuation of the active mono therapy;
randomising the patients with a combo therapy in a group with an active mono therapy and with a continuation of the combo treatment.

The invention claimed is:

1. A pharmaceutical composition for treating a mood disorder or an anxiety disorder comprising:
    (a) pipamperone in a dose of 5-15 mg,
    (b) escitalopram in a dose of 10-20 mg,
    or a pharmaceutically acceptable salt of pipamperone and/or escitalopram, and
    (c) a pharmaceutically acceptable carrier.
2. The pharmaceutical composition of claim 1 for treating a mood disorder.
3. The pharmaceutical composition of claim 1 for treating an anxiety disorder.
4. A pharmaceutical composition comprising:
    (a) pipamperone in a dose of 5-15 mg,
    (b) escitalopram in a dose of 10-20 mg,
    or a pharmaceutically acceptable salt of pipamperone and/or escitalopram, and
    (c) a pharmaceutically acceptable carrier.
5. The pharmaceutical composition of claim 4, wherein pipamperone and escitalopram are present in an amount effective to treat a mood disorder.
6. The pharmaceutical composition of claim 4, wherein pipamperone and escitalopram are present in an amount effective to treat an anxiety disorder.
7. The pharmaceutical composition of claim 1 comprising pipamperone in a dose of 15 mg.
8. The pharmaceutical composition of claim 4 comprising pipamperone in a dose of 15 mg.
9. The pharmaceutical composition of claim 1 comprising escitalopram in a dose of 10 mg.
10. The pharmaceutical composition of claim 4 comprising escitalopram in a dose of 10 mg.
11. The pharmaceutical composition of claim 1 comprising pipamperone in a dose of 15 mg and escitalopram in a dose of 10 mg.
12. The pharmaceutical composition of claim 4 comprising pipamperone in a dose of 15 mg and escitalopram in a dose of 10 mg.
13. The pharmaceutical composition of claim 1 formulated for daily administration.
14. The pharmaceutical composition of claim 4 formulated for daily administration.
15. The pharmaceutical composition of claim 1, wherein the daily dose of pipamperone is 5-15 mg per day.
16. The pharmaceutical composition of claim 4, wherein the daily dose of pipamperone is 5-15 mg per day.
17. The pharmaceutical composition of claim 1, wherein the daily dose of pipamperone is 15 mg per day.
18. The pharmaceutical composition of claim 4, wherein the daily dose of pipamperone is 15 mg per day.
19. The pharmaceutical composition of claim 1, wherein the daily dose of escitalopram is 10-20 mg per day.
20. The pharmaceutical composition of claim 4, wherein the daily dose of escitalopram is 10-20 mg per day.
21. The pharmaceutical composition of claim 1, wherein the daily dose of escitalopram is 10 mg per day.
22. The pharmaceutical composition of claim 4, wherein the daily dose of escitalopram is 10 mg per day.
23. The pharmaceutical composition of claim 1, wherein the daily dose of pipamperone is 15 mg per day and the daily dose of escitalopram is 10 mg per day.
24. The pharmaceutical composition of claim 4, wherein the daily dose of pipamperone is 15 mg per day and the daily dose of escitalopram is 10 mg per day.
25. The pharmaceutical composition of claim 1, wherein pipamperone is provided as a pharmaceutically acceptable salt.
26. The pharmaceutical composition of claim 4, wherein pipamperone is provided as a pharmaceutically acceptable salt.
27. The pharmaceutical composition of claim 1, wherein escitalopram is provided as a pharmaceutically acceptable salt.
28. The pharmaceutical composition of claim 4, wherein escitalopram is provided as a pharmaceutically acceptable salt.
29. The pharmaceutical composition of claim 1 formulated for twice daily administration.
30. The pharmaceutical composition of claim 4 formulated for twice daily administration.
31. A pharmaceutical composition for treating a mood disorder or an anxiety disorder comprising pipamperone in a dose of 5-15 mg and escitalopram in a dose of 10-20 mg.
32. A method of treating an anxiety disorder in a patient comprising administering to the patient the pharmaceutical composition of any of claim 1, 3-4 or 6-31.
33. A method of treating a mood disorder in a patient comprising administering to the patient the pharmaceutical composition of any of claim 1-2, 4-5 or 7-31.

* * * * *